(12) United States Patent
Castellote Alvaro et al.

(10) Patent No.: US 11,453,657 B2
(45) Date of Patent: Sep. 27, 2022

(54) COMPOUNDS FOR THE TREATMENT OF PARASITIC INFECTIONS

(71) Applicant: GlaxoSmithKline Intellectual Property Development Limited, Middlesex (GB)

(72) Inventors: Maria Isabel Castellote Alvaro, Madrid (ES); Maria Luisa León Diaz, Madrid (ES); Jose Ignacio Martin Hernando, Madrid (ES)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 0 days.

(21) Appl. No.: 16/963,539

(22) PCT Filed: Jan. 23, 2019

(86) PCT No.: PCT/EP2019/051633
§ 371 (c)(1),
(2) Date: Jul. 21, 2020

(87) PCT Pub. No.: WO2019/145360
PCT Pub. Date: Aug. 1, 2019

(65) Prior Publication Data
US 2021/0047299 A1 Feb. 18, 2021

(30) Foreign Application Priority Data
Jan. 24, 2018 (EP) .................................. 18382040

(51) Int. Cl.
*C07D 403/12* (2006.01)
*A61P 33/06* (2006.01)

(52) U.S. Cl.
CPC ............ *C07D 403/12* (2013.01); *A61P 33/06* (2018.01)

(58) Field of Classification Search
CPC .................................................. C07D 403/12
See application file for complete search history.

*Primary Examiner* — Brian E McDowell
(74) *Attorney, Agent, or Firm* — James K. Leonard

(57) ABSTRACT

The present invention relates to novel compounds or pharmaceutically acceptable salts thereof, corresponding compositions, and methods and/or uses in therapy, for example in the treatment of parasitic infections such as malaria, in particular infection by *Plasmodium falciparum*.

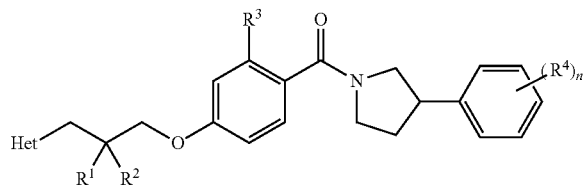

19 Claims, No Drawings

COMPOUNDS FOR THE TREATMENT OF PARASITIC INFECTIONS

This application is a § 371 of International Application No. PCT/EP2019/051633, filed 23 Jan. 2019, which claims the priority of EP18382040.6, filed 24 Jan. 2018.

FIELD OF THE INVENTION

The present invention relates to novel compounds or pharmaceutically acceptable salts thereof, corresponding compositions, and methods and/or uses in therapy, for example in the treatment of parasitic infections such as malaria, in particular infection by *Plasmodium falciparum*.

BACKGROUND OF THE INVENTION

Parasitic protozoal infections are responsible for a wide variety of diseases of medical and veterinary importance, including malaria in man and various coccidiosis in birds, fish and mammals. Many of the diseases are life-threatening to the host and cause considerable economic loss in animal husbandry, such as diseases caused by infection by species of *Eimeria, Theileria, Babesia, Cryptosporidium, Toxoplasma* (such as *Toxoplasma brucei*, African sleeping sickness and *Toxoplasma cruzi*, Chagas disease) and *Plasmodium* (such as *Plasmodium falciparum*), and the Mastigophora such as species of *Leishmania* (such as *Leishmania donovani*). Another parasitic organism of increasing concern is *Pneumocytis carinii*, which can cause an often fatal pneumonia in immunodeficient or immunocompromised hosts, including those infected with HIV.

Malaria is a mosquito-borne disease that, in humans, can be caused by five species of *Plasmodium* parasite, of which *Plasmodium falciparum* is the most virulent. In 2016, there were an estimated 216 million of people infected with malaria worldwide and malarial disease was responsible for an estimated 445,000 deaths (91% of them in sub-saharian Africa), young children and pregnant women being the most affected groups (WORLD HEALTH ORGANIZATION. (2017. *World malaria report*. Geneva, Switzerland, World Health Organization).

Resistance to classical treatments and emerging resistance to the current treatment of choice (artemisinins-based combination therapies) reveals the urgent need for new therapeutic agents with novel mechanisms of action (WORLD HEALTH ORGANIZATION. Joint assessment of the response to artemisinin resistance in the greater Mekong sub-region. November 2011-February 2012. Summary report).

In 2010, GSK released details of more than 13,500 chemical compounds that have already shown to inhibit *Plasmodium falciparum* parasite growth in the phenotypic screening approach (Gamo, F. J. et al., Thousands of chemical starting points for antimalarial lead identification. *Nature*, 2010, 465, 305-310). Molecular structures and descriptions of these compounds were made publicly available in accessible databases under the name of TCAMS (Tres Cantos Antimalarial set) (http//www.ebi.ac.uk/chemblntd). One such compound disclosed in TCAMS is:

Owing to the ever growing emergence of drug resistant strains of malaria and continued high incidence of malaria, there exists an urgent need to provide further drug compounds for the treatment of malaria.

SUMMARY OF THE INVENTION

In a first aspect of the invention, there is provided a compound of Formula (I) or pharmaceutically acceptable salt thereof:

(I)

wherein
$R^1$ is hydrogen, fluoro or methyl, wherein
when $R^1$ is hydrogen, $R^2$ is fluoro, methyl, hydroxyl or amino,
when $R^1$ is fluoro, $R^2$ is fluoro, and
when $R^1$ is methyl, $R^2$ is methyl or hydroxyl;
$R^3$ is hydrogen or fluoro;
$R^4$ is fluoro, chloro, cyano or methoxy;
n is 1 or 2; and
Het is imidazole, pyrazole, thiazole, isothiazole, oxazole, isoxazole, triazole or tetrazole, wherein each Het is optionally substituted by $C_1$-$C_4$ alkyl, cyano or —C(O)NH$_2$.

In a second aspect of the invention, there is provided a pharmaceutical composition comprising (a) a compound of Formula (I) or pharmaceutically acceptable salt thereof; and (b) a pharmaceutically acceptable excipient.

In a third aspect of the invention, there is provided a compound of Formula (I) or pharmaceutically acceptable salt thereof, for use in therapy.

In a fourth aspect of the invention, there is provided a compound of Formula (I) or a pharmaceutically acceptable salt thereof, for use in the treatment of malaria.

In a fifth aspect of the invention, there is provided a method for the treatment of a parasitic protozoal infection, comprising administering a pharmaceutically effective amount of a compound of Formula (I) or pharmaceutically acceptable salt thereof to a human in need thereof.

In a sixth aspect of the invention, there is provided the use of a compound of Formula (I) or pharmaceutically acceptable salt thereof in the manufacture of a medicament for use in the treatment of a parasitic protozoal infection.

In a seventh aspect of the invention, there is provided a combination of (a) a compound of Formula (I) or pharmaceutically acceptable salt thereof; and (b) at least one other anti-malarial agent.

DETAILED DESCRIPTION OF THE INVENTION

As described above, in one aspect of the invention, there is provided a compound of Formula (I) or a pharmaceutically acceptable salt thereof:

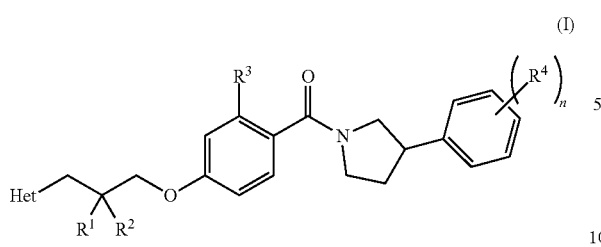

(I)

wherein
R¹ is hydrogen, fluoro or methyl, wherein
when R¹ is hydrogen, R² is fluoro, methyl, hydroxyl or amino,
when R¹ is fluoro, R² is fluoro, and
when R¹ is methyl, R² is methyl or hydroxyl;
R³ is hydrogen or fluoro;
R⁴ is fluoro, chloro, cyano or methoxy;
n is 1 or 2; and
Het is imidazole, pyrazole, thiazole, isothiazole, oxazole, isoxazole, triazole or tetrazole, wherein each Het is optionally substituted by $C_1$-$C_4$ alkyl, cyano or —C(O)NH₂.

In one embodiment, when n is 1, R⁴ is at the para position, also depicted as Formula (Ia):

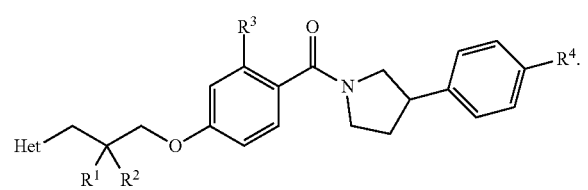

(Ia)

In other words, when n is 1, R⁴ is at the para position of the phenyl ring to which it is attached in Formula (I).

In one embodiment, R⁴ is fluoro or chloro. In a particular embodiment, R⁴ is fluoro.

In one embodiment, R¹ is hydrogen, such that R² is fluoro, methyl, hydroxyl or amino. In a particular embodiment, R¹ is hydrogen and R² is hydroxyl or amino, particularly R² is hydroxyl.

In one embodiment, the compound of the invention is defined according to any one of the following (particularly when R¹ is hydrogen):

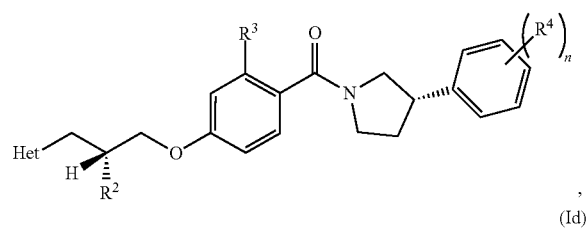

(Ix)

,

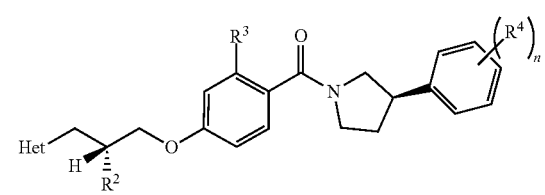

(Id)

or

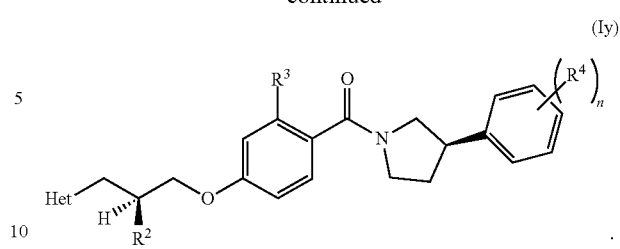

(Iy)

.

Thus, in such embodiment, the chiral centres in the compound of the invention, when R¹ is hydrogen, both chiral centres (i.e. the carbon R² centre and the phenyl-pyrrolidine centre) are not both S configuration.

In one embodiment, the compound of the invention is defined according to Formula (Ib):

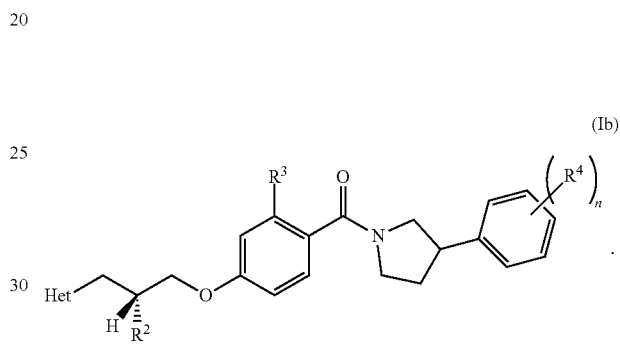

(Ib)

In another embodiment, the compound of the invention is defined according to Formula (Ic):

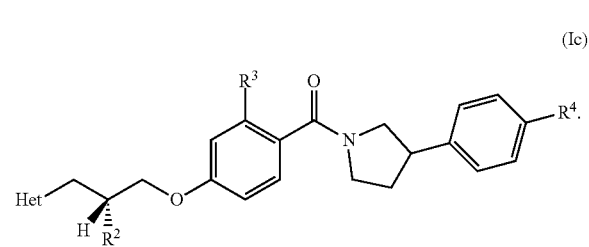

(Ic)

In another embodiment, the compound of the invention is defined according to Formula (Id):

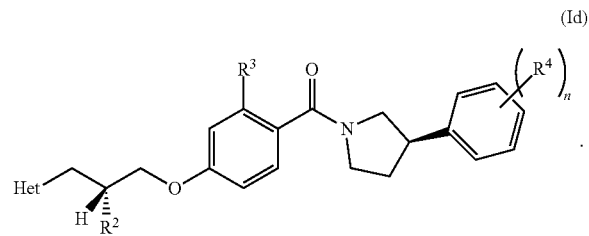

(Id)

In another embodiment, the compound of the invention is defined according to Formula (Ie):

(Ie)

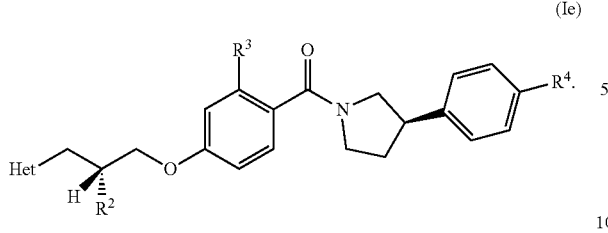

In other words, in an embodiment (according to Formula (Id) or (Ie)), both chiral centres in the molecule (i.e. the carbon $R^2$ centre and the phenyl-pyrrolidine centre) have an R configuration.

In an embodiment, when $R^1$ is hydrogen, the chiral centre on the right-hand side of the molecule, as depicted, has an R configuration (as depicted in Formula (Ie), for example). In other words, the chiral centre on the pyrrolidine has an R configuration.

In an embodiment, when $R^1$ is hydrogen, the chiral centre on the left-hand side of the molecule, as depicted, has an R configuration.

In one embodiment, the invention relates to a compound of Formula (I) or (Ia) to (Ie) or (Ix) or (Iy), as defined above. It should be noted that any reference to a compound of Formula (I) is also a reference to any one of Formulae (Ia) to (Ie), (Ix) or (Iy).

In one embodiment, $R^3$ is hydrogen.

In one embodiment, n is 1.

In one embodiment, Het is attached through a nitrogen atom.

In one embodiment, Het is tetrazole or triazole which is optionally substituted by $C_1$-$C_4$ alkyl, cyano or —C(O)NH$_2$.

In one embodiment, Het is selected from one of the groups depicted below, where * represents the point of attachment.

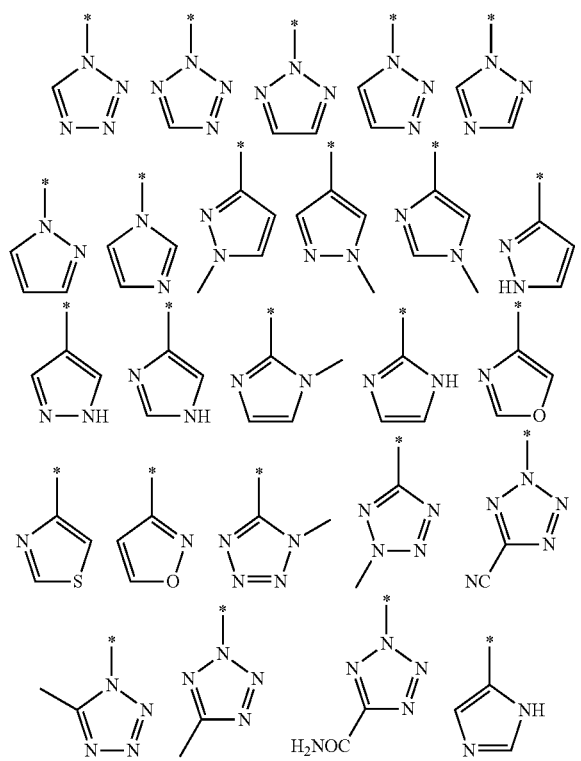

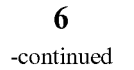

In one embodiment, Het is selected from one of the groups depicted below, where * represents the point of attachment:

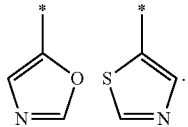

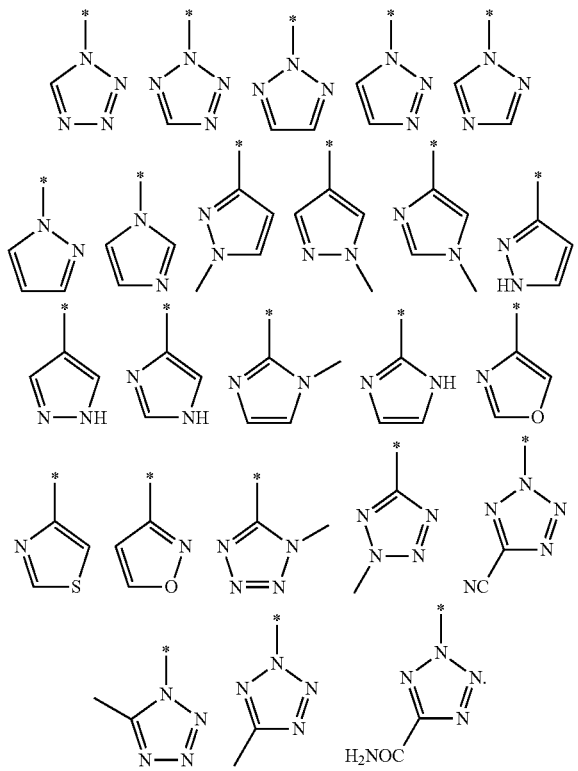

In one embodiment, Het is selected from one of the groups depicted below, where * represents the point of attachment:

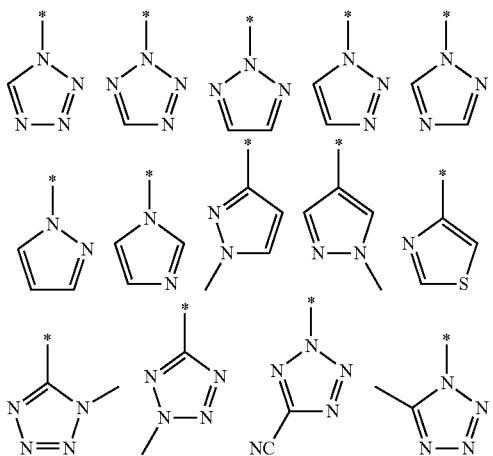

-continued

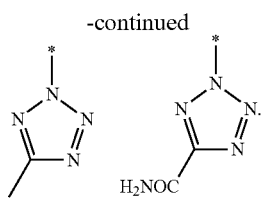

In another embodiment, Het is unsubstituted tetrazole or triazole. In a specific embodiment, Het is unsubstituted tetrazole.

In one embodiment, Het is not selected from:

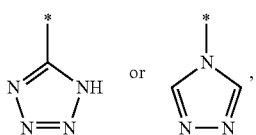

where * represents the point of attachment.

Therefore, in one embodiment, Het is triazole or tetrazole selected from one of the groups depicted below, where * represents the point of attachment:

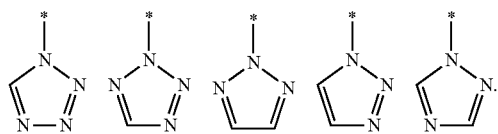

In particular, Het is tetrazole selected from one of the groups depicted below, where* represents the point of attachment:

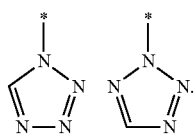

In one embodiment, the compound of Formula (I) is selected from the list consisting of:
((R)-3-(4-fluorophenyl)pyrrolidin-1-yl)(4-(2-methyl-3-(1H-tetrazol-1-yl) propoxy)phenyl)methanone (Example 1a and 1b);
(R)-(4-(2,2-dimethyl-3-(1H-tetrazol-1-yl)propoxy)phenyl) (3-(4-fluorophenyl)pyrrolidin-1-yl)methanone (Example 2);
(4-(2-fluoro-3-(1H-tetrazol-1-yl)propoxy)phenyl)((R)-3-(4-fluorophenyl)pyrrolidin-1-yl)methanone (Example 3a and 3b);
(R)-(4-(2,2-difluoro-3-(1H-tetrazol-1-yl)propoxy)phenyl) (3-(4-fluorophenyl)-pyrrolidin-1-yl)methanone (Example 4);
((R)-3-(4-fluorophenyl)pyrrolidin-1-yl)(4-((R)-2-hydroxy-3-(1H-tetrazol-1-yl) propoxy)phenyl)methanone (Example 5);
((R)-3-(4-fluorophenyl)pyrrolidin-1-yl)(4-((S)-2-hydroxy-3-(1H-tetrazol-1-yl) propoxy)phenyl)methanone (Example 6);
((R)-3-(4-fluorophenyl)pyrrolidin-1-yl)(4-((R)-2-hydroxy-3-(2H-tetrazol-2-yl) propoxy)phenyl)methanone (Example 7);
((R)-3-(4-fluorophenyl)pyrrolidin-1-yl)(4-((S)-2-hydroxy-3-(2H-tetrazol-2-yl)propoxy)phenyl)methanone (Example 8);
((R)-3-(4-fluorophenyl)pyrrolidin-1-yl)(4-(2-hydroxy-2-methyl-3-(2H-tetrazol-2-yl)propoxy)phenyl)methanone (Example 9);
((R)-3-(4-fluorophenyl)pyrrolidin-1-yl)(4-(2-hydroxy-2-methyl-3-(1H-tetrazol-1-yl)propoxy)phenyl)methanone (Example 10);
(4-((R)-2-fluoro-3-(2H-tetrazol-2-yl)propoxy)phenyl)((R)-3-(4-fluorophenyl) pyrrolidin-1-yl)methanone) (Example 11);
(4-((S)-2-fluoro-3-(2H-tetrazol-2-yl)propoxy)phenyl)((R)-3-(4-fluorophenyl) pyrrolidin-1-yl)methanone) (Example 12);
((S)-3-(4-fluorophenyl)pyrrolidin-1-yl)(4-((R)-2-hydroxy-3-(2H-tetrazol-2-yl)propoxy)phenyl)methanone (Example 13);
((S)-3-(4-fluorophenyl)pyrrolidin-1-yl)(4-((S)-2-hydroxy-3-(2H-tetrazol-2-yl)propoxy)phenyl)methanone (Example 14);
((R)-3-(4-fluorophenyl)pyrrolidin-1-yl)(4-((R)-2-hydroxy-3-(1H-1,2,4-triazol-1-yl) propoxy)phenyl)methanone (Example 15);
((R)-3-(4-fluorophenyl)pyrrolidin-1-yl)(4-((R)-2-hydroxy-3-(2H-1,2,3-triazol-2-yl) propoxy)phenyl)methanone (Example 16);
((R)-3-(4-fluorophenyl)pyrrolidin-1-yl)(4-((R)-2-hydroxy-3-(1H-1,2,3-triazol-1-yl) propoxy)phenyl)methanone (Example 17);
((R)-3-(4-fluorophenyl)pyrrolidin-1-yl)(4-((R)-2-hydroxy-3-(4H-1,2,4-triazol-4-yl)propoxy)phenyl)methanone (Example 18);
((R)-3-(4-fluorophenyl)pyrrolidin-1-yl)(4-((R)-2-hydroxy-3-(1H-pyrazol-1-yl) propoxy)phenyl)methanone (Example 19);
((R)-3-(4-fluorophenyl)pyrrolidin-1-yl)(4-((R)-2-hydroxy-3-(1H-imidazol-1-yl) propoxy)phenyl)methanone (Example 20);
((R)-3-(4-fluorophenyl)pyrrolidin-1-yl)(4-((R)-2-hydroxy-3-(5-methyl-1H-tetrazol-1-yl)propoxy)phenyl)methanone (Example 21);
((R)-3-(4-fluorophenyl)pyrrolidin-1-yl)(4-((R)-2-hydroxy-3-(5-methyl-2H-tetrazol-2-yl)propoxy)phenyl)methanone (Example 22);
((R)-3-(4-fluorophenyl)pyrrolidin-1-yl)(4-((R)-2-hydroxy-3-(2-methyl-2H-tetrazol-5-yl)propoxy)phenyl)methanone (Example 23);
((R)-3-(4-fluorophenyl)pyrrolidin-1-yl)(4-((R)-2-hydroxy-3-(1-methyl-1H-tetrazol-5-yl)propoxy)phenyl)methanone (Example 24);
((R)-3-(4-fluorophenyl)pyrrolidin-1-yl)(4-((R)-2-hydroxy-3-(1H-tetrazol-5-yl) propoxy)phenyl)methanone (Example 25);
(2-fluoro-4-((R)-2-hydroxy-3-(1H-tetrazol-1-yl)propoxy) phenyl)((R)-3-(4-fluoro phenyl)pyrrolidin-1-yl)methanone (Example 26);
(2-fluoro-4-((R)-2-hydroxy-3-(2H-tetrazol-2-yl)propoxy) phenyl)((R)-3-(4-fluoro phenyl)pyrrolidin-1-yl)methanone (Example 27);
((R)-3-(4-chlorophenyl)pyrrolidin-1-yl)(4-((R)-2-hydroxy-3-(1H-tetrazol-1-yl) propoxy)phenyl)methanone (Example 28);
((R)-3-(4-chlorophenyl)pyrrolidin-1-yl)(4-((R)-2-hydroxy-3-(2H-tetrazol-2-yl) propoxy)phenyl)methanone (Example 29);

((R)-3-(4-chlorophenyl)pyrrolidin-1-yl) (4-((R)-2-hydroxy-3-(1H-1,2,4-triazol-1-yl) propoxy)phenyl)methanone (Example 30);

((R)-3-(4-chlorophenyl)pyrrolidin-1-yl)(4-((R)-2-hydroxy-3-(2H-1,2,3-triazol-2-yl) propoxy)phenyl)methanone (Example 31);

((R)-3-(4-chlorophenyl)pyrrolidin-1-yl)(4-((R)-2-hydroxy-3-(1H-1,2,3-triazol-1-yl) propoxy)phenyl)methanone (Example 32);

((R)-3-(4-chlorophenyl)pyrrolidin-1-yl) (2-fluoro-4-((R)-2-hydroxy-3-(1H-tetrazol-1-yl)propoxy)phenyl)methanone (Example 33);

((R)-3-(4-chlorophenyl)pyrrolidin-1-yl) (2-fluoro-4-((R)-2-hydroxy-3-(2H-tetrazol-2-yl)propoxy)phenyl)methanone (Example 34);

((R)-3-(4-fluorophenyl)pyrrolidin-1-yl)(4-(2-hydroxy-3-(thiazol-4-yl)propoxy) phenyl)methanone (Example 35);

((R)-3-(4-fluorophenyl)pyrrolidin-1-yl)(4-(2-methoxy-3-(1-methyl-1H-pyrazol-3-yl)propoxy)phenyl)methanone (Example 36);

((R)-3-(4-fluorophenyl)pyrrolidin-1-yl)(4-(2-hydroxy-3-(1-methyl-1H-pyrazol-4-yl)propoxy)phenyl)methanone (Example 37);

2-((R)-3-(4-((R)-3-(4-fluorophenyl)pyrrolidine-1-carbonyl) phenoxy)-2-hydroxypropyl)-2H-tetrazole-5-carboxamide (Example 38);

2-((R)-3-(4-((R)-3-(4-fluorophenyl)pyrrolidine-1-carbonyl) phenoxy)-2-hydroxypropyl)-2H-tetrazole-5-carbonitrile (Example 39);

(3-(2-fluorophenyl)pyrrolidin-1-yl)(4-((R)-2-hydroxy-3-(2H-tetrazol-2-yl)propoxy)phenyl)methanone (Example 40);

(3-(3-fluorophenyl)pyrrolidin-1-yl)(4-((R)-2-hydroxy-3-(2H-tetrazol-2-yl)propoxy)phenyl)methanone (Example 41);

(3-(3-fluorophenyl)pyrrolidin-1-yl)(4-((R)-2-hydroxy-3-(2H-tetrazol-2-yl)propoxy)phenyl)methanone (Example 42);

4-(1-(4-((R)-2-hydroxy-3-(2H-tetrazol-2-yl)propoxy)benzoyl) pyrrolidin-3-yl)benzonitrile
(Example 43);

(4-((R)-2-hydroxy-3-(2H-tetrazol-2-yl)propoxy)phenyl)(3-(4-methoxyphenyl)pyrrolidin-1-yl)methanone (Example 44);

(4-((R)-2-amino-3-(2H-tetrazol-2-yl)propoxy)phenyl)((R)-3-(4-fluorophenyl) pyrrolidin-1-yl)methanone (Example 45);

(4-((R)-2-amino-3-(1H-tetrazol-1-yl)propoxy)phenyl)((R)-3-(4-fluorophenyl) pyrrolidin-1-yl)methanone (Example 46);

(4-((R)-2-amino-3-(1H-tetrazol-1-yl) propoxy)phenyl)((R)-3-(4-chlorophenyl) pyrrolidin-1-yl)methanone (Example 47);

(4-((R)-2-amino-3-(2H-tetrazol-2-yl) propoxy)phenyl)((R)-3-(4-chlorophenyl) pyrrolidin-1-yl)methanone (Example 48);

(4-((S)-2-amino-3-(2H-tetrazol-2-yl) propoxy)phenyl)((R)-3-(4-fluorophenyl) pyrrolidin-1-yl)methanone, Hydrochloride (Example 49);

(4-((R)-2-amino-3-(2H-tetrazol-2-yl) propoxy)phenyl)((S)-3-(4-fluorophenyl) pyrrolidin-1-yl)methanone, Hydrochloride (Example 50);

(4-((S)-2-amino-3-(2H-tetrazol-2-yl) propoxy)phenyl)((S)-3-(4-fluorophenyl) pyrrolidin-1-yl)methanone, Hydrochloride (Example 52);

(4-((R)-2-amino-3-(2H-1,2,3-triazol-2-yl) propoxy)phenyl) ((R)-3-(4-fluorophenyl) pyrrolidin-1-yl)methanone, Hydrochloride (Example 53);

(4-((R)-2-amino-3-(1H-1,2,3-triazol-1-yl) propoxy)phenyl) ((R)-3-(4-fluorophenyl) pyrrolidin-1-yl)methanone, Hydrochloride (Example 54);

(4-((R)-2-amino-3-(1H-pyrazol-1-yl) propoxy)phenyl)((R)-3-(4-fluorophenyl) pyrrolidin-1-yl)methanone, Hydrochloride (Example 55); and (4-((R)-2-amino-3-(2H-tetrazol-2-yl)propoxy)-2-fluorophenyl)((R)-3-(4-fluoro phenyl)pyrrolidin-1-yl)methanone, Hydrochloride (Example 56), or a pharmaceutically acceptable salt thereof.

Terms and Definitions

As used herein, the term "alkyl" represents a saturated, straight, or branched hydrocarbon moiety. The term "$C_1$-$C_4$ alkyl" refers to an alkyl moiety containing from 1 to 4 carbon atoms. Exemplary alkyls include, but are not limited to methyl, ethyl, n-propyl, isopropyl, n-butyl, isobutyl, s-butyl and t-butyl.

As used herein, the term "cyano" represents —CN.

The term "a compound of the invention" means any one of the compounds of the invention as defined above. Specifically, the term "compounds of the invention" as used herein, includes, but is not limited to a compound of Formula (I) or a pharmaceutically acceptable salt thereof and also is a reference to any one of the Formulas described herein, which include the Formulas (Ia) to (Ie).

It will further be appreciated that a compound of the invention, such as a compound of Formula (I) may exist in different tautomeric forms. All possible tautomers are contemplated to be within the scope of the present invention.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, and this phrase also encompasses a mixture of a compound of Formula (I) and a pharmaceutically acceptable salt of a compound of Formula (I).

It is to be understood that references herein to a compound of Formula (I) or a pharmaceutically acceptable salt thereof includes a compound of Formula (I) as a free base or as a pharmaceutically acceptable salt thereof. Thus, in one embodiment, the invention is directed to a compound of Formula (I). In another embodiment, the invention is directed to a pharmaceutically acceptable salt of a compound of Formula (I). Thus, it is to be understood that the aforementioned definitions of this paragraph also applies to the fact that compounds of the present invention are understood to encompass compounds of Formula(s) (I), (Ia), (Ib), (Ic), (Id), (Ie), (Ix), (Iy) or any other corresponding Formula(s) as defined herein, respectively.

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://www.wiley.com/WileyCDA/Wiley-Title/prouctCd-3906390519.html).

Where the compound functionality allows, suitable pharmaceutically acceptable salts of a compound of Formula (I) can be formed, which include acid or base addition salts. Acid addition salts may be formed by reaction with the appropriate acid, optionally in a suitable solvent such as an organic solvent, to give the salt which can be isolated by crystallisation and filtration. Base addition salts may be formed by reaction with the appropriate base, optionally in a suitable solvent such as an organic solvent, to give the salt which can be isolated by crystallisation and filtration.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

In one embodiment, the compound of Formula (I) is a hydrochloride salt of a compound of Formula (I).

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The invention includes within its scope all possible stoichiometric and non-stoichiometric forms of the salts of compounds of Formula (I).

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

An appropriate "therapeutically effective amount" will depend upon a number of factors including, for example, the age and weight of the subject, the precise condition requiring treatment and its severity, the nature of the formulation, and the route of administration, and will ultimately be at the discretion of the attendant physician.

The compounds according to Formula (I) may contain one or more asymmetric centres (also referred to as a chiral centres) and may, therefore, exist as individual enantiomers, diastereomers, or other stereoisomeric forms, or as mixtures thereof. Chiral centres, such as chiral carbon atoms, may also be present in a substituent such as an alkyl group. Where the stereochemistry of a chiral centre present in Formula (I), or in any chemical structure illustrated herein, is not specified, the structure is intended to encompass any stereoisomer and all mixtures thereof. Thus, compounds according to Formula (I) containing one or more chiral centres may be used as racemic modifications including racemic mixtures and racemates, enantiomerically-enriched mixtures, or as enantiomerically-pure individual stereoisomers.

For solvates of the compounds of the invention, or salts thereof, that are in crystalline form, the skilled artisan will appreciate that pharmaceutically-acceptable solvates may be formed wherein solvent molecules are incorporated into the crystalline lattice during crystallization. Solvates may involve non-aqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The invention also includes various deuterated forms of the compounds of Formula(s) (I), (Ia), (Ib), (Ic), (Id), (Ie), (Ix), (Iy) or any other corresponding Formula(s) as defined herein, respectively, or a pharmaceutically acceptable salt thereof. Each available hydrogen atom attached to a carbon atom may be independently replaced with a deuterium atom. A person of ordinary skill in the art will know how to synthesize deuterated forms of the compounds of Formulas (I) to (VI), respectively, or a pharmaceutically acceptable salt thereof of the present invention. For example, deuterated materials, such as alkyl groups may be prepared by conventional techniques (see for example: methyl-$d_3$-amine available from Aldrich Chemical Co., Milwaukee, Wis., Cat. No. 489,689-2).

The subject invention also includes isotopically-labeled compounds which are identical to those recited in Formula(s) (I), (Ia), (Ib), (Ic), (Id), (Ie), (Ix), (Iy) or any other corresponding Formula(s) as defined herein, respectively, respectively, or a pharmaceutically acceptable salt thereof but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3$H, $^{11}$C, $^{14}$C, $^{18}$F, $^{123}$I or $^{125}$I.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3$H or $^{14}$C have been incorporated, are useful in drug and/or substrate tissue distribution assays. Tritiated, ie. $^3$H, and carbon-14, ie. $^{14}$C, isotopes are particularly preferred for their ease of preparation and detectability. $^{11}$C and $^{18}$F isotopes are particularly useful in PET (positron emission tomography).

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

As used herein, the term "optionally" means that the subsequently described event(s) may or may not occur, and include both event(s) that occur and event(s) that do not occur. For example, when used in connection with the term "substituted", i.e. "optionally substituted", it means that the subsequently described substituents may be present or not present.

Compound Preparation

The compounds of the invention may be made by a variety of methods, i.e., which includes those methods conventionally known in the field of chemistry. Any previously defined variable will continue to have the previously defined meaning unless otherwise indicated. Illustrative general synthetic methods are set out in the following schemes, and can be readily adapted to prepare other compounds of the invention. Specific compounds of the invention can be prepared according to the experimental procedures disclosed in the Examples section.

The general procedures used to synthesise the compounds of Formula (I) are described in reaction schemes 1 to 13 below and illustrated in the examples.

Intermediates 3a-c, wherein X is F or Cl, may be prepared by the procedure illustrated in scheme 1.

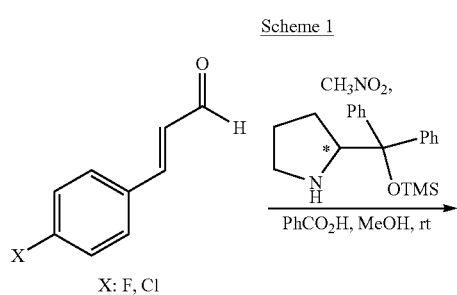

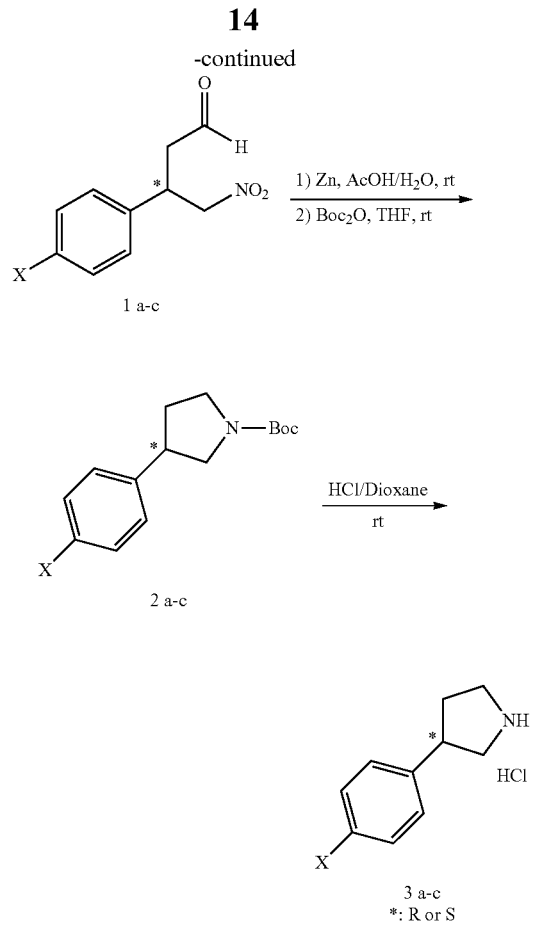

Catalytic asymmetric Michael reaction of 4-substituted cinnamaldehydes with nitromethane in presence of benzoic acid and the corresponding R or S-diphenylprolinol silyl ether affords nitro intermediates 1a-c with excellent enantioselectivity. The nitro group is then reduced with, for example, zinc and acetic acid. Subsequent reductive amination and simultaneous Boc-amine protection gives intermediate 2a-c. Boc deprotection under acidic conditions (for example, HCl/dioxane) afford intermediates 3a-c. Intermediates 3a-c can be (R) or (S) enantiomer.

N-1-substituted tetrazole intermediates 17-18 and example 4 are prepared by, for example, route A or route B depicted in scheme 2.

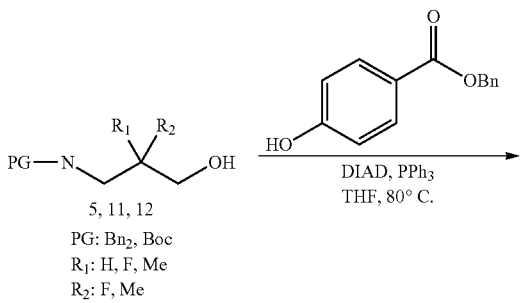

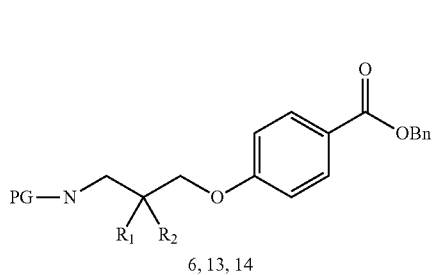
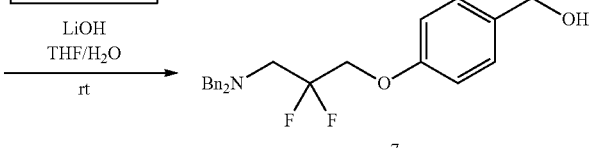
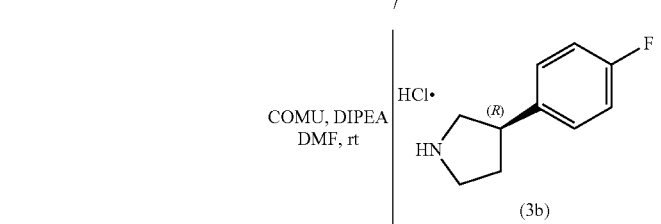
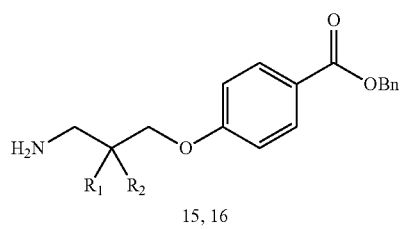
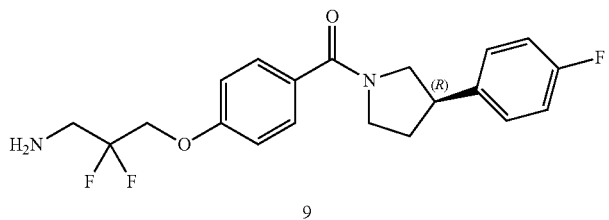
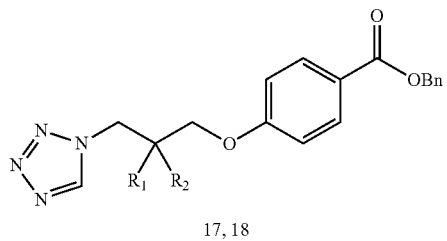
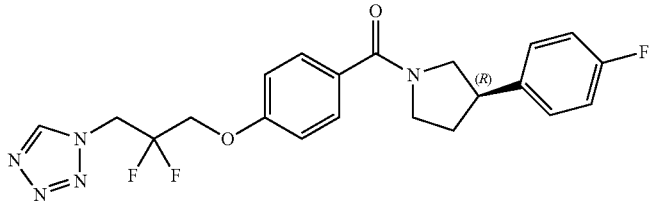

Example 4

As shown in scheme 2, the Mitsunobu reaction of a protecting amino alcohol such as 5, 11, 12, wherein the protecting group (PG) is Bn₂ or Boc, with benzyl 4-hydroxybenzoate affords the corresponding ether intermediates 6, 13 and 14. R₁ and R₂ are both fluoro or methyl, or R₁ is hydrogen and R₂ is methyl.

Example 4, containing a difluoro-substituted alkyl chain, is prepared by route A. Hydrolysis of benzyl ester 6 under basic conditions affords carboxylic acid intermediate 7. Acid-amine coupling between carboxylic acid 7 and chiral R-3-(4-fluorophenyl)pyrrolidine 3b in the presence of, for example, COMU as a coupling reagent gives amide intermediate 8. Hydrogenation followed by condensation with orthoformiate and sodium azide affords example 4.

Alternatively, intermediates 17 and 18, containing a methyl or dimethyl-substituted alkyl chain, can be prepared by route B. Boc-deprotection of benzyl ester 13, 14 under acid conditions followed by condensation with orthoformiate and sodium azide afford the N-1-substituted tetrazole intermediates 17, 18.

Intermediates 25a-b and 28a-b, containing a racemic methyl or hydroxy-substituted alkyl chain, may be prepared by the procedure illustrated in scheme 3.

Scheme 3

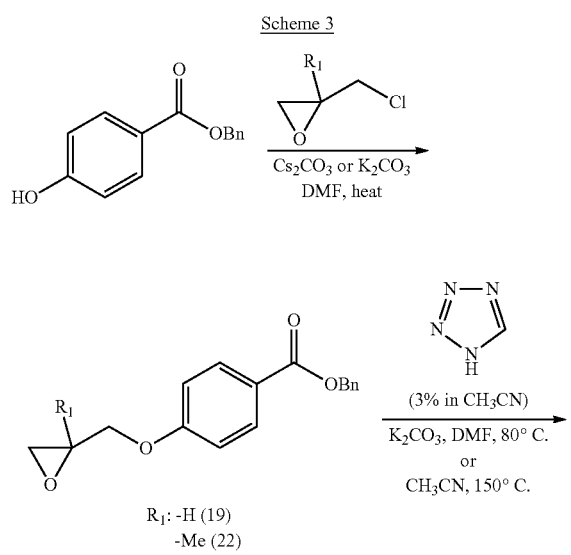

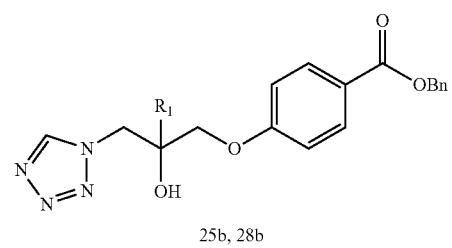

Benzyl 4-hydroxybenzoate is O-alkylated with epichlorohydrin or 2-substituted epichlorohydrins such as 2-methyl epichlorohydrin in the presence of a base to yield the corresponding aryl glycidyl ether derivative 19, 22. Epoxide opening of intermediate 19, 22 with heterocycles such as tetrazole affords N-1 and N-2 tetrazole intermediates 25a-b and 28a-b.

Intermediates such as 26, 27, 29-35, 54, 55, 82 and 83, containing a chiral hydroxy-substituted alkyl chain, can be prepared either by route A or route B (scheme 4).

Scheme 4

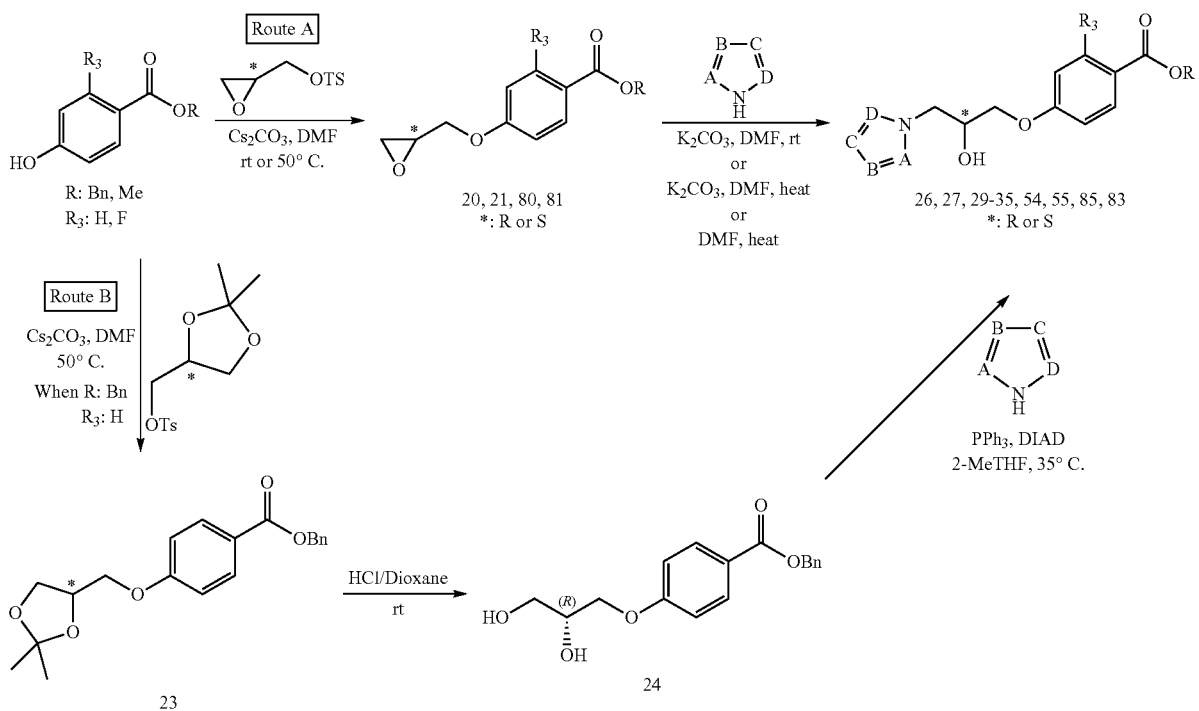

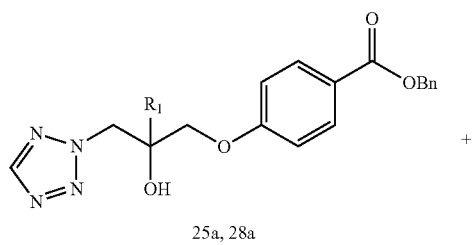

As shown in scheme 4, nucleophilic displacement of a leaving group, such as a tosylate in a chiral oxirane (route A) or in a chiral dimethyl-1,3-dioxolane (route B), by a 4-hydroxybenzoate derivative in presence of a base give chiral intermediates 20, 21, 80, 81 or 23 respectively.

Intermediates 20, 21, 80, 81 can thereafter be converted into corresponding chiral alcohols 26, 27, 29-35, 54, 55, 82 and 83 by epoxide ring opening reaction that is generally carried out under basic conditions or high temperature. A five-membered heterocycle, such as tetrazole, triazole, pyrazole or imidazole, in the presence of a base is used as a nucleophile in the ring opening of the epoxide.

Alternatively, intermediate 23 may also be converted into corresponding chiral alcohols 26 by diol deprotection in acidic conditions followed by reaction with a five-membered heterocycle such as tetrazole under Mitsunobu conditions.

Intermediates 49-51, containing a methoxy-substituted alkyl chain wherein a five-membered heterocycle is linked to the alkyl chain through a carbon atom of the heterocycle moiety, may be prepared by the procedure illustrated in scheme 5.

These intermediates can thereafter be converted into corresponding alcohols 46-48 by reduction with LAH and then subjected to Mitsunobu conditions (PPh$_3$/DIAD) to afford the racemic intermediates 49-51.

Alternatively intermediates 53a-b, wherein a five-membered heterocycle is linked to the chain through a carbon atom of the heterocycle and contain a chiral hydroxy-substituted alkyl chain, may also be prepared by the procedure illustrated in scheme 6.

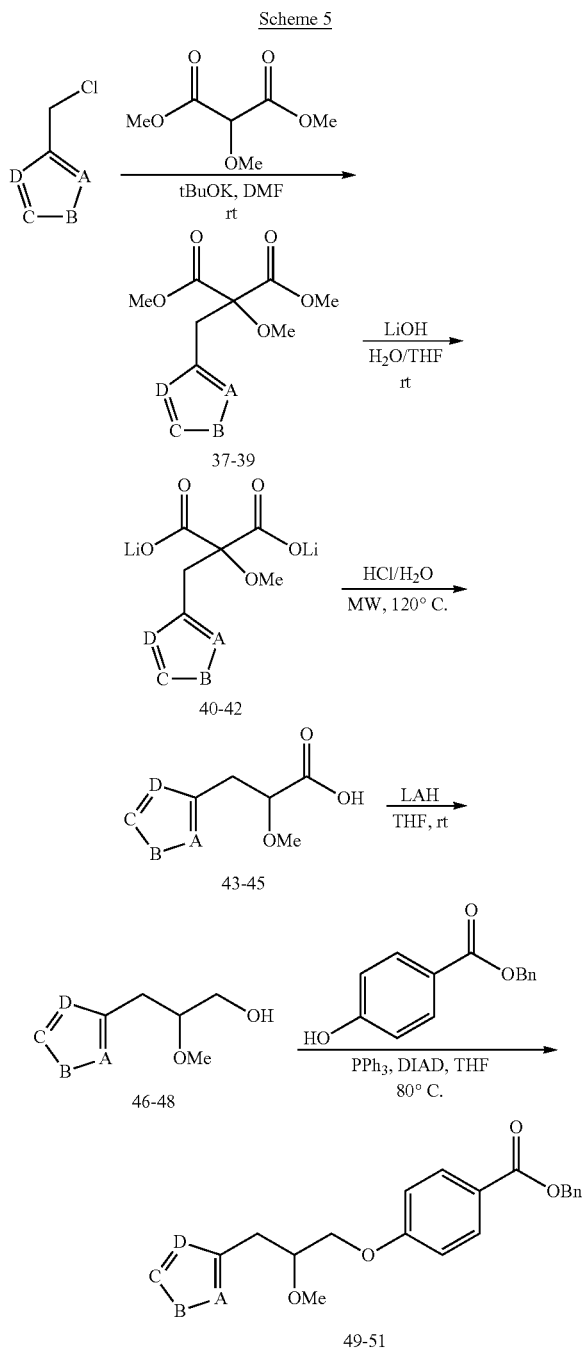

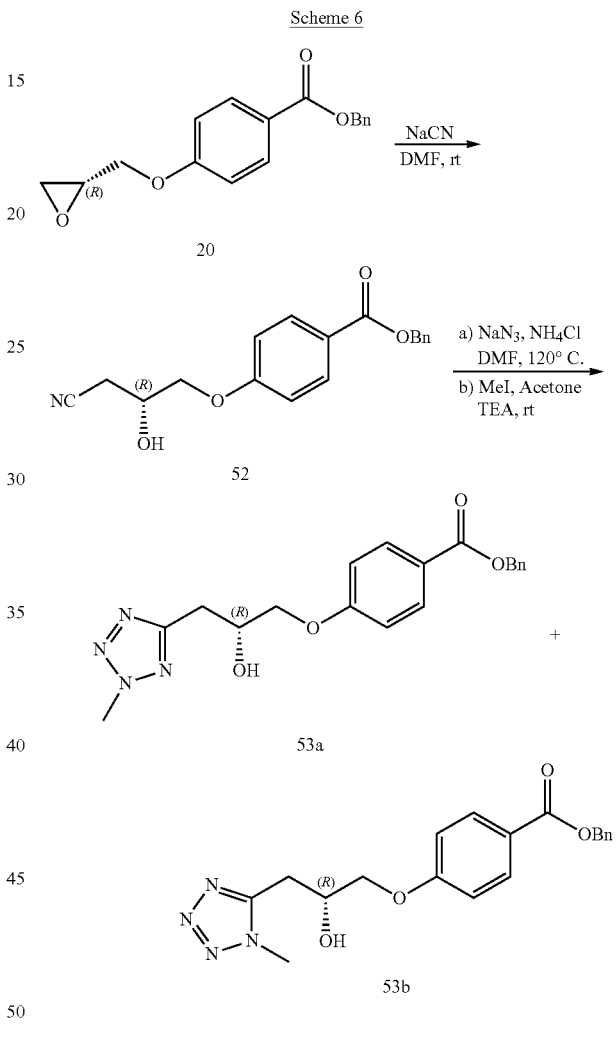

Intermediates 53a-b, described in scheme 6, are synthesized by ring opening of intermediate 20 (a chiral oxirane with fixed R configuration) with, for example, NaCN and the successive reaction of the corresponding nitrile 52 with sodium azide. The methylation of the formed 1H-tetrazole with methyl iodide in the presence of, for example, triethylamine (TEA) as a base provide both 1N- and 2N-methyl substituted tetrazoles 53a and 53b.

Examples 1-3, 5, 6, 9, 10, 35-37, wherein there is a substituted alkyl chain, may be prepared by the procedure illustrated in scheme 7. $R_1$ is typically fluoro, hydrogen, methyl or methoxy and $R_2$ is typically methyl, hydroxy or hydrogen. Heterocycle (Het) is a five-membered heterocycle linked to the chain through a carbon atom or a nitrogen atom of the heterocycle moiety.

Alkylation of dimethyl 2-methoxymalonate with a chloromethyl-five membered heterocycle, such as pyrazole or thiazole, followed by hydrolysis and decarboxylation reactions yield the racemic carboxylic acid intermediates 43-45.

21

Scheme 7

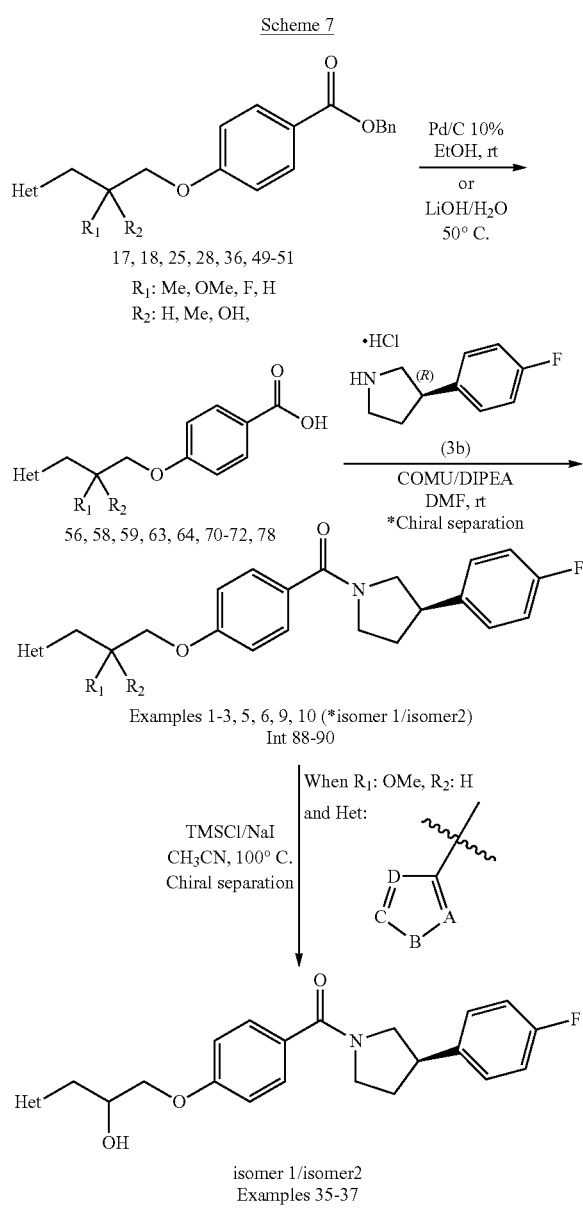

Hydrogenation of a racemic benzyl ester intermediate such as 17, 18, 25, 28, 36, 49-51 affords the corresponding racemic carboxylic acid 56, 58, 59, 63, 64, 70-72, 78. An acid-amine coupling of the racemic carboxylic acid intermediate with a chiral R-3-(4-fluorophenyl)pyrrolidine 3b in the presence of, for example, COMU/DIPEA gives examples 1-3, 5, 6, 9-10 and intermediates 88-90.

22

Examples 35-37 are prepared via O-demethylation of intermediates 89-90 using TMSCl/NaI/MeCN reagent followed by chiral separation.

Examples 5-8, 13-34 and intermediates 86, 87, 91, wherein there is a chiral hydroxy-substituted alkyl chain, can be prepared by the procedure described in scheme 8. Het is a five-membered heterocycle and may be imidazole, pyrazole, triazole or tetrazole, each of which can be substituted. $R_3$ is hydrogen or fluoro and X is fluoro or chloro.

Scheme 8

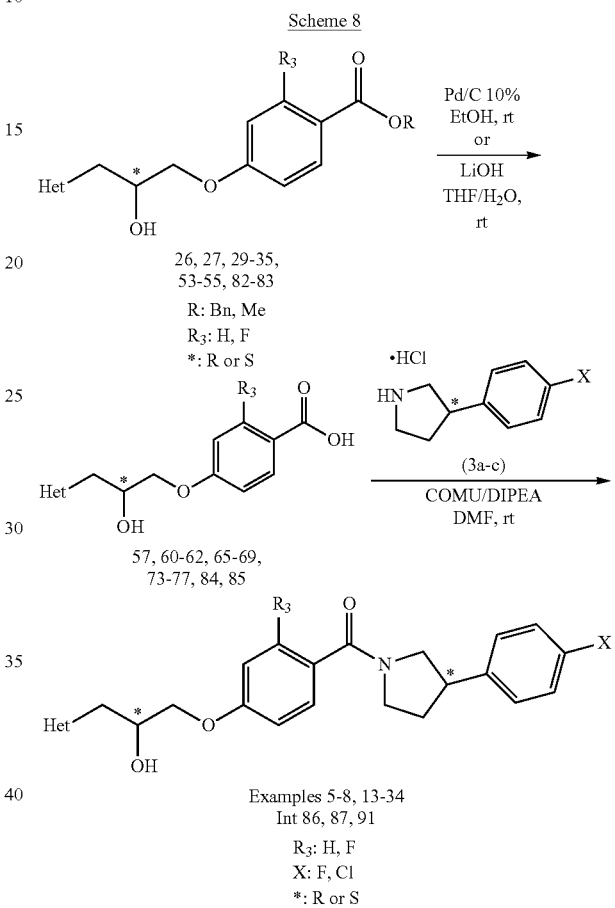

Hydrogenation, wherein R is benzyl, or hydrolysis under basic conditions, wherein R is methyl, affords chiral carboxylic acid intermediates 57, 60-62, 65-69, 73-77, 84, 85. An acid-amine coupling of the corresponding chiral carboxylic acid intermediate with a chiral 3-(4-halo-phenyl)pyrrolidine 3a-c in the presence of, for example, COMU/DIPEA gives examples 5-8, 13-34 and the intermediates 86, 87, 91.

Examples 38 and 39 may be prepared by the procedure illustrated in scheme 9.

Scheme 9

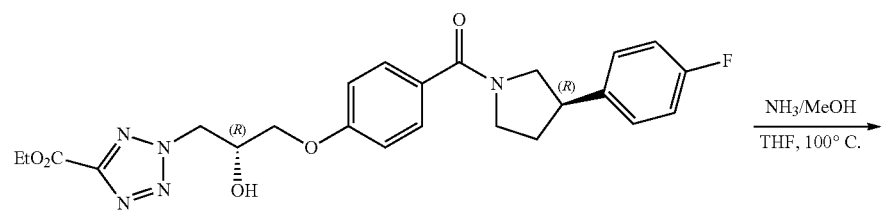

91

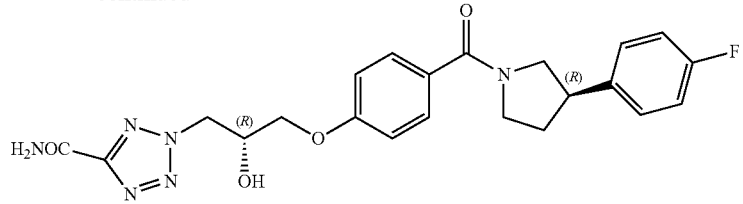

Example 38

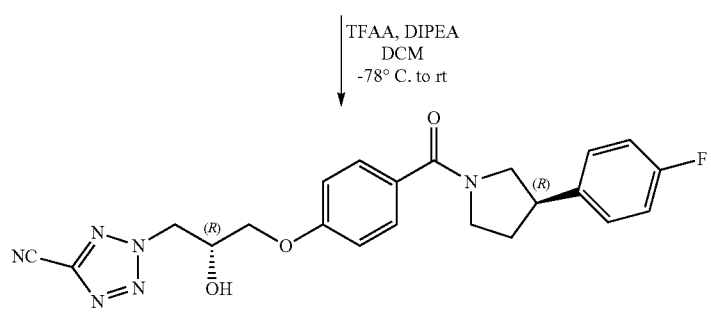

Example 39

Aminolysis of the chiral methyl ester intermediate 91, prepared following the procedure indicated in scheme 8, using NH₃ in MeOH give the primary amide derivative (example 38). The primary amide is converted under mild conditions to the corresponding nitrile (example 39) using trifluoroacetic anhydride (TFAA) in DIPEA.

Examples 40-44 a-b can be prepared using the procedure described in scheme 10. An acid-amine coupling of the corresponding R-chiral carboxylic acid intermediate 57 with a racemic functionalized 3-arylpyrrolidine derivative in the presence of, for example, COMU/DIPEA afford the corresponding amides (examples 40-44 a-b). Stereoisomers are isolated by chiral chromatography. The racemic functionalized 3-arylpyrrolidine derivative can be substituted in ortho, meta and/or para position of the phenyl ring wherein the $R_4$ and $R_4'$ substitution can be groups such as fluoro, methoxy or cyano.

Examples 11 and 12, containing a chiral fluoro-substituted alkyl chain, may be prepared by fluorination reaction. SN2 displacement of hydroxyl by fluorine with DAST occurs with a complete inversion of configuration (scheme 11). Alcohol and fluoro configuration in Examples 7, 8, 11 and 12 can be (R) or (S).

Scheme 11

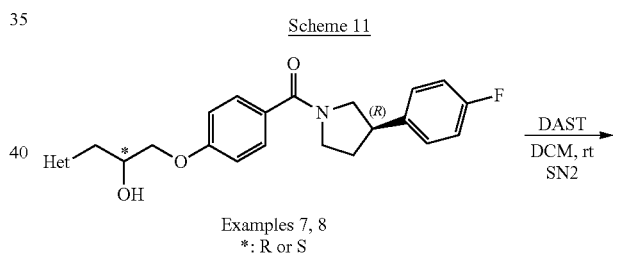

Examples 7, 8
*: R or S

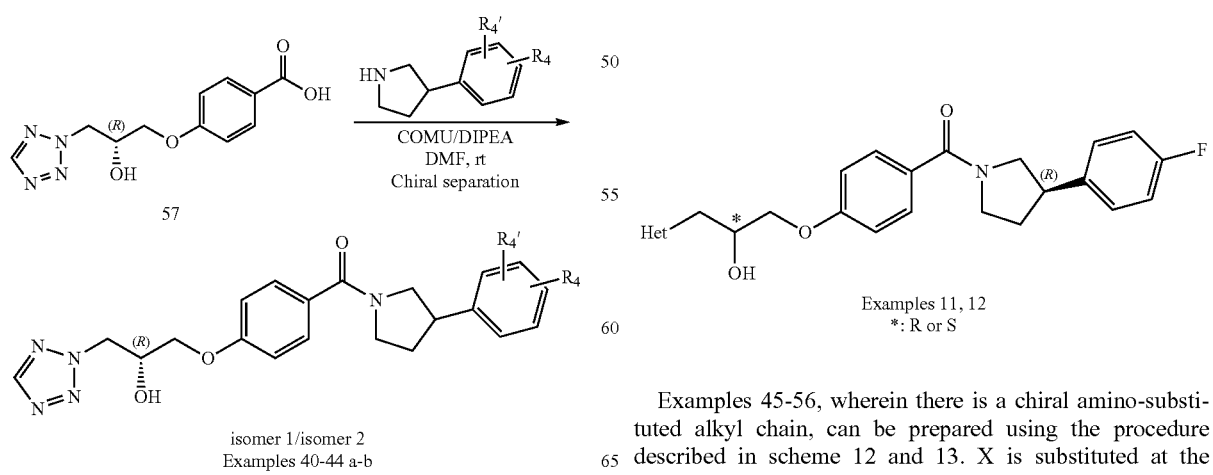

Examples 45-56, wherein there is a chiral amino-substituted alkyl chain, can be prepared using the procedure described in scheme 12 and 13. X is substituted at the 4-position of the phenyl ring and is fluoro or chloro. $R_3$ is hydrogen or fluoro.

Scheme 12

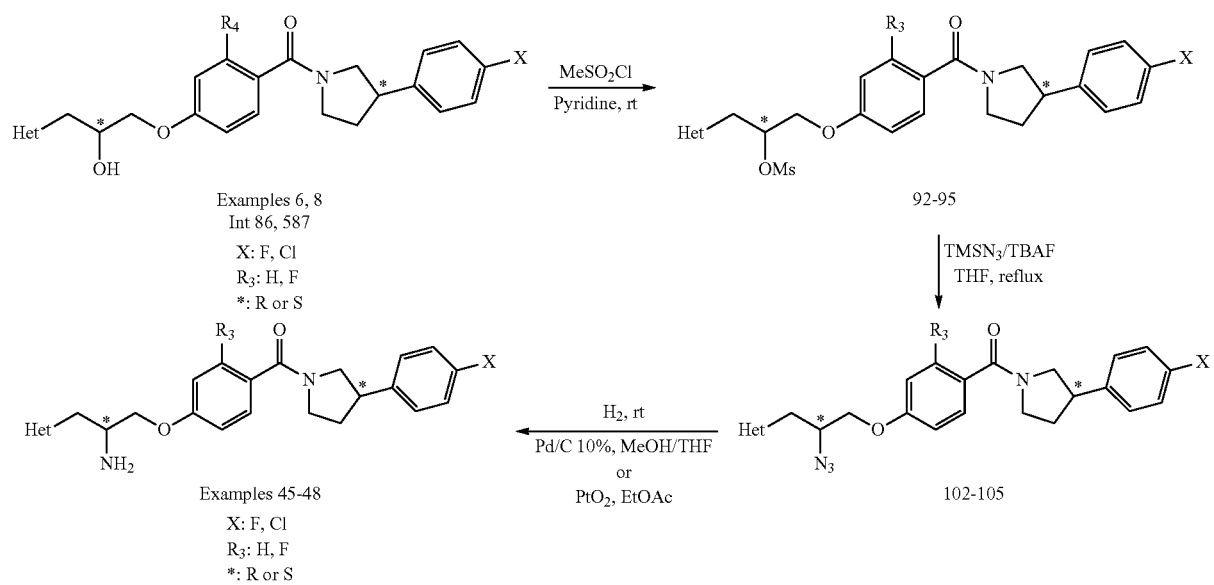

Mesylation of the corresponding chiral secondary alcohol derivative (examples 6, 8 and intermediates 86, 87), prepared following the procedure indicate in scheme 8, by careful reaction with methanesulfonyl chloride in pyridine give the desired mesylate intermediates 92-95. The use of azidotrimethylsilane (TMSN$_3$) as azide source in the presence of tetrabutylammonium fluoride (TBAF) enables a simple and efficient synthesis of azide intermediates 102-105. Finally, the azide intermediate is converted to the corresponding chiral amine derivative (Examples 45-48) by hydrogenation (H$_2$, Pd/C or H$_2$, PtO$_2$).

Alternatively, examples 45, 49-56 may also be prepared by the procedure illustrated in scheme 13.

Scheme 13

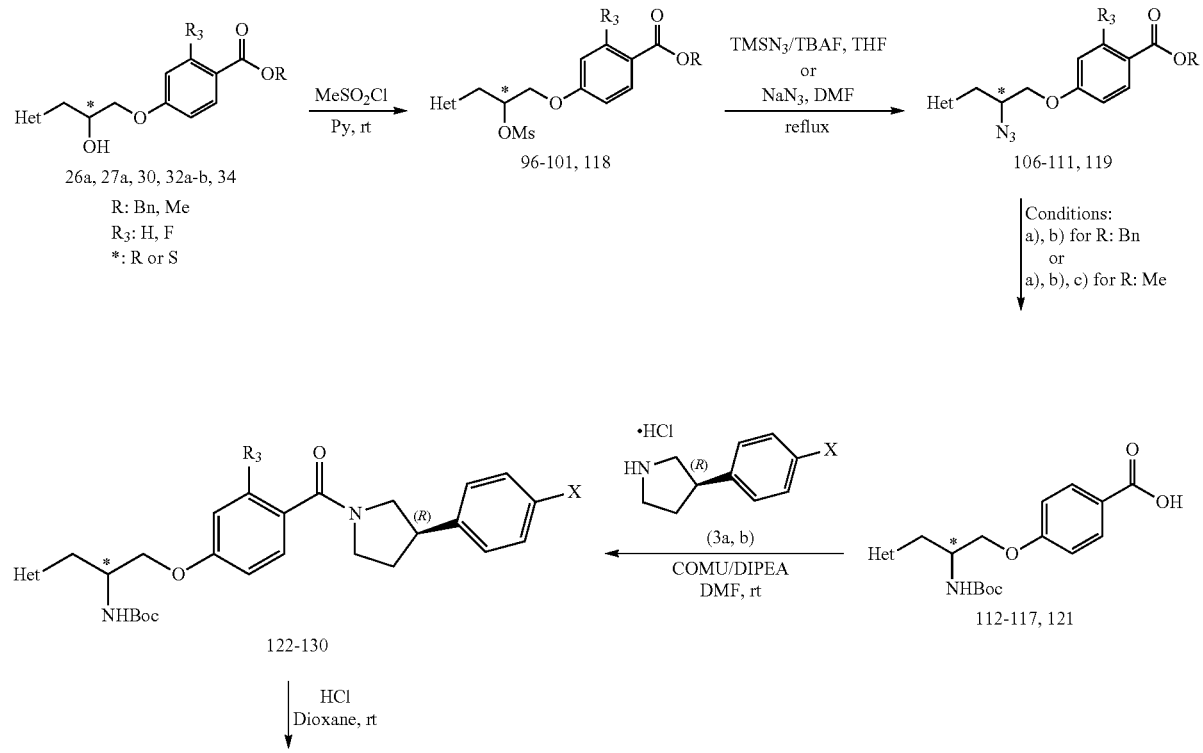

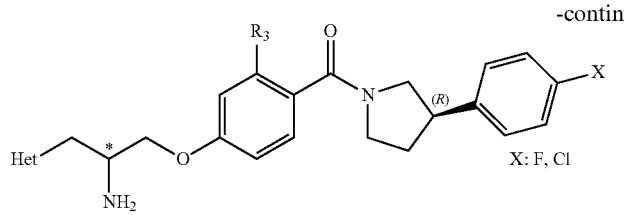

Examples 45, 49-56
X: F, Cl
R₃: H, F
*: R or S

Conditions: a) H₂, Pd/C 10%, MeOH/THF, rt
b) Boc₂O, DCM/DMF, rt
c) LiOH, H₂O/THF, rt The hydroxyl group of chiral esters 26a, 27a, 30, 32a-b, 34, wherein R is benzyl or methyl and $R_1$ is hydrogen or fluoro, is activated with methanesulfonyl chloride to obtain the corresponding mesylate intermediates 95-101, 118. Nucleophilic displacement reaction of mesylate group with TMSN₃ or NaN₃ affords the azide intermediate 106-111, 119. This azide is converted to the corresponding chiral N-Boc-protected carboxylic acid 112-117, 121 by hydrogenation and Boc protection wherein R is a benzyl group or by hydrogenation, Boc protection and hydrolysis wherein R is a methyl group.

An acid-amine coupling of the chiral N-Boc-protected carboxylic acid intermediate with (R)-3-(4-halophenyl)pyrrolidine 3a-b in the presence of, for example, COMU/DIPEA afford amide intermediates 122-130. Finally, deprotection of chiral N-Boc-protected amide using acid conditions (for example, HCl/dioxane) afford the desired chiral amine compounds (Examples 45, 49-56).

Methods of Use

In one aspect, the invention relates to a compound of Formula (I), or a pharmaceutically acceptable salt thereof, for use in therapy.

Compounds of Formula (I) or a pharmaceutically acceptable salt thereof can be useful in the treatment of certain parasitic infections such as parasitic protozoal infections by the malarial parasite *Plasmodium falciparum*, species of *Eimeria, Pneumocytis carinii, Trypanosoma cruzi, Trypanosoma brucei* or *Leishmania donovani*.

In particular, compounds of Formula (I) or pharmaceutically acceptable salts thereof can be useful for treatment of infection by *Plasmodium falciparum*. Accordingly, the invention is directed to methods of treating such infections. Alternatively, the compounds of Formula (I) or pharmaceutically acceptable salts thereof can be useful for the treatment of infection by *Plasmodium* species other than *Plasmodium falciparum* causing human malaria. For example, the compounds of Formula (I) or pharmaceutically acceptable salts thereof can be useful for the treatment of infection by *Plasmodium Vivax*, i.e., malaria caused by infection by *Plasmodium Vivax*.

In one embodiment, the invention relates to a compound of Formula (I) or a pharmaceutically acceptable salt thereof for use in the treatment of a protozoal infection. In a particular embodiment, said protozoal infection is malaria or infection by *Plasmodium falciparum*. In one embodiment, the invention relates to a compound of Formula (I) or a pharmaceutically acceptable salt thereof for use in the treatment of malaria resulting from infection by *Plasmodium falciparum*.

In another aspect of the invention, there is provided a method for the treatment of a parasitic protozoal infection, comprising administering a pharmaceutically effective amount of a compound of Formula (I) or a pharmaceutically acceptable salt thereof to a human in need thereof. In one embodiment, said protozoal infection is malaria or infection by *Plasmodium falciparum*.

In one embodiment, the subject is human.

In another aspect of the invention, there is provided the use of a compound of Formula (I) or a pharmaceutically acceptable salt thereof in the manufacture of a medicament for the treatment of a protozoal infection. In one embodiment, said protozoal infection is malaria or infection by *Plasmodium falciparum*.

Accordingly, a compound of Formula (I) or a pharmaceutically acceptable salt thereof may be used in the treatment of malaria. Therefore, the invention also relates to a method for the treatment of malaria comprising administering a pharmaceutically effective amount of a compound of Formula (I) or a pharmaceutically acceptable salt thereof to a human in need thereof. In addition, the invention relates to the use of a compound of Formula (I) or a pharmaceutically acceptable salt thereof in the manufacture of a medicament for the treatment of malaria.

It will be appreciated by those skilled in the art that references herein to treatment refer to the treatment of established conditions, such as malaria. However, compounds of the invention may also be useful in the prevention of such diseases, such as in the prevention of malaria. Thus, in one embodiment, there is provided the treatment or prevention of a disease such as malaria. In another embodiment, there is provided the treatment of a disease such as malaria. In a further embodiment, there is provided the prevention of a disease such as malaria.

In one embodiment, the malaria is multi-drug resistant malaria. Therefore, in one embodiment, a compound of Formula (I) or a pharmaceutically acceptable salt thereof may be useful in the treatment of sensitive and/or multi-drug resistant malaria.

Formulations

The compounds of Formula (I) and pharmaceutically acceptable salts thereof will normally, but not necessarily, be formulated into pharmaceutical formulations prior to administration to a patient. Accordingly, in another aspect there is provided a pharmaceutical formulation comprising (a) a compound of Formula (I), or a pharmaceutically acceptable salt thereof; and (b) a pharmaceutically acceptable excipient.

Suitable pharmaceutically acceptable excipients include the following types of excipients: binders, disintegrants, lubricants, glidants, granulating agents, coating agents, wetting agents, solvents, co-solvents, suspending agents, emulsifiers, sweeteners, flavouring agents, flavour masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation. The carrier excipient must be "acceptable" in the sense of being compatible with the other ingredients of the formulation and not deleterious to the recipient thereof.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

In one aspect, the invention is directed to a solid or liquid oral dosage form such as a liquid, tablet, lozenge or a capsule, comprising a safe and effective amount of a compound of the invention and a carrier. The carrier may be in the form of a diluent or filler. Suitable diluents and fillers in general include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. A liquid dosage form will generally consist of a suspension or solution of the compound or pharmaceutically acceptable salt in a liquid carrier for example, ethanol, olive oil, glycerine, glucose (syrup) or water (e.g. with an added flavouring, suspending, or colouring agent). Where the composition is in the form of a tablet or lozenge, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers or a semi solid e.g. mono di-glycerides of capric acid, Gelucire and Labrasol, or a hard capsule shell e.g. gelatin. Where the composition is in the form of a soft shell capsule e.g. gelatin, any pharmaceutical carrier routinely used for preparing dispersions or suspensions may be considered, for example aqueous gums or oils, and may be incorporated in a soft capsule shell.

Pharmaceutical compositions may be administered by any appropriate route, for example by the oral (including buccal or sublingual), inhaled, intranasal, topical (including buccal, sublingual or transdermal), parenteral (including subcutaneous, intramuscular, intravenous or intradermal) route. In particular, pharmaceutical compositions are administered via an oral route of administration.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

An oral solid dosage form may further comprise an excipient in the form of a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise an excipient in the form of a disintegrant. Suitable disintegrants include crospovidone, sodium starch glycolate, croscarmelose, alginic acid, and sodium carboxymethyl cellulose. The oral solid dosage form may further comprise an excipient in the form of a lubricant. Suitable lubricants include stearic acid, magnesium stearate, calcium stearate, and talc.

When a compound of Formula (I) or pharmaceutically acceptable salt thereof is used in the treatment of malaria, or *Plasmodium falciparum*, it may be employed alone or in combination with at least one other therapeutic agent, such as at least one other anti-parasitic agents, for example an anti-malarial agent.

For example, the present invention relates to a combination of (a) a compound of Formula (I) or a pharmaceutically acceptable salt thereof; and (b) at least one other anti-malarial agent.

In an embodiment, the combination comprises one or two or three additional anti-malarial agents. For the avoidance of doubt, the at least one other anti-malarial agent is not a compound of Formula (I).

The at least one other anti-malarial agentisanagent in development, approved of recommended for the treatment of malaria.

The at least one other anti-malarial agent may be selected from chloroquine, mefloquine, primaquine, pyrimethamine, quinine, artemisinin, halofantrine, doxycycline, amodiaquine, atovaquone, tafenoquinedapsone, proguanil, sulfadoxine, cycloguanil, fansidar, piperaquine, lumenfantrine, artesunate, dihydroartemisinin, artheneter, fosmidomycin and azithromycin.

The at least one other anti-malarial agent may be tafenoquine.

In an embodiment, the additional anti-malarial agents are atovaquone and proguanil.

The at least one other anti-malarial agent may also be selected from ferroquine, KAF156, cipargamin, DSM265, artemisone, artemisinone, artefenomel, MMV048, SJ733, P218, MMV253, PA92, DDD498, AN13762, DSM421, UCT947 and ACT451840.

The at least one other anti-malarial agent may also be selected from OZ609, OZ277 and SAR97276.

In the treatment of *P. falciparum* infections, the at least one or two or three additional anti-malarial agents are selected as follows, wherein at least one of the anti-malarial agents is an artemisinin-based agent:
  artemether+lumefantrine
  artesunate+amodiaquine
  artesunate+mefloquine
  dihydroartemisinin+piperaquine
  artesunate+sulfadoxine-pyrimethamine (SP)

The above combination treatments are known as artemisinin-based combination therapies (ACTs). The choice of ACT is usually based on the results of therapeutic efficacy studies against local strains of *P. falciparum* malaria.

In the treatment of *P. vivax* infections, an ACT may be used, as described above. Alternatively, the at least one other anti-malarial agent may be chloroquine, particularly in areas without chloroquine resistant *P. vivax*. In areas where resistant *P. vivax* has been identified, infections may be treated with an ACT, as described above.

The combinations may conveniently be presented for use in the form of a pharmaceutical composition or formulation. Therefore, also contemplated herein is a pharmaceutical composition comprising (a) a compound of Formula (I) or a pharmaceutically acceptable salt thereof, as herein described, together with (b) at least one other anti-malaria agent and (c) one or more pharmaceutically acceptable excipients as herein described.

A compound of Formula (I) or pharmaceutically acceptable salt thereof and at least one other therapeutic agent may be administered together or separately and, when administered separately, this may occur separately or sequentially in any order (by the same or by different routes of administration). The amount of a compound of the invention or pharmaceutically acceptable salt thereof and the further therapeutically active agent(s) and the relative timings of administration will be selected in order to achieve the desired combined therapeutic effect.

Examples

The invention will now be illustrated by way of the following non-limiting examples. While particular embodiments of the invention are described below a skilled person will appreciate that various changes and modifications can be made. References to preparations carried out in a similar manner to, or by the general method of, other preparations, may encompass variations in routine parameters such as time, temperature, workup conditions, minor changes in reagents amounts, etc.

In certain of the following Intermediates and Examples, starting materials are identified by reference to other Intermediate or Example numbers. This does not signify that the actual material from any particular Intermediate or Example was necessarily used in a subsequent step exemplified herein, but is used as a short-hand means of denoting the relevant compound name.

Where materials were commercially available, this is indicated in parentheses after the compound name, in capitals. Commercial reagents and solvents were used as received. All solvents used in the reaction were high purity grade or anhydrous grade. Proton nuclear magnetic resonance ($^1$H NMR) spectra were recorded, and chemical shifts are reported in parts per million (δ) downfield from the internal standard tetramethylsilane (TMS). Abbreviations for NMR data are as follows: s=singlet, doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Where diastereomers are represented and the absolute stereochemistry is known, the stereocentre, i.e. the chiral carbon atom, is labelled with R or S. Where the stereochemistry at a particular stereocentre is unknown, but both isomers have been isolated, the terminology used is "isomer 1/Isom 1" and "isomer 2/Isom 2".

Abbreviations

The following list provides definitions of certain abbreviations and symbols as used herein. It will be appreciated that the list is not exhaustive, but the meaning of those abbreviations and symbols not herein below defined will be readily apparent to those skilled in the art. In describing the invention, chemical elements are identified in accordance with the Periodic Table of the Elements.

| | |
|---|---|
| AcOH | acetic acid |
| Anh. | anhydrous |
| aq. | aqueous |
| Boc$_2$O | di-tert-butyl dicarbonate |
| ° C. | degrees centigrade |
| CDCl$_3$ | deuterated chloroform |
| Celite | a filter aid composed of acid-washed diatomaceous silica |
| CyHex | cyclohexane |
| CO$_2$ | carbon dioxide |
| COMU | (1-cyano-2-ethoxy-2-oxoethylidenaminooxy) dimethylamino-morpholino-carbenium hexafluorophosphate |
| Cs$_2$CO$_3$ | cesium carbonate |
| DAST | diethylaminosulfur trifluoride |
| DCM | dichloromethane |
| DEA | diethylamine |
| DIAD | diisopropyl azodicarboxylate |
| DIPEA | diisoproylethylamine |
| DMAP | 4-dimethylaminopyridine |
| DMF | dimethylformamide |
| DMSO-d$_6$ | deuterated dimethylsulfoxide |
| ee | enantiomeric excess |
| eq | equivalents |
| ES MS | electrospray mass spectrometry |
| Et$_2$O | diethylether |
| EtOAc | ethyl acetate |
| EtOH | ethanol |
| Ex | example |
| g | grams |
| h | hours |
| Hex | hexane |
| $^1$H NMR | proton nuclear magnetic resonance spectroscopy |
| HPLC | high performance liquid chromatography |
| Int. | Intermediate |
| iPrOH | 2-propanol |
| K$_2$CO$_3$ | potassium carbonate |
| L | litre |
| LAH | lithium aluminium hydride |
| LiOH•H$_2$O | lithium hydroxide monohydrate |
| M | Molar |
| MeOH | methanol |
| mg | miligrams |
| MHz | megahertzs |
| min(s). | minutes |
| MgSO$_4$ | magnesium sulfate |
| mL | mililitres |
| mmol | milimoles |
| MTBE | methyl tert-butyl ether |
| 2-MeTHF | 2-methyltetrahydrofuran |
| N | Normal |
| NaHCO$_3$ | sodium bicarbonate |
| NaCl | sodium chloride |
| NaCN | sodium cyanide |
| NaI | sodium iodide |
| NaN$_3$ | sodium azide |
| NaOH | sodium hydroxide |
| Na$_2$SO$_4$ | sodium sulfate |
| NH$_4$Cl | ammonium chloride |
| OPPh$_3$ | triphenylphosphine oxide |
| Pf | Plasmodium falciparum |
| PPh$_3$ | triphenylphosphine |
| quant. | quantitative |
| Rt | retention time |
| rt | room temperature |
| sat. | saturated |

-continued

| | |
|---|---|
| SFC | Supercritical Fluid Chromatography |
| TFAA | 2,2,2-trifluoroacetic anhydride |
| TEA | triethylamine |
| TMSN$_3$ | trimethylsilyl azide |
| tBuOK | potassium tert-butoxide |
| THF | tetrahydrofurane |
| TMSCl | trimethylsilyl chloride |
| δ ppm | chemical shift in parts per million |

Compound Preparation

INTERMEDIATES

Intermediate 1a:
(R)-3-(4-Chlorophenyl)-4-nitrobutanal

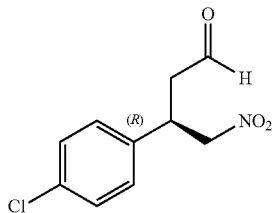

To a MeOH solution (20 mL) of (R)-2-(diphenyl((trimethylsilyl)oxy)methyl)pyrrolidine (SIGMA-ALDRICH, 293 mg, 0.9 mmol) and 4-chlorocinnamaldehyde (SIGMA-ALDRICH, 1.5 g, 9 mmol) at room temperature under argon atmosphere was added benzoic acid (MERCK CHEMICALS, 220 mg, 1.8 mmol). After stirring for 15 min, nitromethane (SIGMA-ALDRICH, 1.5 mL, 27.8 mmol) was added dropwise and the mixture was stirred at room temperature for 23 hours. Upon completion of the reaction, the reaction mixture was quenched with sat. aq. NaHCO$_3$ (100 mL) and the organic materials were extracted with EtOAc twice (100 mL and 50 mL). The organic phases were combined and dried over anh. Na$_2$SO$_4$, filtered and concentrated under reduced pressure. The residue was purified by silica gel flash chromatography (eluting with CyHex:EtOAc 10% to 25%) to obtain the title compound (1.23 g, 60% yield, yellowish oil) and 235 mg of more impure material. This material was used without further purification. $^1$H NMR (300 MHz, CDCl$_3$) ppm: 9.75 (s, 1H), 7.36 (d, J=8.4 Hz, 2H), 7.22 (d, J=8.6 Hz, 2H), 4.75-4.59 (m, 2H), 4.16-4.05 (m, 1H), 2.98 (d, J=7.1 Hz, 2H).

Intermediate 1b:
(R)-3-(4-Fluorophenyl)-4-nitrobutanal

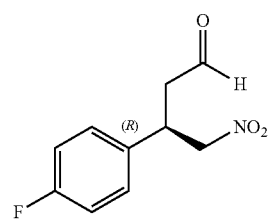

To a stirred solution of (E)-3-(4-fluorophenyl) acryl aldehyde (COMBI-BLOCKS, 200 g, 1.33 mmol) in MeOH (2 L) was added (R)-2-(diphenyl((trimethylsilyl)oxy)methyl)pyrrolidine (SIGMA-ALDRICH, 8.6 g, 0.026 mmol), nitromethane (AVRA, 243 g, 3.99 mmol) and benzoic acid (SPECTROCHEM, 6.4 g, 0.053 mol) at 27° C. under N$_2$ atmosphere. The resultant reaction mixture was stirred for 16 h at 27° C. Upon completion, reaction mixture was evaporated under reduced pressure. The resultant residue was diluted with EtOAc (3 L), and washed with sat. NaHCO$_3$ solution (2×750 mL) and water (3×500 mL). Combined organic layers were washed with brine solution (2×500 mL), dried over anh. Na$_2$SO$_4$, filtered and concentrated under reduced pressure. The residue was purified by silica gel chromatography (product eluted at 20% petroleum ether:EtOAc) to obtain the title compound (165 g, 56% yield, as a brown gummy liquid). $^1$H NMR (400 MHz, CDCl$_3$) δ ppm: 9.77-9.67 (m, 1H), 7.29-7.17 (m, 2H), 7.10-6.98 (m, 2H), 4.70-4.55 (m, 2H), 4.13-4.01 (m, 1H), 2.97-2.90 (m, 2H).

Intermediate 1c:
(S)-3-(4-Fluorophenyl)-4-nitrobutanal

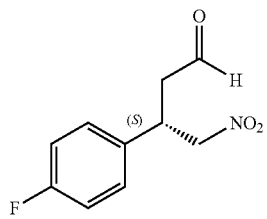

To a stirred solution of (E)-3-(4-fluorophenyl) acryl aldehyde (COMBIBLOCKS, 1.0 g, 6.662 mmol) and (S)-2-(diphenyl((trimethylsilyl)oxy)methyl)pyrrolidine (ARK PHARMA, 43 mg, 0.133 mmol) in MeOH (4 mL) under argon, benzoic acid (AVRA, 32.2 mg, 0.266 mmol), nitromethane (SPECTROCHEM, 1.2 g, 19.98 mmol) were added at 27° C. The resultant reaction mixture was stirred for 48 h at 27° C. On completion, the reaction mixture diluted with water (30 mL) and extracted with EtOAc (2×50 mL). Combined organic layers were washed with brine solution (30 mL), dried over Na$_2$SO$_4$, filtered and concentrated under reduced pressure. Purification by silica gel chromatography (9% EtOAc in petroleum ether) afforded the title compound (500 mg, 33% yield, as a brown liquid). $^1$H NMR (400 MHz, CDCl$_3$) δ ppm: 9.71 (s, 1H), 7.23-7.18 (m, 2H), 7.09-7.01 (m, 2H), 4.71-4.56 (m, 2H), 4.15-4.00 (m, 1H), 2.94-2.90 (m, 2H).

Intermediate 2a: (R)-tert-Butyl
3-(4-chlorophenyl)pyrrolidine-1-carboxylate

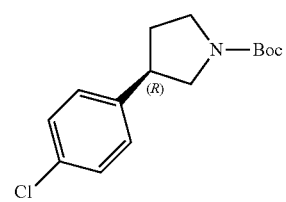

Zinc powder (SIGMA-ALDRICH, 6.7 g, 103 mmol) was added slowly to a cold (ice-water bath) solution of intermediate 1a (1.2 g, 5.27 mmol) in 1:1 AcOH/H₂O mixture (110 mL). The cooling bath was removed and the resulting mixture was vigorously stirred for 2.5 h at room temperature. The solid was filtered off and washed with THF (200 mL).

A solution of NaOH (prepared by dissolving 34 g of NaOH in 300 mL of H₂O) was slowly added to the previously obtained solution cooled to 0° C. Saturated solution of NaHCO₃ (120 mL) was then added, followed by Boc₂O (SIGMA-ALDRICH, 2.3 g, 10.54 mmol). The cooling bath was removed and the resulting mixture stirred for 1 h at room temperature. The reaction mixture was extracted with EtOAc (2×75 mL). The combined organic layers were washed with brine (75 mL) and dried (Na₂SO₄). The solvents were removed under vacuum and the crude was purified by silica gel flash chromatography (eluting with CyHex:EtOAc 0% to 10%) to obtain the title compound (605 mg, 40.7% yield, 100% ee, colourless oil which solidified in the fridge).

¹H NMR (300 MHz, CDCl₃) ppm: 7.30 (d, J=8.6 Hz, 2H), 7.17 (d, J=8.4 Hz, 2H), 3.90-3.72 (m, 1H), 3.68-3.50 (m, 1H), 3.46-3.20 (m, 3H), 2.32-2.21 (m, 1H), 2.01-1.89 (m, 1H), 1.49 (s, 9H).

Chiral SFC: Chiral Pak IC, 150×3 mm column, CO₂/MeOH-EtOH (0.2% DEA) 97:3 (v/v), 1.0 mL/min, R$_t$=8.55 min (100% yield of R enantiomer).

Intermediate 2b: (R)-tert-Butyl 3-(4-fluorophenyl)pyrrolidine-1-carboxylate

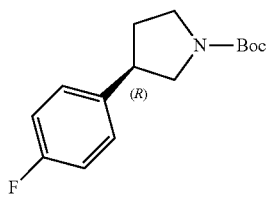

To a stirred solution of intermediate 1b (165 g, 0.781 mol) in AcOH (ADVENT, 4.95 L) and H₂O (4.95 L), zinc powder (AVRA, 1022 g, 15.63 mol) was slowly added at 0° C. The resultant reaction mixture was stirred for 2 h at 26° C. On completion, the reaction mixture was filtered through Celite bed, washed with THF (8.25 L). The reaction mixture was directly taken for next step in the solution form (18.6 L).

The previously obtained solution (18.6 L) cooled at 0° C. was basified with a solution NaOH 24 N (14.5 L) and sat. NaHCO₃ sol. (966 mL) until pH-8. When pH was reached, Boc₂O (AVRA, 18.2 g) was added slowly at 26° C. The resultant reaction mixture was stirred for 5 h at 26° C. On completion of the reaction, organic layer was separated and the aqueous layer was extracted with EtOAc (4×1.5 L). Combined organic layer were washed with brine solution (3×1 L), dried over anh. Na₂SO₄, filtered and filtrate was concentrated under reduced pressure. The crude material was purified by silica gel chromatography (product eluted at 10% petroleum ether:EtOAc) to obtain the title compound (149.98 g, 65% yield, as a pale yellow liquid). ¹H NMR (400 MHz, CDCl₃) δ ppm: 7.22-7.12 (m, 2H), 7.05-6.95 (m, 2H), 3.87-3.73 (m, 1H), 3.67-3.50 (m, 1H), 3.44-3.19 (m, 3H), 2.29-2.19 (m, 1H), 2.01-1.88 (m, 1H), 1.48 (s, 9H). [ES+ MS] m/z 266.2 (MH⁺).

Intermediate 2c: (S)-tert-Butyl 3-(4-fluorophenyl)pyrrolidine-1-carboxylate

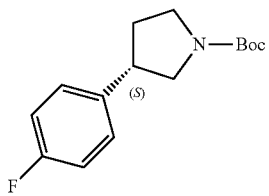

To a stirred solution of intermediate 1c (500 mg, 2.367 mmol) in AcOH (ADVENT, 23.6 mL) and H₂O (23.6 mL), zinc powder (AVRA, 3.0 g, 47.35 mmol) was slowly added at 0° C. The resultant reaction mixture was stirred for 1 h at 26° C. On completion, the reaction mixture was filtered through Celite bed, washed with THF (100 mL) and forwarded to next step with crude reaction mixture.

The previously obtained reaction mixture solution in THF cooled at 0° C. was basified with a solution of NaOH (15.5 g in 143 mL of water) and sat. NaHCO₃ sol. (54 mL), followed by the addition of (Boc)₂O (AVRA, 1.08 mL) at 0° C. The resultant reaction mixture was stirred for 1 h at 26° C. On completion, the reaction mixture was diluted with water (50 mL) and extracted with EtOAc (2×150 mL). Combined organic layers were dried over anh. Na₂SO₄, filtered and filtrate was concentrated under reduced pressure to afford the title compound (400 mg, as a yellow liquid). ¹H NMR (400 MHz, CDCl₃) ppm: 7.19 (dd, J=5.6, 8.4 Hz, 2H), 7.00 (t, J=8.7 Hz, 2H), 3.88-3.20 (m, 5H), 2.32-2.22 (m, 1H), 2.02-1.89 (m, 1H), 1.48-1.38 (s, 9H).

Intermediate 3a: (R)-3-(4-Chlorophenyl)pyrrolidine, hydrochloride

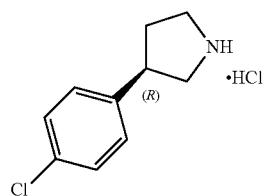

Intermediate 2a (590 mg, 2.1 mmol) was dissolved in 4 M HCl in 1,4-dioxane (SIGMA-ALDRICH, 7.5 mL, 30 mmol) at 0° C. under nitrogen atmosphere. The solution was stirred at rt under nitrogen atmosphere for 2 h. Toluene (3×10 mL) was added and the solvents were removed under vacuum to yield the title compound (456 mg, quant. yield, off-white solid). ¹H NMR (300 MHz, DMSO-d₆) δ ppm: 9.35 (br.s, 2H), 7.42 (d, J=8.6 Hz, 2H), 7.38 (d, J=8.6 Hz, 2H), 3.65-3.54 (m, 1H), 3.49-3.36 (m, 2H), 3.26-3.13 (m, 1H), 3.09-2.98 (m, 1H), 2.40-2.29 (m, 1H), 1.96-1.84 (m, 1H).

Intermediate 3b: (R)-3-(4-Fluorophenyl)pyrrolidine, hydrochloride

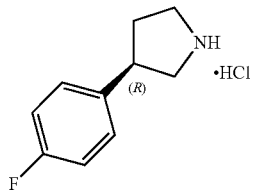

To a stirred solution of intermediate 2b (149 g, 0.562 mmol) in DCM (224 mL) was added 4 M HCl in EtOAc (HYCHEM, 492 mL) at 0° C. slowly. Reaction mixture was stirred at 26° C. for 3 h. After completion, reaction mixture was concentrated under reduced pressure to afford a pink solid that was triturated with $Et_2O$ (5×500 mL). The precipitated solid was filtered off and dried over high vacuum to afford a crude material (100 g, 96% purity, pale pink solid). Solid was further purified by trituration with hot $CH_3CN$ (5×400 mL) and cold $Et_2O$ (5×400 mL) to afford 80 g of material (98.9% purity, off-white solid). Compound was further purified by recrystallization in iPrOH. The obtained solid was dried over high vacuum to afford the title compound as off-white solid (67.75 g, 60% yield, 99% ee). $^1$H NMR (400 MHz, DMSO-$d_6$) δ ppm: 9.38-9.27 (m, 2H), 7.46-7.36 (m, 2H), 7.21-7.13 (m, 2H), 3.64-3.54 (m, 1H), 3.49-3.34 (m, 2H), 3.25-3.14 (m, 1H), 3.08-2.97 (m, 1H), 2.39-2.29 (m, 1H), 1.98-1.84 (m, 1H). [ES+MS]m/z 166.1 (MH$^+$).

Chiral HPLC: Lux Amylose-2, 4.6×250 mm column, $CO_2$/EtOH (0.5% DEA), 3.0 mL/min, $R_t$=7.49 min (99.5% yield of R enantiomer). Chiral HPLC showed 99.5:0.5 R:S enantiomeric ratio (99% ee).

Intermediate 3c: (S)-3-(4-Fluorophenyl)pyrrolidine, hydrochloride

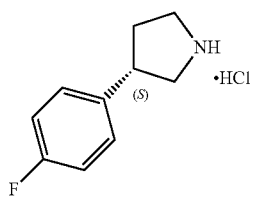

To a stirred solution of intermediate 2c in EtOAc (4 mL), 4 M HCl in EtOAc (4.0 mL) was slowly added at 0° C. The resultant reaction mixture was stirred for 2 h at 26° C. On completion, reaction mixture was concentrated under reduced pressure to obtain a crude mixture that was triturated with $Et_2O$ to afford title compound (330 mg, 80% yield, as an off-white solid). $^1$H NMR (400 MHz, DMSO-$d_6$) δ ppm: 9.42 (br.s, 2H), 7.45-7.35 (m, 2H), 7.21-7.11 (m, 2H), 3.64 (br.s, 1H), 3.50-3.37 (m, 2H), 3.24-3.12 (m, 1H), 3.07-2.94 (m, 1H), 2.42-2.31 (m, 1H), 1.95-1.85 (m, 1H).

Intermediate 4: Ethyl 3-(dibenzylamino)-2,2-difluoropropanoate

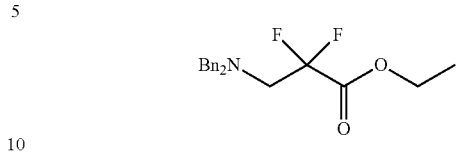

To a solution of 1H-benzotriazole (SIGMA-ALDRICH, 3.0 g, 25.2 mmol) in MeOH (18 mL), dibenzylamine (SIGMA-ALDRICH, 5.16 mL, 27.7 mmol) and formaldehyde (~37 wt. % in $H_2O$, SIGMA-ALDRICH, 2.62 mL, 35.3 mmol) were added, and the mixture was stirred at room temperature for 10 min. $Et_2O$ (9.00 mL) was added and solution was heated to reflux at this temperature overnight. Solvent was removed in vacuo. Crude material was dissolved in EtOAc, washed with sat. $NH_4Cl$ solution, dried over $Na_2SO_4$, filtered, and concentrated to give a mixture of isomers (1H-1,2,3-benzotriazol-1-yl-N,N-dibenzylmethanamine and 2H-1,2,3-benzotriazol-2-yl-N,N-dibenzylmethanamine) (in a ratio 1:0.2, 8.08 g, 98% yield), which was used in the next step without further purification.

To a suspension of zinc powder (SIGMA-ALDRICH, 3.22 g, 49.2 mmol) in THF (96 mL), at rt, was added TMSCl (SIGMA-ALDRICH, 3.14 mL, 24.60 mmol). The mixture was stirred for 10 min and then ethyl bromodifluoroacetate (FLUOROCHEM, 3.48 mL, 27.1 mmol) was added. After stirring at rt for 10 min, a solution of mixture of 1H- and 2H-1,2,3-benzotriazol-1-yl-N,N-dibenzylmethanamine (8.08 g, 24.60 mmol) in THF (27.3 mL) was added and the reaction mixture was stirred at rt for 3 h. A saturated solution of $NaHCO_3$ sat. was added, and the mixture was stirred for 15 min and filtered through a plug of Celite washing with EtOAc. Layers were separated, and the aqueous layer was extracted with EtOAc two times. The combined organic layers were dried, filtered and the solvent was removed in vacuo to obtain ethyl 3-(dibenzylamino)-2,2-difluoropropanoate (8.11 g, 99% yield). This material was used without further purification. $^1$H NMR (300 MHz, CDCl$_3$) δ ppm: 7.39-7.26 (m, 10H), 4.19 (q, J=7.1 Hz, 2H), 3.70 (s, 4H), 3.16 (t, J=13.1 Hz, 2H), 1.24 (t, J=7.1 Hz, 3H).

Intermediate 5: 3-(Dibenzylamino)-2,2-difluoropropan-1-ol

To a mixture of LAH (SIGMA-ALDRICH, 1.849 g, 48.7 mmol) in THF (122 mL) at 0° C. under nitrogen atmosphere, a solution of intermediate 4 (8.12 g, 24.36 mmol) in THF (122 mL) was added. The mixture was stirred at rt overnight. Upon completion of the reaction, the mixture was filtered off through a plug of Celite (washing with EtOAc). The filtrate was evaporated to afford the crude product, which was purified by column chromatography over silica gel (applying a gradient up to 20% EtOAc in CyHex) to give the title compound (3.56 g, 50% yield).

$^1$H NMR (300 MHz, CDCl$_3$) δ ppm: 7.39-7.28 (m, 10H), 3.69 (s, 4H), 3.69-3.64 (m, 2H), 2.96 (t, J=12.7 Hz, 2H).

Intermediate 6: Benzyl 4-(3-(dibenzylamino)-2,2-difluoropropoxy)benzoate

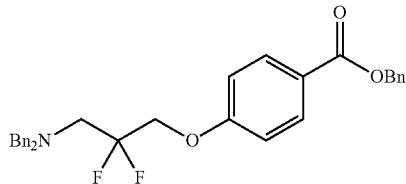

A solution of benzyl 4-hydroxybenzoate (SIGMA-ALDRICH, 1.636 g, 7.17 mmol), intermediate 5 (1.74 g, 5.97 mmol) and PPh$_3$ (SIGMA-ALDRICH, 1.723 g, 6.57 mmol) in THF (44.8 mL) was cooled to 0° C. under nitrogen atmosphere. DIAD (ALFA-AESAR, 1.889 mL, 8.96 mmol) in THF (14.93 mL) was added dropwise and the solution was heated to reflux overnight. Upon completion of the reaction, the solvent was removed in vacuo to afford the crude material which was purified by column chromatography over silica gel (applying a gradient up to 30% EtOAc in CyHex). The desired fractions were evaporated to afford the title compound (2.34 g, 78% yield). $^1$H NMR (300 MHz, CDCl$_3$) ppm: 8.04 (d, J=8.8 Hz, 2H), 7.51-7.35 (m, 5H), 7.31-7.23 (m, 10H), 6.77 (d, J=9.1 Hz, 2H), 5.39 (s, 2H), 4.16 (t, J=12.1 Hz, 2H), 3.75 (s, 4H), 3.10 (t, J=13.1 Hz, 2H).

Intermediate 7: 4-(3-(Dibenzylamino)-2,2-difluoropropoxy)benzoic acid

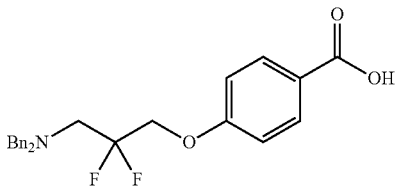

A solution of intermediate 6 (2.6 g, 5.18 mmol) in THF (39.9 mL) was added to a stirred solution of LiOH.H$_2$O (SIGMA-ALDRICH, 1.305 g, 31.1 mmol) in water (11.96 mL) under nitrogen atmosphere, and the mixture was heated at 60° C. overnight. After this time, a second addition of LiOH.H$_2$O (SIGMA-ALDRICH, 0.218 g, 5.18 mmol) was requiered and the mixture was stirred at 60° C. for additional 18 h. The mixture was diluted with EtOAc and water, and the two phases were separated. 2 N aq. HCl sol. was added to the aqueous layer until pH=3. EtOAc was added and the aqueous phase was extracted several times with EtOAc. The combined organic layers were dried, and the solvent was removed in vacuo to afford a brown solid that was washed several times with water and dried under vacuum to give title compound (2.13 g, quant. yield). $^1$H NMR (300 MHz, DMSO-d$_6$) δ ppm: 12.70 (s, 1H), 7.87 (d, J=8.8 Hz, 2H), 7.35-7.26 (m, 8H), 7.24-7.91 (m, 2H), 6.91 (d, J=9.1 Hz, 2H), 4.29 (t, J=12.7 Hz, 2H), 3.68 (s, 4H), 3.07 (t, J=14.1 Hz, 2H).

Intermediate 8: (R)-(4-(3-(Dibenzylamino)-2,2-difluoropropoxy)phenyl)(3-(4-fluorophenyl)-pyrrolidin-1-yl)methanone

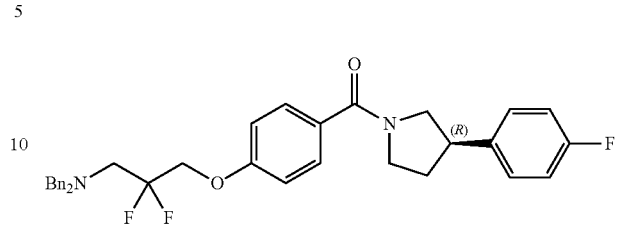

To a solution of intermediate 7 (1.6 g, 3.89 mmol), (R)-3-(4-fluorophenyl)pyrrolidine hydrochloride (3b) (0.941 g, 4.67 mmol) and DIPEA (SIGMA-ALDRICH, 2.038 mL, 11.67 mmol) in DMF (38.9 mL) at 0° C. under nitrogen atmosphere was added COMU (ALFA AESAR, 2.165 g, 5.06 mmol), and the reaction mixture was stirred at 0° C. for 1 h and then at room temperature overnight. The mixture was quenched by the dropwise addition of water. The resulting mixture was then partitioned between EtOAc and sat. aq. NaHCO$_3$. The phases were separated and the aqueous one was re-extracted with EtOAc. The organic layers were combined and washed with sat NaHCO$_3$, 1 N aq. NH$_4$Cl and brine. The organic layer was dried over anh. Na$_2$SO$_4$, filtered and evaporated to dryness under vacuum. The crude material was purified by column chromatography over silica gel (applying a gradient of 0-50% EtOAc in CyHex). The desired fractions were collected and the solvent was removed in vacuo to obtain the title compound (2.13 g, 98% yield). $^1$H NMR (300 MHz, CDCl$_3$) δ ppm: 7.58-7.47 (m, 2H), 7.35-7.12 (m, 12H), 7.09-6.95 (m, 2H), 6.80-6.69 (m, 2H), 4.18-4.05 (m, 2H), 3.95-3.28 (m, 9H), 3.14-2.99 (m, 2H), 2.45-2.24 (m, 1H), 2.15-1.92 (m, 1H).

Intermediate 9: (R)-(4-(3-Amino-2,2-difluoropropoxy)phenyl)(3-(4-fluorophenyl)pyrrolidin-1-yl)methanone

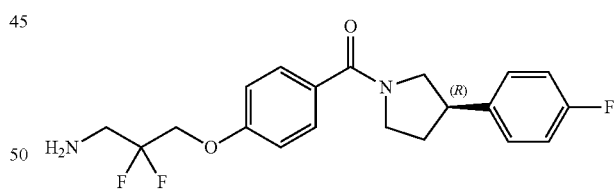

To a solution of intermediate 8 (2.13 g, 3.81 mmol) and 3.0 M HCl (0.381 mL, 1.144 mmol) in EtOH (76 mL) was added palladium hydroxide on carbon (Pd(OH)$_2$/C) (SIGMA-ALDRICH, 0.803 g, 1.144 mmol, 20 wt %) and the solution purged with N$_2$. The resultant suspension was stirred at rt under hydrogen atmosphere overnight. 4 M NH$_3$ in MeOH (SIGMA-ALDRICH, 20 mL) was added to the mixture and the reaction mixture was filtered through Celite, rinsing with MeOH and the combined organic phase was concentrated to obtain the title compound (1.3 g, 90% yield). $^1$H NMR (300 MHz, CDCl$_3$) δ ppm: 7.64-7.52 (m, 2H), 7.36-7.14 (m, 2H), 7.11-6.93 (m, 4H), 4.40-4.24 (m, 2H), 3.98-3.58 (m, 3H), 3.56-3.22 (m, 4H), 2.48-2.25 (m, 1H), 2.22-1.92 (m, 1H).

Intermediate 10: 3-Amino-2-methyl propan-1-ol, Hydrochloride

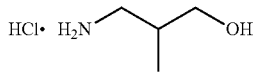

Borane-THF complex (SIGMA-ALDRICH, 1M, 49 mL, 49.0 mmol) was added to a rt stirred solution of DL-3-aminoisobutyric acid (SIGMA-ALDRICH, 2.0 g, 19.39 mmol) in THF (50 mL). The reaction was stirred at rt for 2.5 h and heated at reflux for 18 h. After cooling down to rt, the reaction was quenched by careful addition of MeOH, stirred for 15 min and then solvents were removed under reduced pressure (275 mbar, 4° C.). The residue was dissolved in Et$_2$O (50 mL) and treated with 4 M HCl in dioxane solution (SIGMA-ALDRICH, 10 mL, 40.0 mmol). After 20 min. stirring, solvents were removed under reduced pressure and the residue was triturated with EtOAc and hexane. Solvents were removed under reduced pressure to give the title compound (2.77 g, quant. yield) as a gummy solid. It was used as such in next step. $^1$H NMR (300 MHz, DMSO-d$_6$) δ ppm: 7.30 (br.s, 2H), 3.34-3.22 (m, 3H), 2.88-2.78 (m, 1H), 2.65-2.55 (m, 1H), 1.90-1.74 (m, 1H), 1.44-1.23 (m, 1H), 0.87 (d, J=7.1 Hz, 3H).

Intermediate 11: tert-Butyl (3-hydroxy-2-methylpropyl)carbamate

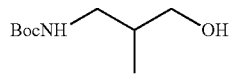

Boc$_2$O (SIGMA-ALDRICH, 4.73 g, 21.69 mmol) in CH$_3$CN (45 mL) was added to a rt solution of intermediate 10 (2.27 g, 18.07 mmol) and TEA (SIGMA-ALDRICH, 3.27 mL, 23.50 mmol) in CH$_3$CN (45 mL). The reaction was then stirred at 40° C. for 18 h. Upon completion of the reaction, solvents were removed under reduced pressure. The residue was diluted with DCM, and the solution was washed with water and brine. The organic layer was dried over anh. MgSO$_4$, filtered and the solvent was removed in vacuo to obtain the title compound (3.02 g, 88% yield). $^1$H NMR (300 MHz, DMSO-d$_6$) ppm: 6.37 (br.s, 1H), 4.39 (t, J=5.3 Hz, 1H), 3.31-3.15 (m, 2H), 2.96-2.87 (m, 1H), 2.79-2.69 (m, 1H), 1.67-1.56 (m, 1H), 1.37 (s, 9H), 0.78 (d, J=6.8 Hz, 3H).

Intermediate 12: tert-Butyl (3-hydroxy-2,2-dimethylpropyl)carbamate

Boc$_2$O (SIGMA-ALDRICH, 1.80 g, 8.26 mmol) was added to a solution of 3-amino-2,2-dimethyl-1-propanol (LANCASTER, 710 mg, 6.88 mmol), DMAP (SIGMA-ALDRICH, 84 mg, 0.688 mmol), and TEA (SIGMA-ALDRICH, 1.92 mL, 13.76 mmol) in DCM (50 mL) at 0° C., and the mixture was stirred at rt overnight. The reaction mixture was washed with sat. NaHCO$_3$ solution (30 mL) and brine (30 mL). The organic layer was dried over Na$_2$SO$_4$, filtered and concentrated to give title compound (1.15 g, 82% yield) which was used in the next step without further purification. $^1$H NMR (300 MHz, CDCl$_3$) δ ppm: 4.94-4.82 (m, 1H), 3.71 (br.s, 1H), 3.20 (s, 2H), 2.97 (d, J=7.1 Hz, 2H), 1.45 (s, 9H), 0.86 (s, 6H).

Intermediate 13: Benzyl 4-(3-((tert-butoxycarbonyl)amino)-2-methylpropoxy)benzoate

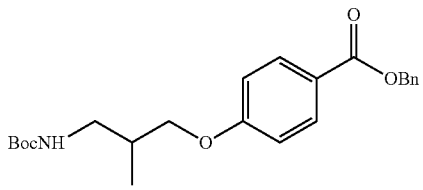 [SMILES: CC(CNC(=O)OC(C)(C)C)COc1ccc(C(=O)OCc2ccccc2)cc1]

DIAD (ALFA-AESAR 1.24 mL, 6.34 mmol) was added to a rt stirred solution of benzyl 4-hydroxybenzoate (SIGMA-ALDRICH, 1.20 g, 5.28 mmol), intermediate 11 (1.00 g, 5.28 mmol) and PPh$_3$ (SIGMA-ALDRICH, 1.66 g, 6.34 mmol) in 1,4-dioxane (50 mL). The mixture was then heated at reflux for 19 h. Solvent was removed in vacuo and the residue was purified by flash chromatography (SiO$_2$, using a gradient of CyHex to EtOAc) to afford the title compound (1.27 g, 52% yield). $^1$H NMR (300 MHz, CDCl$_3$) δ ppm: 8.06 (d, J=8.8 Hz, 2H), 7.51-7.34 (m, 5H), 6.94 (d, 2H), 5.38 (s, 2H), 4.78 (br.s, 1H), 3.94 (d, J=5.5 Hz, 2H), 3.30-3.22 (m, 2H), 2.26-2.15 (m, 1H), 1.47 (d, J=3.5 Hz, 9H), 1.09 (d, J=6.8 Hz, 3H).

Intermediate 14: tert-Butyl (3-hydroxy-2,2-dimethylpropyl)carbamate

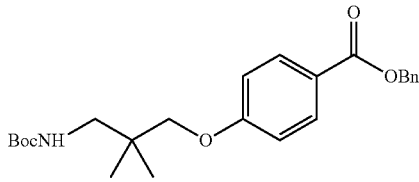 [SMILES: CC(C)(CNC(=O)OC(C)(C)C)COc1ccc(C(=O)OCc2ccccc2)cc1]

A solution of benzyl 4-hydroxybenzoate (SIGMA-ALDRICH, 846 mg, 3.71 mmol), intermediate 12 (628 mg, 3.09 mmol) and PPh$_3$ (SIGMA-ALDRICH, 891 mg, 3.40 mmol) in THF (18.00 mL) was cooled to 0° C. DIAD (ALFA-AESAR, 0.912 mL, 4.63 mmol) in THF (9 mL) was added dropwise and the solution stirred at rt overnight. Solvent was evaporated, and the crude was dissolved in MTBE and washed with NaOH 2 N (×3). The organic layer was dried over Na$_2$SO$_4$, filtered and concentrated. The residue was purified by flash chromatography on silica gel using a gradient of CyHex:EtOAc (100:0 to 80:20) to give title compound (517 mg, 40.5% yield). $^1$H NMR (300 MHz, CDCl$_3$) δ ppm: 8.03 (d, J=8.8 Hz, 2H), 7.48-7.33 (m, 5H), 6.92 (d, J=8.8 Hz, 2H) 5.35 (s, 2H), 4.75 (br.s, 1H), 3.72 (s, 2H), 3.18 (d, J=6.3 Hz, 2H), 1.44 (s, 9H), 1.04 (s, 6H).

Intermediate 15: Benzyl 4-(3-amino-2-methylpropoxy)benzoate, Hydrochloride

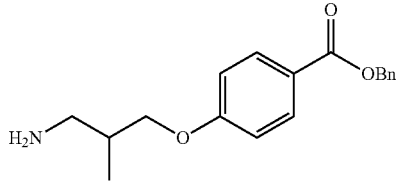 [SMILES: CC(CN)COc1ccc(C(=O)OCc2ccccc2)cc1]

A sol. of 4 M HCl in dioxane (SIGMA-ALDRICH, 1.6 mL, 6.40 mmol) was added to a rt solution of intermediate 13 (625 mg, 1.565 mmol) in Et$_2$O (10 mL). The mixture was stirred for 4 h, and then a new addition 4 M HCl in dioxane (3.2 mL) was done and stirring was continued for 18 h. Two more additions of 4 M HCl in dioxane (3.2 mL) were required until completion of the reaction. Solvent was removed in vacuo, and EtOAc was added and partially removed in vacuo, and hexane was added to the stirred solution. Solid was collected by filtration to give the title compound (406 mg, 77% yield). $^1$H NMR (300 MHz, CDCl$_3$) δ ppm: 7.96 (d, J=8.8 Hz, 2H), 7.92 (br.s, 3H), 7.48-7.33 (m, 5H), 7.06 (d, J=9.1 Hz, 2H), 5.31 (s, 2H), 4.00 (d, J=6.1 Hz, 2H), 3.01-2.92 (m, 1H), 2.82-2.74 (m, 1H), 2.29-2.20 (m, 1H), 1.04 (d, J=6.8 Hz, 3H).

Intermediate 16: Benzyl 4-(3-amino-2,2-dimethylpropoxy)benzoate

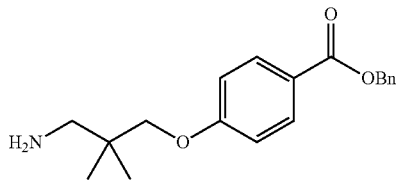 [SMILES: CC(C)(CN)COc1ccc(C(=O)OCc2ccccc2)cc1]

A sol. of 4 M HCl in dioxane (SIGMA-ALDRICH, 5.0 mL, 20.00 mmol) was added to intermediate 14 (477 mg, 1.154 mmol). The mixture was stirred at rt overnight, then partitioned between 0.5 M aq. Na$_2$CO$_3$ solution and DCM. The layers were separated and the aqueous phase was extracted with DCM. The combined organic layers were dried over Na$_2$SO$_4$, filtered and concentrated under reduced pressure to give title compound (360 mg, quant. yield). $^1$H NMR (300 MHz, CDCl$_3$) ppm: 8.02 (d, J=9.1 Hz, 2H), 7.48-7.33 (m, 5H), 6.93 (d, J=9.1 Hz, 2H), 5.35 (s, 2H), 3.77 (s, 2H), 2.69 (s, 2H), 1.02 (s, 6H).

Intermediate 17: Benzyl 4-(2-methyl-3-(1H-tetrazol-1-yl)propoxy)benzoate

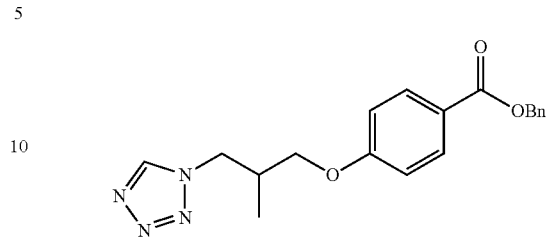

Sodium azide (SIGMA-ALDRICH, 118 mg, 1.813 mmol) and triethyl orthoformate (SIGMA-ALDRICH, 0.805 mL, 4.84 mmol) were added to a rt solution of intermediate 15 (406 mg, 1.209 mmol) in AcOH (1 mL). The reaction was stirred at reflux for 20 h. Solvents were removed under reduced pressure. Residue was diluted with DCM, washed sequentially with sat. aq. NaHCO$_3$ and brine, and dried over anh. MgSO$_4$ to give a crude material. The residue was purified by flash chromatography on silica gel using a gradient of CyHex:EtOAc (100-0% to 0-100%) to afford the title compound (250 mg; 59% yield). $^1$H NMR (300 MHz, CDCl$_3$) δ ppm: 8.55 (s, 1H), 8.05 (d, J=8.8 Hz, 2H), 7.48-7.32 (m, 5H), 6.89 (d, J=8.8 Hz, 2H), 5.36 (s, 2H), 4.65 (dd, J=13.9, 6.3 Hz, 1H), 4.53 (dd, J=13.9, 6.3 Hz, 1H), 3.93 (dd, J=9.6, 4.3 Hz, 1H), 3.83 (dd, J=9.6, 6.8 Hz, 1H), 2.73-2.63 (m, 1H), 1.14 (d, J=6.8 Hz, 3H).

Intermediate 18: Benzyl 4-(2,2-dimethyl-3-(1H-tetrazol-1-yl)propoxy)benzoate

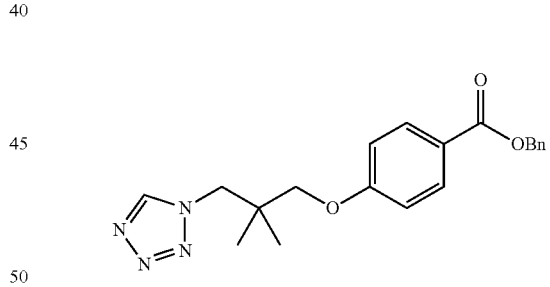

AcOH (0.6 mL) was added to a mixture of intermediate 16 (454 mg, 1.449 mmol), sodium azide (SIGMA-ALDRICH, 141 mg, 2.173 mmol), and triethyl orthoformate (SIGMA-ALDRICH, 0.875 mL, 5.79 mmol). The resulting mixture was heated at reflux overnight, then cooled to rt, and the solvent removed under reduced pressure. The crude material was dissolved in DCM, and washed with sat. NaHCO$_3$ solution, dried over Na$_2$SO$_4$, filtered, and concentrated. The residue was purified by flash chromatography on silica gel using a gradient of CyHex:EtOAc as eluents (100:0 to 30:70) to give title compound (194 mg, 36.5% yield). $^1$H NMR (300 MHz, CDCl$_3$) ppm: 8.47 (s, 1H), 8.06 (d, J=8.8 Hz, 2H), 7.48-7.33 (m, 5H), 6.92 (d, J=8.8 Hz, 2H), 5.36 (s, 2H), 4.50 (s, 2H), 3.65 (s, 2H), 1.56 (s, 2H), 1.15 (s, 6H).

Intermediate 19: Benzyl 4-(oxiran-2-ylmethoxy)benzoate

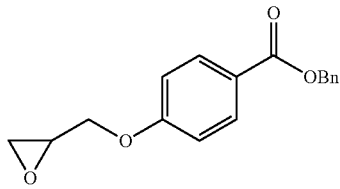 [SMILES: O=C(OCc1ccccc1)c1ccc(OCC2CO2)cc1]

Epichlorhydrin (SIGMA-ALDRICH, 1.237 mL, 15.77 mmol) was added to a suspension of $Cs_2CO_3$ (SIGMA-ALDRICH 4.28 g, 13.14 mmol) and benzyl 4-hydroxybenzoate (SIGMA-ALDRICH, 1.5 g, 6.57 mmol) in DMF (16.43 mL) under nitrogen atmosphere. The mixture was heated to 50° C. overnight. A new addition of epichlorhydrin (1.237 mL, 15.77 mmol) was done and the solution was heated to 70° C. for additional 5 h. Upon completion of the reaction, the solvent was removed under vacuo. The crude material was dissolved in EtOAc, washed with brine, dried over $Na_2SO_4$, filtered, and concentrated under reduced pressure. The residue was purified by flash chromatography on silica gel and eluted with CyHex:EtOAc (100:0 to 70:30). The desired fractions were collected and the solvent was removed in vacuo to obtain the title compound (1.14 g, 61% yield). $^1$H NMR (300 MHz, $CDCl_3$) δ ppm: 8.07 (d, J=9.1 Hz, 2H), 7.50-7.34 (m, 5H), 6.98 (d, J=9.1 Hz, 2H), 5.38 (s, 2H), 4.34 (dd, J=11.1, 3.0 Hz, 1H), 4.03 (dd, J=11.1, 5.8 Hz, 1H), 3.43-3.38 (m, 1H), 2.98-2.95 (m, 1H), 2.78 (dd, J=5.1, 2.8 Hz, 1H).

Intermediate 20: (R)-Benzyl 4-(oxiran-2-ylmethoxy)benzoate

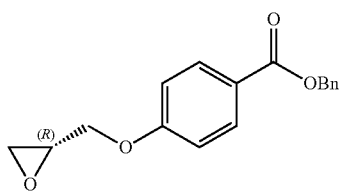

$Cs_2CO_3$ (SIGMA-ALDRICH, 114 g, 0.350 mol) was added to a suspension of (R)-oxiran-2-ylmethyl 4-methylbenzenesulfonate (CHEM-IMPEX, 40.0 g, 0.175 mol) and benzyl 4-hydroxybenzoate (SIGMA-ALDRICH, 40 g, 0.175 mol) in DMF (0.876 L) under nitrogen atmosphere. The solution was stirred at rt overnight. The solvent was removed under vacuo, then the crude mixture was dissolved in EtOAc, and washed with water (2×) and brine (2×), dried over $Na_2SO_4$, filtered, and concentrated to give the title compound (51.8 g, quant. yield; e.e 97.5%). $^1$H NMR (300 MHz, $CDCl_3$) δ ppm: 8.10-7.97 (m, 2H), 7.49-7.31 (m, 5H), 6.99-6.91 (m, 2H), 5.35 (s, 2H), 4.30 (dd, J=11.1, 3.0 Hz, 1H), 4.00 (dd, J=11.1, 5.8 Hz, 1H), 3.41-3.33 (m, 1H), 2.98-2.86 (m, 1H), 2.78 (dd, J=4.9, 2.7 Hz, 1H).

Chiral SFC: ChiralPak IC, 150×3 mm column, $CO_2$/MeOH (1% DEA) 95:5 (v/v), 2.0 mL/min, $R_t$=3.52 min. Chiral HPLC showed 96.6:1.2 R:S enantiomeric ratio (97.5% ee).

Intermediate 21: (S)-Benzyl 4-(oxiran-2-ylmethoxy)benzoate

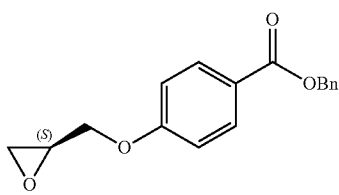

$Cs_2CO_3$ (SIGMA-ALDRICH, 10.11 g, 31.0 mmol) was added to a suspension of (S)-oxiran-2-ylmethyl 4-methylbenzenesulfonate (SIGMA-ALDRICH, 4.25 g, 18.61 mmol) and benzyl 4-hydroxybenzoate (SIGMA-ALDRICH, 3.54 g, 15.51 mmol) in DMF (40 mL) under nitrogen atmosphere. The solution was heated to 50° C. overnight. After the solvent was removed under vacuo, the crude was dissolved in EtOAc and the solution washed with water and brine, dried over $Na_2SO_4$, filtered, and concentrated under reduced pressure. The residue was purified by flash chromatography on silica gel and eluted with CyHex:EtOAc (100:0 to 85:15). The desired fractions were collected and the solvent was removed in vacuo to obtain the title compound (4.4 g, quant. yield). $^1$H NMR (300 MHz, $CDCl_3$) δ ppm: 8.07-8.02 (m, 2H), 7.48-7.31 (m, 5H), 6.98-6.92 (m, 2H), 5.35 (s, 2H), 4.31 (dd, J=11.1, 3.0 Hz, 1H), 4.00 (dd, J=11.1, 5.8 Hz, 1H), 3.41-3.35 (m, 1H), 2.96-2.91 (m, 1H), 2.78 (dd, J=4.8, 2.5 Hz, 1H).

Intermediate 22: Benzyl 4-((2-methyloxiran-2-yl)methoxy)benzoate

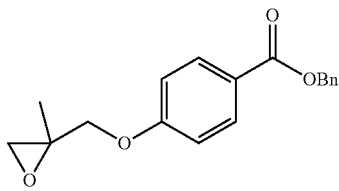 [SMILES: CC1(COc2ccc(C(=O)OCc3ccccc3)cc2)CO1]

2-(Chloromethyl)-2-methyloxirane (COMBI-BLOCKS, 1.698 mL, 17.52 mmol) was added to a suspension of $K_2CO_3$ (SIGMA-ALDRICH, 1.817 g, 13.14 mmol) and benzyl 4-hydroxybenzoate (SIGMA-ALDRICH, 2 g, 8.76 mmol) in DMF (8.76 mL) under nitrogen atmosphere. The solution was stirred and heated at 80° C. overnight. After cooling to rt, the mixture was partitioned between EtOAc and water. The layers were separated, and the organic layer was washed with brine, dried over $Na_2SO_4$, filtered, and concentrated under reduced pressure. The residue was purified by flash chromatography on silica gel and eluted with CyHex:EtOAc (100:0 to 70:30). The desired fractions were collected and the solvent was removed in vacuo to obtain the title compound (1.77 g, 67.7% yield). $^1$H NMR (300 MHz, $CDCl_3$) ppm: 8.08-8.02 (m, 2H), 7.50-7.34 (m, 5H), 6.97-6.91 (m, 2H), 5.35 (s, 2H), 4.11 (d, J=10.5 Hz, 1H), 3.99 (d, J=10.5 Hz, 1H), 2.89 (d, J=4.6 Hz, 1H), 2.76 (d, J=4.6 Hz, 1H), 1.50 (s, 3H).

Intermediate 23: Benzyl (S)-4-((2,2-dimethyl-1,3-dioxolan-4-yl)methoxy)benzoate

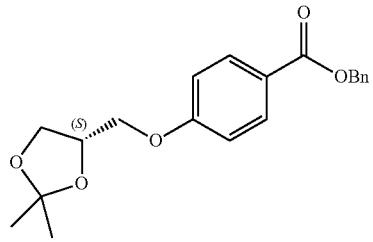

Cs$_2$CO$_3$ (SIGMA-ALDRICH, (11.42 g, 35.0 mmol) was added to a suspension of (R)-(2,2-dimethyl-1,3-dioxolan-4-yl)methyl 4-methylbenzenesulfonate (SIGMA-ALDRICH, 5.02 g, 17.52 mmol) and benzyl 4-hydroxybenzoate (SIGMA-ALDRICH, 4 g, 17.52 mmol) in DMF (175 mL) under nitrogen atmosphere. The solution was stirred at 50° C. overnight. After cooling to rt, the solvent was removed under vacuo. The crude mixture was dissolved in EtOAc (20 mL), and washed with water (20 mL) and brine (20 mL), dried over Na$_2$SO$_4$, filtered, and concentrated under reduced pressure. The residue was purified by chromatography on silica gel and eluted with CyHex:EtOAc (from 100:0 to 70:30) to afford the title compound (5.16 g, 15.07 mmol, 86% yield, ee 100%). $^1$H NMR (300 MHz, CDCl$_3$) δ ppm: 8.10-8.03 (m, 2H), 7.52-7.34 (m, 5H), 7.01-6.92 (m, 2H), 5.38 (s, 2H), 4.53 (quin, J=5.9 Hz, 1H), 4.22 (dd, J=8.6, 6.3 Hz, 1H), 4.14 (dd, J=9.6, 5.6 Hz, 1H), 4.04 (dd, J=9.6, 5.8 Hz, 1H), 3.95 (dd, J=8.6, 5.8 Hz, 1H), 1.50 (s, 3H), 1.45 (s, 3H).

Chiral SFC: ChiralPak IG, 150×4.6 mm column, CO$_2$/MeOH (1% DEA) 60:40 (v/v), 3.0 mL/min, R$_t$=4.92 min (100% ee).

Intermediate 24: Benzyl(R)-4-(2,3-dihydroxypropoxy)benzoate

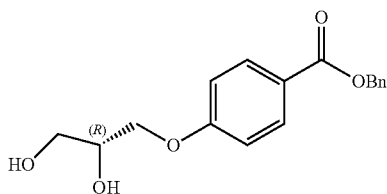

To benzyl (S)-4-((2,2-dimethyl-1,3-dioxolan-4-yl)methoxy)benzoate (intermediate 23, 5.4 g, 15.77 mmol) was added 4 M HCl in MeOH (SIGMA-ALDRICH, 35 mL, 140 mmol). The mixture was stirred at rt for 5 h and then concentrated under reduced pressure to afford the title compound (5.1 g, quant. yield, ee 100%). $^1$H NMR (300 MHz, CDCl$_3$) δ ppm: 7.97-7.91 (m, 2H), 7.49-7.33 (m, 5H), 7.08-7.01 (m, 2H), 5.31 (s, 2H), 5.00 (d, J=5.1 Hz, 1H), 4.69 (t, J=5.7 Hz, 1H), 4.08 (dd, J=10.1, 4.0 Hz, 1H), 3.94 (dd, J=10.0, 6.2 Hz, 1H), 3.85-3.75 (m, 1H), 3.45 (t, J=6.1 Hz, 2H).

Chiral SFC: ChiralPak IG, 150×4.6 mm column, CO$_2$/MeOH (1% DEA) 80:20 (v/v), 3.0 mL/min, R$_t$=8.9 min (100% ee).

Intermediates 25a and 25b: Benzyl 4-(2-hydroxy-3-(2H-tetrazol-2-yl)propoxy)benzoate (25a) and benzyl 4-(2-hydroxy-3-(1H-tetrazol-1-yl)propoxy)benzoate (25b)

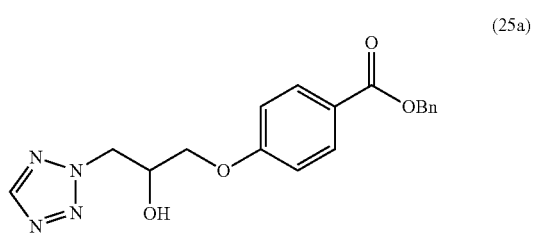
(25a)

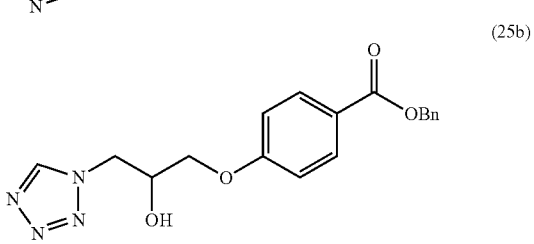
(25b)

1H-Tetrazole (ACROS, 3 wt. % in CH$_3$CN, 10.30 g, 4.41 mmol) was added to a solution of benzyl 4-(oxiran-2-ylmethoxy)benzoate (intermediate 19, 1.14 g, 4.01 mmol) in CH$_3$CN under nitrogen atmosphere. The solvent was removed in vacuo, and the residue was stirred and heated to 150° C. overnight under nitrogen atmosphere. After cooling at rt, the residue was purified by flash chromatography on silica gel (eluted with CyHex:EtOAc/EtOH(3/1), gradient 100:0 to 70:30). The desired fractions were collected and the solvent was removed in vacuo to obtain:

intermediate 25a: Benzyl 4-(2-hydroxy-3-(2H-tetrazol-2-yl)propoxy)benzoate (396 mg, 27.9% yield). $^1$H NMR (300 MHz, CDCl$_3$) ppm: 8.58 (s, 1H), 8.06 (d, J=8.8 Hz, 2H), 7.48-7.32 (m, 5H), 6.94 (d, J=8.8 Hz, 2H), 5.35 (s, 2H), 5.03-4.89 (m, 2H), 4.69-4.59 (m, 1H), 4.19-4.11 (m, 2H), 2.92 (d, J=5.8 Hz, 1H).

intermediate 25b: Benzyl 4-(2-hydroxy-3-(1H-tetrazol-1-yl)propoxy)benzoate (556 mg, 39.1% yield). $^1$H NMR (300 MHz, CDCl$_3$) ppm: 8.78 (s, 1H), 8.06 (d, J=8.8 Hz, 2H), 7.49-7.32 (m, 5H), 6.93 (d, J=8.8 Hz, 2H), 5.35 (s, 2H), 4.80 (dd, J=14.4, 3.3 Hz, 1H), 4.64 (dd, J=14.2, 7.1 Hz, 1H), 4.55-4.44 (m, 1H), 4.13 (dd, J=9.6, 4.8 Hz, 1H), 4.01 (dd, J=9.6, 5.8 Hz, 1H), 2.88-2.82 (m, 1H).

Intermediates 26a and 26b: (R)-Benzyl 4-(2-hydroxy-3-(2H-tetrazol-2-yl)propoxy)benzoate (26a) and (R)-benzyl 4-(2-hydroxy-3-(1H-tetrazol-2-yl)propoxy)benzoate (26b)

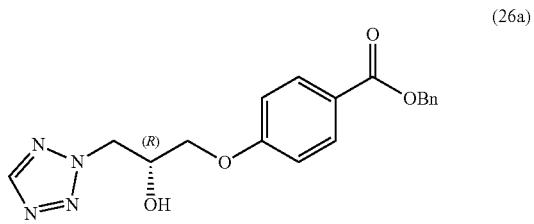
(26a)

-continued

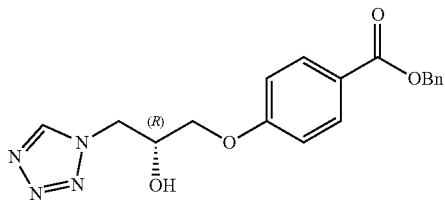

(26b)

Procedure A:

Benzyl (R)-4-(oxiran-2-ylmethoxy)benzoate (intermediate 20, 128.7 g, 0.453 mol) was dissolved in DMF (2.3 L) under nitrogen atmosphere and K₂CO₃ (SIGMA-ALDRICH, 125 g, 0.905 mol) was added. 1H-tetrazole (ACROS, 3 wt. % in CH₃CN, 2 L, 0.905 mol) was added to the suspension, and the mixture was heated at 80° C. overnight. After cooling at rt, the mixture was partitioned between EtOAc (2.5 L), water (1.5 L) and sat. NaCl solution (1 L), the layers were separated and the aqueous layer was extracted with EtOAc (1 L) twice. The organic layer was washed with sat. NaCl solution (1 L), dried over Na₂SO₄, filtered, and concentrated under reduced pressure. The crude material was purified by chromatography on silica gel and eluted with CyHex:EtOAc (from 100:0 to 0:100). The desired fractions were collected and the solvent was removed in vacuo to obtain the isomers 26a (64 g, 39.9% yield) and 26b (70 g, 43.6%) in a ratio aprox. 0.9/1.1.

intermediate 26a: Benzyl (R)-4-(2-hydroxy-3-(2H-tetrazol-2-yl)propoxy)benzoate. 1H NMR (300 MHz, CDCl₃) δ ppm: 8.58 (s, 1H), 8.15-7.98 (m, 2H), 7.53-7.33 (m, 5H), 7.01-6.83 (m, 2H), 5.35 (s, 2H), 5.02-4.88 (m, 2H), 4.69-4.59 (m, 1H), 4.19-4.09 (m, 2H), 2.98 (dd, J=5.8, 1.3 Hz, 1H). [ES+MS] m/z 355 (MH⁺).

intermediate 26b: Benzyl (R)-4-(2-hydroxy-3-(1H-tetrazol-1-yl)propoxy)benzoate. 1H NMR (300 MHz, CDCl₃) δ ppm: 8.77 (s, 1H), 8.10-8.00 (m, 2H), 7.49-7.31 (m, 5H), 6.97-6.88 (m, 2H), 5.35 (s, 2H), 4.81 (dd, J=14.1, 3.3 Hz, 1H), 4.67-4.57 (m, 1H), 4.55-4.44 (m, 1H), 4.17-4.10 (m, 1H), 4.07-4.00 (m, 1H), 3.30 (br.s, 1H). [ES+MS] m/z 355 (MH⁺).

Procedure B:

A solution of benzyl (R)-4-(2,3-dihydroxypropoxy)benzoate (intermediate 24, 2.00 g, 6.62 mmol) and 1H-Tetrazole (ACROS, 3 wt. % in CH₃CN, 38.6 mL, 13.23 mmol) in 2-MeTHF (33.1 mL) was heated to 36° C. DIAD (ALFA-AESAR, 2.79 mL, 13.23 mmol) in 2-MeTHF (17 mL) and PPh₃ (SIGMA-ALDRICH, 3.47 g, 13.23 mmol) in 2-MeTHF (17 mL) under nitrogen atmosphere was slowly added at the same time via syringe over 30 min. The mixture was heated at 36° C. for 2 h. Solvent was removed under vacuo, and the mixture was dissolved in EtOAc (100 mL) and washed with 1 M HCl (2×100 mL), NaHCO₃ sat (100 mL) and NaCl sat. (100 mL). The organic layer was dried with MgSO₄ and the organic solvent was removed under reduced pressure. The crude was redissolved in Et₂O (150 mL), stirred for 30 min at rt and filtered to removed most of the OPPh₃. The mother liquor was concentrated, and the residue was purified by chromatography on silica gel and eluted with CyHex:EtOAc mixture (from 100:0 to 0:100) to afford benzyl (R)-4-(2-hydroxy-3-(2H-tetrazol-2-yl)propoxy)benzoate (isomer 26a, 2.1 g, 4.15 mmol, 62.7% yield) with additional 30% approx. of OPPh₃. The isomer 26b was discarded.

Intermediates 27a and 27b: (S)-Benzyl 4-(2-hydroxy-3-(2H-tetrazol-2-yl)propoxy)benzoate (27a) and (S)-benzyl 4-(2-hydroxy-3-(1H-tetrazol-1-yl)propoxy)benzoate (27b)

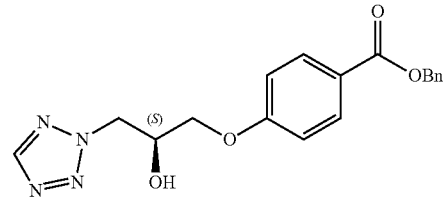

(27a)

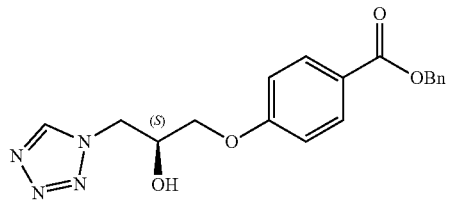

(27b)

Benzyl (S)-4-(oxiran-2-ylmethoxy)benzoate (intermediate 21) (4.41 g, 15.51 mmol) was dissolved in DMF (59.7 mL) and 1H-Tetrazole (ACROS, 3 wt. % in CH₃CN, 72.4 g, 31.0 mmol) was added. The CH₃CN was evaporated under reduced pressure, and K₂CO₃ (SIGMA-ALDRICH, 4.29 g, 31.0 mmol) was added to the mixture under nitrogen atmosphere. The mixture was heated at 80° C. overnight. After cooling, the mixture was partitioned between EtOAc and water. Layers were separated and the organic layer was washed with brine, dried over Na₂SO₄, filtered, and concentrated under reduced pressure. The crude material was purified by chromatography on silica gel and eluted with CyHex:EtOAc/EtOH(3/1) (from 100:0 to 70:30). The desired fractions were collected and the solvent was removed in vacuo to obtain the isomers 27a and 27b in a ratio 1.1/0.9 intermediate 27a: Benzyl (S)-4-(2-hydroxy-3-(2H-tetrazol-2-yl)propoxy)benzoate (2.44 g, 44.4% yield). ¹H NMR (300 MHz, CDCl₃) ppm: 8.58 (s, 1H), 8.06 (d, J=9.1 Hz, 2H), 7.48-7.32 (m, 5H), 6.94 (d, J=8.8 Hz, 2H), 5.35 (s, 2H), 5.02-4.89 (m, 2H), 4.68-4.59 (m, 1H), 4.20-4.10 (m, 2H), 2.96 (d, J=5.8 Hz, 1H), 1.58 (s, 3H).

intermediate 27b: Benzyl (S)-4-(2-hydroxy-3-(1H-tetrazol-1-yl)propoxy)benzoate (2.28 g, 41.5% yield). ¹H NMR (300 MHz, CDCl₃) δ ppm: 8.81 (s, 1H), 8.08 (d, J=9.1 Hz, 2H), 7.51-7.35 (m, 5H), 6.95 (d, J=8.9 Hz, 2H), 5.38 (s, 2H), 4.84 (dd, J=14.1, 3.0 Hz, 1H), 4.65 (dd, J=14.1, 7.6 Hz, 1H), 4.57-4.48 (m, 1H), 4.15 (dd, J=9.6, 4.8 Hz, 1H), 4.07 (dd, J=9.6, 5.6 Hz, 1H), 3.43 (d, J=5.1 Hz, 1H), 1.67 (s, 3H).

Intermediates 28a & 28b: Benzyl 4-(2-hydroxy-2-methyl-3-(2H-tetrazol-2-yl)propoxy) benzoate (28a) and benzyl 4-(2-hydroxy-2-methyl-3-(1H-tetrazol-1-yl)propoxy)benzoate (28b)

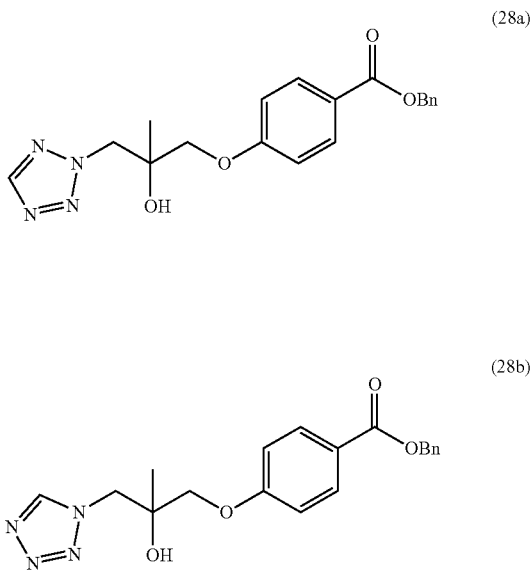

(28a)

(28b)

1H-Tetrazole (ACROS, 3 wt. % in $CH_3CN$, 27.7 g, 11.87 mmol) was added to a solution of benzyl 4-((2-methyloxiran-2-yl)methoxy)benzoate (intermediate 22, 1.77 g, 5.93 mmol) in DMF (19.78 mL) under nitrogen atmosphere. The solvents were removed in vacuo and the crude was re-dissolved in DMF (19.78 mL) under nitrogen atmosphere. $K_2CO_3$ (SIGMA-ALDRICH, 1.640 g, 11.87 mmol) was added and the mixture was heated at 80° C. overnight. After cooling, the mixture was partitioned between EtOAc and water. The layers were separated, and the organic layer was washed with brine, dried over $Na_2SO_4$, filtered, and concentrated under reduced pressure. The crude material was purified by chromatography on silica gel and eluted with CyHex:EtOAc/EtOH (3/1) (100:0 to 60:40). The desired fractions were collected and the solvent was removed in vacuo to obtain the isomers 28a and 28b in a ratio 1/1.

intermediate 28a: Benzyl 4-(2-hydroxy-2-methyl-3-(2H-tetrazol-2-yl)propoxy)benzoate (1.04 g, 47.6% yield). $^1$H NMR (300 MHz, $CDCl_3$) ppm: 8.56 (s, 1H), 8.05 (d, J=8.8 Hz, 2H), 7.48-7.32 (m, 5H), 6.90 (d, J=8.8 Hz, 2H), 5.35 (s, 2H), 4.97 (d, J=13.9 Hz, 1H), 4.87 (d, J=13.9 Hz, 1H), 3.99 (d, J=9.3 Hz, 1H), 3.89 (d, J=9.1 Hz, 1H), 3.17-3.12 (m, 1H), 1.44 (s, 3H).

intermediate 28b: Benzyl 4-(2-hydroxy-2-methyl-3-(1H-tetrazol-1-yl)propoxy)benzoate (1.09 g, 49.9% yield). $^1$H NMR (300 MHz, $CDCl_3$) δ ppm: 8.56 (s, 1H), 8.058-8.01 (m, 2H), 7.48-7.31 (m, 5H), 6.91 (d, J=8.8 Hz, 2H), 5.34 (s, 2H), 4.69 (d, J=14.4 Hz, 1H), 4.63 (d, J=14.4 Hz, 1H), 3.94-3.83 (m, 2H), 2.98-2.86 (m, 1H), 1.43 (s, 3H).

Intermediate 29: Benzyl(R)-4-(2-hydroxy-3-(1H-1,2,4-triazol-1-yl)propoxy)benzoate

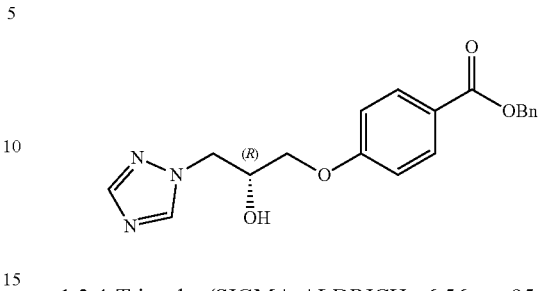

1,2,4-Triazole (SIGMA-ALDRICH, 6.56 g, 95 mmol) was added to a stirred suspension of $K_2CO_3$ (SIGMA-ALDRICH, 13.12 g, 95 mmol) and benzyl (R)-4-(oxiran-2-ylmethoxy)benzoate (intermediate 20, 9 g, 31.7 mmol) in DMF (158 mL) under nitrogen atmosphere. The mixture was stirred at 80° C. overnight. After cooling, the mixture was dissolved in EtOAc, washed with water, dried over $Na_2SO_4$, filtered, and concentrated under reduced pressure. The residue was purified by chromatography on silica gel and eluted with CyHex:EtOAc/EtOH(3/1) (from 100:0 to 0:100). The desired fractions were collected and the solvent was removed in vacuo to afford the title compound (8.7 g, 78% yield, ee 99.5%). $^1$H NMR (300 MHz, $CDCl_3$) δ ppm: 8.15 (s, 1H), 8.05 (d, J=9.1 Hz, 2H), 7.96 (s, 1H), 7.48-7.31 (m, 5H), 6.93 (d, J=8.9 Hz, 2H), 5.35 (s, 2H), 4.52 (dd, J=13.1, 2.5 Hz, 1H), 4.48-4.34 (m, 2H), 4.07 (dd, J=9.6, 5.1 Hz, 1H), 4.00 (dd, J=9.6, 5.5 Hz, 1H), 3.64 (d, J=4.8 Hz, 1H).

Chiral SFC: ChiralPak IA, 150×3 mm column, $CO_2$/MeOH (1% DEA) 60:40 (v/v), 3.0 mL/min, $R_t$=3.9 min. Chiral HPLC showed 96.3:0.2 R:S enantiomeric ratio (99.5% ee).

Intermediate 30: Benzyl (S)-4-(2-hydroxy-3-(1H-1,2,4-triazol-1-yl)propoxy)benzoate

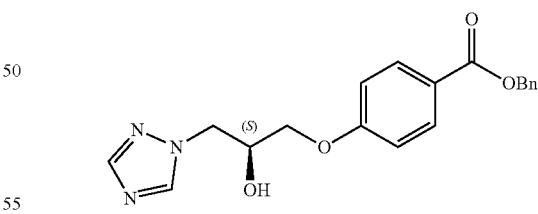

Intermediate 30 was prepared using analogous conditions to that described for intermediate 29, replacing benzyl (R)-4-(oxiran-2-ylmethoxy)benzoate by benzyl (S)-4-(oxiran-2-ylmethoxy)benzoate (intermediate 21, 800 mg, 2.81 mmol). 714 mg (71.8% yield) of the title intermediate was obtained after chromatographic purification. $^1$H NMR (300 MHz, $CDCl_3$) δ ppm: 8.16 (s, 1H), 8.05 (d, J=8.8 Hz, 2H), 7.98 (s, 1H), 7.48-7.31 (m, 5H), 6.93 (d, J=9.1 Hz, 2H), 5.35 (s, 2H), 4.56-4.36 (m, 3H), 4.10-3.96 (m, 2H), 4.00 (dd, J=9.6, 5.5 Hz, 1H), 3.51-3.43 (m, 1H).

Intermediates 31a and 31b: (R)-Benzyl 4-(2-hydroxy-3-(2H-1,2,3-triazol-2-yl)propoxy) benzoate (31a) and (R)-benzyl 4-(2-hydroxy-3-(1H-1,2,3-triazol-1-yl)propoxy)benzoate (31b)

(31a)

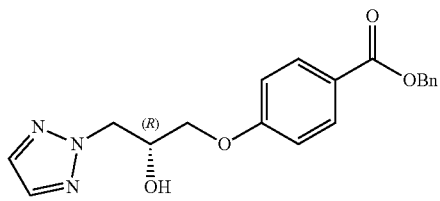

(31b)

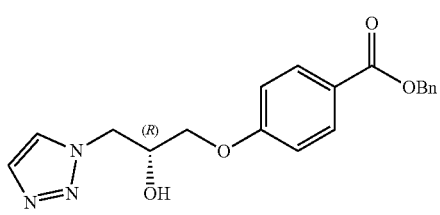

1H-1,2,3-Triazole (SIGMA-ALDRICH, 219 mg, 3.17 mmol) was added to a solution of (R)-benzyl 4-(oxiran-2-ylmethoxy)benzoate (intermediate 20, 300 mg, 1.055 mmol) and K$_2$CO$_3$ (SIGMA-ALDRICH, 438 mg, 3.17 mmol) in DMF (4 mL) under nitrogen atmosphere. The mixture was heated at 80° C. for 3 h. After cooling, the mixture was partitioned between EtOAc and water. The layers were separated, and the organic layer was washed with brine, dried over Na$_2$SO$_4$, filtered, and concentrated. The crude material was purified by chromatography on silica gel and eluted with CyHex:EtOAc (100:0 to 40:60) to obtain the isomers 31a and 31b in a ratio 1/1.

intermediate 31a: (R)-benzyl 4-(2-hydroxy-3-(2H-1,2,3-triazol-2-yl)propoxy)benzoate (187 mg, 50.2% yield). $^1$H NMR (300 MHz, CDCl$_3$) δ ppm: 8.04 (d, J=9.1 Hz, 2H), 7.67 (s, 2H), 7.48-7.31 (m, 5H), 6.93 (d, J=8.8 Hz, 2H), 5.35 (s, 2H), 4.80 (dd, J=13.9, 3.8 Hz, 1H), 4.69 (dd, J=13.9, 6.8 Hz, 1H), 4.59-4.49 (m, 1H), 4.11 (dd, J=9.6, 5.1 Hz, 1H), 4.01 (dd, J=9.6, 5.8 Hz, 1H), 3.50 (d, J=5.1 Hz, 1H).

intermediate 31b: (R)-benzyl 4-(2-hydroxy-3-(1H-1,2,3-triazol-1-yl)propoxy)benzoate (190 mg, 51.0% yield). $^1$H NMR (300 MHz, CDCl$_3$) δ ppm: 8.04 (d, J=8.8 Hz, 2H), 7.73 (d, J=1.0 Hz, 1H), 7.70 (d, J=1.0 Hz, 1H), 7.48-7.31 (m, 5H), 6.92 (d, J=8.8 Hz, 2H), 5.35 (s, 2H), 4.73 (dd, J=14.1, 3.5 Hz, 1H), 4.60 (dd, J=14.1, 6.8 Hz, 1H), 4.55-4.47 (m, 1H), 4.08-3.97 (m, 2H), 3.16 (br.s, 1H).

Intermediates 32a and 32b: (S)-Benzyl 4-(2-hydroxy-3-(2H-1,2,3-triazol-2-yl)propoxy) benzoate (32a) and (S)-benzyl 4-(2-hydroxy-3-(1H-1,2,3-triazol-1-yl)propoxy)benzoate (32b)

(32a)

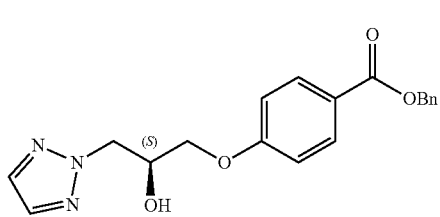

-continued (32b)

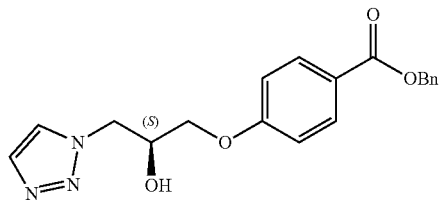

Intermediates 32a-b were prepared using analogous conditions to that described for intermediates 31a-b, replacing benzyl (R)-4-(oxiran-2-ylmethoxy)benzoate by benzyl (S)-4-(oxiran-2-ylmethoxy)benzoate (intermediate 21, 1.5 g, 5.28 mmol). Isomer 32a and 32b were obtained in a ratio 1/1 after chromatography on silica gel.

intermediate 32a: (S)-benzyl 4-(2-hydroxy-3-(2H-1,2,3-triazol-2-yl)propoxy)benzoate (885 mg, 47.5% yield). $^1$H NMR (300 MHz, CDCl$_3$) ppm: 8.04 (d, J=9.1 Hz, 2H), 7.67 (s, 2H), 7.48-7.31 (m, 5H), 6.93 (d, J=8.8 Hz, 2H), 5.35 (s, 2H), 4.80 (dd, J=13.9, 3.8 Hz, 1H), 4.69 (dd, J=13.9, 6.8 Hz, 1H), 4.59-4.49 (m, 1H), 4.11 (dd, J=9.6, 5.1 Hz, 1H), 4.01 (dd, J=9.6, 5.8 Hz, 1H), 3.49 (d, J=5.1 Hz, 1H).

intermediate 32b: (S)-benzyl 4-(2-hydroxy-3-(1H-1,2,3-triazol-1-yl)propoxy)benzoate (896 mg, 48.1% yield). $^1$H NMR (300 MHz, CDCl$_3$) ppm: 8.04 (d, J=8.8 Hz, 2H), 7.73 (d, J=1.0 Hz, 1H), 7.70 (d, J=1.0 Hz, 1H), 7.48-7.31 (m, 5H), 6.92 (d, J=8.8 Hz, 2H), 5.35 (s, 2H), 4.73 (dd, J=14.1, 3.5 Hz, 1H), 4.61 (dd, J=14.1, 6.8 Hz, 1H), 4.55-4.47 (m, 1H), 4.08-3.97 (m, 2H), 3.09 (d, J=5.1 Hz, 1H).

Intermediate 33: Benzyl (R)-4-(2-hydroxy-3-(1H-pyrazol-1-yl)propoxy)benzoate

Benzyl (R)-4-(oxiran-2-ylmethoxy)benzoate (intermediate 20, 0.200 g, 0.703 mmol) was dissolved in DMF (3.52 mL) under nitrogen atmosphere and K$_2$CO$_3$ (SIGMA-ALDRICH, 0.194 g, 1.407 mmol) was added. 1H-pyrazole (SIGMA-ALDRICH, 0.048 g, 0.703 mmol) was added to the suspension and the mixture was heated at 80° C. overnight. After cooling, the mixture was partitioned between EtOAc and water, the layers were separated and the aqueous layer was extracted with EtOAc twice. The organic layer was washed with sat. NaCl solution, dried over Na$_2$SO$_4$, filtered, and concentrated under reduced pressure. The residue was purified by chromatography on silica gel and eluted with CyHex:EtOAc (from 0% to 100%) to obtain the title compound (110 mg, 44.4% yield). $^1$H NMR (300 MHz, DMSO-d$_6$) δ ppm: 7.97-7.92 (m, 2H), 7.70 (d, J=2.0 Hz, 1H), 7.47-7.33 (m, 6H), 7.06-7.02 (m, 2H), 6.22 (t, J=2.0 Hz, 1H), 5.32 (d, J=5.0 Hz, 1H), 5.32 (s, 2H), 4.35-4.05 (m, 3H), 4.02-3.89 (m, 2H).

Intermediate 34: Benzyl (S)-4-(2-hydroxy-3-(1H-pyrazol-1-yl)propoxy)benzoate

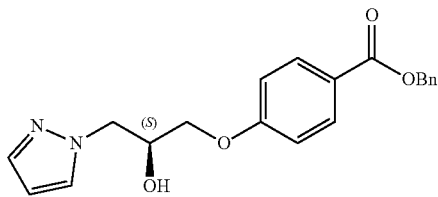

Intermediates 34 was prepared using analogous conditions to that described for intermediates 33, replacing benzyl (R)-4-(oxiran-2-ylmethoxy)benzoate by benzyl (S)-4-(oxiran-2-ylmethoxy)benzoate (intermediate 21, 700 mg, 2.462 mmol). 660 mg (76% yield) of the title intermediate was obtained after chromatographic purification. $^1$H NMR (300 MHz, CDCl$_3$) δ ppm: 8.03 (d, J=9.1 Hz, 2H), 7.70-7.66 (m, 1H), 7.56 (d, J=2.0 Hz, 1H), 7.47-7.33 (m, 5H), 6.90 (d, J=8.8 Hz, 2H), 6.38 (br.s, 1H), 6.28 (t, J=2.0 Hz, 1H), 5.35 (s, 2H), 4.49-4.32 (m, 3H), 4.07-3.76 (m, 2H).

Intermediate 35: Benzyl (R)-4-(2-hydroxy-3-(1H-imidazol-1-yl)propoxy)benzoate

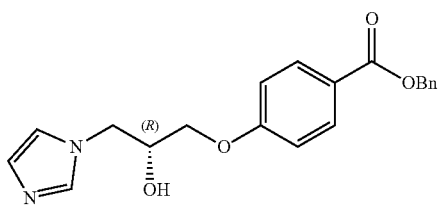

Intermediates 35 was prepared using analogous conditions to that described for intermediates 33, replacing 1H-pyrazole by 1H-imidazole (SIGMA-ALDRICH, 0.096 g, 1.407 mmol). 140 mg (56.5% yield) of the title intermediate was obtained after chromatographic purification. $^1$H NMR (300 MHz, DMSO-d$_6$) δ ppm: 7.95 (d, J=8.8 Hz, 2H), 7.58 (s, 1H), 7.49-7.32 (m, 5H), 7.15 (s, 1H), 7.07 (d, J=8.8 Hz, 2H), 6.87 (s, 1H), 5.53 (d, J=5.3 Hz, 1H), 5.32 (s, 2H), 4.18 (dd, J=12.9, 2.8 Hz, 1H), 4.13-4.01 (m, 2H), 3.91 (d, J=4.8 Hz, 2H).

Intermediate 36: Benzyl 4-(2-fluoro-3-(1H-tetrazol-1-yl)propoxy)benzoate

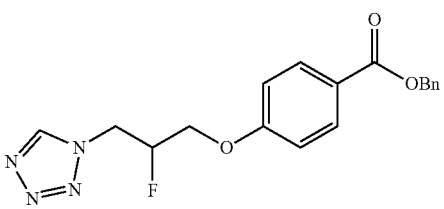 [SMILES: O=C(OCc1ccccc1)c1ccc(OCC(F)Cn2cnnn2)cc1]

DAST (SIGMA-ALDRICH, 0.138 mL, 1.044 mmol) was added to a solution of benzyl 4-(2-hydroxy-3-(1H-tetrazol-1-yl)propoxy)benzoate (intermediate 25b, 185 mg, 0.522 mmol) in DCM (10 mL) at 0° C., and the mixture was stirred at rt. After overnight, a new addition of DAST (SIGMA-ALDRICH, 0.069 mL, 0.522 mmol) was done and the mixture stirred at room temperature for additional 6 h. The reaction was quenched with sat. NaHCO$_3$ solution, diluted with DCM and extracted three times. The combined organics were dried over Na$_2$SO$_4$, filtered and concentrated under reduced pressure. Chromatography on silica gel eluting with CyHex:EtOAc (from 100:0 to 50:50) give the title compound (114 mg, 61% yield). $^1$H NMR (300 MHz, CDCl$_3$) δ ppm: 8.76 (s, 1H), 8.05 (d, J=8.8 Hz, 2H), 7.47-7.31 (m, 5H), 6.93 (d, J=8.8 Hz, 2H), 5.34 (s, 2H), 5.31-5.11 (m, 1H), 4.99-4.88 (m, 2H), 4.37-4.18 (m, 2H).

Intermediate 37: Dimethyl 2-methoxy-2-((1-methyl-1H-pyrazol-3-yl)methyl)malonate

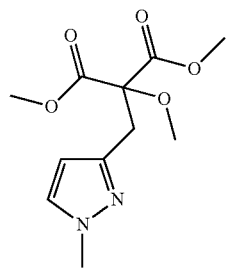

To a solution of 3-(chloromethyl)-1-methyl-1H-pyrazole hydrochloride (ENAMINE, 1 g, 5.99 mmol) and dimethyl 2-methoxymalonate (TCI SHANGHAI, 2.10 mL, 15.27 mmol) in DMF (37.4 mL) was added tBuOK (SIGMA-ALDRICH, 2.01 g, 17.96 mmol) at 0° C. The reaction mixture was stirred at rt. After overnight, the mixture was diluted with water and extracted with EtOAc. The organic extract was washed with sat. NH$_4$Cl and brine, dried over anh. Na$_2$SO$_4$, filtered and concentrated under reduced pressure. The residue was purified by chromatography on silica gel and eluted with CyHex:EtOAc (from 100:0 to 0:100) to give the title compound (892 mg, 58% yield) as a colorless oil. $^1$H NMR (300 MHz, CDCl$_3$) δ ppm: 7.23 (d, J=2.0 Hz, 1H), 6.04 (d, J=2.0 Hz, 1H), 3.83 (s, 2H), 3.81 (s, 6H), 3.46 (s, 6H).

Intermediate 38: Dimethyl 2-methoxy-2-(thiazol-4-ylmethyl)malonate

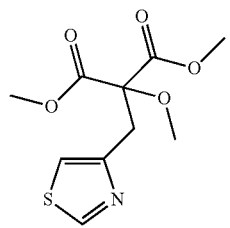

Intermediate 38 was prepared using analogous conditions to that described for intermediate 37, replacing 3-(chloromethyl)-1-methyl-1H-pyrazole hydrochloride by 4-(chloromethyl)thiazole hydrochloride (CHEMBRIDGE, 3.0 g, 17.64 mmol). 2.22 g (48.5% yield) of the title intermediate was obtained after chromatographic purification. $^1$H NMR (300

MHz, CDCl$_3$) δ ppm: 8.72 (d, J=2.0 Hz, 1H), 7.16 (d, J=2.0 Hz, 1H), 3.82 (s, 6H), 3.69 (s, 2H), 3.47 (s, 6H).

Intermediate 39: Dimethyl 2-methoxy-2-((1-methyl-1H-pyrazol-4-yl)methyl)malonate

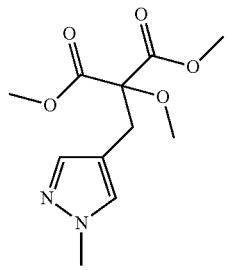

Intermediate 39 was prepared using analogous conditions to that described for intermediate 37, replacing 3-(chloromethyl)-1-methyl-1H-pyrazole hydrochloride by 4-(chloromethyl)-1-methyl-1H-pyrazole hydrochloride (ENAMINE, 1 g, 5.99 mmol). 400 mg (26.1% yield) of the title intermediate was obtained after chromatographic purification. $^1$H NMR (300 MHz, CDCl$_3$) δ ppm: 7.23 (s, 1H), 7.25 (s, 1H), 3.84 (s, 3H), 3.77 (s, 6H), 3.46 (s, 3H), 3.24 (s, 2H).

Intermediate 40: Lithium 2-methoxy-2-((1-methyl-1H-pyrazol-3-yl)methyl)malonate

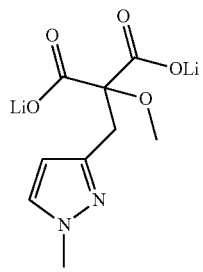

To a solution of intermediate 37 (890 mg, 3.47 mmol) in THF (15 mL) was added a solution of LiOH.H$_2$O (SIGMA-ALDRICH, 364 mg, 8.68 mmol) in water (5 mL). The reaction mixture was stirred for 2 h at rt until a white solid precipitated. The precipitate was filtered, washed with THF, and dried to give the title compound (850 mg, quant. yield) as white solid. $^1$H NMR (300 MHz, DMSO-d$_6$) δ ppm: 7.36 (d, J=2.0 Hz, 1H), 6.04 (d, J=2.0 Hz, 1H), 3.69 (s, 3H), 3.19 (s, 2H), 3.15 (s, 3H).

Intermediate 41: Lithium 2-methoxy-2-(thiazol-4-ylmethyl)malonate

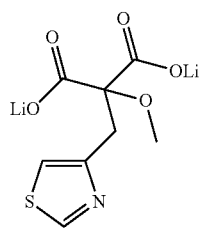

Intermediate 41 was prepared using analogous conditions to that described for intermediate 40, using as starting material intermediate 38 (2.2 g, 8.49 mmol). 1.9 g (92% yield) of the title intermediate, as a white solid, was obtained after precipitation. $^1$H NMR (300 MHz, DMSO-d$_6$) δ ppm: 8.88 (d, J=2.0 Hz, 1H), 7.27 (br.s, 1H), 3.47 (s, 2H), 3.15 (s, 3H).

Intermediate 42: Lithium 2-methoxy-2-((1-methyl-1H-pyrazol-4-yl)methyl)malonate

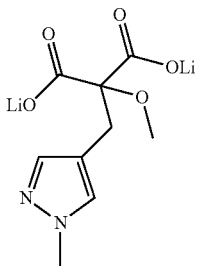

Intermediate 42 was prepared using analogous conditions to that described for intermediate 40, using as starting material intermediate 39 (1.86 g, 7.26 mmol). 2.7 g of the title intermediate (impurified with salts, 60% purity) was obtained after concentration under reduced pressure.
$^1$H NMR (300 MHz, D$_2$O) ppm: 7.38 (s, 1H), 7.34 (s, 1H), 3.78 (s, 2H), 3.23 (s, 3H), 3.10 (s, 2H).

Intermediate 43: 2-Methoxy-3-(1-methyl-1H-pyrazol-3-yl)propanoic acid

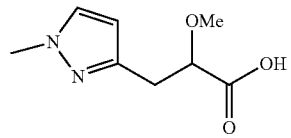

To a solution of lithium 2-methoxy-2-((1-methyl-1H-pyrazol-3-yl)methyl)malonate (intermediate 40, 850 mg, 3.54 mmol) in water (30 mL) was added 6 M HCl in H$_2$ (SIGMA-ALDRICH, 1.475 mL, 8.85 mmol). The reaction mixture was stirred for 1 h at 120° C. in a microwave system. The product was purified using a column of Diaion HP20 resin which was eluted initially with water to remove the salts. Then, the resin was eluted with MeOH and the product was collected and concentrated to give the title compound (590 mg, 90% yield, as a yellow oil). $^1$H NMR (300 MHz, DMSO-d$_6$) δ ppm: 12.61 (br.s, 1H), 7.52 (d, J=2.0 Hz, 1H), 6.03 (d, J=2.0 Hz, 1H), 3.92 (dd, J=7.8, 4.8 Hz, 1H), 3.74 (s, 3H), 3.24 (s, 3H), 2.93-2.75 (m, 2H).

Intermediate 44: 2-Methoxy-3-(thiazol-4-yl)propanoic acid

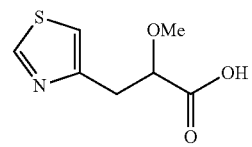 [SMILES: COC(Cc1cscn1)C(=O)O]

Intermediate 44 was prepared using analogous conditions to that described for intermediate 43, using as starting material lithium 2-methoxy-2-(thiazol-4-ylmethyl)malonate (intermediate 41, 1.87 g, 7.69 mmol). 1.15 g (80% yield) of the title intermediate, as a white solid, was obtained. $^1$H NMR (300 MHz, DMSO-d$_6$) δ ppm: 12.78 (br.s, 1H), 9.01 (d, J=2.0 Hz, 1H), 7.39 (d, J=2.0 Hz, 1H), 4.11 (dd, J=8.1, 4.8 Hz, 1H), 3.23 (s, 3H), 3.17-3.02 (m, 2H).

Intermediate 45: 2-Methoxy-3-(1-methyl-1H-pyrazol-4-yl)propanoic acid

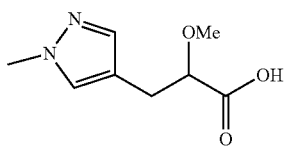

Intermediate 45 was prepared using analogous conditions to that described for intermediate 43, using as starting material lithium 2-methoxy-2-((1-methyl-1H-pyrazol-4-yl)methyl)malonate (intermediate 42, 2.70 g, 6.75 mmol, 60% purity). 550 mg (42.2% yield) of the title intermediate was obtained. $^1$H NMR (300 MHz, DMSO-d$_6$) ppm: 7.45 (s, 1H), 7.22 (s, 1H), 3.83-3.77 (m, 1H), 3.87-3.66 (br.s, 1H), 3.76 (s, 2H), 3.27 (s, 3H), 2.83-2.63 (m, 2H).

Intermediate 46: 2-Methoxy-3-(1-methyl-1H-pyrazol-3-yl)propan-1-ol

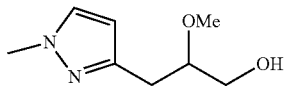

To a solution of 2-methoxy-3-(1-methyl-1H-pyrazol-3-yl)propanoic acid (intermediate 43, 590 mg, 3.20 mmol) in THF (32 mL) was added LAH (SIGMA-ALDRICH, 250 mg, 6.59 mmol) at 0° C. under nitrogen atmosphere. The reaction mixture was warmed to rt and stirred overnight. The reaction was cooled to 0° C., diluted with Et$_2$O, and water (0.25 mL) was slowly added. Then, NaOH 15% (0.25 mL) was added with continuous stirring, followed by water (0.75 mL). The suspension was warmed to rt and stirred 15 min. MgSO$_4$ was added and the mixture was filtered to remove the salts. The solvent was removed in vacuo to obtain the title compound (578 mg, quant. yield) as a brown oil. $^1$H NMR (300 MHz, DMSO-d$_6$) δ ppm: 7.51 (d, J=2.3 Hz, 1H), 6.02 (d, J=2.3 Hz, 1H), 4.58-4.51 (m, 1H), 3.74 (s, 3H), 3.62-3.56 (m, 1H), 3.45-3.33 (m, 2H), 3.26 (s, 3H), 2.67-2.61 (m, 2H).

Intermediate 47: 2-Methoxy-3-(thiazol-4-yl)propan-1-ol

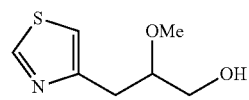 [SMILES: COC(CO)Cc1cscn1]

Intermediate 47 was prepared using analogous conditions described for intermediate 46, using 2-methoxy-3-(thiazol-4-yl)propanoic acid (intermediate 44, 1.15 g, 6.14 mmol). 812 mg (76% yield) of the title compound, as a brown oil, was obtained after extraction. $^1$H NMR (300 MHz, CDCl$_3$) δ ppm: 8.77 (d, J=2.0 Hz, 1H), 7.08 (d, J=2.0 Hz, 1H), 3.74-3.64 (m, 2H), 3.58-3.49 (m, 1H), 3.42 (s, 3H), 3.0-2.01 (m, 2H), 2.64 (br.s, 1H).

Intermediate 48: 2-Methoxy-3-(1-methyl-1H-pyrazol-4-yl)propan-1-ol

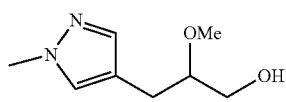

Intermediate 48 was prepared using analogous conditions described for intermediate 46, using 2-methoxy-3-(1-methyl-1H-pyrazol-4-yl)propanoic acid (intermediate 45, 376 mg, 2.041 mmol). 262 mg (75% yield) of the title compound was obtained after extraction. $^1$H NMR (300 MHz, CDCl$_3$) δ ppm: 7.36 (s, 1H), 7.24 (s, 1H), 3.89 (s, 3H), 3.74-3.65 (m, 1H), 3.55-3.39 (m, 2H), 3.47 (s, 3H), 2.80-2.64 (m, 2H), 2.03 (br.s, 1H).

Intermediate 49: Benzyl 4-(2-methoxy-3-(1-methyl-1H-pyrazol-3-yl)propoxy)benzoate

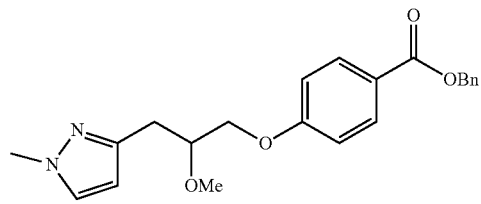 [SMILES: COC(COc1ccc(C(=O)OCc2ccccc2)cc1)Cc1ccn(C)n1]

A solution of benzyl 4-hydroxybenzoate (SIGMA-ALDRICH, 925 mg, 4.05 mmol), 2-methoxy-3-(1-methyl-1H-pyrazol-3-yl)propan-1-ol (intermediate 46, 575 mg, 3.38 mmol) and PPh$_3$ (SIGMA-ALDRICH, 975 mg, 3.72 mmol) in THF (30 mL) was cooled to 0° C. under nitrogen atmosphere. DIAD (ALFA-AESAR, 1.1 mL, 5.22 mmol) was added dropwise and the solution was stirred at 80° C. overnight. Upon completion of the reaction, the solvent was removed in vacuo and the residue was purified by column chromatography over silica gel (applying a gradient up to 100% EtOAc in CyHex). The desired fractions were evaporated, Et$_2$O was added and a white solid precipitated. It was filtered off and the solvent was removed in vacuo. This process was repeated two time more to give the title compound (1 g, 66% yield, 15% of OPPh$_3$ remain). It was used in the next step without further purification. $^1$H NMR (300 MHz, CDCl$_3$) δ ppm: 8.04-7.98 (m, 2H), 7.51-7.31 (m, 5H), 7.26 (d, J=2.3 Hz, 1H), 6.95-6.89 (m, 2H), 6.08 (d, d, J=2.3 Hz, 1H), 5.34 (s, 2H), 4.12 (dd, J=10.1, 3.5 Hz, 1H), 4.02 (dd, J=10.1, 5.8 Hz, 1H), 3.91-3.85 (m, 1H), 3.86 (s, 3H), 3.06-2.91 (m, 2H).

Intermediate 50: Benzyl 4-(2-methoxy-3-(thiazol-4-yl)propoxy)benzoate

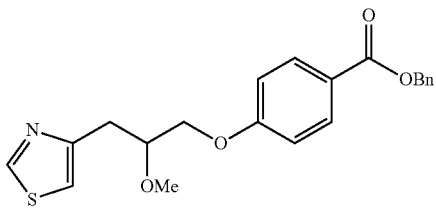 [SMILES: COC(COc1ccc(C(=O)OCc2ccccc2)cc1)Cc1cscn1]

Intermediate 50 was prepared using analogous conditions described for intermediate 49, using 2-methoxy-3-(thiazol-4-yl)propan-1-ol (intermediate 47, 810 mg, 4.68 mmol). 1.0 g (27.9% yield, 50% purity, impurified with diisopropyl hydrazine-1,2-dicarboxylate) of the title compound was obtained after chromatography on silica gel. Compound was used without further purification. $^1$H NMR (300 MHz, CDCl$_3$) ppm: 8.77 (d, J=1.8 Hz, 1H), 8.02 (d, J=8.8 Hz, 2H), 7.48-7.31 (m, 5H), 7.08 (d, J=2.0 Hz, 1H), 6.92 (d, J=8.8 Hz, 2H), 5.34 (s, 2H), 4.17-3.99 (m, 2H), 3.53-3.47 (m, 1H), 3.47 (s, 3H), 3.23-2.18 (m, 2H).

Intermediate 51: Benzyl 4-(2-methoxy-3-(1-methyl-1H-pyrazol-4-yl)propoxy)benzoate

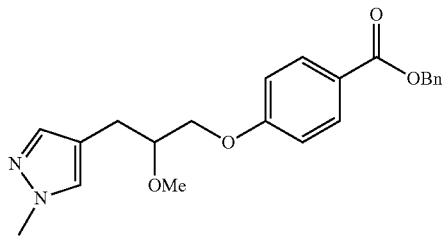 [SMILES: COC(COc1ccc(C(=O)OCc2ccccc2)cc1)Cc1cnn(C)c1]

Intermediate 51 was prepared using analogous conditions described for intermediate 49, using 2-methoxy-3-(1-methyl-1H-pyrazol-4-yl)propan-1-ol (intermediate 48, 209 mg, 1.227 mmol). 247 mg (52.9% yield, impurified with OPPh$_3$) of the title compound was obtained after chromatography on silica gel. Compound was used without further purification. 1H NMR (300 MHz, CDCl$_3$) δ ppm: 8.03 (d, J=8.8 Hz, 2H), 7.73-7.64 (m, 2H), 7.59-7.31 (m, 4H), 7.21 (s, 1H), 6.91 (d, J=8.8 Hz, 2H), 5.34 (s, 2H), 3.98 (d, J=5.1 Hz, 2H), 3.86 (s, 3H), 3.73-3.65 (m, 1H), 3.50 (s, 3H), 2.91-2.71 (m, 2H).

Intermediate 52: Benzyl(R)-4-(3-cyano-2-hydroxypropoxy)benzoate

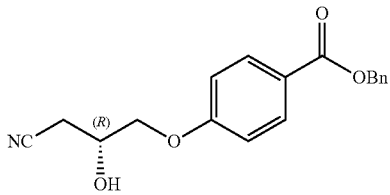

Benzyl (R)-4-(oxiran-2-ylmethoxy)benzoate (intermediate 20, 0.500 g, 1.759 mmol) was dissolved in DMF/water (1.759 mL/1.759 mL) under nitrogen atmosphere and NaCN (MERCK CHEMICALS, 0.086 g, 1.759 mmol) was added. The mixture was stirred at rt overnight. The mixture was partitioned between EtOAc and water, the layers were separated and the aqueous layer was extracted with EtOAc twice. The organic layer was washed with sat. NaCl solution, dried over Na$_2$SO$_4$, filtered, and concentrated under reduced pressure. The crude residue was purified by chromatography on silica gel and eluted with CyHex:EtOAc (from 100:0 to 0:100) to give the title compound (160 mg, 29.2% yield). $^1$H NMR (300 MHz, DMSO-d$_6$) δ ppm: 7.95 (d, J=8.8 Hz, 2H), 7.49-7.31 (m, 5H), 7.07 (d, J=9.1 Hz, 2H), 5.81 (d, J=5.3 Hz, 1H), 5.32 (s, 2H), 4.17-4.09 (m, 1H), 4.06-3.95 (m, 2H), 2.81 (dd, J=16.9, 4.5 Hz, 1H), 2.71 (dd, J=16.9, 6.8 Hz, 1H).

Intermediates 53a and 53b: Benzyl (R)-4-(2-hydroxy-3-(2-methyl-2H-tetrazol-5-yl)propoxy)benzoate (53a) and benzyl (R)-4-(2-hydroxy-3-(1-methyl-1H-tetrazol-5-yl)propoxy)benzoate (53b)

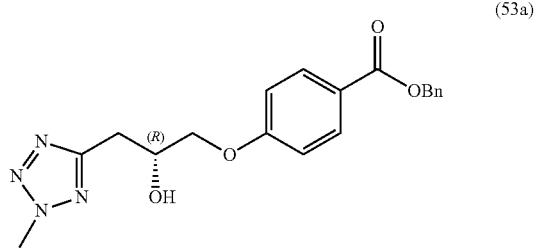

(53a)

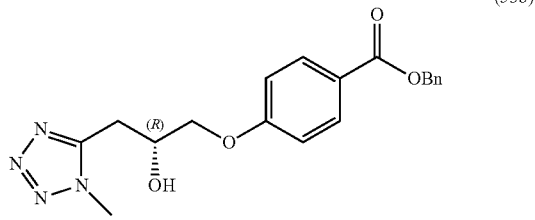

(53b)

Benzyl (R)-4-(3-cyano-2-hydroxypropoxy)benzoate (intermediate 52, 0.160 g, 0.514 mmol) was dissolved in DMF (3.43 mL) under nitrogen atmosphere. NaN$_3$ (PANREAC, 0.334 g, 5.14 mmol) and NH$_4$Cl (SIGMA-ALDRICH, 0.275 g, 5.14 mmol) were added. The mixture was heated at 120° C. for 16 h. After cooling, the mixture was partitioned between EtOAc and water, the layers were separated and the aqueous layer was extracted with EtOAc twice. The organic layer was washed with sat. NaCl solution, dried over Na$_2$SO$_4$, filtered, and concentrated under reduced pressure. The crude material was purified by chromatography on silica gel and eluted with CyHex/EtOAc (from 0% to 100%). The desired fractions were collected and the solvent was removed in vacuo to give benzyl (R)-4-(2-hydroxy-3-(1H-tetrazol-5-yl)propoxy)benzoate (110 mg, 60.4% yield).

Benzyl (R)-4-(2-hydroxy-3-(2H-tetrazol-5-yl)propoxy)benzoate intermediate (100 mg, 0.282 mmol) was dissolved in acetone (0.941 mL) under nitrogen atmosphere, and TEA (SIGMA-ALDRICH, 0.235 mL, 1.693 mmol) and MeI (0.105 mL, 1.693 mmol) were added. The mixture was stirred at rt for 16 h. The mixture was partitioned between DCM and water, the layers were separated and the aqueous layer was extracted with DCM twice. The organic layer was dried over Na$_2$SO$_4$, filtered, and concentrated under reduced pressure. The crude material was purified by chromatography on silica gel and eluted with CyHex:EtOAc/EtOH (3/1) (from 0% to 100%). The desired fractions were collected and the solvent was removed in vacuo to obtain 53a and 53b.

intermediate 53a: Benzyl (R)-4-(2-hydroxy-3-(2-methyl-2H-tetrazol-5-yl)propoxy) benzoate (20 mg, 19.24% yield). [ES+MS] m/z 369 (MH$^+$).

intermediate 53b: Benzyl (R)-4-(2-hydroxy-3-(1-methyl-1H-tetrazol-5-yl)propoxy) benzoate (20 mg, 19.24% yield). [ES+MS] m/z 369 (MH$^+$).

Intermediate 54: Ethyl (R)-2-(3-(4-((benzyloxy)carbonyl)phenoxy)-2-hydroxypropyl)-2H-tetrazole-5-carboxylate

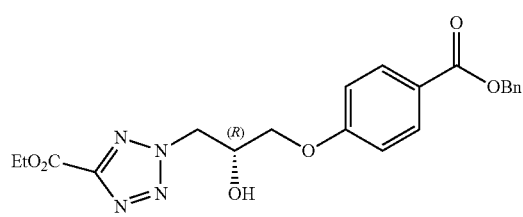

Benzyl (R)-4-(oxiran-2-ylmethoxy)benzoate (intermediate 20, 0.60 g, 2.110 mmol) was dissolved in DMF (10.55 mL) under nitrogen atmosphere and sodium 5-(ethoxycarbonyl)tetrazol-2-ide (ALFA AESAR, 0.346 g, 2.110 mmol) was added. The mixture was heated at 80° C. overnight. After cooling, the mixture was partitioned between EtOAc and water, layers were separated and the aqueous layer was extracted with EtOAc twice. The organic layer was washed with brine, dried over Na$_2$SO$_4$, filtered, and concentrated under reduced pressure. The crude material was purified by chromatography on silica gel and eluted with CyHex:EtOAc (from 100:0 to 0:100) to afford the title compound (90 mg, 10% yield). $^1$H NMR (300 MHz, DMSO-d$_6$) ppm: 7.96 (d, J=8.8 Hz, 2H), 7.49-7.32 (m, 5H), 7.08 (d, J=9.0 Hz, 2H), 5.67 (d, J=5.8 Hz, 1H), 5.32 (s, 2H), 5.02-4.84 (m, 2H), 4.47-4.40 (m, 1H), 4.41 (q, J=7.1 Hz, 2H), 4.18-4.11 (m, 2H), 1.33 (t, J=7.1 Hz, 3H).

Intermediates 55a and 55b: Benzyl (R)-4-(2-hydroxy-3-(5-methyl-2H-tetrazol-2-yl)propoxy)benzoate (55a) and benzyl (R)-4-(2-hydroxy-3-(5-methyl-1H-tetrazol-1-yl)propoxy)benzoate (55b)

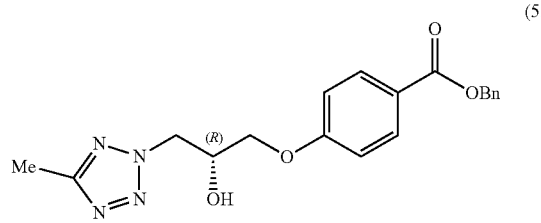

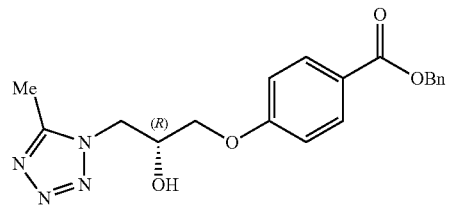

Benzyl (R)-4-(oxiran-2-ylmethoxy)benzoate (intermediate 20, 0.250 g, 0.879 mmol) was dissolved in DMF (4.40 mL) under nitrogen atmosphere and K$_2$CO$_3$ (SIGMA-ALDRICH, 0.243 g, 1.759 mmol) was added. 5-methyl-1H-tetrazole (AK SCIENTIFIC, 0.148 g, 1.759 mmol) was added to the suspension and the mixture was heated at 80° C. overnight. After cooling, the mixture was partitioned between EtOAc and water, the layers were separated and the aqueous layer was extracted with EtOAc twice. The organic layer was washed with sat. NaCl solution, dried over Na$_2$SO$_4$, filtered, and concentrated under reduced pressure. The crude material was purified by chromatography on silica gel and eluted with CyHex:EtOAc (from 100:0 to 0:100). The desired fractions were collected and the solvent was removed in vacuo to obtain the isomers 55a and 55b.

intermediate 55a: Benzyl (R)-4-(2-hydroxy-3-(5-methyl-2H-tetrazol-2-yl) propoxy)benzoate (100 mg, 30.9% yield). $^1$H NMR (300 MHz, DMSO-d$_6$) ppm: 7.96 (d, J=8.8 Hz, 2H), 7.48-7.31 (m, 5H), 7.07 (d, J=8.8 Hz, 2H), 5.61 (d, J=5.6 Hz, 1H), 5.35 (s, 2H), 4.82-4.67 (m, 2H), 4.42-4.30 (m, 1H), 4.16-4.06 (m, 2H), 2.45 (s, 3H).

intermediate 55b: Benzyl (R)-4-(2-hydroxy-3-(5-methyl-1H-tetrazol-1-yl) propoxy)benzoate (130 mg, 40.1% yield). $^1$H NMR (300 MHz, DMSO-d$_6$) ppm: 7.96 (d, J=9.1 Hz, 2H), 7.49-7.33 (m, 5H), 7.08 (d, J=9.1 Hz, 2H), 5.65 (d, J=5.6 Hz, 1H), 5.32 (s, 2H), 4.58 (dd, J=14.4, 3.8 Hz, 1H), 4.41 (dd, J=14.4, 7.8 Hz, 1H), 4.27-4.18 (m, 1H), 4.13-4.04 (m, 2H), 2.68 (s, 3H).

Intermediate 56: 4-(2,2-Dimethyl-3-(1H-tetrazol-1-yl)propoxy)benzoic acid

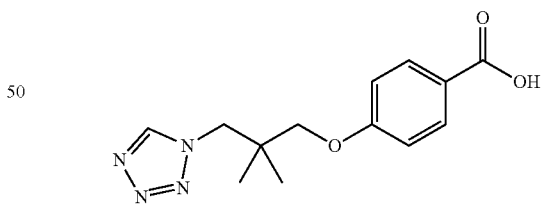

To a solution of benzyl 4-(2,2-dimethyl-3-(1H-tetrazol-1-yl)propoxy)benzoate (intermediate 18, 192 mg, 0.524 mmol) in EtOH (6 mL) was added Palladium 10% on activated carbon (SIGMA-ALDRICH, 20 mg, 0.188 mmol) and the solution purged with nitrogen. The solution was stirred under H$_2$ atmosphere at rt. overnight. The solution was filtered through a Celite pad, further eluted with MeOH and the solvent evaporated to give the title compound (137 mg, 95% yield). $^1$H NMR (300 MHz, CDCl$_3$) δ ppm: 8.49 (s, 1H), 8.08 (d, J=8.8 Hz, 2H), 6.94 (d, J=8.8 Hz, 2H), 4.51 (s, 2H), 3.68 (s, 2H), 1.16 (s, 6H).

Intermediate 57: (R)-4-(2-Hydroxy-3-(2H-tetrazol-2-yl)propoxy)benzoicacid

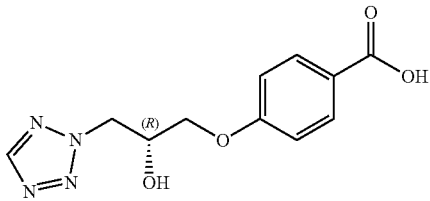

To a solution of benzyl (R)-4-(2-hydroxy-3-(2H-tetrazol-2-yl)propoxy)benzoate (intermediate 26a, 73 g, 0.206 mol) in EtOH (2 L) under nitrogen atmosphere at 0° C., Palladium 10% on activated carbon (SIGMA-ALDRICH, 3.29 g, 30.9 mmol) was added. The suspension was purged with hydrogen/vacuum cycles and the mixture was stirred under hydrogen atmosphere at rt overnight. The catalyst was removed by filtration through a nylon filter membrane and washing with DCM:MeOH(10:1). Filtrate and washes were combined and evaporated to dryness under vacuum to give the title compound (50.4 g, 93% yield, ee >95%). $^1$H NMR (DMSO-$d_6$) δ ppm: 12.66 (br.s., 1H), 8.98 (s, 1H), 8.01-7.76 (m, 2H), 7.14-6.91 (m, 2H), 5.63 (br. s., 1H), 4.97-4.71 (m, 2H), 4.40 (br.s, 1H), 4.20-4.00 (m, 2H). [ES+MS] m/z 263 (MH$^+$). Chiral SFC: ChiralPak IA, 150×3 mm column, $CO_2$/MeOH (1% DEA) 70:30 (v/v), 3.0 mL/min, $R_t$=1.71 min. Chiral HPLC showed ee >95%

Intermediate 58-78 were prepared using analogous conditions to that described for Intermediate 56 but replacing intermediate 18 with that indicated in Table 1. Modifications in the protocol are also indicated.

TABLE 1

| Int. | Structure | starting int. | Physical data/Yield |
|---|---|---|---|
| 58 | 4-(2-methyl-3-(1H-tetrazol1yl)propoxy) | 17 | $^1$H NMR (300 MHz, DMSO-$d_6$) δ ppm: 12.71 (br.s, 1H), 9.43 (s, 1H), 7.87 (d, J = 8.8 Hz, 2H), 6.96 (d, J = 8.8 Hz, 2H), 4.63 (dd, J = 13.9, 6.3 Hz, 1H), 4.51 (dd, J = 13.9, 7.0 Hz, 1H), 4.02-3.91 (m, 2H), 2.61-2.50 (m, 1H), 0.96 (d, J = 6.8 Hz, 3H). quant. yield See footnote a) |
| 59 | 4-(2-hydroxy-3-(1H-tetrazol-1yl)propoxy) benzoic acid | 25b | $^1$H NMR (300 MHz, DMSO-$d_6$) δ ppm: 12.63 (br.s, 1H), 9.38 (s, 1H), 7.92 (d, J = 8.8 Hz, 2H), 7.04 (d, J = 8.8 Hz, 2H), 5.71 (br.s, 1H), 4.71 (dd, J = 14.1, 3.8 Hz, 1H), 4.57 (dd, J = 14.1, 8.1 Hz, 1H), 4.31-4.21 (m, 1), 4.06 (d, J = 5.3 Hz, 2H). 80% yield |
| 60 | (R)-4-(2-hydroxy-3-(1H-tetrazol-1yl)propoxy)benzoic acid | 26b | $^1$H NMR (300 MHz, DMSO-$d_6$) δ ppm: 12.67 (br.s, 1H), 9.38 (s, 1H), 7.90 (d, J = 8.8 Hz, 2H), 7.03 (d, J = 8.8 Hz, 2H), 5.73 (br.s, 1H), 4.71 (dd, J = 14.1, 3.8 Hz, 1H), 4.57 (dd, J = 14.1, 8.1 Hz, 1H), 4.30-4.21 (m, 1), 4.05 (d, J = 5.1 Hz, 2H). 76% yield |
| 61 | (S)-4-(2-hydroxy-3-(2H-tetrazol-2-yl)propoxy)benzoic acid | 27a | $^1$H NMR (DMSO-$d_6$) δ ppm; 12.67 (br.s, 1H), 8.99 (s, 1H), 7.90 (d, J = 8.8 Hz, 2H), 7.05 (d, J = 8.8 Hz, 2H), 5.64 (br. s., 1H), 4.94-4.78 (m, 2H), 4.47-4.36 (m, 1H), 4.17-4.06 (m, 2H) 88% yield |

TABLE 1-continued

| Int. | Structure | starting int. | Physical data/ Yield |
|---|---|---|---|
| 62 | (S)-4-(2-hydroxy-3-(1H-tetrazol-1yl)propoxy)benzoic acid | 27b | ¹H NMR (300 MHz, DMSO-d₆) δ ppm: 12.67 (br.s, 1H), 9.39 (s, 1H), 7.90 (d, J = 8.8 Hz, 2H), 7.03 (d, J = 8.8 Hz, 2H), 5.71 (br.s, 1H), 4.71 (dd, J = 13.9, 3.5 Hz, 1H), 4.57 (dd, J = 13.9, 8.1 Hz, 1H), 4.30-4.21 (m, 1), 4.06 (d, J = 5.3 Hz, 2H). 81% yield |
| 63 | 4-(2-hydroxy-2-methyl-3-(1H-tetrazol-1yl)propoxy)benzoic acid | 28b | ¹H NMR (300 MHz, DMSO-d₆) δ ppm: 12.61 (br.s, 1H), 9.28 (s, 1H), 7.90 (d, J = 8.8 Hz, 2H), 7.02 (d, J = 8.8 Hz, 2H), 5.55 (br.s, 1H), 4.61 (dd, J = 13.9, 6.3 Hz, 2H), 3.85 (dd, J = 14.4, 9.6 Hz, 2H), 1.17 (s, 3H). 77% yield |
| 64 | 4-(2-hydroxy-2-methyl-3-(2H-tetrazol-2-yl)propoxy)benzoic acid | 28a | ¹H NMR (300 MHz, DMSO-d₆) δ ppm: 12.68 (br.s, 1H), 9.94 (s, 1H), 7.89 (d, J = 8.8 Hz, 2H), 7.02 (d, J = 8.8 Hz, 2H), 5.41 (br.s, 1H), 4.82 (s, 2H), 3.95 (d, J = 9.6 Hz, 1H), 3.87 (d, J = 9.4 Hz, 1H), 1.25 (s, 3H). 73% yield |
| 65 | (R)-4-(2-hydroxy-3-(1H-1,2,4-triazol-1-yl)propoxy)benzoic acid | 29 | ¹H NMR (300 MHz, DMSO-d₆) δ ppm: 12.63 (br.s, 1H), 8.47 (s, 1H), 7.97 (s, 1H), 7.89 (d, J = 8.8 Hz, 2H), 7.03 (d, J = 8.8 Hz, 2H), 5.53 (br.s, 1H), 4.40-4.26 (m, 2H), 4.24-4.17 (m, 1H), 4.08-3.97 (m, 2H). [ES + MS] m/z 262 (MH⁺). 87% yield See footnote a) |
| 66 | (R)-4-(2-hydroxy-3-(2H-1,2,3-triazol-2-yl)propoxy)benzoic acid | 31a | ¹H NMR (300 MHz, DMSO-d₆) δ ppm: 12.66 (br. s., 1H), 7.89 (d, J = 9.1 Hz, 2H), 7.79 (s, 2H), 7.01 (d, J = 8.8 Hz, 2H), 5.49 (br.s, 1H), 4.63-4.49 (m, 2H), 4.39-4.31 (m, 1H), 4.09-3.99 (m, 2H). 92% yield |

TABLE 1-continued

| Int. | Structure | starting int. | Physical data/ Yield |
|---|---|---|---|
| 67 | (R)-4-(2-hydroxy-3-(1H-1,2,3-triazol-1-yl)propoxy)benzoic acid | 31b | ¹H NMR (300 MHz, CDCl₃) δ ppm: 12.60 (br.s, 1H), 8.09 (d, J = 0.7 Hz, 1H), 7.89 (d, J = 9.1 Hz, 2H), 7.72 (d, J = 0.7 Hz, 1H), 7.02 (d, J = 9.1 Hz, 2H), 5.59 (br s, 1H), 4.61 (dd, J = 13.9, 4.4 Hz, 1H), 4.47 (dd, J = 7.6, 4.4 Hz), 4.28-4.21 (m, 1H), 4.05-3.96 (m, 2H). 96% yield |
| 68 | (R)-4-(2-hydroxy-3-(1H-pyrazol-1-yl)propoxy)benzoic acid | 33 | ¹H NMR (300 MHz, DMSO-d₆) δ ppm: 12.74 (br.s, 1H), 7.87 (d, J = 8.8 Hz, 2H), 7.70 (d, J = 2.0 Hz, 1H), 7.44 (d, J = 2.0 Hz, 1H), 6.98 (d, J = 8.8 Hz, 2H), 6.22 (t, J = 2.0 Hz, 1H), 5.42 (br.s, 1H), 4.36-4.26 (m, 1H), 4.24-4.14 (m, 2H), 4.01-3.87 (m, 2H). 75% yield |
| 69 | (R)-4-(2-hydroxy-3-(1H-imidazol-1-yl)propoxy)benzoic acid | 35 | ¹H NMR (300 MHz, DMSO-d₆) δ ppm: 12.60 (br.s, 1H), 7.89 (d, J = 8.8 Hz, 2H), 7.59 (s, 1H), 7.15 (s, 1H), 7.03 (d, J = 8.8 Hz, 2H), 6.87 (s, 1H), 5.51 (d., J = 5.1 Hz, 1H), 4.21-4.01 (m, 3H), 4.93-3.83 (m, 2H). 61% yield |
| 70 | 4-(2-fluoro-3-(1H-tetrazol-1-yl)propoxy)benzoic acid | 36 | ¹H NMR (300 MHz, DMSO-d₆) δ ppm: 12.69 (br.s, 1H), 9.50 (s, 1H), 7.92 (d, J = 8.8 Hz, 2H), 7.07 (d, J = 8.8 Hz, 2H), 5.48-5.26 (m, 1H), 5.11-4.89 (m, 2H), 4.54-4.25 (m, 2H). 91% yield See footnote a) |
| 71 | 4-(2-methoxy-3-(1-methyl-1H-pyrazol-3-yl)propoxy)benzoic acid | 49 | ¹H NMR (300 MHz, DMSO-d₆) δ ppm: 12.64 (br.s, 1H), 7.86 (d, J = 8.8 Hz, 2H), 7.74-7.58 (m, 1H), 6.99 (d, J = 8.8 Hz, 2H), 6.07 (d, J = 2.3,1H), 4.15-3.97 (m, 2H), 3.83-3.75 (m, 1H), 3.76 (s, 3H), 3.34 (s, 3H), 2.89-2.73 (m, 2H). 83% yield See footnote b) |

TABLE 1-continued

| Int. | Structure | starting int. | Physical data/ Yield |
|---|---|---|---|
| 72 | 4-(2-methoxy-3-(1-methyl-1H-pyrazol-4-yl)propoxy)benzoic acid | 51 | $^1$H NMR (300 MHz, CDCl$_3$) δ ppm: 8.04 (d, J = 8.8 Hz, 2H), 7.38 (s, 1H), 7.22 (s, 1H), 6.93 (d, J = 8.8 Hz, 2H), 3.99 (d, J = 5.1 Hz, 2H), 3.87 (s, 3H), 3.74-3.36 (m, 1H), 3.49 (s, 3H), 2.91-2.75 (m, 2H). 75% yield |
| 73 | (R)-4-(2-hydroxy-3-(2-methyl-2H-tetrazol-5-yl)propoxy)benzoic acid | 53a | [ES + MS] m/z 279 (MH$^+$) 99% yield |
| 74 | (R)-4-(2-hydroxy-3-(1-methyl-1H-tetrazol-5-yl)propoxy)benzoic acid | 53b | [ES + MS] m/z 279 (MH$^+$) 99% yield |
| 75 | (R)-4-(3-(5-(ethoxycarbonyl)-2H-tetrazol-2-yl)-2-hydroxypropoxy)benzoic acid | 54 | [ES + MS] m/z 337 (MH$^+$) 85% yield |
| 76 | (R)-4-(2-hydroxy-3-(5-methyl-2H-tetrazol-2-yl)propoxy)benzoic acid | 55a | $^1$H NMR (300 MHz, DMSO-d$_6$) δ ppm: 12.76 (br.s, 1H), 7.90 (d, J = 8.8 Hz, 2H), 7.02 (d, J = 8.8 Hz, 2H), 5.60 (br.s, 1H), 4.83-4.67 (m, 2H), 4.43-4.32 (m, 1H), 4.15-4.05 (m, 2H), 2.45 (s, 3H). 90% yield |

| Int. | Structure | starting int. | Physical data/Yield |
|---|---|---|---|
| 77 | 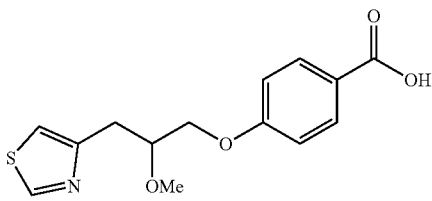 [SMILES: COC(COc1ccc(C(=O)O)cc1)Cc1cscn1]

(R)-4-(2-hydroxy-3-(5-methyl-1H-tetrazol-1-yl)propoxy)benzoic acid | 55b | $^1$H NMR (300 MHz, DMSO-d$_6$) δ ppm: 12.71 (br. s., 1H), 7.90 (d, J = 8.8 Hz, 2H), 7.04 (d, J = 8.8 Hz, 2H), 5.71 (br.s., 1H), 4.64-4.54 (m, 1H), 4.47-4.37 (m, 1H), 4.27-4.18 (m, 1H), 4.12-4.01 (m, 2H), 2.53 (s, 3H).
71.3% yield | a) The hydrogenation reaction was performed in EtOH/EtOAc 1/1
b) The hydrogenation reaction was performed in EtOH/EtOAc 1/1.5

Intermediate 78:
4-(2-Methoxy-3-(thiazol-4-yl)propoxy) benzoic acid

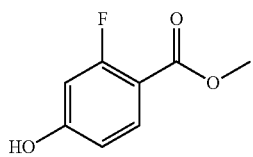

To a solution of LiOH.H$_2$O (0.109 g, 2.61 mmol) in THF (8.00 mL) was added benzyl 4-(2-methoxy-3-(thiazol-4-yl)propoxy)benzoate (intermediate 50, 1 g, 1.304 mmol) in water (2 mL) and the mixture was stirred under hydrogen atmosphere at rt overnight. LiOH.H$_2$O (0.109 g, 2.61 mmol) was added again and the mixture was heated at 50° C. overnight. A new addition of LiOH.H$_2$O (0.109 g, 2.61 mmol) was required to complete the reaction. After cooling, the mixture was partitioned between DCM and water, the layers were separated and the aqueous layer washed with DCM. The aqueous layer was acidified with aq. 6 N HCl until pH 2-3, then the product was extracted with DCM, dried over Na$_2$SO$_4$, filtered and concentrated to afford the title compound (293 mg, 77% yield). 1H NMR (300 MHz, DMSO-d$_6$) δ ppm: 12.60 (br.s, 1H), 9.04 (d, J=2.0 Hz, 1H), 7.87 (d, J=8.8 Hz, 2H), 7.44 (d, J=2.0 Hz, 1H), 7.01 (d, J=8.8 Hz, 2H), 4.20-4.14 (m, 1H), 4.08-4.02 (m, 1H), 3.99-3.91 (m, 1H), 3.32 (s, 3H), 3.07 (d, J=6.1 Hz, 2H).

Intermediate 79: Methyl 2-fluoro-4-hydroxybenzoate

To a round bottom containing 2-fluoro-4-hydroxybenzoic acid (COMBI-BLOCKS, 1 g, 6.41 mmol) was added a solution of MeOH (10 mL, 247 mmol) and H$_2$SO$_4$ (SIGMA-ALDRICH, 0.400 mL, 7.50 mmol). The mixture was heated to 80° C. overnight. The solvent was removed, and the mixture was diluted with EtOAc. The organic phase was washed with sat. aq. NaHCO$_3$, and with brine, and then dried over anh. Na$_2$SO$_4$. After filtration, the organic solvent was removed in vacuo to yield the title compound (1 g, 92% yield) as a pale brown solid. $^1$H NMR (300 MHz, CDCl$_3$) ppm: 7.88 (t, J=8.6 Hz, 1H), 6.66 (dd, J=8.6, 2.5 Hz, 1H), 6.62 (dd, J=11.6, 2.3 Hz, 1H), 5.52 (br.s, 1H), 3.91 (s, 3H).

Intermediate 80: (R)-Methyl 2-fluoro-4-(oxiran-2-ylmethoxy)benzoate

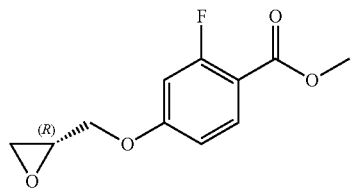

(R)-oxiran-2-ylmethyl 4-methylbenzenesulfonate (CHEM-IMPEX, 1.610 g, 7.05 mmol) was added to a suspension of methyl 2-fluoro-4-hydroxybenzoate (intermediate 79, 1 g, 5.88 mmol) and Cs$_2$CO$_3$ (SIGMA-ALDRICH, 5.75 g, 17.63 mmol) in DMF (15 mL) under nitrogen atmosphere. The solution was stirred and heated to 50° C. overnight. After cooling, the solvent was removed under vacuo. The crude material was dissolved in EtOAc, washed with brine, dried over Na$_2$SO$_4$, filtered, and concentrated under reduced pressure. The residue was purified by chromatography on silica gel and eluted with CyHex:EtOAc (from 100:0 to 80:20) to obtain title compound (1.42 g, 89% yield) impurified with (R)-oxiran-2-ylmethyl 4-methylbenzenesulfonate. It was used without additional purification. $^1$H NMR (300 MHz, CDCl$_3$) δ ppm: 7.92 (t, J=8.6 Hz, 1H), 6.76 (dd, J=8.6, 2.4 Hz, 1H), 6.67 (dd, J=12.4, 2.4 Hz, 1H), 4.31 (dd, J=11.0, 2.9 Hz, 1H), 3.96 (dd, J=11.0, 5.9 Hz, 1H), 3.91 (s, 3H), 3.40-3.35 (m, 1H), 2.94 (t, J=4.8 Hz, 1H), 2.77 (dd, J=4.8, 2.5 Hz, 1H).

Intermediate 81: (S)-Methyl 2-fluoro-4-(oxiran-2-ylmethoxy)benzoate

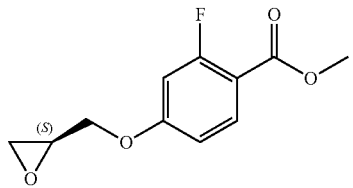

Intermediate 81 was prepared using analogous conditions to that described for intermediate 80, replacing (R)-oxiran-2-ylmethyl 4-methylbenzenesulfonate by (S)-oxiran-2-ylmethyl 4-methylbenzenesulfonate (SIGMA-ALDRICH, 2.82 g, 12.34 mmol, 1.0 eq). Title intermediate was obtained as a colorless oil (2.7 g, 97% yield). $^1$H NMR (300 MHz, CDCl$_3$) δ ppm: 7.91 (t, J=8.6 Hz, 1H), 6.75 (dd, J=8.6, 2.5 Hz, 1H), 6.67 (dd, J=12.4, 2.5 Hz, 1H), 4.31 (dd, J=11.1, 2.9 Hz, 1H), 3.96 (dd, J=11.0, 5.8 Hz, 1H), 3.91 (s, 3H), 3.40-3.34 (m, 1H), 2.94 (t, J=4.8 Hz, 1H), 2.77 (dd, J=4.8, 2.5 Hz, 1H).

Intermediate 82a and 82b: (R)-Methyl 2-fluoro-4-(2-hydroxy-3-(2H-tetrazol-2-yl)propoxy)benzoate (82a) and (R)-methyl 2-fluoro-4-(2-hydroxy-3-(1H-tetrazol-1-yl)propoxy)benzoate (82b)

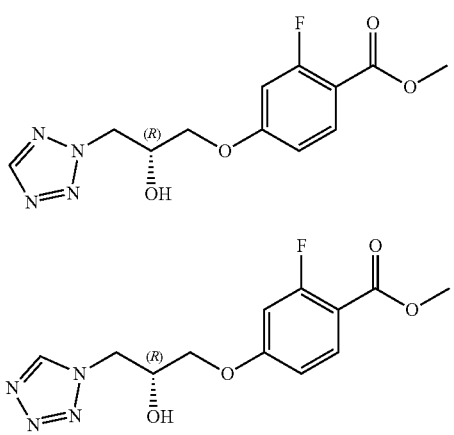

(R)-Methyl 2-fluoro-4-(oxiran-2-ylmethoxy)benzoate (intermediate 80, 400 mg, 1.768 mmol) was added to a solution of 1H-tetrazole (ACROS, 3 wt. % in CH$_3$CN, 310 mg, 4.42 mmol) and K$_2$CO$_3$ (SIGMA-ALDRICH, 611 mg, 4.42 mmol) in DMF (8 mL) under nitrogen atmosphere. The mixture was heated to 80° C. overnight. After cooling, the mixture was partitioned between water and EtOAc, the layers were separated and the organic layer was washed with brine, dried over Na$_2$SO$_4$, filtered, and concentrated under reduced pressure. The crude material was purified by chromatography on silica gel and eluted with DCM:MeOH (from 100:00 to 95:5). The desired fractions were collected and the solvent was removed in vacuo to obtain the isomers 82a and 82b.

intermediate 82a: (R)-methyl 2-fluoro-4-(2-hydroxy-3-(2H-tetrazol-2-yl)propoxy) benzoate (196 mg, 37.4% yield). $^1$H NMR (300 MHz, CDCl$_3$) δ ppm: 8.59 (s, 1H), 7.94 (t, J=8.6 Hz, 1H), 6.75 (dd, J=8.8, 2.3 Hz, 1H), 6.67 (dd, J=12.4, 2.5 Hz, 1H), 5.01-4.89 (m, 2H), 4.69-4.60 (m, 1H), 4.18-4.09 (m, 2H), 3.92 (s, 3H), 2.96 (d, J=5.8 Hz, 1H).

intermediate 82b: (R)-methyl 2-fluoro-4-(2-hydroxy-3-(1H-tetrazol-1-yl)propoxy) benzoate (197 mg, 37.6% yield). $^1$H NMR (300 MHz, CDCl$_3$) δ ppm: 8.78 (s, 1H), 7.94 (t, J=8.6 Hz, 1H), 6.74 (dd, J=8.6, 2.3 Hz, 1H), 6.67 (dd, J=12.1, 2.3 Hz, 1H), 4.80 (dd, J=14.1, 3.0 Hz, 1H), 4.63 (dd, J=14.4, 7.3 Hz, 1H), 4.54-4.46 (m, 1H), 4.12 (dd, J=9.6, 4.8 Hz, 1H), 4.01 (dd, J=9.6, 6.1 Hz, 1H), 3.92 (s, 3H), 2.95 (d, J=4.8 Hz, 1H).

Intermediate 83a and 83b: (S)-Methyl 2-fluoro-4-(2-hydroxy-3-(2H-tetrazol-2-yl)propoxy)benzoate (83a) and (S)-methyl 2-fluoro-4-(2-hydroxy-3-(1H-tetrazol-1-yl)propoxy)benzoate (83b)

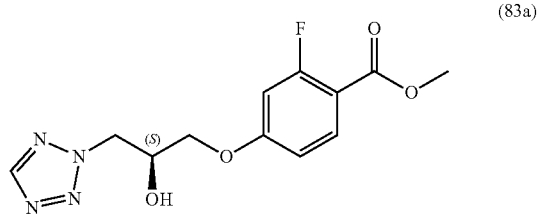

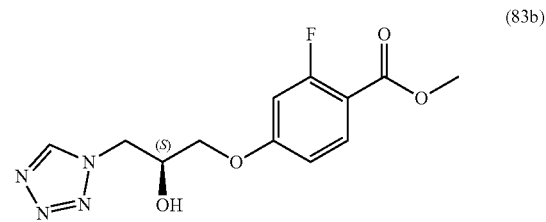

Intermediates 83a-b were prepared using analogous conditions to that described for intermediates 82a-b, using (S)-methyl 2-fluoro-4-(oxiran-2-ylmethoxy)benzoate (intermediate 81, 2.78 g, 12.29 mmol). Title intermediates were obtained after chromatographic purification.

Intermediate 83a: (S)-methyl 2-fluoro-4-(2-hydroxy-3-(2H-tetrazol-2-yl)propoxy) benzoate (982 mg, 27% yield). $^1$H NMR (300 MHz, CDCl$_3$) δ ppm: 8.59 (s, 1H), 7.94 (t, J=8.6 Hz, 1H), 6.75 (dd, J=8.8, 2.5 Hz, 1H), 6.67 (dd, J=12.1, 2.5 Hz, 1H), 5.01-4.89 (m, 2H), 4.68-4.59 (m, 1H), 4.18-4.09 (m, 2H), 3.92 (s, 3H), 2.96 (d, J=5.3 Hz, 1H).

intermediate 83b: (S)-methyl 2-fluoro-4-(2-hydroxy-3-(1H-tetrazol-1-yl)propoxy) benzoate (900 mg, 24.7% yield). $^1$H NMR (300 MHz, CDCl$_3$) ppm: 8.78 (s, 1H), 7.94 (t, J=8.6 Hz, 1H), 6.74 (dd, J=8.8, 2.8 Hz, 1H), 6.67 (dd, J=12.1, 2.5 Hz, 1H), 4.80 (dd, J=14.1, 3.0 Hz, 1H), 4.63 (dd, J=14.1, 7.1 Hz, 1H), 4.55-4.45 (m, 1H), 4.12 (dd, J=9.6, 4.8 Hz, 1H), 4.01 (dd, J=9.6, 6.1 Hz, 1H), 3.92 (s, 3H), 2.95 (d, J=5.0 Hz, 1H).

Intermediate 84: (R)-2-Fluoro-4-(2-hydroxy-3-(2H-tetrazol-2-yl)propoxy)benzoic acid

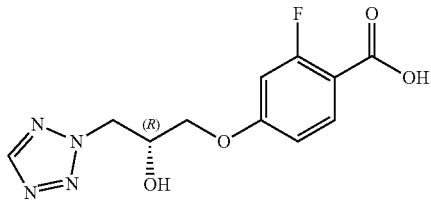

(R)-Methyl 2-fluoro-4-(2-hydroxy-3-(2H-tetrazol-2-yl)propoxy)benzoate (intermediate 82a, 126 mg, 0.425 mmol) was dissolved in THF (3 mL) and LiOH.H₂O (SIGMA-ALDRICH, 57 mg, 1.358 mmol) in water (1.00 mL) was added. The mixture was stirred at rt overnight. 6 N HCl (0.226 mL, 1.357 mmol) was added to the mixture and it was concentrated under reduced pressure. The crude material was triturated with water and filtered, rinsed with water and dried under vacuum to give the title compound (108 mg, 90% yield) as a white solid. ¹H NMR (300 MHz, DMSO-d₆) δ ppm: 12.89 (br.s, 1H), 8.97 (s, 1H), 7.82 (t, J=8.8 Hz, 1H), 6.94-6.85 (m, 2H), 5.64 (d, J=5.8 Hz, 1H), 4.91-4.77 (m, 2H), 4.43-4.36 (m, 1H), 4.18-4.06 (m, 2H).

Intermediate 85: (R)-2-Fluoro-4-(2-hydroxy-3-(1H-tetrazol-1-yl)propoxy)benzoicacid

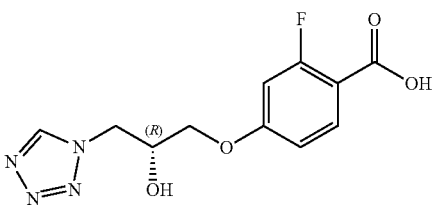

(R)-Methyl 2-fluoro-4-(2-hydroxy-3-(1H-tetrazol-1-yl)propoxy)benzoate (intermediate 82b, 324 mg, 1.094 mmol) was dissolved in THF (8 mL) and LiOH. H₂O (SIGMA-ALDRICH, 184 mg, 4.37 mmol) in water (2.67 mL) was added. The mixture was stirred at room temperature overnight. 6 N HCl (0.729 mL, 4.37 mmol) was added to the mixture and it was concentrated under reduced pressure. The crude was triturated with water and filtered, rinsed with water and dried to give the title compound (271 mg, 88% yield) as a white solid. ¹H NMR (300 MHz, DMSO-d₆) δ ppm: 12.90 (br.s, 1H), 9.37 (s, 1H), 7.83 (t, J=8.7 Hz, 1H), 6.92 (dd, J=12.9, 2.3 Hz, 1H), 6.88 (dd, J=8.8, 2.3 Hz, 1H), 5.72 (br.s, 1H), 4.69 (dd, J=14.0, 3.7 Hz, 1H), 4.54 (dd, J=13.9, 8.1 Hz, 1H), 4.28-4.21 (m, 1H), 4.11-4.04 (m, 2H).

Examples 1a-b: ((R)-3-(4-Fluorophenyl)pyrrolidin-1-yl)(4-(2-methyl-3-(1H-tetrazol-1-yl) propoxy) phenyl)methanone (isomer 1 and isomer 2)

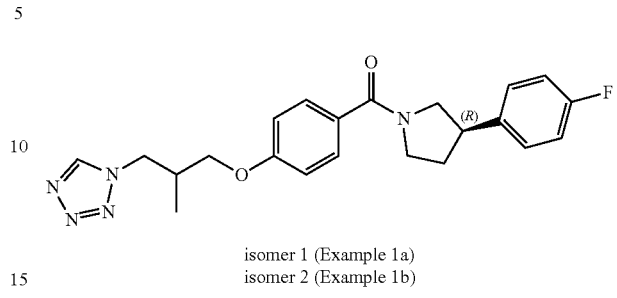

isomer 1 (Example 1a)
isomer 2 (Example 1b)

To a solution of 4-(2,2-dimethyl-3-(1H-tetrazol-1-yl) propoxy)benzoic acid (intermediate 58, 100 mg, 0.381 mmol), (R)-3-(4-fluorophenyl)pyrrolidine hydrochloride (Intermediate 3b, 85 mg, 0.419 mmol) and DIPEA (SIGMA-ALDRICH, 0.200 mL, 1.144 mmol) in DMF (2 mL) at 0° C. under nitrogen atmosphere was added COMU (ALFA AESAR, 212 mg, 0.496 mmol). The reaction was allowed to warm to rt and stirred for 18 h. The reaction was quenched at 0° C. with water and then it was partitioned between EtOAc and sat. aq. NH₄Cl solution. Layers were separated, and the aqueous layer was extracted with EtOAc twice. Combined organic layers were washed with sat. aq. NH₄Cl solution (×2), sat. aq. NaHCO₃ solution and brine, and then dried over anh. MgSO₄ and evaporation under reduced pressure. The crude was purified by chromatography on silica gel and eluted with CyHex:EtOAc/EtOH (3/1) (from 100:0 to 50:50 and then 0:100). The desired fractions were collected and the solvent was removed in vacuo to obtain to give a mixture of diastereoisomers (128 mg, 82% yield) that was separated by chiral SFC separation (ChiralPak AD-H 250×20 mm column, CO₂/EtOH (1% DEA) 70:30 (v/v), F=70.0 mL/min). Both diastereoisomers were collected, dissolved in EtOAc and then washed with water 3 times. Organic layer was dried over anh. MgSO₄, and evaporated to obtain a residue that was dissolved in CH₃CN/H₂O and lyophilised to give isomer 1 (Example 1a, 36.8 mg, ee 100%) and isomer 2 (Example 1b, 31.5 mg, ee 100%).

isomer 1 (Example 1a)—First eluted in SFC. ¹H NMR (300 MHz, DMSO-d₆) δ ppm: 9.43 (s, 1H), 7.53 (d, J=8.6 Hz, 2H), 7.42-7.28 (m, 2H), 7.22-7.08 (m, 2H), 6.98-6.98 (m, 2H), 4.68-4.55 (m, 2H), 4.02-3.36 (m, 7H), 2.62-2.58 (m, 1H), 2.33-1.89 (m, 2H), 0.99-0.92 (m, 3H). [ES+MS] m/z 410 (MH⁺).

isomer 2 (Example 1b)—Second eluted in SFC. ¹H NMR (300 MHz, DMSO-d₆) δ ppm: 9.43 (s, 1H), 7.53 (d, J=8.6 Hz, 2H), 7.42-7.28 (m, 2H), 7.22-7.08 (m, 2H), 6.98-6.98 (m, 2H), 4.68-4.55 (m, 2H), 4.02-3.36 (m, 7H), 2.62-2.58 (m, 1H), 2.33-1.89 (m, 2H), 0.99-0.92 (m, 3H). [ES+MS] m/z 410 (MH⁺).

Chiral SFC determination using ChiralPak AD-H 150×3 mm column (CO₂/MeOH (1% DEA) 60:40 (v/v), F=3.0 mL/min, R_t isomer 1=3.44 min, R_t isomer 2=4.38 min).

Example 2: (R)-(4-(2,2-Dimethyl-3-(1H-tetrazol-1-yl)propoxy)phenyl)(3-(4-fluorophenyl) pyrrolidin-1-yl)methanone

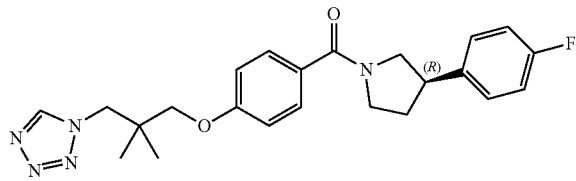

To a solution of 4-(2,2-dimethyl-3-(1H-tetrazol-1-yl) propoxy)benzoic acid (intermediate 56, 88 mg, 0.319 mmol), (R)-3-(4-fluorophenyl)pyrrolidine hydrochloride (Intermediate 3b, 70.7 mg, 0.350 mmol) and DIPEA (SIGMA-ALDRICH, 0.167 mL, 0.956 mmol) in DMF (5 mL) at 0° C. under nitrogen atmosphere was added COMU (ALFA AESAR, 177 mg, 0.414 mmol) and the reaction mixture was stirred at 0° C. for 1 h and then at rt overnight. The mixture was quenched by the dropwise addition of water, and then partitioned between EtOAc and sat. aq. NH$_4$Cl. The phases were separated and the aqueous one was re-extracted with EtOAc. The organic layers were combined and washed with sat. aq. NH$_4$Cl, sat. NaHCO$_3$ and brine. The organic layer was dried over anh. Na$_2$SO$_4$, filtered and evaporated to dryness under vacuum. The crude was purified by chromatography on silica gel and eluted with CyHex:EtOAc/EtOH (3/1) (from 100:0 to 30:70) to give the title compound (129 mg, 96%). $^1$H NMR (300 MHz, CDCl$_3$) δ ppm: 8.47 (s, 1H), 7.61-7.52 (m, 2H), 7.26-7.14 (m, 2H), 7.08-6.97 (m, 2H), 6.95-6.86 (m, 2H), 4.54-4.56 (m, 2H), 4.15-3.29 (m, 7H), 2.44-2.25 (m, 1H), 2.18-1.94 (m, 1H), 1.14 (s, 6H). [ES+MS] m/z 424 (MH$^+$).

Examples 3a-b: (4-(2-Fluoro-3-(1H-tetrazol-1-yl)propoxy)phenyl)((R)-3-(4-fluorophenyl) pyrrolidin-1-yl)methanone ((isomer 1 and isomer 2)

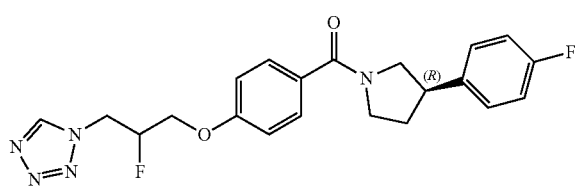

isomer 1 (Example 3a)
isomer 2 (Example 3b)

To a solution of 4-(2-fluoro-3-(1H-tetrazol-1-yl)propoxy) benzoic acid (intermediate 70, 145 mg, 0.545 mmol), (R)-3-(4-fluorophenyl)pyrrolidine hydrochloride (intermediate 3b, 132 mg, 0.654 mmol) and DIPEA (SIGMA-ALDRICH, 0.285 mL, 1.634 mmol) in anh. DMF (10 mL) at 0° C. under nitrogen atmosphere was added COMU (ALFA AESAR, 303 mg, 0.708 mmol) and the reaction mixture was stirred at 0° C. for 1 h and then at rt overnight. The mixture was quenched by the dropwise addition of water. The resulting mixture was then partitioned between EtOAc and sat. aq. NH$_4$Cl. The phases were separated and the aqueous one was re-extracted with EtOAc. The organic layers were combined and washed with sat. aq. NH$_4$Cl, sat. NaHCO$_3$ and brine. The organic layer was dried over anh. Na$_2$SO$_4$, filtered and evaporated to dryness under vacuum. The crude was purified by chromatography on silica gel and eluted with CyHex:EtOAc/EtOH(3/1) (from 100:0 to 40:60) to give a mixture of diastereoisomers (235 mg, quant. yield) that was separated by chiral SFC separation (ChiralPak IC 250×20 mm column, CO$_2$/MeOH (1% DEA) 60:40 (v/v), F=70 mL/min). The desired fractions were concentrated under reduced pressure and the residues were dissolved in CH$_3$CN/H$_2$O and lyophilised to give isomer 1 (Example 3a, 87 mg, ee 100%) and isomer 2 (Example 3b, 90 mg, ee 100%).

isomer 1 (Example 3a)—First eluted in SFC. $^1$H NMR (300 MHz, CDCl$_3$) δ ppm: 8.77 (br.s, 1H), 7.64-7.56 (m, 2H), 7.30-7.14 (m, 2H), 7.12-6.90 (m, 3H), 5.35-5.14 (m, 1H), 5.04-4.90 (m, 2H), 4.39-4.07 (m, 3H), 3.98-3.30 (m, 5H), 2.50-2.27 (m, 1H), 2.20-1.94 (m, 1H). [ES+MS] m/z 414 (MH$^+$).

isomer 2 (Example 3b)—Second eluted in SFC. $^1$H NMR (300 MHz, CDCl$_3$) δ ppm: 8.77 (br.s, 1H), 7.64-7.56 (m, 2H), 7.30-7.14 (m, 2H), 7.12-6.90 (m, 3H), 5.35-5.14 (m, 1H), 5.04-4.90 (m, 2H), 4.39-4.07 (m, 3H), 3.98-3.30 (m, 5H), 2.50-2.27 (m, 1H), 2.20-1.94 (m, 1H). [ES+MS] m/z 414 (MH$^+$).

Chiral SFC determination using ChiralPak IC 150×3 mm column (CO$_2$/MeOH (1% DEA) 80:20 (v/v), F=2.0 mL/min, R$_t$ isomer 1=5.58 min, R$_t$ isomer 2=6.32 min).

Example 4: (R)-(4-(2,2-Difluoro-3-(1H-tetrazol-1-yl)propoxy)phenyl)(3-(4-fluorophenyl)-pyrrolidin-1-yl)methanone

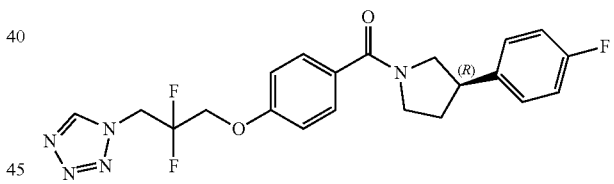

AcOH (SIGMA-ALDRICH, 3.44 mL) was added to a mixture of (R)-(4-(3-amino-2,2-difluoropropoxy)phenyl)(3-(4-fluorophenyl)pyrrolidin-1-yl)methanone (Intermediate 9, 1.3 g, 3.44 mmol), NaN$_3$ (SIGMA-ALDRICH, 0.335 g, 5.15 mmol) and triethyl ortoformate (SIGMA-ALDRICH, 2.076 mL, 13.74 mmol). The resulting mixture was refluxed for 20 h. The reaction mixture was cooled to rt, and solvent was removed under reduced pressure. The crude material was dissolved in EtOAc, washed with sat. NH$_4$Cl solution, dried over Na$_2$SO$_4$, filtered, and concentrated under reduced pressure. The crude was purified by chromatography on silica gel and eluted with CyHex:EtOAc/EtOH (3/1) (from 100:0 to 50:50) to obtain the title compound (287 mg, 19.4%). $^1$H NMR (300 MHz, CDCl$_3$) δ ppm: 8.77 (s, 1H), 7.62-7.54 (m, 2H), 7.26-7.12 (m, 2H), 7.08-6.88 (m, 4H), 5.17-5.05 (m, 2H), 4.25 (m, 2H), 4.15-3.32 (m, 5H), 2.45-2.25 (m, 1H), 2.18-1.91 (m, 1H). [ES+MS] m/z 432 (MH$^+$).

Example 5: ((R)-3-(4-Fluorophenyl)pyrrolidin-1-yl) (4-((R)-2-hydroxy-3-(1H-tetrazol-1-yl) propoxy) phenyl)methanone

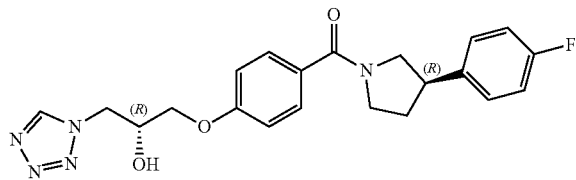

To a solution of (R)-4-(2-hydroxy-3-(1H-tetrazol-1-yl) propoxy)benzoic acid (intermediate 60, 1 g, 3.78 mmol), (R)-3-(4-fluorophenyl)pyrrolidine hydrochloride (Intermediate 3b, 0.916 g, 4.54 mmol) and DIPEA (SIGMA-ALDRICH, 1.983 mL, 11.35 mmol) in anh. DMF (37.8 mL) at 0° C. under nitrogen atmosphere was added COMU (ALFA AESAR, 2.107 g, 4.92 mmol) and the reaction mixture was stirred at 0° C. for 1 h and then at rt overnight. The mixture was quenched by the dropwise addition of water, and then partitioned between EtOAc and sat. aq. NaHCO$_3$. The phases were separated and the aqueous one was re-extracted with EtOAc. The organic layers were combined and washed with sat. NaHCO$_3$, 1 N aq. NH$_4$Cl and brine. The organic layer was dried over anh. Na$_2$SO$_4$, filtered and evaporated to dryness under vacuum. The crude was purified by chromatography on silica gel and eluted with CyHex:EtOAc/EtOH (3/1) (from 100:0 to 50:50). The desired fractions were collected and the solvent was removed in vacuo to obtain the desired product as a dark red oil. It was dissolved in EtOAc and washed with 2 N HCl twice. The organic layer was dried over anh. Na$_2$SO$_4$, filtered and evaporated to dryness under vacuum to obtain the desired product as a colourless oil. It was lyophilized to obtain the title compound (1.38 g, 89% yield, 95% purity by chiral SFC analysis, ee 90%) as a white solid. The title compound was purified by chiral SFC (ChiralPak IA 250×20 mm column, CO$_2$/MeOH (1% DEA) 70:30 (v/v), F=80 mL/min). The desired fractions were concentrated under reduced pressure and the residue was dissolved in EtOAc and then washed with sat. aq. NaHCO$_3$. Organic layer was dried over anh. MgSO$_4$, evaporated to dryness under vacuum and the residue was lyophilized to obtain the title compound (656 mg, ee 100%). $^1$H NMR (300 MHz, CDCl$_3$) δ ppm: 8.85 (d, J=5.3 Hz, 1H), 7.53-7.43 (m, 2H), 7.29-7.13 (m, 2H), 7.11-6.99 (m, 2H), 6.81 (dd, J=11.4, 8.6 Hz, 2H), 4.98 (br.s, 1H), 4.83-4.74 (m, 1H), 4.63-4.52 (m, 1H), 4.22 (br.s, 1H), 3.92-3.32 (m, 7H), 2.46-2.27 (m, 1H), 2.20-1.96 (m, 1H). [ES+MS] m/z 412 (MH$^+$). Chiral SFC determination using ChiralPak IA 150×3 mm column (CO$_2$/EtOH (1% DEA) 60:40 (v/v), F=3.0 mL/min, R$_t$=2.70 min).

Example 6: ((R)-3-(4-Fluorophenyl)pyrrolidin-1-yl) (4-((S)-2-hydroxy-3-(1H-tetrazol-1-yl) propoxy) phenyl)methanone

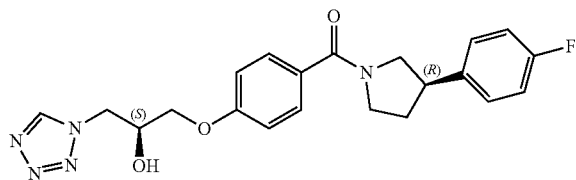

The title compound was prepared using analogous conditions described in Example 5 using (S)-4-(2-hydroxy-3-(1H-tetrazol-1-yl)propoxy)benzoic acid (intermediate 62, 350 mg, 1.32 mmol). 256 mg (ee 100%) of the title compound as a white solid was obtained after chiral purification. $^1$H NMR (300 MHz, CDCl$_3$) ppm: 8.85 (d, J=5.3 Hz, 1H), 7.56-7.46 (m, 2H), 7.29-7.14 (m, 2H), 7.12-6.99 (m, 2H), 6.84 (dd, J=11.4, 8.6 Hz, 2H), 4.86-4.74 (m, 1H), 4.68-4.55 (m, 1H), 4.34 (br.s, 1H), 4.19 (br.s, 1H), 3.92-3.32 (m, 7H), 2.48-2.27 (m, 1H), 2.20-1.95 (m, 1H). [ES+MS] m/z 412 (MH$^+$). Chiral SFC determination using ChiralPak IA 150×3 mm column (CO$_2$/MeOH (1% DEA) 70:30 (v/v), F=3.0 mL/min, R$_t$=6.72 min).

Example 5 and Example 6 were also prepared using analogous conditions described in Example 1a-b, using (4-(2-hydroxy-3-(1H-tetrazol-1-yl)propoxy)benzoic acid (intermediate 59, 85 mg, 0.322 mmol). The diastereomer mixture was separate by chiral SFC to afford isomer 1 (17 mg, ee 100%, that correspond with Example 6—S isomer) and isomer 2 (11 mg, ee 100%, that correspond with Example 5—R isomer).

Chiral SFC determination using ChiralPak IA 150×3 mm column (CO$_2$/MeOH (1% DEA) 70:30 (v/v), F=3.0 mL/min, R$_t$ isomer 1$_{(example\ 6)}$=5.8 min, R$_t$ isomer 2$_{(example5)}$=8.0 min).

Example 7: ((R)-3-(4-Fluorophenyl)pyrrolidin-1-yl) (4-((R)-2-hydroxy-3-(2H-tetrazol-2-yl) propoxy) phenyl)methanone

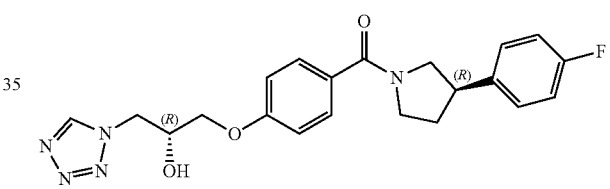

To a solution of (R)-4-(2-hydroxy-3-(2H-tetrazol-2-yl) propoxy)benzoic acid (intermediate 57, 50 g, 0.189 mol), (R)-3-(4-fluorophenyl)pyrrolidine hydrochloride (intermediate 3b, 45.8 g, 0.227 mol) and DIPEA (SIGMA-ALDRICH, 99 mL, 0.568 mol) in anh. DMF (1.9 L) at 0° C. under nitrogen atmosphere was added COMU (ALFA AESAR, 105 g, 0.246 mol) and the reaction mixture was stirred at 0° C. for 1 h and then at rt overnight. The mixture was quenched by the dropwise addition of water (1 L), 1 M HCl (0.5 L) and sat. NaCl (0.5 L). The resulting mixture was then partitioned with EtOAc (2 L), the phases were separated and the aqueous one was re-extracted with EtOAc (1 L). The organic layers were combined and washed sat. aq. NH$_4$C (1 L), sat. aq. Na$_2$CO$_3$ (1 L) and brine. The organic layer was dried over anh. Na$_2$SO$_4$, filtered and evaporated to dryness under vacuum to obtain 125 g of crude material. The crude was purified by chromatography on silica gel column and eluted with CyHex:EtOAc/EtOH (3/1) (from 100:0 to 50:50). The desired fractions were collected and the solvent was removed in vacuo to obtain the title compound impurified with by-products derived of COMU. For remove these impurities, the product was dissolved in EtOAc (1 L) and washed with 2 M HCl (×3) and sat. aq. Na$_2$CO$_3$ sol. (×1) and brine. The organic layer was dried over anh. Na$_2$SO$_4$, filtered and evaporated to dryness under vacuum to obtain 75 g of ((R)-3-(4-fluorophenyl)pyrrolidin-1-yl)(4-((R)-2-hydroxy-3-(2H-tetrazol-2-yl)propoxy)phenyl) methanone.

((R)-3-(4-fluorophenyl)pyrrolidin-1-yl)(4-((R)-2-hydroxy-3-(2H-tetrazol-2-yl)propoxy)phenyl) methanone (75 g) was dissolved in acetone (0.250 L) and Et$_2$O (1 L) was slowly added. After 24 h of crystallization, the solid was filtered to give ((R)-3-(4-fluorophenyl)pyrrolidin-1-yl)(4-((R)-2-hydroxy-3-(2H-tetrazol-2-yl)propoxy)phenyl)methanone (49 g, 0.119 mol, 62.9% yield, with an ee >97%). The mother liquor was concentrated to obtain ((R)-3-(4-fluorophenyl)pyrrolidin-1-yl)(4-((R)-2-hydroxy-3-(2H-tetrazol-2-yl)propoxy)phenyl)methanone (26 g, 63.2 mmol, 33.4% yield, with a ee 95%). $^1$H NMR (300 MHz, DMSO-d$_6$) δ ppm: 8.97 (s, 1H), 7.55 (d, J=8.6 Hz, 2H), 7.43-7.27 (m, 2H), 7.21-7.07 (m, 2H), 7.05-6.92 (m, 2H), 5.60 (d, J=5.3 Hz, 1H), 4.95-4.74 (m, 2H), 4.40 (br.s., 1H), 4.15-4.02 (m, 2H), 3.98-3.72 (m, 1H), 3.71-3.34 (m, 4H), 2.31-2.16 (m, 1H), 2.07-1.87 (m, 1H). [ES+MS] m/z 412 (MH$^+$). Chiral SFC determination using ChiralPak IA 150×3 mm column (CO$_2$/MeOH (1% DEA) 60:40 (v/v), F=3.0 mL/min, R$_t$=3.54 min).

Example 8: ((R)-3-(4-Fluorophenyl)pyrrolidin-1-yl)(4-((S)-2-hydroxy-3-(2H-tetrazol-2-yl)propoxy)phenyl)methanone

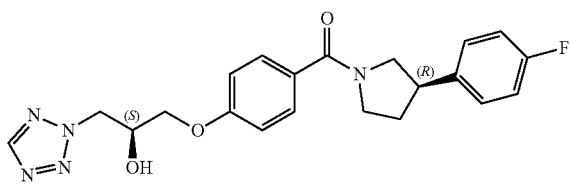

Example 8 was prepared with analogous conditions as described in Example 7, using (S)-4-(2-hydroxy-3-(2H-tetrazol-2-yl)propoxy)benzoic acid (intermediate 61, 0.600 g, 2.271 mmol) and (R)-3-(4-fluorophenyl)pyrrolidine hydrochloride (intermediate 3b, 0.550 g, 2.72 mmol). Crude material was purified by chiral SFC (ChiralPak IG, 250×20 mm column, CO$_2$/EtOH 60:40 (v/v), F=80.0 mL/min) to afford the title compound (684 mg, 72.5% yield, ee 100%) as a yellow solid. $^1$H NMR (300 MHz, DMSO-d$_6$) δ ppm: 8.96 (s, 1H), 7.54 (d, J=8.6 Hz, 2H), 7.41-7.27 (m, 2H), 7.19-7.07 (m, 2H), 7.03-6.93 (m, 2H), 5.63-5.56 (m, 1H), 4.92-4.74 (m, 2H), 4.44-4.33 (m, 1H), 4.13-4.01 (m, 2H), 3.95-3.34 (m, 5H), 2.31-2.16 (m, 1H), 2.10-1.88 (m, 1H). [ES+MS] m/z 412 (MH$^+$).

Examples 9a-b: ((R)-3-(4-Fluorophenyl)pyrrolidin-1-yl)(4-(2-hydroxy-2-methyl-3-(2H-tetrazol-2-yl)propoxy)phenyl)methanone (isomer 1 and isomer 2)

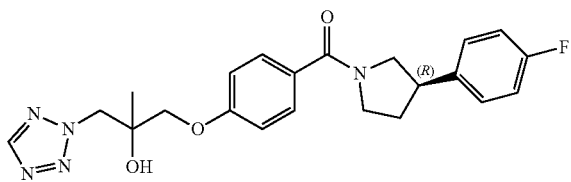

isomer 1 (Example 9a)
isomer 2 (Example 9b)

To a solution of 4-(2-hydroxy-2-methyl-3-(2H-tetrazol-2-yl)propoxy)benzoic acid (intermediate 64, 250 mg, 0.898 mmol), (R)-3-(4-fluorophenyl)pyrrolidine hydrochloride (intermediate 3b, 217 mg, 1.078 mmol) and DIPEA (SIGMA-ALDRICH, 0.297 mL, 1.703 mmol) in anh. DMF (8.98 mL) at 0° C. under nitrogen atmosphere was added COMU (ALFA AESAR, 500 mg, 1.168 mmol) and the reaction mixture was stirred at 0° C. for 1 h and then at room temperature overnight. The mixture was quenched by the dropwise addition of water. The resulting mixture was then partitioned between EtOAc and sat. aq. NaHCO$_3$ solution. The phases were separated and the aqueous one was re-extracted with ethyl acetate. The organic layers were combined and washed with sat. NaHCO$_3$, 1 N aq. NH$_4$Cl and brine. The organic layer was dried over anh. Na$_2$SO$_4$, filtered and evaporated to dryness under vacuum. The crude was purified by chromatography on silica gel and eluted with CyHex:EtOAc/EtOH (3/1) (from 100:0 to 50:50). The desired fractions were collected and the solvent was removed in vacuo to obtain to give a mixture of diastereoisomers (415 mg, quant. yield) that was separated by chiral SFC separation (ChiralPak IA 250×20 mm column, CO$_2$/EtOH (1% DEA) 70:30 (v/v), F=70.0 mL/min). The desired fractions were collected, dissolved in EtOAc and then washed with water 3 times. Organic layer was dried over anh. MgSO$_4$, and evaporated to obtain a residue that were dissolved in CH$_3$CN/H$_2$O and lyophilised to give isomer 1 (68 mg) and isomer 2 (45 mg).

isomer 1 (Example 9a)—First eluted in SFC (68 mg, ee 100%). $^1$H NMR (300 MHz, CDCl$_3$) δ ppm: 8.57 (s, 1H), 7.62-7.50 (m, 2H), 7.35-7.14 (m, 2H), 7.13-6.98 (m, 2H), 6.97-6.83 (m, 2H), 5.04-4.85 (m, 2H), 4.18-3.31 (m, 8H), 2.47-2.26 (m, 1H), 2.21-1.94 (m, 1H), 1.39 (s, 3H). [ES+MS] m/z 426 (MH$^+$).

isomer 2 (Example 9b)—Second eluted in SFC (45 mg, ee 100%). $^1$H NMR (300 MHz, CDCl$_3$) δ ppm: 8.57 (s, 1H), 7.62-7.50 (m, 2H), 7.35-7.14 (m, 2H), 7.13-6.98 (m, 2H), 6.97-6.83 (m, 2H), 5.04-4.85 (m, 2H), 4.18-3.31 (m, 8H), 2.47-2.26 (m, 1H), 2.21-1.94 (m, 1H), 1.39 (s, 3H). [ES+MS] m/z 426 (MH$^+$).

Chiral SFC determination using ChiralPak IA 150×3 mm column (CO$_2$/EtOH (1% DEA) 60:40 (v/v), F=2.0 mL/min, R$_t$ isomer 1=4.25 min, R$_t$ isomer 2=6.40 min).

Examples 10a-b: ((R)-3-(4-Fluorophenyl)pyrrolidin-1-yl)(4-(2-hydroxy-2-methyl-3-(1H-tetrazol-1-yl)propoxy)phenyl)methanone (isomer 1 and isomer 2)

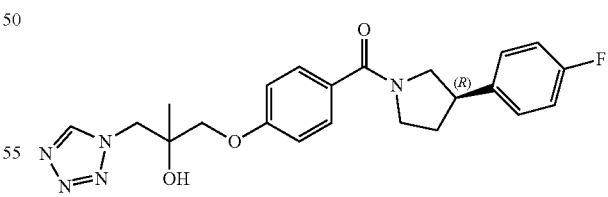

isomer 1 (Example 10a)
isomer 2 (Example 10b)

Examples 10a-b were also prepared using analogous conditions described in Examples 9a-b using 4-(2-hydroxy-2-methyl-3-(1H-tetrazol-1-yl)propoxy)benzoic acid (intermediate 63, 250 mg, 0.898 mmol). The diastereomer mixture was separate by chiral SFC to afford isomer 1 (123 mg, ee 100%, Example 10a) and isomer 2 (125 mg, ee 100%, Example 10b).

isomer 1 (Example 10a)—First eluted in SFC. $^1$H NMR (300 MHz, CDCl$_3$) δ ppm: 8.84 (d, J=5.5 Hz, 1H), 7.58-7.48 (m, 2H), 7.30-7.15 (m, 2H), 7.12-6.99 (m, 2H), 6.90-6.80 (m, 2H), 4.76-4.57 (m, 2H), 4.16-3.32 (m, 8H), 2.47-2.27 (m, 1H), 2.21-1.94 (m, 1H), 1.35 (d, J=6.0 Hz, 3H). [ES+MS] m/z 426 (MH$^+$).

isomer 2 (Example 10b)—Second eluted in SFC. $^1$H NMR (300 MHz, CDCl$_3$) δ ppm: 8.84 (d, J=5.5 Hz, 1H), 7.58-7.48 (m, 2H), 7.30-7.15 (m, 2H), 7.12-6.99 (m, 2H), 6.90-6.80 (m, 2H), 4.76-4.57 (m, 2H), 4.16-3.32 (m, 8H), 2.47-2.27 (m, 1H), 2.21-1.94 (m, 1H), 1.35 (d, J=6.0 Hz, 3H). [ES+MS] m/z 426 (MH$^+$).

Chiral SFC determination using ChiralPak AD-H 150×3 mm column (CO$_2$/MeOH 60:40 (v/v), F=2.0 mL/min, R$_t$ isomer 1=3.26 min, R$_t$ isomer 2=5.34 min).

Example 11: (4-((R)-2-Fluoro-3-(2H-tetrazol-2-yl) propoxy)phenyl)((R)-3-(4-fluorophenyl) pyrrolidin-1-yl)methanone)

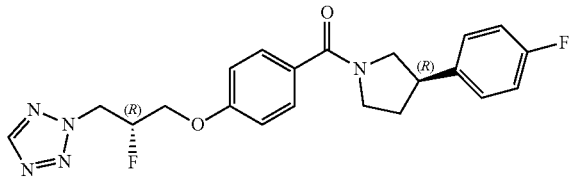

Diethylaminosulfur trifluoride (DAST, SIGMA-ALDRICH, 65 µL, 0.492 mmol) was added to a solution of ((R)-3-(4-fluorophenyl)pyrrolidin-1-yl)(4-((S)-2-hydroxy-3-(2H-tetrazol-2-yl)propoxy) phenyl) methanone (Example 8, 100 mg, 0.243 mmol) in DCM (3 mL) at 0° C. The mixture was stirred at rt for 5 h. Then, a new addition of diethylaminosulfur trifluoride (SIGMA-ALDRICH, 32.1 µL, 0.243 mmol) was done and the mixture was stirred at rt overnight. The reaction was quenched with sat. NaHCO$_3$ solution (5 mL), diluted with DCM (5 mL) and extracted three times with DCM (10 mL). The combined organics were dried over Na$_2$SO$_4$, filtered and concentrated under reduced pressure. The crude was purified by chromatography on silica gel and eluted with CyHex:EtOAc/EtOH (3/1) (from 100:0 to 65:35) to obtain the title compound (42 mg, 41.8% yield, ee 98.5%) as a white solid. $^1$H NMR (300 MHz, DMSO-d$_6$) δ ppm: 9.06 (s, 1H), 7.57 (d, J=8.6 Hz, 2H), 7.43-7.28 (m, 2H), 7.21-6.98 (m, 4H), 5.54-5.31 (m, 1H), 5.30-5.14 (m, 2H), 4.54-4.23 (m, 2H), 3.99-3.34 (m, 5H), 2.37-2.15 (m, 1H), 2.10-1.87 (m, 1H). [ES+MS] m/z 414 (MH$^+$). Chiral SFC determination using Chiral Pak IC 150×3 mm column (CO$_2$/MeOH (1% DEA) 70:30 (v/v), F=2.0 mL/min, R$_t$=5.06 min).

Example 12: (4-((S)-2-Fluoro-3-(2H-tetrazol-2-yl) propoxy)phenyl)((R)-3-(4-fluorophenyl) pyrrolidin-1-yl)methanone)

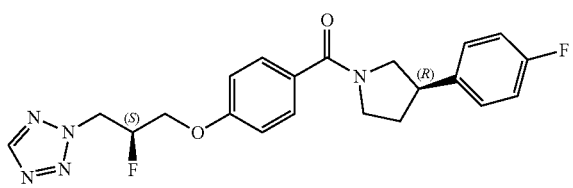

The title compound was prepared using analogous conditions described in Example 11 using ((R)-3-(4-fluorophenyl)pyrrolidin-1-yl)(4-((R)-2-hydroxy-3-(2H-tetrazol-2-yl) propoxy)phenyl) methanone (Example 7, 100 mg, 0.243 mmol). 40 mg (39.8% yield, ee 99.2%) of title compound as a white solid was obtained. $^1$H NMR (300 MHz, DMSO-d$_6$) δ ppm: 9.06 (s, 1H), 7.57 (d, J=8.6 Hz, 2H), 7.43-7.28 (m, 2H), 7.21-6.98 (m, 4H), 5.54-5.31 (m, 1H), 5.30-5.14 (m, 2H), 4.54-4.23 (m, 2H), 3.99-3.34 (m, 5H), 2.37-2.15 (m, 1H), 2.10-1.87 (m, 1H). [ES+MS]m/z 414 (MH$^+$). Chiral SFC determination using Chiral Pak IC 150×3 mm column (CO$_2$/MeOH (1% DEA) 70:30 (v/v), F=2.0 mL/min, R$_t$=4.5 min).

Example 13: ((S)-3-(4-Fluorophenyl)pyrrolidin-1-yl)(4-((R)-2-hydroxy-3-(2H-tetrazol-2-yl)propoxy) phenyl)methanone

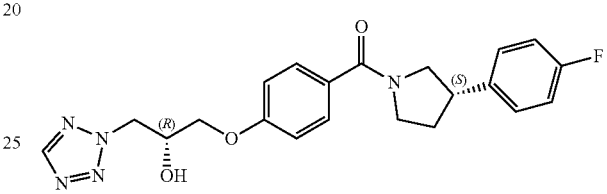

Example 13 was prepared with analogous conditions as described in Example 7, using (R)-4-(2-hydroxy-3-(2H-tetrazol-2-yl)propoxy)benzoic acid (intermediate 57, 0.100 g, 0.378 mmol) and (R)-3-(4-fluorophenyl)pyrrolidine hydrochloride (intermediate 3c, 0.092 g, 0.454 mmol). Crude material was purified by chiral SFC (ChiralPak IG, 250×20 mm column, CO$_2$/EtOH 60:40 (v/v), F=80.0 mL/min) to afford the title compound (90 mg, 57.2% yield, ee 100%) as a white foam. $^1$H NMR (300 MHz, DMSO-d$_6$) ppm: 8.97 (s, 1H), 7.55 (d, J=8.6 Hz, 2H), 7.42-7.28 (m, 2H), 7.20-7.08 (m, 2H), 7.04-6.95 (m, 2H), 5.64-5.57 (m, 1H), 4.94-4.75 (m, 2H), 4.45-4.34 (m, 1H), 4.13-4.02 (m, 2H), 3.95-3.34 (m, 5H), 2.33-2.16 (m, 1H), 2.10-1.88 (m, 1H). [ES+MS] m/z 412 (MH$^+$).

Example 14: ((S)-3-(4-Fluorophenyl)pyrrolidin-1-yl)(4-((S)-2-hydroxy-3-(2H-tetrazol-2-yl)propoxy) phenyl)methanone

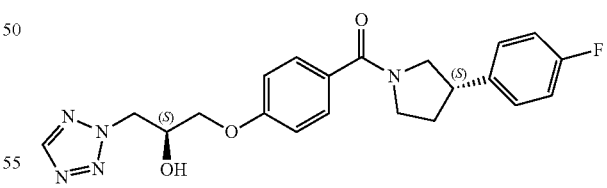

Example 14 was prepared with analogous conditions as described in Example 7, using (S)-4-(2-hydroxy-3-(2H-tetrazol-2-yl)propoxy)benzoic acid (intermediate 61, 0.100 g, 0.378 mmol) and (S)-3-(4-fluorophenyl)pyrrolidine hydrochloride (intermediate 3c, 0.092 g, 0.454 mmol). Crude material was purified by chiral SFC (ChiralPak IG, 250×20 mm column, CO$_2$/EtOH 60:40 (v/v), F=80.0 mL/min) to afford the title compound (90 mg, 57.2% yield, ee 100%) as a white foam. $^1$H NMR (300 MHz, DMSO-d$_6$) ppm: 8.97 (s, 1H), 7.54 (d, J=8.6 Hz, 2H), 7.42-7.29 (m, 2H), 7.21-7.10 (m, 2H), 7.04-6.95 (m, 2H), 5.64-5.57 (m, 1H), 4.93-4.76 (m, 2H), 4.44-4.35 (m, 1H), 4.14-4.02 (m, 2H), 3.96-3.34 (m, 5H), 2.32-2.16 (m, 1H), 2.10-1.89 (m, 1H). [ES+MS] m/z 412 (MH⁺).

Examples 15-34 were prepared using analogous conditions to that described for example 2 but replacing intermediates with that indicated in Table 2. Modifications in the protocol are also indicated.

TABLE 2

| Ex. | Structure | Int. | Physical data/Yield |
|---|---|---|---|
| 15 | ((R)-3-(4-fluorophenyl)pyrrolidin-1-yl)(4-((R)-2-hydroxy-3-(1H-1,2,4-triazol-1-yl)propoxy)phenyl)methanone | 65/3b | $^1$H NMR (300 MHz, DMSO-d$_6$) δ ppm: 8.46 (s, 1H), 7.96 (s, 1H), 7.54 (d, J = 8.6 Hz, 2H), 7.43-7.28 (m, 2H), 7.22-7.09 (m, 2H), 7.03-6.93 (m, 2H), 5.55-5.47 (m, 1H), 4.43-4.13 (m, 3H), 4.05-3.87 (m, 2H), 3.82-3.33 (m, 5H), 2.32-2.16 (m, 1H), 2.09-1.87 (m, 1H). [ES + MS] m/z 411 (MH⁺). 81% yield |
| 16 | ((R)-3-(4-fluorophenyl)pyrrolidin-1-yl)(4-((R)-2-hydroxy-3-(2H-1,2,3-triazol-2-yl)propoxy)phenyl)methanone | 66/3b | $^1$H NMR (300 MHz, DMSO-d$_6$) δ ppm: 7.78 (s, 2H), 7.56 (d, J = 8.8 Hz, 2H), 7.43-7.28 (m, 2H), 7.20-7.08 (m, 2H), 7.02-6.91 (m, 2H), 5.46 (br.s, 1H), 4.65-4.46 (m, 2H), 4.40-4.29 (m, 1H), 4.08-3.92 (m, 2H), 3.81-3.34 (m, 5H), 2.33-2.15 (m, 1H), 2.11-1.88 (m, 1H). [ES + MS] m/z 411 (MH⁺). 88% yield |
| 17 | ((R)-3-(4-fluorophenyl)pyrrolidin-1-yl)(4-((R)-2-hydroxy-3-(1H-1,2,3-triazol-1-yl)propoxy)phenyl)methanone | 67/3b | $^1$H NMR (300 MHz, DMSO-d$_6$) δ ppm: 8.09 (s, 1H), 7.78 (s, 1H), 7.54 (d, J = 8.6 Hz, 2H), 7.43-7.28 (m, 2H), 7.21-7.08 (m, 2H), 7.04-6.93 (m, 2H), 5.61-5.53 (m, 1H), 4.66-4.41 (m, 2H), 4.28-4.18 (m, 1H), 4.03-3.90 (m, 2H), 3.82-3.34 (m, 5H), 2.32-2.15 (m, 1H), 2.09-1.90 (m, 1H). [ES + MS] m/z 411 (MH⁺). 94% yield |
| 18 | ((R)-3-(4-fluorophenyl)pyrrolidin-1-yl)(4-((R)-2-hydroxy-3-(4H-1,2,4-triazol-4-yl)propoxy)phenyl)methanone | —/3b | $^1$H NMR (300 MHz, DMSO-d$_6$) δ ppm: 8.48 (s, 2H), 7.54 (d, J = 8.6 Hz, 2H), 7.43-7.28 (m, 2H), 7.21-7.09 (m, 2H), 7.04-6.94 (m, 2H), 5.64-5.57 (m, 1H), 4.33-4.06 (m, 3H), 3.98-3.86 (m, 3H), 3.81-3.34 (m, 6H), 2.34-2.16 (m, 1H), 2.10-1.88 (m, 1H). [ES + MS] m/z 411 (MH⁺). 16% yield |
| 19 | ((R)-3-(4-fluorophenyl)pyrrolidin-1-yl)(4-((R)-2-hydroxy-3-(1H-pyrazol-1-yl)propoxy)phenyl)methanone | 68/3b | $^1$H NMR (300 MHz, DMSO-d$_6$) δ ppm: 7.70 (br.s, 1H), 7.53 (d, J = 8.6 Hz, 2H), 7.44 (br.s, 1H), 7.42-7.28 (m, 2H), 7.21-7.08 (m, 2H), 7.01-6.90 (m, 2H), 6.22 (br.s, 1H), 5.46-5.38 (m, 1H), 4.36-4.25 (m, 1H), 4.24-4.14 (m, 2H), 4.00-3.84 (m, 2H), 3.81-3.34 (m, 5H), 2.33-2.17 (m, 1H), 2.10-1.89 (m, 1H). [ES + MS] m/z 410 (MH⁺). 74.5% yield See footnote a) |

TABLE 2-continued

| Ex. | Structure | Int. | Physical data/Yield |
|---|---|---|---|
| 20 | ((R)-3-(4-fluorophenyl)pyrrolidin-1-yl)(4-((R)-2-hydroxy-3-(1H-imidazol-1-yl)propoxy)phenyl)methanone | 69/3b | $^1$H NMR (300 MHz, DMSO-d$_6$) δ ppm: 7.65 (br.s, 1H), 7.54 (d, J = 8.6 Hz, 2H), 7.43-7.29 (m, 2H), 7.22-7.09 (m, 3H), 7.03-6.94 (m, 2H), 6.91 (br.s, 1H), 5.55-5.46 (m, 1H), 4.25-4.13 (m, 1H), 4.12-4.00 (m, 2H), 3.95-3.33 (m, 2H), 3.80-3.25 (m, 5H), 2.33-2.16 (m, 1H), 2.11-1.86 (m, 1H). [ES + MS] m/z 410 (MH$^+$). 64.8% yield See footnote a) |
| 21 | ((R)-3-(4-fluorophenyl)pyrrolidin-1-yl)(4-((R)-2-hydroxy-3-(5-methyl-1H-tetrazol-1-yl)propoxy)phenyl)methanone | 77/3b | $^1$H NMR (300 MHz, DMSO-d$_6$) δ ppm: 7.56 (d, J = 8.8 Hz, 2H), 7.43-7.29 (m, 2H), 7.21-7.10 (m, 2H), 7.05-6.96 (m, 2H), 5.66-5.61 (m, 1H), 4.64-4.53 (m, 1H), 4.47-4.36 (m, 1H), 4.27-4.15 (m, 1H), 4.10-3.97 (m, 2H), 3.81-3.34 (m, 5H), 2.53 (s, 3H), 2.32-2.16 (m, 1H), 2.11-1.89 (m, 1H). [ES + MS] m/z 426 (MH$^+$). 88% yield See footnote b) |
| 22 | ((R)-3-(4-fluorophenyl)pyrrolidin-1-yl)(4-((R)-2-hydroxy-3-(5-methyl-2H-tetrazol-2-yl)propoxy)phenyl)methanone | 76/3b | $^1$H NMR (300 MHz, DMSO-d$_6$) δ ppm: 7.55 (d, J = 8.8 Hz, 2H), 7.43-7.29 (m, 2H), 7.20-7.08 (m, 2H), 7.03-6.93 (m, 2H), 5.62-5.55 (m, 1H), 4.84-4.64 (m, 2H), 4.42-4.30 (m, 1H), 4.12-4.00 (m, 2H), 3.96-3.35 (m, 5H), 2.45 (s, 3H), 2.33-2.15 (m, 1H), 2.09-1.88 (m, 1H). [ES + MS] m/z 426 (MH$^+$). 70% yield See footnote b) |
| 23 | ((R)-3-(4-fluorophenyl)pyrrolidin-1-yl)(4-((R)-2-hydroxy-3-(2-methyl-2H-tetrazol-5-yl)propoxy)phenyl)methanone | 73/3b | $^1$H NMR (300 MHz, CD$_3$OD) δ ppm: 7.60-7.52 (m, 2H), 7.40-7.32 (m, 1H), 7.31-7.24 (m, 1H), 7.12-6.98 (m, 4H), 4.48-4.37 (m, 1H), 4.33 (d, J = 5.3 Hz, 3H), 4.17-4.03 (m, 3H), 3.90-3.36 (m, 5H), 3.29-3.09 (m, 2H), 2.43-2.24 (m, 1H), 2.21-1.98 (m, 1H). [ES + MS] m/z 426 (MH$^+$). 86% yield See footnote b) |
| 24 | ((R)-3-(4-fluorophenyl)pyrrolidin-1-yl)(4-((R)-2-hydroxy-3-(1-methyl-1H-tetrazol-5-yl)propoxy)phenyl)methanone | 74/3b | $^1$H NMR (300 MHz, CD$_3$OD) δ ppm: 7.61-7.54 (m, 2H), 7.41-7.34 (m, 1H), 7.32-7.26 (m, 1H), 7.13-7.00 (m, 4H), 4.46-4.36 (m, 1H), 4.12 (d, J = 5.3 Hz, 3H), 4.16-4.03 (m, 2H), 3.90-3.16 (m, 9H), 2.43-2.25 (m, 1H), 2.21-1.99 (m, 1H). [ES + MS] m/z 426 (MH$^+$). 86% yield See footnote b) |

TABLE 2-continued

| Ex. | Structure | Int. | Physical data/Yield |
|---|---|---|---|
| 25 | ((R)-3-(4-fluorophenyl)pyrrolidin-1-yl)(4-((R)-2-hydroxy-3-(1H-tetrazol-5-yl)propoxy)phenyl)methanone | —/3b | $^1$H NMR (300 MHz, DMSO-d$_6$) δ ppm: 7.56 (d, J = 8.8 Hz, 1H), 7.42-7.26 (m, 3H), 7.21-7.08 (m, 3H), 7.07-6.98 (m, 1H), 5.73-5.60 (m, 1H), 4.59-4.40 (m, 1H), 3.97-3.84 (m, 1H), 3.79-3.35 (m, 8H), 2.34-2.22 (m, 1H), 2.02-1.85 (m, 1H)<br>18% yield<br>See footnote b) |
| 26 | (2-fluoro-4-((R)-2-hydroxy-3-(1H-tetrazol-1-yl)propoxy)phenyl((R)-3-(4-fluorophenyl)pyrrolidin-1-yl)methanone | 85/3b | $^1$H NMR (300 MHz, DMSO-d$_6$) δ ppm: 9.37 (d, J = 6.1 Hz, 1H), 7.43-7.36 (m, 2H), 7.33-7.28 (m,1H), 7.21-7.09 (m, 2H), 6.98-6.83 (m, 2H), 5.68 (dd, J = 7.6, 5.6 Hz, 1H), 4.75-4.65 (m, 1H), 4.60-4.48 (m, 1H), 4.29-4.18 (m, 1H), 4.09-4.00 (m, 2H), 3.75-3.22 (m, 5H), 2.35-2.17 (m, 1H), 2.11-1.90 (m, 1H). [ES + MS] m/z 430 (MH$^+$).<br>87% yield |
| 27 | (2-fluoro-4-((R)-2-hydroxy-3-(2H-tetrazol-2-yl)propoxy)phenyl((R)-3-(4-fluorophenyl)pyrrolidin-1-yl)methanone | 84/3b | $^1$H NMR (300 MHz, DMSO-d$_6$) δ ppm: 8.97 (d, J = 5.3 Hz, 1H), 7.44-7.35 (m, 2H), 7.34-7.27 (m, 1H), 7.21-7.08 (m, 2H), 6.98-6.83 (m, 2H), 5.66-5.59 (m, 1H), 4.93-4.75 (m, 2H), 4.44-4.34 (m, 1H), 4.16-4.03 (m, 2H), 3.75-3.22 (m, 5H), 2.35-2.19 (m, 1H), 2.09-1.90 (m, 1H). [ES + MS] m/z 430 (MH$^+$).<br>27% yield |
| 28 | ((R)-3-(4-chlorophenyl)pyrrolidin-1-yl)(4-((R)-2-hydroxy-3-(1H-tetrazol-1-yl)propoxy)phenyl)methanone | 60/3a | $^1$H NMR (300 MHz, DMSO-d$_6$) δ ppm: 9.37 (s, 1H), 7.55 (d, J = 8.6 Hz, 2H), 7.43-7.27 (m, 4H), 7.06-6.93 (m, 2H), 5.71-5.63 (m, 1H), 4.76-4.51 (m, 2H), 4.24 (br.s, 1H), 4.08-3.98 (m, 2H), 3.96-3.34 (m, 5H), 2.35-2.18 (m, 1H), 2.09-1.89 (m, 1H). [ES + MS] m/z 428 (MH$^+$).<br>81% yield |
| 29 | ((R)-3-(4-chlorophenyl)pyrrolidin-1-yl)(4-((R)-2-hydroxy-3-(2H-tetrazol-2-yl)propoxy)phenyl)methanone | 57/3a | $^1$H NMR (300 MHz, CDCl$_3$) δ ppm: 8.57 (s, 1H), 7.59-7.49 (m, 2H), 7.36-7.10 (m, 4H), 6.96-6.86 (m, 2H), 5.03-4.86 (m, 2H), 4.61 (br.s, 1H), 4.14-4.04 (m, 2H), 3.93-3.14 (m, 6H), 2.44-2.24 (m, 1H), 2.17-1.92 (m, 1H). [ES + MS] m/z 428 (MH$^+$).<br>82% yield |

TABLE 2-continued

| Ex. | Structure | Int. | Physical data/Yield |
|---|---|---|---|
| 30 | ((R)-3-(4-chlorophenyl)pyrrolidin-1-yl)(4-((R)-2-hydroxy-3-(1H-1,2,4-triazol-1-yl)propoxy)phenyl)methanone | 65/3a | $^1$H NMR (300 MHz, DMSO-d$_6$) δ ppm: 8.47 (s, 1H), 7.96 (s, 1H), 7.54 (d, J = 8.6 Hz, 2H), 7.44-7.27 (m, 4H), 7.04-6.92 (m, 2H), 5.51 (br.s, 1H), 4.43-4.13 (m, 3H), 4.06-3.89 (m, 2H), 3.82-3.35 (m, 5H), 2.33-2.17 (m, 1H), 2.09-1.90 (m, 1H). [ES + MS] m/z 427 (MH$^+$). 98% yield |
| 31 | ((R)-3-(4-chlorophenyl)pyrrolidin-1-yl)(4-((R)-2-hydroxy-3-(2H-1,2,3-triazol-2-yl)propoxy)phenyl)methanone | 66/3a | $^1$H NMR (300 MHz, DMSO-d$_6$) δ ppm: 7.78 (s, 2H), 7.54 (d, J = 8.8 Hz, 2H), 7.43-7.28 (m, 4H), 7.02-6.91 (m, 2H), 5.50 (br.s, 1H), 4.65-4.46 (m, 2H), 4.39-4.27 (m, 1H), 4.09-3.94 (m, 2H), 3.84-3.35 (m, 5H), 2.33-2.17 (m, 1H), 2.07-1.86 (m, 1H). [ES + MS] m/z 427 (MH$^+$). 74% yield |
| 32 | ((R)-3-(4-chlorophenyl)pyrrolidin-1-yl)(4-((R)-2-hydroxy-3-(1H-1,2,3-triazol-1-yl)propoxy)phenyl)methanone | 67/3a | $^1$H NMR (300 MHz, DMSO-d$_6$) δ ppm: 8.09 (s, 1H), 7.72 (s, 1H), 7.54 (d, J = 8.8 Hz, 2H), 7.43-7.27 (m, 4H), 7.04-6.93 (m, 2H), 5.61-5.53 (m, 1H), 4.67-4.41 (m, 2H), 4.29-4.17 (m, 1H), 4.03-3.89 (m, 2H), 3.83-3.34 (m, 5H), 2.33-2.17 (m, 1H), 2.09-1.88 (m, 1H). [ES + MS] m/z 427 (MH$^+$). 98% yield |
| 33 | ((R)-3-(4-chlorophenyl)pyrrolidin-1-yl)(2-fluoro-4-((R)-2-hydroxy-3-(1H-tetrazol-1-yl)propoxy)phenyl)methanone | 85/3a | $^1$H NMR (300 MHz, DMSO-d$_6$) δ ppm: 9.37 (d, J = 5.6 Hz, 1H), 7.43-7.27 (m, 5H), 6.98-6.83 (m, 2H), 5.72-5.66 (m, 1H), 4.74-4.65 (m, 1H), 4.60-4.49 (m, 1H), 4.29-4.19 (m, 1H), 4.08-3.99 (m, 2H), 3.75-3.25 (m, 5H), 2.36-2.20 (m, 1H), 2.08-1.89 (m, 1H). [ES + MS] m/z 446 (MH$^+$). 95% yield |
| 34 | ((R)-3-(4-chlorophenyl)pyrrolidin-1-yl)(2-fluoro-4-((R)-2-hydroxy-3-(2H-tetrazol-2-yl)propoxy)phenyl)methanone | 84/3a | $^1$H NMR (300 MHz, DMSO-d$_6$) δ ppm: 8.98 (d, J = 5.1 Hz, 1H), 7.43-7.26 (m, 5H), 6.99-6.83 (m, 2H), 5.65-5.60 (m, 1H), 4.94-4.75 (m, 2H), 4.45-4.33 (m, 1H), 4.16-4.03 (m, 2H), 3.76-3.23 (m, 5H), 2.37-2.17 (m, 1H), 2.09-1.90 (m, 1H). [ES + MS] m/z 446 (MH$^+$). 76% yield | a) The mixture was partitioned between EtOAc and water.
b) The reaction was quenched by the addition of sat. aq Na$_2$CO$_3$. EtOAc (50 mL) was added and the layers were separated.

Intermediate 86-91 were prepared using analogous conditions to that described for Example 2 but replacing intermediates with that indicated in Table 3. Modifications in the protocol are also indicated.

TABLE 3

| Int. | Structure | Int. | Physical data/Yield |
|---|---|---|---|
| 86 | ((R)-3-(4-chlorophenyl)pyrrolidin-1-yl)(4-((S)-2-hydroxy-3-(1H-tetrazol-1-yl)propoxy)phenyl)methanone | 62/3a | $^1$H NMR (300 MHz, CDCl$_3$) δ ppm: 8.84-8.80 (m, 1H), 7.51-7.43 (m, 2H), 7.36-7.18 (m, 3H), 7.13 (d, J = 8.3 Hz, 1H), 6.79 (dd, J = 11.1, 8.8 Hz, 2H), 4.82-4.52 (m, 2H), 4.42 (d, J = 5.1 Hz, 1H), 4.28 (br.s, 1H), 3.92-3.28 (m, 7H), 2.45-2.24 (m, 1H), 2.17-1.93 (m, 1H). 92% yield |
| 87 | ((R)-3-(4-chlorophenyl)pyrrolidin-1-yl)(4-((S)-2-hydroxy-3-(2H-tetrazol-2-yl)propoxy)phenyl)methanone | 61/3a | $^1$H NMR (300 MHz, CDCl$_3$) δ ppm: 8.57 (s, 1H), 7.59-7.50 (m, 2H), 7.36-7.18 (m, 3H), 7.14 (d, J = 8.3 Hz, 1H), 6.96-6.86 (m, 2H), 5.03-4.87 (m, 2H), 4.67-4.57 (m, 1H), 4.15-4.04 (m, 2H), 3.94-3.27 (m, 5H), 3.13-3.06 (m, 1H), 2.44-2.23 (m, 1H), 2.17-1.91 (m, 1H). quant. yield |
| 88 | ((R)-3-(4-fluorophenyl)pyrrolidin-1-yl)(4-(2-methoxy-3-(1-methyl-1H-pyrazol-3-yl)propoxy)phenyl)methanone | 71/3b | $^1$H NMR (300 MHz, DMSO-d$_6$) δ ppm: 7.57-7.49 (m, 3H), 7.42-7.27 (m, 2H), 7.20-7.08 (m, 2H), 7.00-6.90 (m, 2H), 6.07 (br.s, 1H), 4.14-3.87 (m, 3H), 3.83-3.32 (m, 8H), 3.75 (s, 3H), 2.87-2.75 (m, 2H), 2.32-2.14 (m, 1H), 2.10-1.87 (m,1H). 88% yield |
| 89 | ((R)-3-(4-fluorophenyl)pyrrolidin-1-yl)(4-(2-methoxy-3-(thiazol-4-yl)propoxy)phenyl)methanone | 78/3b | $^1$H NMR (300 MHz, CDCl$_3$) δ ppm: 8.78 (s, 1H), 7.58-7.47 (m, 2H), 7.28-7.12 (m, 2H), 7.08 (s, 1H), 7.07-6.96 (m, 2H), 6.95-6.86 (m, 2H), 4.12-3.57 (m, 7H), 3.46 (s, 3H), 3.40-3.26 (m, 1H), 3.24-3.15 (m, 2H), 2.42-2.20 (m, 1H), 2.14-1.89 (m, 1H). 92% yield |
| 90 | ((R)-3-(4-fluorophenyl)pyrrolidin-1-yl)(4-(2-methoxy-3-(1-methyl-1H-pyrazol-4- | 72/3b | $^1$H NMR (300 MHz, CDCl$_3$) δ ppm: 7.60-7.51 (m, 2H), 7.36 (s, 1H), 7.30-7.15 (m, 3H), 7.10-6.99 (m, 2H), 6.97-6.88 (m, 2H), 4.05-3.29 (m, 8H), 3.88 (s, 3H), 3.51 (s, 3H), 2.93-2.77 (m, 2H), 2.44-2.24 (m, 1H), 2.16-1.93 (m,1H). 46.7% yield |

TABLE 3-continued

| Int. | Structure | Int. Physical data/Yield |
|---|---|---|
| | yl)propoxy)phenyl)methanone | |
| 91 | 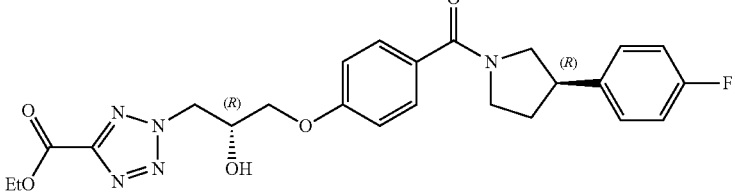<br>Ethyl 2-((R)-3-(4-((R)-3-(4-fluorophenyl)pyrrolidine-1-carbonyl)phenoxy)-2-hydroxypropyl)-2H-tetrazole-5-carboxylate | 75/3b $^1$H NMR (300 MHz, DMSO-d$_6$) δ ppm: 7.56 (d, J = 8.6 Hz, 2H), 7.43-7.29 (m, 2H), 7.21-7.09 (m, 2H), 7.05-6.95 (m, 2H), 5.71-5.62 (m, 1H), 5.02-4.82 (m, 2H), 4.48-4.37 (m, 1H), 4.15-4.05 (m, 2H), 3.80-3.38 (m, 5H), 3.19-3.14 (m, 2H), 2.32-1.90 (m, 2H), 1.38-1.30 (m,3H). quant. yield<br>See footnote b) | a) The mixture was partitioned between EtOAc and water.

Examples 35a-b: ((R)-3-(4-Fluorophenyl)pyrrolidin-1-yl)(4-(2-hydroxy-3-(thiazol-4-yl)propoxy) phenyl)methanone (isomer 1 and isomer 2)

isomer 1 (Example 35a)
isomer 2 (Example 36b)

TMSCl (SIGMA-ALDRICH, 0.5 mL, 3.91 mmol) was added to a solution of NaI (ALFA AESAR, 586 mg, 3.91 mmol) and ((R)-3-(4-fluorophenyl)pyrrolidin-1-yl)(4-(2-methoxy-3-(thiazol-4-yl)propoxy)phenyl)methanone (intermediate 89, 330 mg, 0.749 mmol) in CH$_3$CN (8 mL) at 0° C. under nitrogen atmosphere. The reaction mixture was heated to 50° C. for 5 h. A new addition of TMSCl (SIGMA-ALDRICH, 0.50 mL, 3.91 mmol) and NaI (ALFA AESAR, 586 mg, 3.91 mmol) is required and the mixture was heated to 100° C. overnight. After completion of the reaction, the mixture was allowed to cool down to rt and MeOH was added. The solution was concentrated under reduced pressure, and the remaining oil was dissolved in EtOAc (15 mL) The organic layer was washed with sat. aq. Na$_2$S$_2$O$_3$ (10 mL), NaHCO$_3$ (10 mL) and brine (10 mL), dried over anh. Na$_2$SO$_4$ and concentrated under reduced pressure. The crude material was purified by flash chromatography on silica gel using a gradient of CyHex:EtOAc/EtOH(3/1) (from 100:0 to 50:50) to give a mixture of diastereoisomers (304 mg, 95% yield) that was separated by chiral HPLC (ChiralPak IA 250×20 mm column, Hept:EtOH/MeOH 40:60 (v/v), F=18 mL/min). The desired fractions were concentrated under reduced pressure and the residues were dissolved in CH$_3$CN/H$_2$O and lyophilised to give isomer 1 (Example 35a, 123 mg, 100% ee) and isomer 2 (Example 35b, 126 mg, 100% ee).

isomer 1 (Example 35a)—First eluted in SFC. $^1$H NMR (300 MHz, DMSO-d$_6$) δ ppm: 9.02 (br.s, 1H), 7.52 (d, J=8.8 Hz, 2H), 7.43-7.29 (m, 3H), 7.20-7.08 (m, 2H), 6.99-6.89 (m, 2H), 5.15-5.09 (m, 1H), 4.21 (br.s, 1H), 4.02-3.86 (m, 2H), 3.81-3.34 (m, 5H), 3.10-2.08 (m, 2H), 2.32-2.13 (m, 1H), 2.10-1.86 (m, 1H). [ES+MS] m/z 427 (MH$^+$).

isomer 2 (Example 35b)—Second eluted in SFC. $^1$H NMR (300 MHz, DMSO-d$_6$) δ ppm: 9.02 (br.s, 1H), 7.52 (d, J=8.8 Hz, 2H), 7.43-7.29 (m, 3H), 7.20-7.08 (m, 2H), 6.99-6.89 (m, 2H), 5.13 (br.s, 1H), 4.21 (br.s, 1H), 4.02-3.86 (m, 2H), 3.81-3.34 (m, 5H), 3.10-2.08 (m, 2H), 2.32-2.13 (m, 1H), 2.10-1.86 (m, 1H). [ES+MS] m/z 427 (MH$^+$).

Chiral SFC determination using ChiralPak IA 150×3 mm column (CO$_2$/MeOH (1% DEA) 60:40 (v/v), F=3.0 mL/min, R$_t$ isomer 1=4.68 min, R$_t$ isomer 2=7.21 min).

Examples 36a-b: ((R)-3-(4-Fluorophenyl)pyrrolidin-1-yl)(4-(2-methoxy-3-(1-methyl-1H-pyrazol-3-yl)propoxy)phenyl)methanone (isomer 1 and isomer 2)

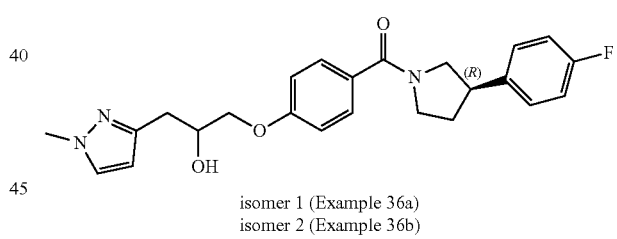

isomer 1 (Example 36a)
isomer 2 (Example 36b)

Example 36a-b were prepared using analogous conditions described in Example 35a-b, using ((R)-3-(4-fluorophenyl)pyrrolidin-1-yl)(4-(2-methoxy-3-(1-methyl-1H-pyrazol-3-yl)propoxy) phenyl)methanone (intermediate 88, 705 mg, 1.611 mmol). The diastereomeric mixture was separate by chiral HPLC to afford isomer 1 (258 mg, ee 100%, Example 36a) and isomer 2 (255 mg, ee 99.2%, Example 36b).

isomer 1 (Example 36a)—First eluted in SFC. $^1$H NMR (300 MHz, DMSO-d$_6$) δ ppm: 7.57-7.49 (m, 3H), 7.43-7.28 (m, 2H), 7.21-7.09 (m, 2H), 7.00-6.89 (m, 2H), 6.07 (br.s, 1H), 5.07-5.00 (m, 1H), 4.12-3.81 (m, 3H), 3.75 (s, 3H), 3.73-3.33 (m, 5H), 2.85-2.64 (m, 2H), 2.32-2.15 (m, 1H), 2.10-1.86 (m, 1H). [ES+MS] m/z 424 (MH$^+$).

isomer 2 (Example 36b)—Second eluted in SFC. $^1$H NMR (300 MHz, DMSO-d$_6$) δ ppm: 7.57-7.49 (m, 3H), 7.43-7.28 (m, 2H), 7.21-7.09 (m, 2H), 7.00-6.89 (m, 2H), 6.07 (br.s, 1H), 5.07-5.00 (m, 1H), 4.12-3.81 (m, 3H), 3.75 (s, 3H), 3.73-3.33 (m, 5H), 2.85-2.64 (m, 2H), 2.32-2.15 (m, 1H), 2.10-1.86 (m, 1H). [ES+MS] m/z 424 (MH$^+$).

Chiral HPLC determination using ChiralPak AD-H 150×3 mm column (Hept/EtOH (0.1% DEA) 10:90 (v/v), F=1.0 mL/min, R$_t$ isomer 1=4.56 min, R$_t$ isomer 2=11.31 min).

Examples 37: ((R)-3-(4-Fluorophenyl)pyrrolidin-1-yl)(4-(2-hydroxy-3-(1-methyl-1H-pyrazol-4-yl)propoxy)phenyl)methanone

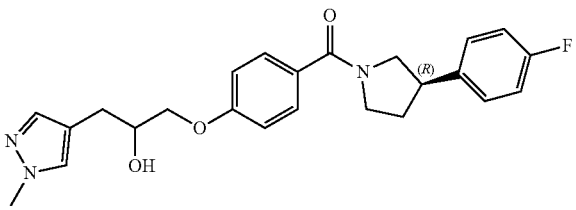

Example 37 were prepared using analogous conditions (although in that case the mixture was heating at 100° C.) described in Example 35a-b, using ((R)-3-(4-fluorophenyl)pyrrolidin-1-yl)(4-(2-methoxy-3-(1-methyl-1H-pyrazol-4-yl)propoxy) phenyl)methanone (intermediate 90, 100 mg, 0.229 mmol). 19 mg, (19.6% yield) of the title compound as a diastereomeric mixture was obtained after chromatography on silica gel. $^1$H NMR (300 MHz, CDCl$_3$) δ ppm: 7.63-7.52 (m, 2H), 7.40 (s, 1H), 7.38-7.16 (m, 3H), 7.11-7.00 (m, 2H), 6.98-6.90 (m, 2H), 4.23-3.31 (m, 9H), 3.91 (s, 3H), 2.91-2.74 (m, 2H), 2.46-2.25 (m, 1H), 2.20-1.94 (m, 1H). [ES+MS] m/z 424 (MH$^+$).

Example 38: 2-((R)-3-(4-((R)-3-(4-Fluorophenyl)pyrrolidine-1-carbonyl)phenoxy)-2-hydroxypropyl)-2H-tetrazole-5-carboxamide ![structure]

To a solution of ethyl 2-((R)-3-(4-((R)-3-(4-fluorophenyl)pyrrolidine-1-carbonyl)phenoxy)-2-hydroxypropyl)-2H-tetrazole-5-carboxylate (intermediate 91, 0.010 g, 0.021 mmol) in THF (0.103 mL) under nitrogen atmosphere, 7 N NH$_3$ in MeOH (SIGMA-ALDRICH, 0.148 mL, 1.034 mmol) was added. The mixture was stirred at 100° C. for 45 min. The solvents were then evaporated under reduced pressure. The crude material was purified by flash chromatography on silica gel using a gradient of CyHex:EtOAc/EtOH (3/1) (from 100:0 to 0:100) to obtain the title compound (5 mg, 52.1% yield). $^1$H NMR (300 MHz, CD$_3$OD) δ ppm: 7.61-7.52 (m, 2H), 7.39-7.23 (m, 2H), 7.12-6.98 (m, 4H), 5.04-4.91 (m, 2H), 4.64-4.53 (m, 1H), 4.22-4.12 (m, 2H), 3.90-3.36 (m, 5H), 2.43-1.96 (m, 2H). [ES+MS] m/z 455 (MH$^+$).

Example 39: 2-((R)-3-(4-((R)-3-(4-Fluorophenyl)pyrrolidine-1-carbonyl)phenoxy)-2-hydroxypropyl)-2H-tetrazole-5-carbonitrile

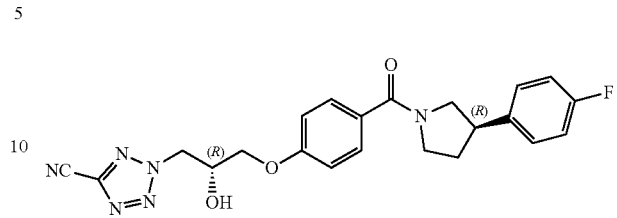

To a solution of 2-((R)-3-(4-((R)-3-(4-fluorophenyl)pyrrolidine-1-carbonyl)phenoxy)-2-hydroxypropyl)-2H-tetrazole-5-carboxamide (example 38, 0.050 g, 0.110 mmol) and DIPEA (SIGMA-ALDRICH, 0.384 mL, 2.200 mmol) in DCM (0.367 mL) under nitrogen atmosphere, was added dropwise TFAA (SIGMA-ALDRICH, 0.077 mL, 0.550 mmol) (½) at −40° C. The mixture was stirred at −78° C. for 1 h. To complete the reaction, additional amount of DIPEA (SIGMA-ALDRICH, 0.384 mL, 2.200 mmol) and TFAA (SIGMA-ALDRICH, 0.077 mL, 0.550 mmol) was added at room temperature. After 30 min, the reaction mixture was diluted with EtOAc and poured into aq. NH$_4$Cl, extracted with EtOAc and washed with brine. The organic layer was dried over Na$_2$SO$_4$, filtered and solvents were removed under reduced pressure. The resulting crude product was purified by column chromatography on silica gel using a gradient of CyHex:EtOAc/EtOH (3/1) (from 100:00 to 50:50) to afford the title compound (38 mg, 78% yield) as a yellow solid. $^1$H NMR (300 MHz, DMSO-d$_6$) δ ppm: 7.57-7.47 (m, 2H), 7.33-7.15 (m, 2H), 7.12-6.98 (m, 2H), 6.89-6.77 (m, 2H), 5.03-4.92 (m, 2H), 4.53-4.41 (m, 1H), 4.12-3.30 (m, 8H), 2.48-1.94 (m, 2H). [ES+MS] m/z 437 (MH$^+$).

Examples 40a and 40b: (3-(2-Fluorophenyl)pyrrolidin-1-yl)(4-((R)-2-hydroxy-3-(2H-tetrazol-2-yl)propoxy)phenyl)methanone (isomer 1 and isomer 2)

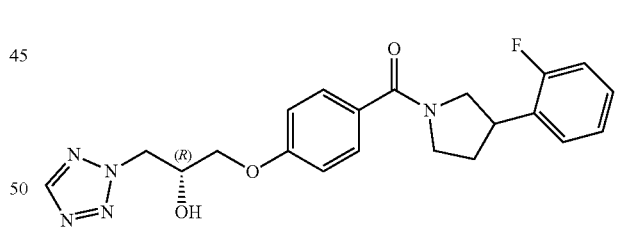

isomer 1 (Example 40a)
isomer 2 (Example 40b)

To a solution of (R)-4-(2-hydroxy-3-(2H-tetrazol-2-yl)propoxy)benzoic acid (intermediate 57, 0.200 g, 0.757 mmol), 3-(2-fluorophenyl)pyrrolidine hydrochloride (ENAMINE, 0.229 g, 1.135 mmol) and DIPEA (SIGMA-ALDRICH, 0.397 mL, 2.271 mmol) in DMF (7.57 mL) at 0° C. under nitrogen atmosphere was added COMU (ALFA AESAR, 0.421 g, 0.984 mmol) and the reaction mixture was stirred at 0° C. for 1 h and then at rt overnight. The mixture was quenched by the dropwise addition of sat. Na$_2$CO$_3$. The resulting mixture was then partitioned with EtOAc and water. The phases were separated and the aqueous one was re-extracted with EtOAc. The organic layers were combined and washed with 1 M HCl, Na$_2$CO$_3$ sat and brine. The organic layer was dried over anh. Na$_2$SO$_4$, filtered and evaporated to dryness under vacuum. The residue was purified by flash chromatography on silica gel using a gradient of CyHex:EtOAc (from 100:0 to 0:100) to afford 320 mg as a mixture of diastereoisomers. The diastereomeric mixture was separated by chiral HPLC purification using an isocratic mixture of Hept:MeOH-EtOH 10:90 with a CHIRALPAK AD 20×250 mm column, F=18 mL/min, 254 nm. Separation was achieved and appropriate fractions were collected to afford:

isomer 1 (Example 40a)—First eluted in HPLC (120 mg, 38.1% yield, ee 100%). $^1$H NMR (300 MHz, DMSO-d$_6$) ppm: 8.98 (s, 1H), 7.56 (d, J=8.6 Hz, 2H), 7.45-6.95 (m, 6H), 5.65-5.58 (m, 1H), 4.95-4.77 (m, 2H), 4.46-4.34 (m, 1H), 4.15-4.02 (m, 2H), 3.97-3.44 (m, 5H), 2.34-1.95 (m, 2H). [ES+MS] m/z 412 (MH$^+$).

isomer 2 (Example 40b)—Second eluted in HPLC (120 mg, 38.1% yield, ee 100%). $^1$H NMR (300 MHz, DMSO-d$_6$) δ ppm: 8.97 (s, 1H), 7.56 (d, J=8.6 Hz, 2H), 7.46-7.10 (m, 4H), 7.05-6.95 (m, 2H), 5.64-5.58 (m, 1H), 4.94-4.76 (m, 2H), 4.45-4.35 (m, 1H), 4.14-4.04 (m, 2H), 3.97-3.43 (m, 5H), 2.35-1.90 (m, 2H). [ES+MS] m/z 412 (MH$^+$).

Chiral HPLC determination using ChiralPak AD-H 150×3 mm column (Hept/MeOH-EtOH (0.1% DEA) 10:90 (v/v), F=1.0 mL/min, R$_t$ isomer 1=5.50 min, R$_t$ isomer 2=11.06 min).

Examples 41a and 41b: (3-(3-Fluorophenyl)pyrrolidin-1-yl)(4-((R)-2-hydroxy-3-(2H-tetrazol-2-yl) propoxy)phenyl)methanone (isomer 1 and isomer 2)

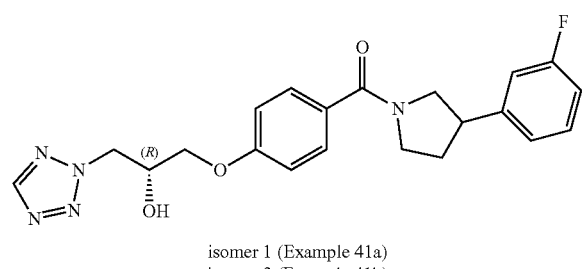

isomer 1 (Example 41a)
isomer 2 (Example 41b)

Examples 41a-b were prepared by method analogous to that described for Examples 40a-b, replacing 3-(2-fluorophenyl)pyrrolidine hydrochloride by 3-(3-fluorophenyl)pyrrolidine hydrochloride (ENAMINE), and the diastereomeric mixture obtained was separated using similar conditions.

isomer 1 (Example 41a)—First eluted in HPLC (119 mg, 37.8% yield, ee 100%). $^1$H NMR (300 MHz, DMSO-d$_6$) ppm: 8.97 (s, 1H), 7.56 (d, J=8.8 Hz, 2H), 7.44-6.94 (m, 6H), 5.62 (br.s, 1H), 4.94-4.76 (m, 2H), 4.40 (br.s, 1H), 4.15-4.04 (m, 2H), 3.97-3.36 (m, 5H), 2.36-1.93 (m, 2H). [ES+MS] m/z 412 (MH$^+$).

isomer 2 (Example 41b)—Second eluted in HPLC (117 mg, 37.2% yield, ee 100%). $^1$H NMR (300 MHz, DMSO-d$_6$) δ ppm: 8.97 (s, 1H), 7.56 (d, J=8.8 Hz, 2H), 7.43-6.94 (m, 6H), 5.64-5.57 (m, 1H), 4.94-4.76 (m, 2H), 4.40 (br.s, 1H), 4.13-4.04 (m, 2H), 3.96-3.36 (m, 5H), 2.36-1.94 (m, 2H). [ES+MS] m/z 412 (MH$^+$).

Chiral HPLC determination using ChiralPak AD-H 150×3 mm column (Hept/MeOH-EtOH (0.1% DEA) 10:90 (v/v), F=1.0 mL/min, R$_t$ isomer 1=6.34 min, R$_t$ isomer 2=10.99 min).

Examples 42a and 42b: (3-(3-Fluorophenyl)pyrrolidin-1-yl)(4-((R)-2-hydroxy-3-(2H-tetrazol-2-yl) propoxy)phenyl)methanone (isomer 1 and isomer 2)

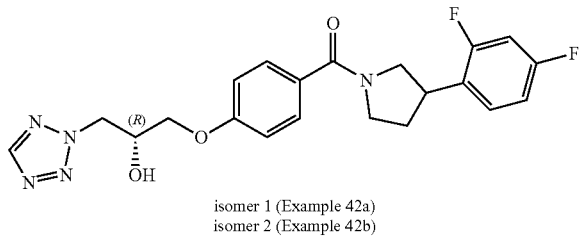

isomer 1 (Example 42a)
isomer 2 (Example 42b)

Examples 42a-b were prepared by method analogous to that described for Examples 40a-b, replacing 3-(2-fluorophenyl)pyrrolidine hydrochloride by 3-(2,4-difluorophenyl) pyrrolidine hydrochloride (ASW MEDCHEM) and the diastereomeric mixture was separated using similar conditions.

isomer 1 (Example 42a)—First eluted in HPLC (111 mg, 33.8% yield, ee 100%). $^1$H NMR (300 MHz, DMSO-d$_6$) ppm: 8.98 (s, 1H), 7.55 (d, J=8.8 Hz, 2H), 7.51-7.34 (m, 1H), 7.30-6.94 (m, 4H), 5.62 (br.s, 1H), 4.94-4.75 (m, 2H), 4.40 (br.s, 1H), 4.15-4.02 (m, 2H), 3.96-3.42 (m, 5H), 2.34-1.95 (m, 2H). [ES+MS] m/z 430 (MH$^+$).

isomer 2 (Example 42b)—Second eluted in HPLC (111 mg, 33.8% yield, ee 100%). $^1$H NMR (300 MHz, DMSO-d$_6$) δ ppm: 8.98 (s, 1H), 7.56 (d, J=8.8 Hz, 2H), 7.51-7.38 (m, 1H), 7.30-6.95 (m, 4H), 5.64-5.57 (m, 1H), 4.94-4.74 (m, 2H), 4.39 (br.s, 1H), 4.14-4.04 (m, 2H), 3.94-3.43 (m, 5H), 2.34-1.94 (m, 2H). [ES+MS] m/z 430 (MH$^+$).

Chiral HPLC determination using ChiralPak AD-H 150×3 mm column (Hept/MeOH-EtOH (0.1% DEA) 10:90 (v/v), F=1.0 mL/min, R$_t$ isomer 1=5.73 min, R$_t$ isomer 2=9.48 min).

Examples 43a and 43b: 4-(1-(4-((R)-2-Hydroxy-3-(2H-tetrazol-2-yl)propoxy)benzoyl) pyrrolidin-3-yl) benzonitrile (isomer 1 and isomer 2)

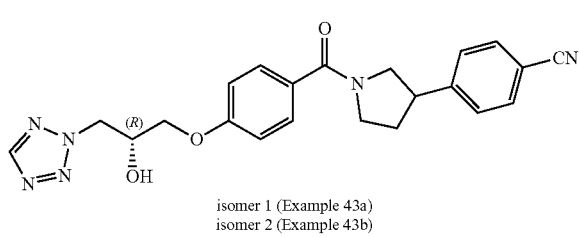

isomer 1 (Example 43a)
isomer 2 (Example 43b)

Examples 43a-b were prepared by method analogous to that described for Example 40a-b, replacing 3-(2-fluorophenyl)pyrrolidine hydrochloride by 4-(pyrrolidin-3-yl)benzonitrile hydrochloride (ASW MEDCHEM) and the diastereomeric mixture was separated using similar conditions.

isomer 1 (Example 43a)—First eluted in HPLC (130 mg, 40.6% yield, ee 100%). $^1$H NMR (300 MHz, DMSO-d$_6$) ppm: 8.98 (s, 1H), 7.86-7.75 (m, 2H), 762-7.45 (m, 4H), 7.05-6.95 (m, 2H), 5.65-5.58 (m, 1H), 4.95-4.76 (m, 2H), 4.40 (br.s, 1H), 4.15-4.04 (m, 2H), 3.99-3.41 (m, 5H), 2.39-1.94 (m, 2H). [ES+MS] m/z 419 (MH$^+$).

isomer 2 (Example 43b)—Second eluted in HPLC (120 mg, 37.5% yield, ee 100%). $^1$H NMR (300 MHz, DMSO-$d_6$) δ ppm: 8.98 (s, 1H), 7.86-7.75 (m, 2H), 762-7.45 (m, 4H), 7.05-6.95 (m, 2H), 5.65-5.58 (m, 1H), 4.95-4.76 (m, 2H), 4.40 (br.s, 1H), 4.15-4.04 (m, 2H), 3.99-3.41 (m, 5H), 2.39-1.94 (m, 2H). [ES+MS] m/z 419 (MH$^+$).

Chiral HPLC determination using ChiralPak AD-H 150×3 mm column (Hept/MeOH-EtOH (0.1% DEA) 10:90 (v/v), F=1.0 mL/min, R$_t$ isomer 1=7.30 min, R$_t$ isomer 2=13.22 min).

Example 44a and 44b: (4-((R)-2-Hydroxy-3-(2H-tetrazol-2-yl)propoxy)phenyl)(3-(4-methoxyphenyl)pyrrolidin-1-yl)methanone (isomer 1 and isomer 2)

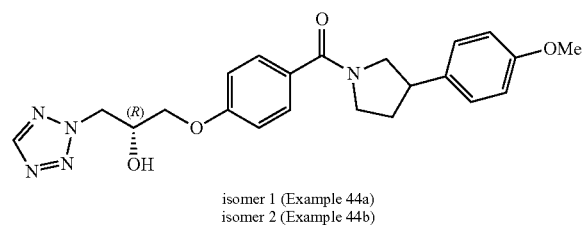

isomer 1 (Example 44a)
isomer 2 (Example 44b)

Examples 44 a-b were prepared by methods analogous to that described for Examples 40a-b, replacing 3-(2-fluorophenyl)pyrrolidine hydrochloride by 3-(4-methoxyphenyl)pyrrolidine hydrochloride (ASW MEDCHEM) and the diastereomeric mixture was separated using similar conditions.

isomer 1 (Example 44a)—First eluted in HPLC (133 mg, 41.1% yield, ee 100%). $^1$H NMR (300 MHz, DMSO-$d_6$) δ ppm: 8.97 (s, 1H), 7.55 (m, 2H), 729-7.17 (m, 2H), 7.04-6.83 (m, 2H), 5.64-5.59 (m, 1H), 4.94-4.76 (m, 2H), 4.40 (br.s, 1H), 4.12-4.04 (m, 2H), 3.80-3.37 (m, 3H), 2.30-1.87 (m, 2H). [ES+MS] m/z 424 (MH$^+$).

isomer 2 (Example 44b)—Second eluted in HPLC (129 mg, 39.8% yield, ee 100%). $^1$H NMR (300 MHz, DMSO-$d_6$) δ ppm: 8.97 (s, 1H), 7.55 (m, 2H), 729-7.17 (m, 2H), 7.04-6.83 (m, 2H), 5.64-5.59 (m, 1H), 4.94-4.76 (m, 2H), 4.40 (br.s, 1H), 4.12-4.04 (m, 2H), 3.80-3.37 (m, 3H), 2.30-1.87 (m, 2H). [ES+MS] m/z 424 (MH$^+$).

Chiral HPLC determination using ChiralPak AD-H 150×3 mm column (Hept/MeOH-EtOH (0.1% DEA) 10:90 (v/v), F=1.0 mL/min, R$_t$ isomer 1=6.30 min, R$_t$ isomer 2=10.48 min).

Intermediate 92: (S)-1-(4-((R)-3-(4-Fluorophenyl)pyrrolidine-1-carbonyl)phenoxy)-3-(2H-tetrazol-2-yl)propan-2-ylmethanesulfonate

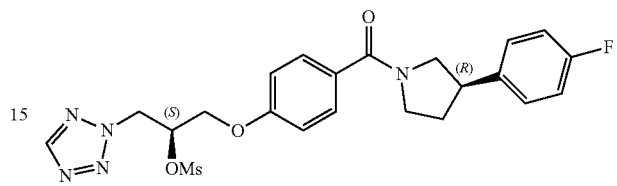

Methanesulfonyl chloride (SIGMA-ALDRICH, 0.091 mL, 1.167 mmol) was added dropwise to a solution of ((R)-3-(4-fluorophenyl)pyrrolidin-1-yl)(4-((S)-2-hydroxy-3-(2H-tetrazol-2-yl) propoxy)phenyl) methanone (Example 8, 320 mg, 0.778 mmol) in dry pyridine (SIGMA-ALDRICH, 2.1 mL, 26.0 mmol) at 0° C. The mixture was stirred at rt for 2 h till completion. The reaction mixture was poured into a mixture of ice, water (3 mL) and 6 M HCl (1 mL). Saturated aq. NH$_4$Cl solution was added and the mixture was extracted exhaustively with EtOAc. The combined organic layers were successively washed with sat. aq. NaHCO$_3$ sol. and brine. The organic layer was dried over Na$_2$SO$_4$, filtered and concentrated under reduced pressure to afford the title compound (368 mg, 97% yield). $^1$H NMR (300 MHz, CDCl$_3$) δ ppm: 8.63-8-58 (m, 1H), 7.61-7.54 (m, 2H), 7.30-7.13 (m, 2H), 7.08-6.89 (m, 4H), 5.53-5.43 (m, 1H), 5.24-5.07 (m, 2H), 4.37-4.28 (m, 2H), 3.95-3.30 (m, 5H), 2.94 (s, 3H), 2.44-2.24 (m, 1H), 2.18-1.92 (m, 1H).

Intermediates 93-95 were prepared using analogous conditions to that described for intermediate 92 but replacing ((R)-3-(4-fluorophenyl)pyrrolidin-1-yl)(4-((S)-2-hydroxy-3-(2H-tetrazol-2-yl)propoxy)phenyl)methanone with that indicated in Table 4.

TABLE 4

| Int. | Structure | starting int. | Physical data/Yield |
|---|---|---|---|
| 93 | (S)-1-(4-((R)-3-(4-fluorophenyl pyrrolidine-1-carbonyl)phenoxy)-3-(1H-tetrazol-1-yl)propan-2-yl methanesulfonate | Ex.6 | $^1$H NMR (300 MHz, CDCl$_3$) δ ppm: 8.82-8-77 (m, 1H), 7.61-7.53 (m, 2H), 7.32-7.13 (m, 2H), 7.09-6.86 (m, 4H), 5.40-5.30 (m, 1H), 4.99-4.93 (m, 2H), 4.32-4.09 (m, 2H), 3.94-3.31 (m, 5H), 2.99 (s, 3H), 2.42-2.24 (m, 1H), 2.16-1.91 (m, 1H). quant. yield |

TABLE 4-continued

| Int. | Structure | starting int. | Physical data/Yield |
|---|---|---|---|
| 94 | (S)-1-(4-((R)-3-(4-chlorophenyl)pyrrolidine-1-carbonyl)phenoxy)-3-(1H-tetrazol-1-yl)propan-2-yl methanesulfonate | 86 | $^1$H NMR (300 MHz, CDCl$_3$) δ ppm: 8.82-8-76 (m, 1H), 7.61-7.52 (m, 2H), 7.36-7.10 (m, 4H), 6.95-6.86 (m, 2H), 5.39-5.31 (m, 1H), 4.99-4.92 (m, 2H), 4.31-4.05 (m, 2H), 3.95-3.28 (m, 5H), 2.99 (s, 3H), 2.44-2.25 (m, 1H), 2.17-1.92 (m, 1H). quant. yield |
| 95 | (S)-1-(4-((R)-3-(4-chlorophenyl)pyrrolidine-1-carbonyl)phenoxy)-3-(2H-tetrazol-2-yl)propan-2-yl methanesulfonate | 87 | $^1$H NMR (300 MHz, CDCl$_3$) δ ppm: 8.70-8-65 (m, 1H), 7.61-7.51 (m, 2H), 7.36-7.10 (m, 4H), 6.99-6.88 (m, 2H), 5.54-5.43 (m, 1H), 5.24-5.05 (m, 2H), 4.38-4.28 (m, 2H), 3.95-3.28 (m, 5H), 2.95 (s, 3H), 2.46-2.24 (m, 1H), 2.19-1.89 (m, 1H). 98% yield |

Intermediate 96: (S)-Benzyl 4-(2-((methylsulfonyl)oxy)-3-(2H-tetrazol-2-yl)propoxy)benzoate

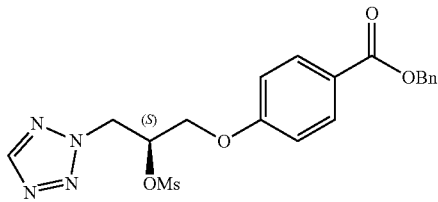

Methanesulfonyl chloride (SIGMA-ALDRICH, 1.187 mL, 15.24 mmol) was added dropwise to a solution of benzyl (S)-4-(2-hydroxy-3-(2H-tetrazol-2-yl)propoxy)benzoate (intermediate 27a, 3.6 g, 10.16 mmol) in dry pyridine (SIGMA-ALDRICH, 24 mL, 297 mmol) at 0° C. The mixture was stirred at room temperature for 3 h till completion. The reaction mixture was poured into a mixture of ice, water (12 mL) and 2 N HCl (4 mL). Saturated aq. NH$_4$Cl solution was added and the mixture was extracted exhaustively with EtOAc. The combined organic layers were successively washed with sat. aq. NaHCO$_3$ sol. and brine. The organic layer was dried over Na$_2$SO$_4$, filtered and concentrated under reduced pressure to afford the title compound (4.36 g, 99% yield)

Intermediate 97-101 were prepared using analogous conditions to that described for Intermediate 96 but replacing intermediate 27a with that indicated in Table 5.

TABLE 5

| Int. | Structure | starting int. | Physical data/Yield |
|---|---|---|---|
| 97 | (R)-benzyl 4-(2-((methylsulfonyl)oxy)-3-(2H-tetrazol-2-yl)propoxy)benzoate | 26a | $^1$H NMR (300 MHz, DMSO-d$_6$) δ ppm: 9.05 (s, 1H), 7.99 (d, J = 8.8 Hz, 2H), 7.50-7.32 (m, 5H), 7.12 (d, J = 9.1 Hz, 2H), 5.48-5.40 (m, 1H), 5.33 (s, 2H), 4.30-4.17 (m, 2H), 4.54-4.44 (m, 2H), 3.12 (s, 3H). 98% yield |

TABLE 5-continued

| Int. | Structure | starting int. | Physical data/Yield |
|---|---|---|---|
| 98 | 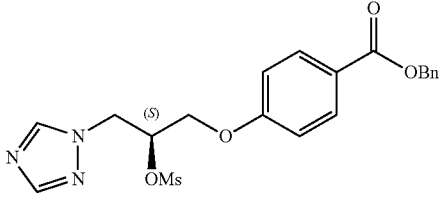<br>(S)-benzyl 4-(2-((methylsulfonyl)oxy)-3-(1H-1,2,4-triazol-1-yl)propoxy)benzoate | 30 | $^1$H NMR (300 MHz, CDCl$_3$) δ ppm: 8.22 (s, 1H), 8.06 (d, J = 8.8 Hz, 2H), 8.02 (s, 1H), 7.49-7.33 (m, 5H), 6.94 (d, J = 9.1 Hz, 2H), 5.35 (s, 2H), 5.35-5.27 (m, 1H), 4.69-4.63 (m, 2H), 4.41-4.21 (m, 2H), 2.87 (s, 3H).<br>quant. yield |
| 99 | 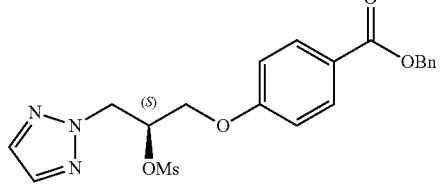<br>(S)-benzyl 4-(2-((methylsulfonyl)oxy)-3-(2H-1,2,3-triazol-2-yl)propoxy)benzoate | 32a | $^1$H NMR (300 MHz, CDCl$_3$) δ ppm: 8.06 (d, J = 8.8 Hz, 2H), 7.79-7.76 (m, 1H), 7.75-7.73 (m, 1H), 7.48-7.31 (m, 5H), 6.96 (d, J = 8.8 Hz, 2H), 5.39-5.30 (m, 3H), 4.91-4.86 (m, 2H), 4.38-4.13 (m, 2H), 2.91 (s, 3H).<br>96% yield |
| 100 | 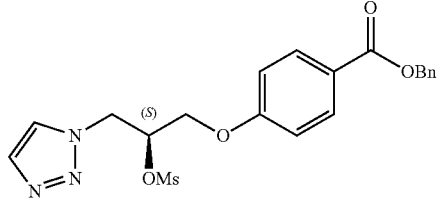<br>(S)-benzyl 4-(2-((methylsulfonyl)oxy)-3-(1H-1,2,3-triazol-1-yl)propoxy)benzoate | 32b | 1H NMR (300 MHz, CDCl$_3$) δ ppm: 8.06 (d, J = 8.8 Hz, 2H), 7.80-7.77 (m, 1H), 7.75-7.73 (m, 1H), 7.47-7.32 (m, 5H), 6.92 (d, J = 8.8 Hz, 2H), 5.38-5.31 (m, 3H), 4.91-4.86 (m, 2H), 4.38-4.15 (m, 2H), 2.91 (s, 3H).<br>87% yield |
| 101 | 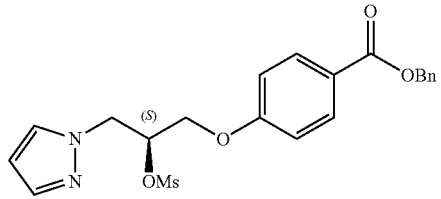<br>(S)-benzyl 4-(2-((methylsulfonyl)oxy)-3-(1H-pyrazol-1-yl)propoxy)benzoate | 34 | $^1$H NMR (300 MHz, CDCl$_3$) δ ppm: 8.05 (d, J = 9.1 Hz, 2H), 7.59 (d, J = 1.7 Hz, 1H), 7.53 (d, J = 2.0 Hz, 1H), 7.48-7.32 (m, 5H), 6.93 (d, J = 8.8 Hz, 2H), 6.34-6.29 (m, 1H), 5.35 (s, 2H), 5.33-5.26 (m, 1H), 4.67-4.51 (m, 2H), 4.40-4.16 (m, 2H), 2.74 (s, 3H).<br>97% yield |

Intermediate 102: (4-((R)-2-Azido-3-(2H-tetrazol-2-yl)propoxy)phenyl)((R)-3-(4-fluorophenyl) pyrrolidin-1-yl)methanone

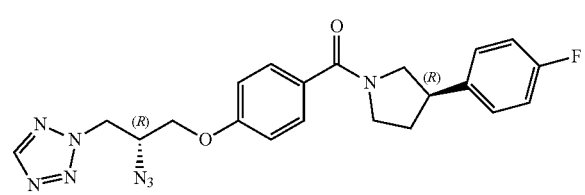

To a solution of (S)-1-(4-((R)-3-(4-fluorophenyl)pyrrolidine-1-carbonyl)phenoxy)-3-(2H-tetrazol-2-yl)propan-2-yl methanesulfonate (intermediate 92, 365 mg, 0.746 mmol) and trimethylsilyl azide (0.148 mL, 1.118 mmol) in THF (8 mL) was added a solution of TBAF in THF (1.0 M) (1.118 mL, 1.118 mmol). The reaction mixture was heated under reflux for 4 h. New additions of trimethylsilyl azide (86 mg×2) and TBAF in THF (1.0 M) (1.118 mL) were done to ensure completion of the reaction and the solution was heated to reflux. Upon completion of the reaction, the solvent was removed under vacuo and the crude material was purified by chromatography on silica gel and eluted with CyHex:EtOAc/EtOH (3/1) (from 100:0 to 50:50). The desired fractions were collected and the solvent was removed in vacuo to obtain the title compound (157 mg, 48.2% yield). $^1$H NMR (300 MHz, CDCl$_3$) δ ppm: 8.75-8-

72 (m, 1H), 7.61-7.53 (m, 2H), 7.36-7.10 (m, 4H), 6.97-6.89 (m, 2H), 4.83-4.56 (m, 2H), 4.41-4.04 (m, 3H), 3.94-3.28 (m, 5H), 2.44-2.25 (m, 1H), 2.17-1.93 (m, 1H).

Intermediates 103-105 were prepared using analogous conditions to that described for intermediate 102 but replacing intermediate 92 with that indicated in Table 6.

(14.78 mL, 14.78 mmol). The mixture was refluxed overnight. Water (100 mL) and EtOAc (300 mL) was added and the layers were separated. The organic layer was washed with brine, dried over $Na_2SO_4$, filtered and concentrated under reduced pressure. The crude material was chromatographed on silica gel and eluted with CyHex:EtOAc (from

TABLE 6

| Int. | Structure | starting int | Physical data/Yield |
|---|---|---|---|
| 103 | (4-((R)-2-azido-3-(1H-tetrazol-1-yl)propoxy)phenyl)((R)-3-(4-fluorophenyl)pyrrolidin-1-yl)methanone | 93 | $^1$H NMR (300 MHz, $CDCl_3$) δ ppm: 8.76-8-71 (m, 1H), 7.62-7.53 (m, 2H), 7.28-7.13 (m, 2H), 7.09-6.88 (m, 4H), 4.84-4.56 (m, 2H), 4.41-4.05 (m, 3H), 3.96-3.31 (m, 5H), 2.45-2.25 (m, 1H), 2.18-1.92 (m, 1H). 90% yield |
| 104 | (4-((R)-2-azido-3-(1H-tetrazol-1-yl)propoxy)phenyl)((R)-3-(4-chlorophenyl)pyrrolidin-1-yl)methanone | 94 | $^1$H NMR (300 MHz, $CDCl_3$) δ ppm: 8.76-8-70 (m, 1H), 7.61-7.52 (m, 2H), 7.36-7.10 (m, 4H), 6.97-6.89 (m, 2H), 4.82-4.56 (m, 2H), 4.40-4.05 (m, 3H), 3.95-3.28 (m, 5H), 2.44-2.25 (m, 1H), 2.17-1.93 (m, 1H). 71.5% yield |
| 105 | (4-((R)-2-azido-3-(2H-tetrazol-2-yl)propoxy)phenyl)((R)-3-(4-chlorophenyl)pyrrolidin-1-yl)methanone | 95 | $^1$H NMR (300 MHz, $CDCl_3$) δ ppm: 8.60 (s, 1H), 7.61-7.52 (m, 2H), 7.35-7.10 (m, 4H), 6.99-6.90 (m, 2H), 5.00-4.91 (m, 2H), 4.28-4.14 (m, 3H), 3.96-3.27 (m, 5H), 2.45-2.24 (m, 1H), 2.16-1.93 (m, 1H). 54.2% yield |

Intermediate 106: (R)-Benzyl 4-(2-azido-3-(2H-tetrazol-2-yl)propoxy)benzoate

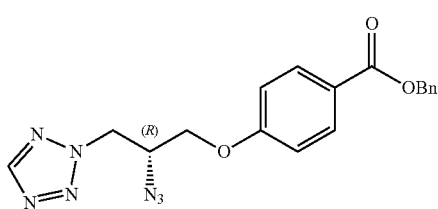

Intermediate 106 was prepared via two alternative routes.

Method A: Using $TMSN_3$ as Azidation Reagent

To a solution of benzyl (S)-4-(2-((methylsulfonyl)oxy)-3-(2H-tetrazol-2-yl)propoxy)benzoate (intermediate 96, 4.26 g, 9.85 mmol) and $TMSN_3$ (2.61 mL, 19.70 mmol) in THF (99 mL) was added a solution of TBAF in THF (1.0 M) 100:0 to 60:40). The desired fractions were collected and the solvent was removed in vacuo to obtain the title compound (1.48 g, 39.6% yield).

Method B: Using $NaN_3$ as as Azidation Reagent

To a solution of benzyl (S)-4-(2-((methylsulfonyl)oxy)-3-(2H-tetrazol-2-yl)propoxy)benzoate (intermediate 96, 1.6 g, 3.70 mmol) in DMF (37.0 mL), $NaN_3$ (0.481 g, 7.40 mmol) was added. The mixture was heated at 80° C. for 6 h. The mixture was partitioned between EtOAc and water, and the layers were separated. The organic layer washed with brine, dried over $Na_2SO_4$, filtered and concentrated under reduced pressure. The crude material was chromatographed on silica gel and eluted with CyHex:EtOAc/EtOH (3/1) (from 100:0 to 70:30). The desired fractions were collected and the solvent was removed in vacuo to obtain the title compound (567 mg, 40.4% yield). $^1$H NMR (300 MHz, $CDCl_3$) δ ppm: 8.60 (s, 1H), 8.05 (d, J=8.8 Hz, 2H), 7.48-7.32 (m, 5H), 6.95 (d, J=8.8 Hz, 2H), 5.36 (s, 2H), 5.00-4.90 (m, 2H), 4.51-4.43 (m, 1H), 4.29-4.18 (m, 2H).

Intermediate 107-111 were prepared using analogous conditions described in Method B for intermediate 106 (Table 7).

TABLE 7

| Int. | Structure | starting int. | Physical data/Yield |
|---|---|---|---|
| 107 | (S)-benzyl 4-(2-azido-3-(2H-tetrazol-2-yl)propoxy)benzoate | 97 | ¹H NMR (300 MHz, DMSO-d₆) δ ppm: 9.08 (s, 1H), 7.99 (d, J = 9.1 Hz, 2H), 7.50-7.32 (m, 5H), 7.11 (d, J = 8.8 Hz, 2H), 5.33 (s, 2H), 5.16-4.96 (m, 2H), 4.67-4.59 (m, 1H), 4.48-4.27 (m, 2H). 43.4% yield. |
| 108 | (R)-benzyl 4-(2-azido-3-(1H-1,2,4-triazol-1-yl)propoxy)benzoate | 98 | ¹H NMR (300 MHz, CDCl₃) δ ppm: 8.16 (s, 1H), 8.06 (d, J = 8.8 Hz, 2H), 8.01 (s, 1H), 7.48-7.32 (m, 5H), 6.94 (d, J = 9.1 Hz, 2H), 5.36 (s, 2H), 4.55-4.30 (m, 3H), 4.27-4.08 (m, 2H). 82% yield. |
| 109 | (R)-benzyl 4-(2-azido-3-(2H-1,2,3-triazol-2-yl)propoxy)benzoate | 99 | ¹H NMR (300 MHz, CDCl₃) δ ppm: 8.06 (d, J = 8.8 Hz, 2H), 7.69 (s, 2H), 7.49-7.32 (m, 5H), 6.94 (d, J = 9.1 Hz, 2H), 5.35 (s, 2H), 4.79-4.68 (m, 2H), 4.47-4.37 (m, 1H), 4.23-4.11 (m, 2H). 83% yield. |
| 110 | (R)-benzyl 4-(2-azido-3-(1H-1,2,3-triazol-1-yl)propoxy)benzoate | 100 | ¹H NMR (300 MHz, CDCl₃) δ ppm: 8.06 (d, J = 8.8 Hz, 2H), 7.76 (d, J = 0.8 Hz, 1H), 7.69 (d, J = 0.8 Hz, 1H), 7.48-7.32 (m, 5H), 6.94 (d, J = 9.1 Hz, 2H), 5.36 (s, 2H), 4.77-4.53 (m, 2H), 4.38-4.31 (m, 1H), 4.28-4.22 (m, 1H), 4.10-4.05 (m, 1H). 94% yield |
| 111 | (R)-benzyl 4-(2-azido-3-(1H-pyrazol-1-yl)propoxy)benzoate | 101 | ¹H NMR (300 MHz, CDCl₃) δ ppm: 8.05 (d, J = 8.8 Hz, 2H), 7.59 (d, J = 1.8 Hz, 1H), 7.49-7.32 (m, 5H), 6.93 (d, J = 9.1 Hz, 2H), 6.30 (t, J = 2.0 Hz, 1H), 5.35 (s, 2H), 4.51-4.27 (m, 3H), 4.22-4.16 (m, 1H), 4.06-4.00 (m, 1H). 71.9% yield |

Intermediate 112: (R)-4-(2-((tert-Butoxycarbonyl)amino)-3-(2H-tetrazol-2-yl)propoxy)benzoic acid

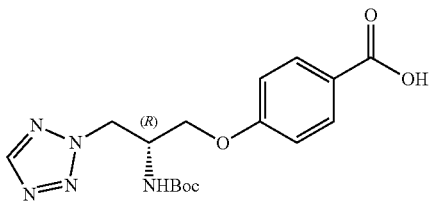

To a solution of benzyl (R)-4-(2-azido-3-(2H-tetrazol-2-yl)propoxy)benzoate (intermediate 106, 3.8 g, 10.02 mmol) in MeOH/THF (71.5 mL/28.6 mL) was added palladium 10% on activated carbon (SIGMA-ALDRICH, 150 mg, 1.410 mmol) and the mixture was stirred under a balloon filled with $H_2$ at room temperature overnight. The mixture was filtered, washed with MeOH and DMF, and the solution obtained was concentrated to give 2.9 g (quant. yield) of intermediate (R)-4-(2-amino-3-(2H-tetrazol-2-yl)propoxy)benzoic acid that was used without further purification.

$Boc_2O$(SIGMA-ALDRICH, 3.28 g, 15.04 mmol) in DCM (25 mL) was added to a solution of (R)-4-(2-amino-3-(2H-tetrazol-2-yl)propoxy)benzoic acid (2.64 g, 10.03 mmol) in DCM/DMF (25 mL/50.0 mL) at r.t. The mixture was stirred at rt for 2 h. Upon completion of the reaction, the mixture was partitioned between water and DCM, and the layers were separated. The organic layer was dried over $Na_2SO_4$, filtered and concentrated to give the title compound (4.35 g, quant. yield) that was used without further purification.

Intermediate 113-117 were prepared using analogous conditions to that described for Intermediate 112 but replacing intermediate 106 with that indicated in Table 8. Modifications in the protocol are also indicated.

TABLE 8

| Int. | Structure | starting int. | Physical data/Yield |
|---|---|---|---|
| 113 | (S)-4-(2-((tert-butoxycarbonyl)amino)-3-(2H-tetrazol-2-yl)propoxy)benzoic acid | 107 | $^1$H NMR (300 MHz, DMSO-$d_6$) 12.68 (br. s, 1H), 8.96 (s, 1H), 7.89 (d, J = 8.8 Hz, 2H), 7.20 (d, J = 8.8 Hz, 1H), 7.01 (d, J = 8.8 Hz, 2H), 4.97 (dd, J = 13.9, 4.5 Hz, 1H), 4.54 (dd, J = 13.6, 8.3 Hz, 1H), 4.39-4.27 (m, 1H), 4.12 (d, J = 6.1 Hz, 2H), 1.31 (s, 9H). 91% yield See footnote a), b), c) |
| 114 | (R)-4-(2-((tert-butoxycarbonyl)amino)-3-(1H-1,2,4-triazol-1-yl)propoxy)benzoic acid | 108 | $^1$H NMR (300 MHz, DMSO-$d_6$) 12.68 (br. s, 1H), 8.42 (s, 1H), 7.97 (s, 1H), 7.88 (d, J = 8.8 Hz, 2H), 7.71 (s, 1H), 7.13 (d, J = 8.3 Hz, 1H), 7.00 (d, J = 8.8 Hz, 2H), 4.43 (dd, J = 13.9, 5.1 Hz, 1H), 4.54 (dd, J = 13.9, 8.6 Hz, 1H), 4.26-4.16 (m, 1H), 4.08-4.00 (m, 2H), 1.33 (s, 9H). quant. yield See footnote a), b), c) |
| 115 | (R)-4-(2-((tert-butoxycarbonyl)amino)-3-(2H-1,2,3-triazol-2-yl)propoxy)benzoic acid | 109 | $^1$H NMR (300 MHz, $CD_2Cl_2$) δ ppm: 12.65 (br. s, 1H), 7.88 (d, J = 8.8 Hz, 2H), 7.83-7.74 (m, 2H), 7.12-7.07 (m, 1H), 6.98 (d, J = 8.6 Hz, 2H), 4.66 (dd, J = 13.6, 5.6 Hz, 1H), 4.54 (dd, J = 13.6, 7.6 Hz, 1H), 4.35-4.26 (m, 1H), 4.01 (d, J = 5.6 Hz, 2H), 1.33 (s, 9H). 99% yield See footnote a), b), c) |

TABLE 8-continued

| Int. | Structure | starting int. | Physical data/Yield |
|---|---|---|---|
| 116 | (R)-4-(2-((tert-butoxycarbonyl)amino)-3-(1H-1,2,3-triazol-1-yl)propoxy) benzoic acid | 110 | $^1$H NMR (300 MHz, DMSO-$d_6$) 12.64 (br. s, 1H), 8.06 (d, J = 0.8 Hz 1H), 7.89 (d, J = 8.6 Hz, 2H), 7.71 (s, 1H), 7.20-7.15 (m, 1H), 7.02 (d, J = 8.8 Hz, 2H), 4.67 (dd, J = 13.9, 5.1 Hz, 1H), 4.54 (dd, J = 13.9, 8.6 Hz, 1H), 4.31-4.18 (m, 1H), 4.05 (d, J = 5.6 Hz, 2H), 1.32 (s, 9H). 99% yield See footnote a), b), c) |
| 117 | (R)-4-(2-((tert-butoxycarbonyl)amino)-3-(1H-pyrazol-1-yl)propoxy)benzoic acid | 111 | $^1$H NMR (300 MHz, DMSO-$d_6$) 12.63 (br. s, 1H), 7.88 (d, J = 8.8 Hz, 2H), 7.66 (d, J = 1.8 Hz, 1H), 7.45 (d, J = 1.3 Hz, 1H), 7.09 (d, J = 7.8 Hz, 1H), 6.99 (d, J = 8.8 Hz, 2H), 6.22 (t, J = 1.8 Hz, 1H), 4.34 (dd, J = 13.4, 5.6 Hz, 1H), 4.28-4.14 (m, 2H), 4.02-3.90 (m, 2H), 1.35 (s, 9H). 89% yield See footnote a), b), c) | b) The hydrogenation reaction was performed in EtOAc c) After completion hydrogenation reaction, the reaction was purged with $N_2$ and vacuum and $Boc_2O$ in DMF was added over.

d) The mixture was filtered thought a Celite pad and washed with MeOH and EtOAc, the solution was concentrated to give a solid. The solid was washed with water and dried to dive the title compound.

Intermediate 118: Methyl (S)-2-fluoro-4-(2-((methylsulfonyl)oxy)-3-(2H-tetrazol-2-yl)propoxy)benzoate Intermediate 119: Methyl(R)-4-(2-azido-3-(2H-tetrazol-2-yl)propoxy)-2-fluorobenzoate

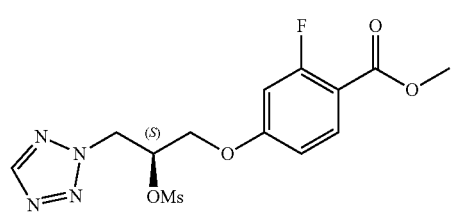

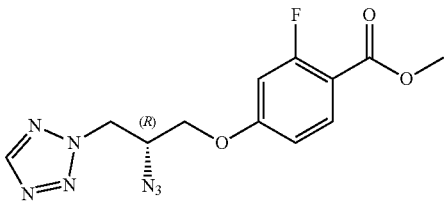

Methanesulfonyl chloride (SIGMA-ALDRICH, 400 µl, 5.13 mmol) was added dropwise to a solution of methyl (S)-2-fluoro-4-(2-hydroxy-3-(2H-tetrazol-2-yl)propoxy) benzoate (intermediate 83a, 980 mg, 3.31 mmol) in dry pyridine (SIGMA-ALDRICH, 8.0 mL, 99 mmol) at 0° C. The mixture was stirred at rt for 2 h. The reaction mixture was poured into a mixture of ice, water (5 mL) and 2 N HCl (10 mL). EtOAc was added and the layer separated. The organic layer was washed with 2 N HCl, sat. $Na_2CO_3$ and brine, dried over $Na_2SO_4$ and concentrated under reduced pressure. The crude material containing pyridine was redissolved in toluene and concentrated, this process was repeated 2 times to eliminate pyridine. The title compound (1.3 g, quant. yield) was used without further purification. $^1$H NMR (300 MHz, CDCl$_3$) δ ppm: 8.61 (s, 1H), 7.96 (t, J=8.6 Hz, 1H), 6.78 (dd, J=8.6, 2.3 Hz, 1H), 6.69 (dd, J=11.9, 2.3 Hz, 1H), 5.53-5.45 (m, 1H), 5.22-5.09 (m, 2H), 4.39-4.29 (m, 2H), 3.92 (s, 3H), 2.96 (s, 3H).

To a solution of methyl (S)-2-fluoro-4-(2-((methylsulfonyl)oxy)-3-(2H-tetrazol-2-yl)propoxy) benzoate (intermediate 118, 1.3 g, 3.47 mmol) in DMF (35 mL) was added $NaN_3$ (PAN REAC APPLICHEM, 0.903 g, 13.89 mmol). The mixture was heated at 80° C. overnight. After cooling, the mixture was partitioned between EtOAc and sat. aq. $NH_4Cl$ solution, the layers were separated and the organic layer washed with sat. aq. $Na_2CO_3$ solution, and brine, dried over $Na_2SO_4$ and concentrated under reduced pressure. The crude material was purified by chromatography on silica gel and eluted with CyHex:EtOAc (from 100:00 to 70:30) to give the title compound (480 mg, 43.0% yield). $^1$H NMR (300 MHz, CDCl$_3$) δ ppm: 8.60 (s, 1H), 7.95 (t, J=8.6 Hz, 1H), 6.76 (dd, J=8.8, 2.3 Hz, 1H), 6.69 (dd, J=12.1, 2.5 Hz, 1H), 4.99-4.91 (m, 2H), 4.52-4.43 (m, 1H), 4.27-4.16 (m, 2H), 3.92 (s, 3H).

Intermediate 120: Methyl(R)-4-(2-((tert-butoxycarbonyl)amino)-3-(2H-tetrazol-2-yl)propoxy)-2-fluorobenzoate

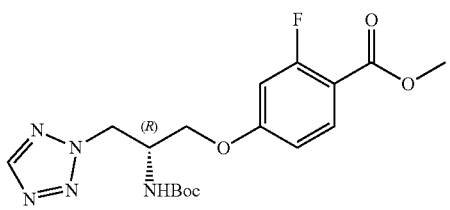

To a solution of palladium 10% on activated carbon (SIGMA-ALDRICH, 50 mg, 0.470 mmol) in EtOAc (15 mL) was added methyl (R)-4-(2-azido-3-(2H-tetrazol-2-yl)propoxy)-2-fluorobenzoate (intermediate 119, 480 mg, 1.494 mmol) and the mixture was stirred under a balloon filled with $H_2$ at rt overnight. Upon completion of the reaction, the reaction was purged with nitrogen and vacuum, and $Boc_2O$ (SIGMA-ALDRICH, 489 mg, 2.241 mmol) in DMF (7.00 mL) was added. The new mixture was stirred at room temperature for 2 h. The mixture was filtered thought a Celite pad, the Celite pad was washed with MeOH and EtOAc, and the solution was concentrated under reduced pressure. It was partitioned between EtOAc and water, the layers were separated and the aqueous layer extracted with EtOAc (×2). The combined organic layers were dried over $Na_2SO_4$, filtered and concentrated to give the title compound (605 mg, quant. yield). $^1$H NMR (300 MHz, $CDCl_3$) δ ppm: 8.55 (s, 1H), 7.93 (t, J=8.6 Hz, 1H), 6.71 (dd, J=8.6, 2.3 Hz, 1H), 6.63 (dd, J=12.1, 2.5 Hz, 1H), 5.25-5.16 (m, 1H), 5.01-4.90 (m, 2H), 4.60 (br.s, 1H), 4.12 (dd, J=9.3, 3.3 Hz, 1H), 4.02 (dd, J=9.3, 5.3 Hz, 1H), 3.91 (s, 3H), 1.43 (s, 9H).

Intermediate 121: (R)-4-(2-((tert-Butoxycarbonyl)amino)-3-(2H-tetrazol-2-yl)propoxy)-2-fluoro benzoic acid

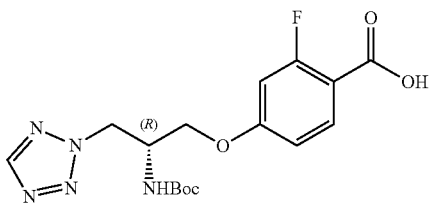

LiOH.$H_2O$ (SIGMA-ALDRICH, 127 mg, 3.03 mmol) in water (4.00 mL) was added to a solution of methyl (R)-4-(2-((tert-butoxycarbonyl)amino)-3-(2H-tetrazol-2-yl)propoxy)-2-fluorobenzoate (intermediate 120, 600 mg, 1.517 mmol) in THF (12 mL). The mixture was stirred at rt overnight. The reaction mixture was partitioned between EtOAc and 2 N HCl, the phases were separated and the aqueous layer was extracted with EtOAc. The combined organic layers were dried over anh. $Na_2SO_4$, filtered and evaporated to dryness under vacuum to give the title compound (515 mg, 89% yield) as a white solid. $^1$H NMR (300 MHz, DMSO-$d_6$) δ ppm: 12.88 (br.s, 1H), 8.96 (s, 1H), 7.84 (t, J=8.7 Hz, 1H), 7.20 (d, J=8.8 Hz, 1H), 6.94-6.83 (m, 2H), 4.96 (dd, J=13.6, 4.6 Hz, 1H), 4.84-4.75 (m, 1H), 4.39-4.26 (m, 1H), 4.18-4.08 (m, 2H), 1.30 (s, 9H).

Intermediate 122: tert-Butyl ((R)-1-(4-((R)-3-(4-fluorophenyl)pyrrolidine-1-carbonyl)phenoxy)-3-(2H-tetrazol-2-yl)propan-2-yl)carbamate

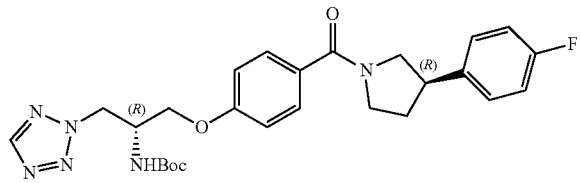

To a solution of (R)-4-(2-((tert-butoxycarbonyl)amino)-3-(2H-tetrazol-2-yl)propoxy)benzoic acid (intermediate 112, 3.64 g, 10.02 mmol), (R)-3-(4-fluorophenyl)pyrrolidine hydrochloride (intermediate 3b, 2.424 g, 12.02 mmol) and DIPEA (SIGMA-ALDRICH, 5.25 mL, 30.1 mmol) in anh. DMF (150 mL) at 0° C. under nitrogen atmosphere was added COMU (ALFA AESAR, 5.58 g, 13.02 mmol) and the reaction mixture was stirred at 0° C. for 1 h and then at rt overnight. The mixture was quenched by the dropwise addition of water, and the resulting mixture was then partitioned between EtOAc and sat. aq. $NH_4Cl$. The phases were separated and the organic layer was washed with sat. $Na_2CO_3$ sol. and brine. The organic layer was dried over anh. $Na_2SO_4$, filtered and evaporated to dryness under vacuum The residue was purified by flash chromatography on silica gel using a gradient of CyHex:EtOAc/EtOH (3/1) (from 100:0 to 70:30). The desired fractions were collected and the solvent was removed in vacuo to obtain 3.86 g of the title compound impurified with COMU. A second purification by chiral SFC was done (CHIRALPAK AD-H 20×250 mm column, $CO_2$:MeOH 70:30, F=70 mL/min) to afford 2.68 g of the title compound (52.4% yield, ee 100%) as a yellow oil. $^1$H NMR (300 MHz, DMSO-$d_6$) δ ppm: 8.95 (s, 1H), 7.54 (d, J=8.6 Hz, 2H), 7.43-7.26 (m, 2H), 7.22-7.07 (m, 2H), 7.02-6.90 (m, 2H), 5.01-4.72 (m, 2H), 4.38-4.25 (m, 1H), 4.14-4.01 (m, 2H), 3.95-3.35 (m, 5H), 2.31-2.13 (m, 1H), 2.09-1.86 (m, 1H), 1.29 (s, 9H)

Intermediate 123-130 were prepared using analogous conditions to that described for example 122 but replacing intermediates with that indicated in Table 9.

TABLE 9

| Int. | Structure | Int. | Physical data/Yield |
|---|---|---|---|
| 123 | tert-butyl ((S)-1-(4-((R)-3-(4-fluoro phenyl)pyrrolidine-1-carbonyl)phenoxy)-3-(2H-tetrazol-2-yl)propan-2-yl) carbamate | 113/3b | $^1$H NMR (300 MHz, DMSO-$d_6$) δ ppm: 8.95 (s, 1H), 7.54 (d, J = 8.6 Hz, 2H), 7.43-7.28 (m, 2H), 7.23-7.09 (m, 2H), 7.02-6.92 (m, 2H), 5.02-4.72 (m, 2H), 4.40-4.25 (m, 2H), 4.17-4.03 (m, 2H), 3.96-3.35 (m, 5H), 2.33-2.18 (m, 1H), 2.11-1.89 (m, 1H), 1.30 (s, 9H) 87.2% yield (ee 100%) See footnote a), e) |
| 124 | tert-butyl ((R)-1-(4-((S)-3-(4-fluoro phenyl)pyrrolidine-1-carbonyl)phenoxy)-3-(2H-tetrazol-2-yl)propan-2-yl) carbamate | 112/3c | [ES + MS] m/z 511 (MH$^+$). 56.7% yield (ee 100%) See footnote a), e) |
| 125 | tert-butyl ((S)-1-(4-((S)-3-(4-fluoro phenyl)pyrrolidine-1-carbonyl)phenoxy)-3-(2H-tetrazol-2-yl)propan-2-yl) carbamate | 113/3c | [ES + MS] m/z 511 (MH$^+$). 73.1% yield (ee 100%) See footnote a), e) |
| 126 | tert-butyl ((R)-1-(4-((R)-3-(4-fluoro phenyl)pyrrolidine-1-carbonyl)phenoxy)-3-(1H-1,2,4-triazol-1-yl)propan-2-yl) carbamate | 114/3b | $^1$H NMR (300 MHz, DMSO-$d_6$) δ ppm: 8.41 (s, 1H), 7.97 (s, 1H), 7.54 (d, J = 8.6 Hz, 2H), 7.42-7.28 (m, 2H), 7.21-7.08 (m, 3H), 7.03-6.90 (m, 2H), 4.47-4.13 (m, 3H), 407-3.96 (m, 2H), 3.82-3.35 (m, 5H), 2.32-2.12 (m, 1H), 2.12-1.89 (m, 1H), 1.32 (s, 9H). 61.6% yield (ee 100%) See footnote c), f) |
| 127 | tert-butyl ((R)-1-(4-((R)-3-(4-fluoro phenyl)pyrrolidine-1-carbonyl)phenoxy)-3-(2H-1,2,3-triazol-2-yl)propan-2-yl) carbamate | 115/3b | $^1$H NMR (300 MHz, DMSO-$d_6$) δ ppm: 7.78 (s, 1H), 7.53 (d, J = 8.6 Hz, 2H), 7.45-7.27 (m, 2H), 7.21-7.04 (m, 3H), 7.01-6.89 (m, 2H), 4.71-4.46 (m, 2H), 4.36-4.22 (m, 1H), 4.06-3.91 (m, 2H), 3.80-3.34 (m, 5H), 2.32-2.13 (m, 1H), 2.11-1.89 (m, 1H), 1.32 (s, 9H). 61.6% yield (ee 100%) See footnote c), g) |

TABLE 9-continued

| Int. | Structure | Int. | Physical data/Yield |
|---|---|---|---|
| 128 | tert-butyl ((R)-1-(4-((R)-3-(4-fluorophenyl)pyrrolidine-1-carbonyl)phenoxy)-3-(1H-1,2,3-triazol-1-yl)propan-2-yl)carbamate | 116/3b | $^1$H NMR (300 MHz, DMSO-d$_6$) δ ppm: 8.05 (s, 1H), 7.71 (s, 1H), 7.54 (d, J = 8.6 Hz, 2H), 7.43-7.27 (m, 2H), 7.22-7.07 (m, 3H), 7.03-6.91 (m, 2H), 4.71-4.40 (m, 2H), 4.29-4.17 (m, 1H), 4.10-3.97 (m, 2H), 3.95-3.35 (m, 5H), 2.32-2.13 (m, 1H), 2.08-1.89 (m,1H), 1.31 (s, 9H). 72.2% yield (ee 100%) See footnote c), h) |
| 129 | tert-butyl ((R)-1-(4-((R)-3-(4-fluorophenyl)pyrrolidine-1-carbonyl)phenoxy)-3-(1H-pyrazol-1-yl)propan-2-yl)carbamate | 117/3b | $^1$H NMR (300 MHz, DMSO-d$_6$) δ ppm: 7.66 (s, 1H), 7.53 (d, J = 8.6 Hz, 2H), 7.45 (s, 1H), 7.41-7.27 (m, 2H), 7.20-7.04 (m, 3H), 7.00-6.88 (m, 2H), 4.38-4.10 (m, 3H), 4.01-3.84 (m, 2H), 3.82-3.33 (m, 5H), 2.33-2.15 (m, 1H), 2.11-1.87 (m,1H), 1.33 (s, 9H). 80.4% yield (ee 100%) See footnote c), h) |
| 130 | tert-butyl ((R)-1-(3-fluoro-4-((R)-3-(4-fluorophenyl)pyrrolidine-1-carbonyl)phenoxy)-3-(2H-tetrazol-2-yl)propan-2-yl)carbamate | 121/3b | $^1$H NMR (300 MHz, CDCl$_3$) δ ppm: 8.57-8.52 (m, 1H), 7.46-7.38 (m, 1H), 7.26-7.13 (m, 2H), 7.08-6.96 (m, 2H), 6.77-6.69 (m, 1H), 6.66-6.57 (m, 1H), 5.09-4.89 (m, 2H), 4.65-4.53 (m, 1H), 4.17-3.87 (m, 3H), 3.79-3.31 (m, 5H), 2.45-2.23 (m, 1H), 2.17-1.94 (m,1H), 1.43 (s, 9H). 65.0% yield (ee 99%) See footnote b), d) | c) Purification on silica gel (CyHex/EtOAc 100/0 to 0/80)
d) Purification on silica gel (CyHex/EtOAc 100/0 to 0/100)
e) Purification on silica gel (DCM/MeOH 100/0 to 95/5)
f) Purification by Chiral SFC (ChiralPak AD-H 250 × 20 mm column, CO$_2$:MeOH 70:30 (v/v)).
g) Purification by Chiral SFC (ChiralPak IA 250 × 20 mm column, CO$_2$:iPrOH 60:40 (v/v)).
h) Purification by Chiral HPLC (ChiralPak AD-H 250 × 20 mm column, Heptane:MeOH/EtOH 50:50 (v/v)).
i) Purification by Chiral HPLC (ChiralPak IA 250 × 20 mm column, Heptane:EtOH 10:90 (v/v)).
j) Purification by Chiral HPLC (ChiralPak IA 250 × 20 mm column, Heptane:iPrOH 65:35 (v/v)).

Example 45: (4-((R)-2-Amino-3-(2H-tetrazol-2-yl)propoxy)phenyl)((R)-3-(4-fluorophenyl) pyrrolidin-1-yl)methanone

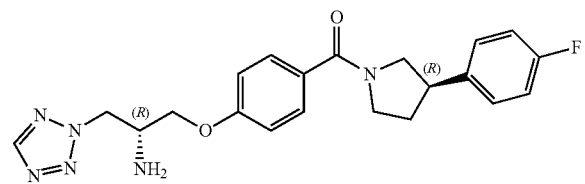

Example 45 was prepared via two alternative routes and could be isolated either as free base or as hydrochloride salt.
Route A: Via Intermediate 102.
To a solution of (4-((R)-2-azido-3-(2H-tetrazol-2-yl)propoxy)phenyl)((R)-3-(4-fluorophenyl) pyrrolidin-1-yl)methanone (intermediate 102, 157 mg, 0.360 mmol) in MeOH/THF (5.56 mL/2.22 mL) was added palladium 10% on activated carbon (SIGMA-ALDRICH, 22.97 mg, 0.216 mmol) and the mixture was stirred under a balloon filled with H$_2$ at rt overnight. Upon completion of the reaction, the mixture was filtered thought a Celite pad, and the solution was evaporated to dryness. The crude material was purified by chromatography on silica gel and eluted with CyHex: EtOAc/EtOH (3/1) (from 100:0 to 0:100). The desired fractions were collected and solvents evaporated in vacuo. The residue was lyophilized to yield the title compound (82 mg, 55.5% yield, white solid) as a free base.
Route B: Via Intermediate 122.
To tert-butyl ((R)-1-(4-((R)-3-(4-fluorophenyl)pyrrolidine-1-carbonyl)phenoxy)-3-(2H-tetrazol-2-yl)propan-2-yl)carbamate (intermediate 122, 2.68 g, 5.25 mmol) was added 4 M HCl solution in dioxane (SIGMA-ALDRICH, 13.12 mL, 52.5 mmol) and the mixture was stirred at rt for 4 h. Upon completion, the mixture was concentrated under reduced pressure to give the crude hydrochloride. The crude material was loaded onto a SCX column, washed with MeOH and then the product was eluted with a 2 M NH₃ in MeOH solution (SIGMA-ALDRICH). The desired fractions were collected and the solvent was removed in vacuo to give the title compound (1.99 g, 92% yield, ee 100%) as a free base (a white solid which became an oil upon standing). Chiral SFC determination using Chiral Pak IA 150×3 mm column (CO$_2$/EtOH (1% DEA) 50:50 (v/v), F=3.0 mL/min, R$_t$=2.77 min). $^1$H NMR (300 MHz, DMSO-d$_6$) δ ppm: 8.98-8.93 (m, 1H), 7.54 (d, J=8.6 Hz, 2H), 7.43-7.28 (m, 2H), 7.20-7.08 (m, 2H), 6.99-6.90 (m, 2H), 4.90-4.66 (m, 2H), 4.03-3.35 (m, 8H), 2.35-2.15 (m, 1H), 2.10-1.88 (m, 1H). [ES+MS] m/z 411 (MH$^+$).

To a solution of (4-((R)-2-amino-3-(2H-tetrazol-2-yl) propoxy)phenyl)((R)-3-(4-fluorophenyl) pyrrolidin-1-yl) methanone (1.9 g, 4.63 mmol) in DCM (5 mL), 3 M HCl solution in MeOH (1.697 mL, 5.09 mmol) was added and the resulting solution was stirred at rt overnight. The solvents were evaporated in vacuo, Et$_2$O was added, and then the solution was concentrated under reduced pressure to give the title compound as a hydrochloride salt (1.9 g, 92% yield, as a white solid). $^1$H NMR (300 MHz, DMSO-d$_6$) δ ppm: 9.06-9.01 (m, 1H), 7.54 (d, J=8.6 Hz, 2H), 7.43-7.28 (m, 2H), 7.21-7.09 (m, 2H), 7.03-6.92 (m, 2H), 6.37 (br.s, 3H), 5.10-4.89 (m, 2H), 4.21-3.34 (m, 8H), 2.32-2.14 (m, 1H), 2.10-1.85 (m, 1H). [ES+MS] m/z 411 (MH$^+$).

Examples 46-48 were prepared using analogous conditions to that described for route A of example 45 but replacing intermediate 102 with that indicated in Table 10. Modifications in the protocol or in purification step are also indicated.

TABLE 10

| Int. | Structure | Int. | Physical data/Yield |
|---|---|---|---|
| 46 | (4-((R)-2-amino-3-(1H-tetrazol-1-yl)propoxy)phenyl)((R)-3-(4-fluorophenyl) pyrrolidin-1-yl)methanone | 103 | $^1$H NMR (300 MHz, DMSO-d$_6$) δ ppm: 9.37 (s, 1H), 7.55 (d, J = 8.6 Hz, 2H), 7.43-7.28 (m, 2H), 7.21-7.09 (m, 2H), 7.01-6.91 (m, 2H), 4.69-4.41 (m, 2H), 4.01-3.35 (m, 8H), 2.36-1.74 (m, 4H). [ES + MS] m/z 411 (MH$^+$). 65.8 % yield See footnote b) |
| 47 | (4-((R)-2-amino-3-(1H-tetrazol-1-yl) propoxy)phenyl)((R)-3-(4-chlorophenyl) pyrrolidin-1-yl)methanone | 104 | $^1$H NMR (300 MHz, DMSO-d$_6$) δ ppm: 9.36 (s, 1H), 7.54 (d, J = 8.6 Hz, 2H), 7.43-7.28 (m, 4H), 7.00-6.92 (m, 2H), 4.69-4.39 (m, 2H), 3.98-3.34 (m, 8H), 2.36-1.66 (m, 4H). [ES + MS] m/z 427 (MH$^+$). 55.4% yield See footnote a), b) |
| 48 | (4-((R)-2-amino-3-(2H-tetrazol-2-yl) propoxy)phenyl)((R)-3-(4-chlorophenyl) pyrrolidin-1-yl)methanone | 105 | $^1$H NMR (300 MHz, CDCl$_3$) δ ppm: 8.56 (s, 1H), 7.59-7.51 (m, 2H), 7.36-7.10 (m, 4H), 6.96-6.88 (m, 2H), 4.97-4.74 (m, 2H), 4.13-3.29 (m, 8H), 2.45-2.24 (m, 1H), 2.17-1.92 (m, 1H). [ES + MS] m/z 427 (MH$^+$). 62.5% yield See footnote a) | a) The reaction was performed on PtO$_2$ (1 eq) and EtOAc was used as solvent b) Purification on silica gel (DCM:MeOH 100:0 to 90:10)

Examples 49-56 were prepared using analogous conditions to that described for route Bof example 45 but replacing intermediate 122 with that indicated in Table 11. Modifications in the protocol are also indicated.

TABLE 11

| Ex. | Structure | Int. | Physical data/Yield |
|---|---|---|---|
| 49 | 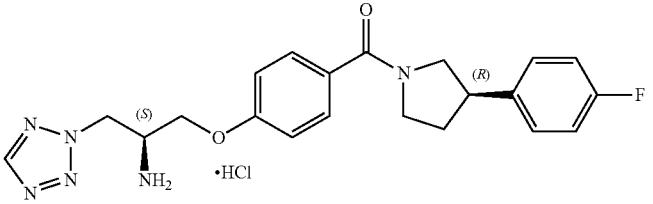<br>(4-((S)-2-amino-3-(2H-tetrazol-2-yl)propoxy)phenyl)((R)-3-(4-fluorophenyl)pyrrolidin-1-yl)methanone, Hydrochloride | 123 | $^1$H NMR (300 MHz, DMSO-$d_6$) δ ppm: 9.12-9.07 (m, 1H), 8.64 (br.s, 3H), 7.57 (d, J = 8.6 Hz, 2H), 7.43-7.28 (m, 2H), 7.21-7.09 (m, 2H), 7.04-6.94 (m, 2H), 5.22-5.10 (m, 2H), 4.39-4.14 (m, 3H), 3.88-3.45 (m, 5H), 2.35-2.17 (m, 1H), 2.11-1.89 (m, 1H). [ES + MS] m/z 411 (MH$^+$).<br>64.8% yield<br>See footnote a), b) |
| 50 | 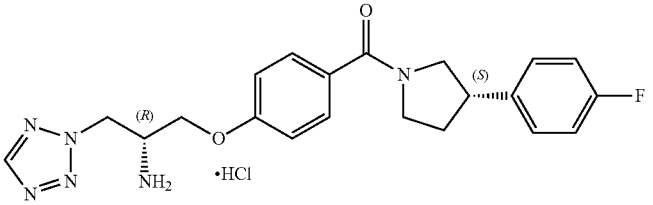<br>(4-((R)-2-amino-3-(2H-tetrazol-2-yl)propoxy)phenyl)((S)-3-(4-fluorophenyl)pyrrolidin-1-yl)methanone, Hydrochloride | 124 | $^1$H NMR (300 MHz, DMSO-$d_6$) δ ppm: 9.12-9.07 (m, 1H), 8.61 (br.s, 3H), 7.57 (d, J = 8.6 Hz, 2H), 7.43-7.28 (m, 2H), 7.20-7.09 (m, 2H), 7.04-6.94 (m, 2H), 5.23-5.07 (m, 2H), 4.36-4.14 (m, 3H), 3.82-3.33 (m, 5H), 2.34-2.16 (m, 1H), 2.10-1.88 (m, 1H). [ES + MS] m/z 411 (MH$^+$).<br>90% yield<br>See footnote a), b) |
| 51 | 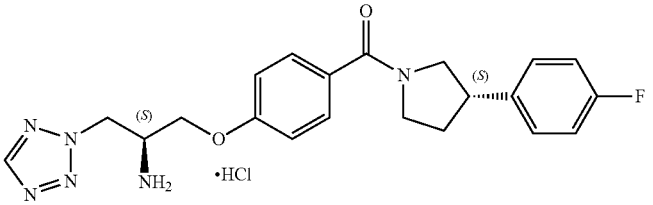<br>(4-((S)-2-amino-3-(2H-tetrazol-2-yl)propoxy)phenyl)((S)-3-(4-fluorophenyl)pyrrolidin-1-yl)methanone, Hydrochloride | 125 | $^1$H NMR (300 MHz, DMSO-$d_6$) δ ppm: 9.13-9.05 (m, 1H), 8.69 (br.s, 3H), 7.57 (d, J = 8.6 Hz, 2H), 7.43-7.28 (m, 2H), 7.21-7.07 (m, 2H), 7.04-6.94 (m, 2H), 5.23-5.11 (m, 2H), 4.38-4.13 (m, 3H), 3.98-3.40 (m, 5H), 2.34-2.16 (m, 1H), 2.10-1.88 (m, 1H). [ES + MS] m/z 411 (MH$^+$).<br>81% yield<br>See footnote a), b) |
| 52 | 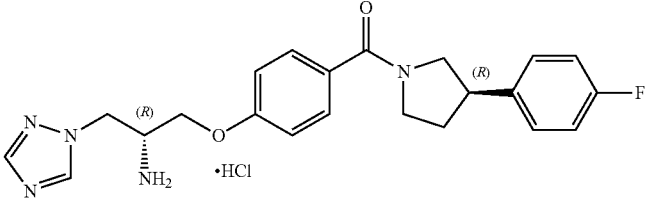<br>(4-((R)-2-amino-3-(1H-1,2,4-triazol-1-yl)propoxy)phenyl)((R)-3-(4-fluorophenyl)pyrrolidin-1-yl)methanone, Hydrochloride | 126 | $^1$H NMR (300 MHz, DMSO-$d_6$) δ ppm: 8.63-8.57 (m, 1H), 8.50 (br.s, 3H), 8.13-8.07 (m, 1H), 7.57 (d, J = 8.6 Hz, 2H), 7.42-7.28 (m, 2H), 7.21-7.09 (m, 2H), 7.05-6.95 (m, 2H), 4.69-4.57 (m, 2H), 4.15-3.89 (m, 3H), 3.80-3.31 (m, 5H), 2.37-2.16 (m, 1H), 2.11-1.87 (m, 1H). [ES + MS] m/z 410 (MH$^+$).<br>99% yield<br>See footnote a), c) |

TABLE 11-continued

| Ex. | Structure | Int. Physical data/Yield |
|---|---|---|
| 53 | 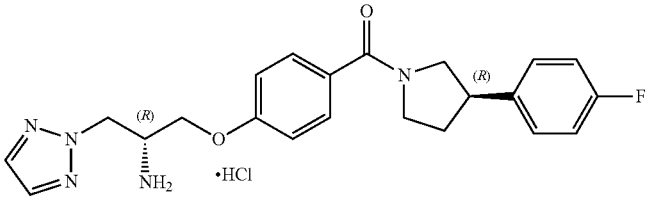<br>(4-((R)-2-amino-3-(2H-1,2,3-triazol-2-yl)propoxy)phenyl)((R)-3-(4-fluorophenyl)pyrrolidin-1-yl)methanone, Hydrochloride | 127 $^1$H NMR (300 MHz, DMSO-d$_6$) δ ppm: 8.49 (br.s, 3H), 7.93-7.88 (m, 2H), 7.57 (d, J = 8.6 Hz, 2H), 7.43-7.28 (m, 2H), 7.21-7.08 (m, 2H), 7.04-6.94 (m, 2H), 4.92-4.76 (m, 2H), 4.33-4.01 (m, 3H), 3.98-3.31 (m, 5H), 2.37-2.16 (m, 1H), 2.13-1.87 (m, 1H). [ES + MS] m/z 410 (MH$^+$).<br>97% yield<br>See footnote a), c) |
| 54 | 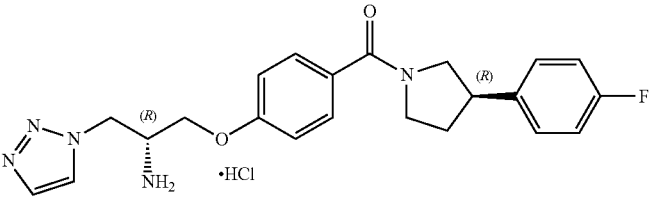<br>(4-((R)-2-amino-3-(1H-1,2,3-triazol-1-yl)propoxy)phenyl)((R)-3-(4-fluorophenyl)pyrrolidin-1-yl)methanone, Hydrochloride | 128 $^1$H NMR (300 MHz, DMSO-d$_6$) δ ppm: 8.68 (br.s, 3H), 8.29-8.21 (m,1H), 7.83-7.78 (m, 1H), 7.57 (d, J = 8.6 Hz, 2H), 7.42-7.28 (m, 2H), 7.21-7.09 (m, 2H), 7.03-6.94 (m, 2H), 4.91-4.76 (m, 2H), 4.30-4.01 (m, 3H), 3.95-3.36 (m, 5H), 2.36-2.15 (m, 1H), 2.10-1.87 (m, 1H). [ES + MS] m/z 410 (MH$^+$).<br>98% yield<br>See footnote a), c) |
| 55 | 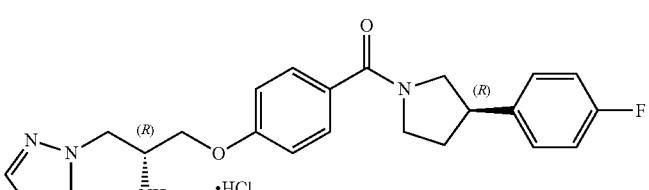<br>(4-((R)-2-amino-3-(1H-pyrazol-1-yl)propoxy)phenyl)((R)-3-(4-fluorophenyl)pyrrolidin-1-yl)methanone, Hydrochloride | 129 $^1$H NMR (300 MHz, DMSO-d$_6$) δ ppm: 8.55 (br.s, 3H), 7.84-7.77 (m, 1H), 7.60-7.52 (m, 3H), 7.43-7.29 (m, 2H), 7.21-7.09 (m, 2H), 7.03-6.94 (m, 2H), 6.34-6.28 (m, 1H), 4.60-4.50 (m, 2H), 4.24-3.93 (m, 3H), 3.79-3.33 (m, 5H), 2.34-2.16 (m, 1H), 2.09-1.89 (m, 1H). [ES + MS] m/z 409 (MH$^+$).<br>97% yield<br>See footnote a), c) |
| 56 | 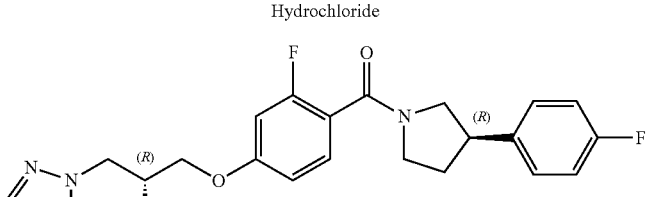<br>(4-((R)-2-amino-3-(2H-tetrazol-2-yl)propoxy)-2-fluorophenyl)((R)-3-(4-fluorophenyl)pyrrolidin-1-yl)methanone, Hydrochloride | 130 $^1$H NMR (300 MHz, DMSO-d$_6$) δ ppm: 9.09 (d, J = 6.3 Hz, 1H), 8.65 (br.s, 3H), 7.48-7.27 (m, 3H), 7.21-7.08 (m, 2H), 6.97-6.81 (m, 2H), 5.20-5.09 (m, 2H), 4.39-4.15 (m, 3H), 3.76-3.20 (m, 5H), 2.35-2.17 (m, 1H), 2.11-1.89 (m, 1H). [ES + MS] m/z 429 (MH$^+$).<br>96% yield<br>See footnote a), c) | a) The hydrochloride salt is isolated of the crude material. No SCX column required.
b) The solvent was removed and the solid was triturated with Et$_2$O and filtered to obtain the title compound
c) The mixture was concentrated, the crude was dissolved in Acetonitrile/Water and lyophilized to give the title compound.

Biological Assays

A compound of this invention may be tested in one of several biological assays to determine the concentration of compound which is required to have a given pharmacological effect. The assays are described below.

In Vitro Potency

P. falciparum Growth Inhibition Assay.

The sensitivity of P. falciparum infected erythrocytes to the compound was determined in duplicate using the [3H] hypoxanthine incorporation method with an inoculum of 0.5% parasitemia (ring stage) and 2% hematocrit. The parasites were grown in RPMI 1640, 25 mM HEPES and supplemented with 5% Albumax. Plates are incubated at 37° C., 5% CO$_2$, 5% O$_2$, 90% N$_2$. After 24 h of incubation, [3H]hypoxanthine is added and plates are incubated for another 24 h. After that period, plates are harvested on a glass fiber filter using a TOMTEC Cell harvester 96. Filters are dried and melt on scintillator sheets and the bound radioactivity is quantified by use of a Wallac Microbeta Trilux (Model 1450 LS—Perkin Elmer). IC50s are determined using Grafit 7 program (Grafit program; Erithacus Software, Horley, Surrey, United Kingdom).

Each example compound was tested generally in accordance with the above-mentioned assay and the PfIC50 value for each compound is reported in the Table below and according to the following:

<0.1 μM=++++
≥0.1 μM to <0.5 μM=+++
≥0.5 μM to <1 μM=++
≥1 μM to <5 μM=+
≥5=|

| Example | Structure | PfIC50 Media (uM) | Isomer[a] |
|---|---|---|---|
| 1a | 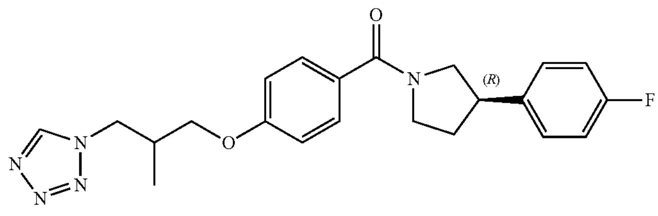 | +++ | Isom1,R |
| 1b | 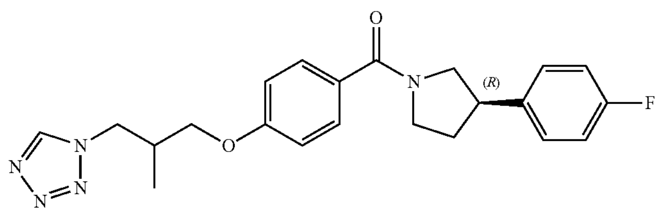 | ++++ | Isom2,R |
| 2 | 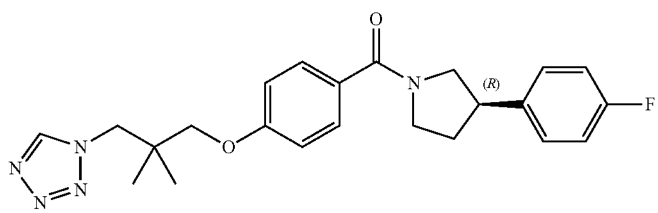 | ++ | R |
| 3a | 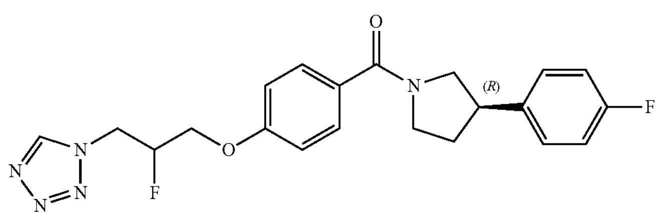 | +++ | Isom1,R |
| 3b | 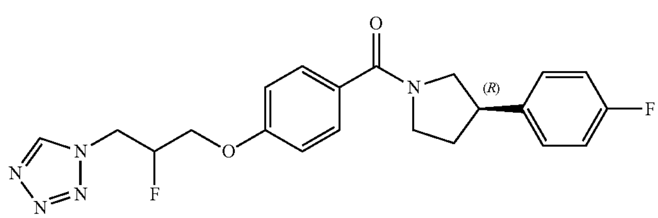 | ++++ | Isom2,R |
| 4 | 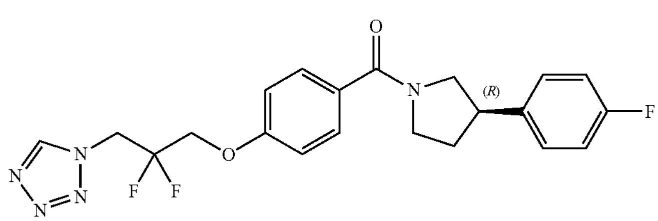 | ++++ | R |

-continued

| Example | Structure | PfIC50 Media (uM) | Isomer[a] |
|---|---|---|---|
| 5 | 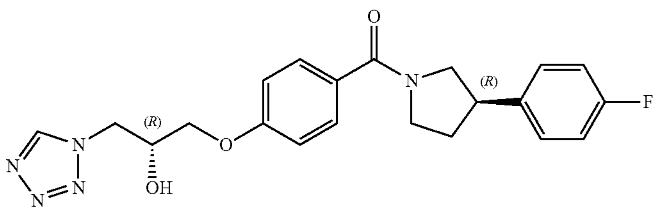 | ++++ | R,R |
| 6 | 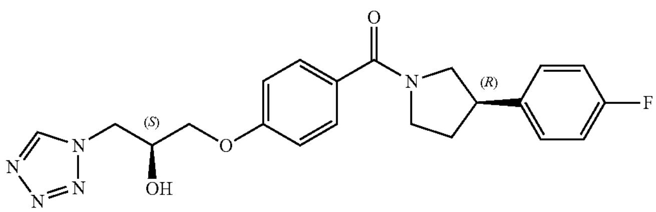 | +++ | S,R |
| 7 | 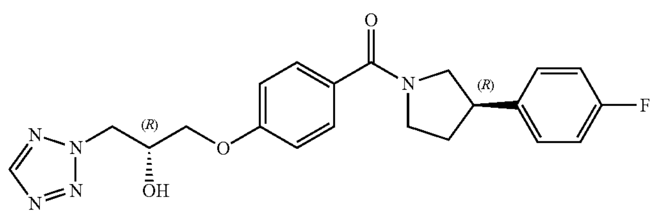 | ++++ | R,R |
| 8 | 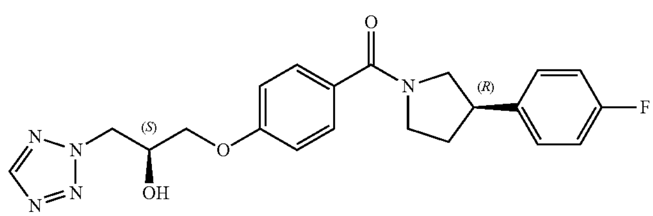 | ++++ | S,R |
| 9a | 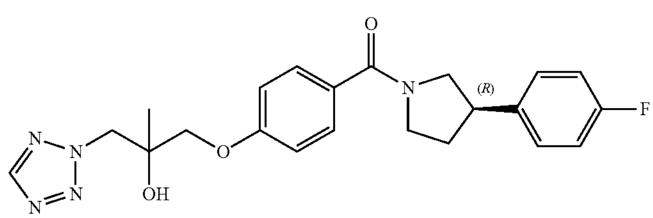 | +++ | Isom 1,R |
| 9b | 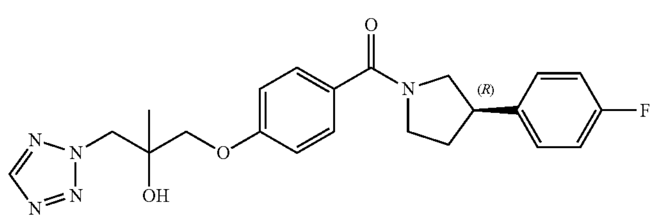 | +++ | Isom 2,R |
| 10a | 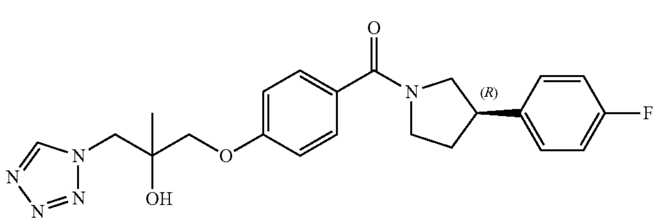 | + | Isom 1,R |

-continued

| Example | Structure | PfIC50 Media (uM) | Isomer[a] |
|---|---|---|---|
| 10b | 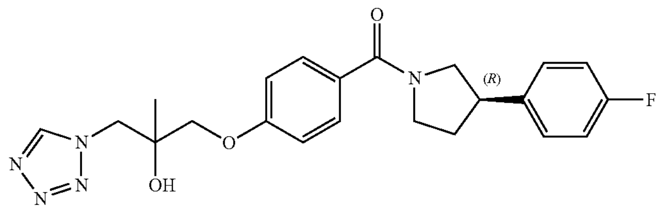 | + | Isom 2,R |
| 11 | 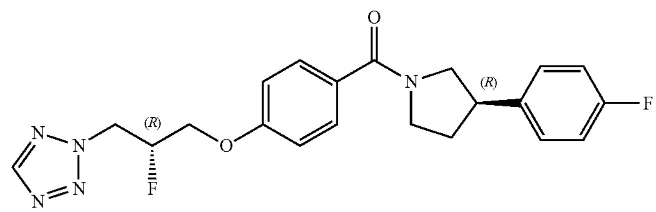 | ++++ | R,R |
| 12 | 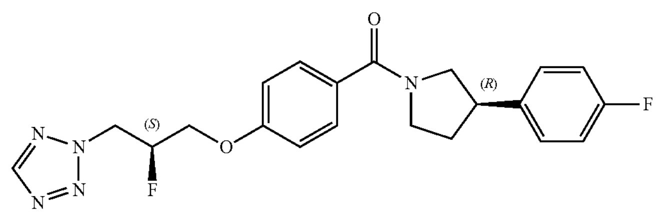 | ++++ | S,R |
| 13 | 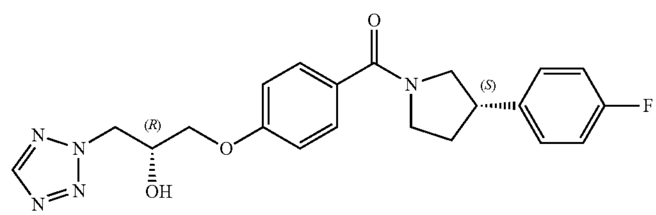 | ++++ | R,S |
| 14 | 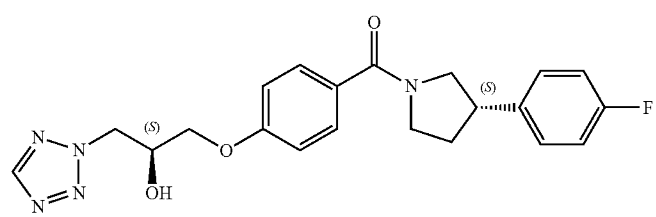 | + | S,S |
| 15 | 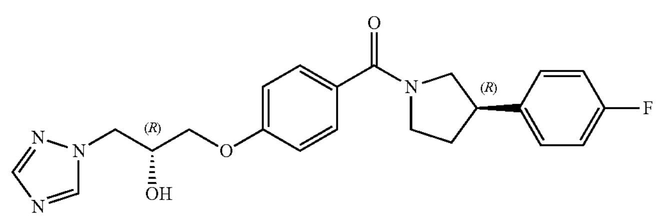 | ++++ | R,R |
| 16 | 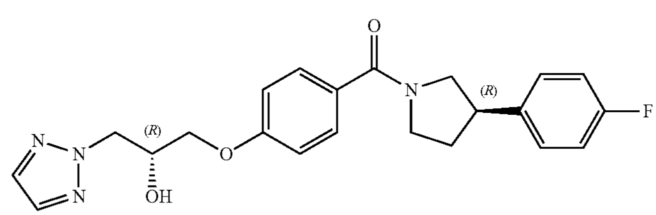 | ++++ | R,R |

-continued

| Example | Structure | PfIC50 Media (uM) | Isomer[a] |
|---|---|---|---|
| 17 | 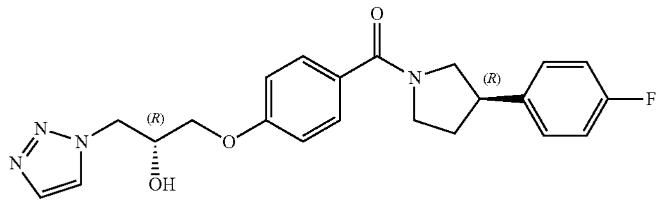 | ++++ | R,R |
| 18 | 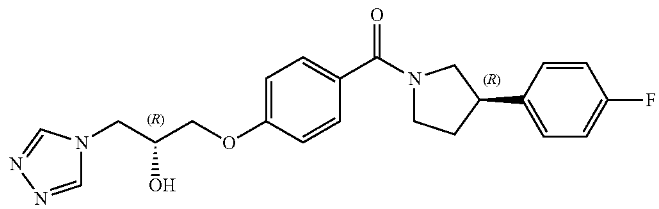 | + | R,R |
| 19 | 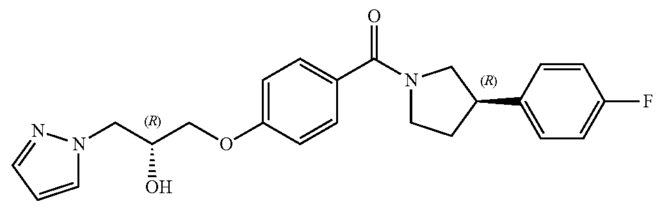 | ++++ | R,R |
| 20 | 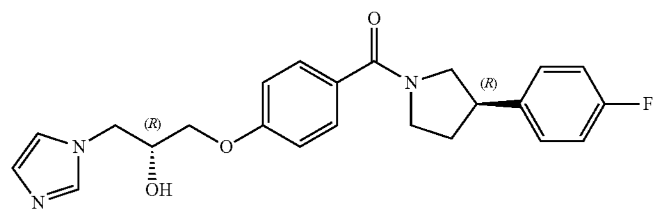 | ++++ | R,R |
| 21 | 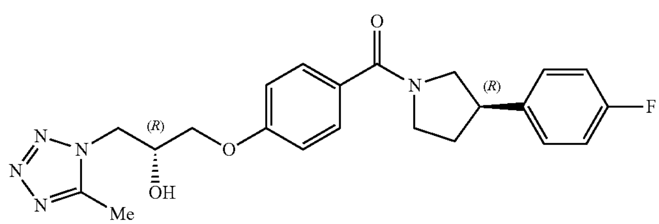 | ++ | R,R |
| 22 | 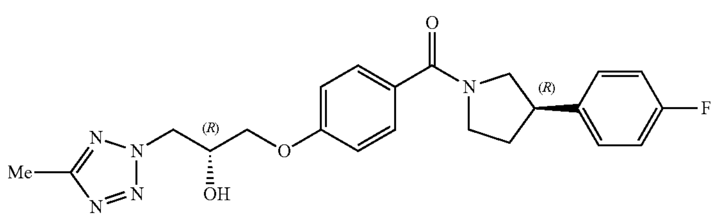 | ++++ | R,R |
| 23 | 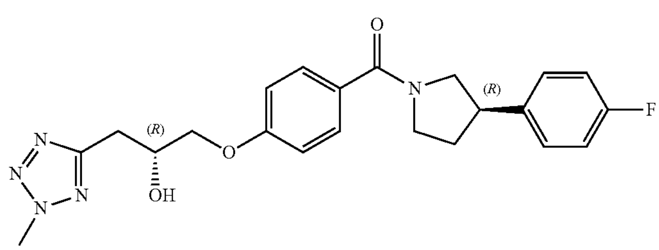 | ++++ | R,R |

-continued

| Example | Structure | PfIC50 Media (uM) | Isomer[a] |
|---|---|---|---|
| 24 | 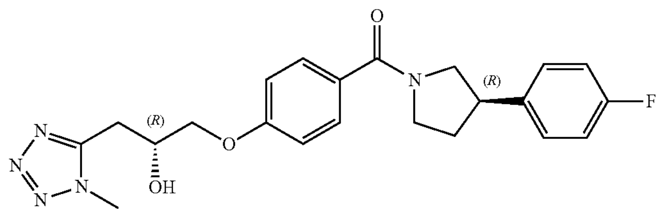 | +++ | R,R |
| 25 | 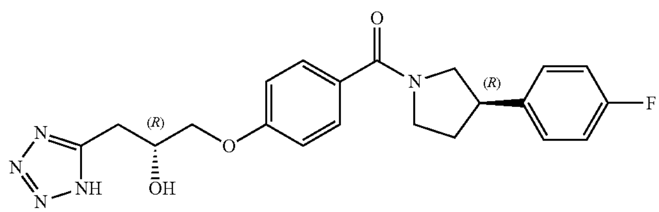 | + | R,R |
| 26 | 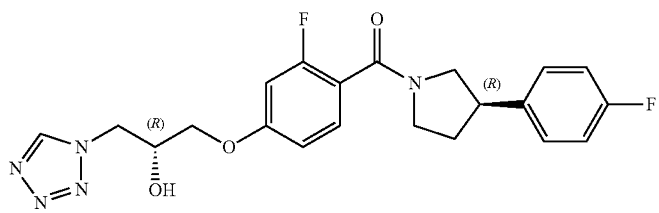 | +++ | R,R |
| 27 | 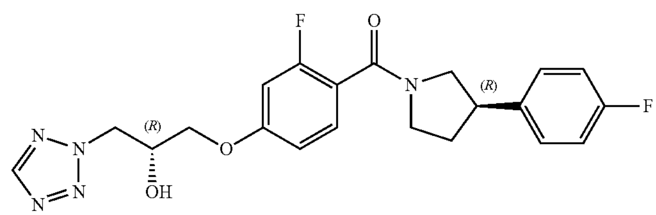 | ++++ | R,R |
| 28 | 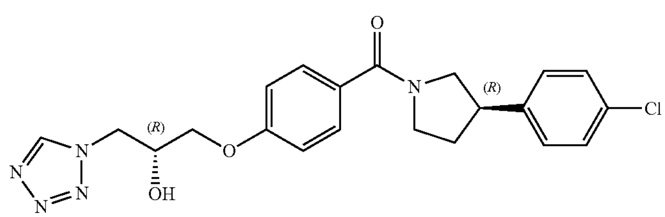 | ++++ | R,R |
| 29 | 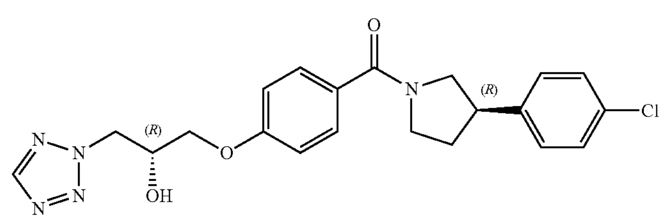 | ++++ | R,R |
| 30 | 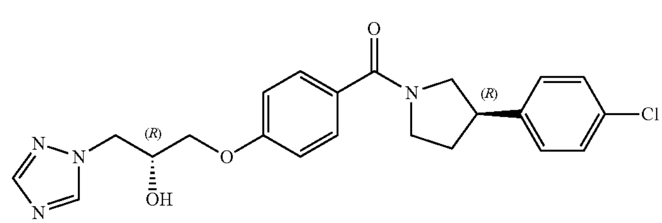 | ++++ | R,R |

-continued

| Example | Structure | PfIC50 Media (uM) | Isomer[a] |
|---|---|---|---|
| 31 | 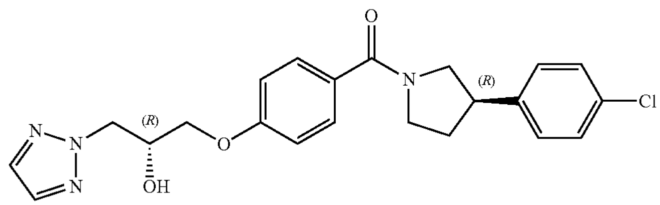 | ++++ | R,R |
| 32 | 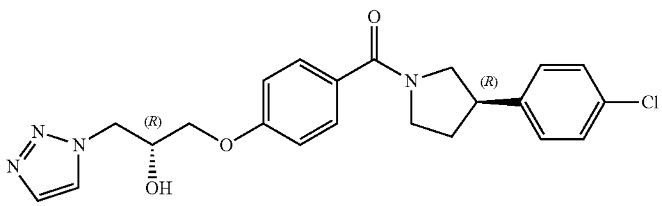 | ++++ | R,R |
| 33 | 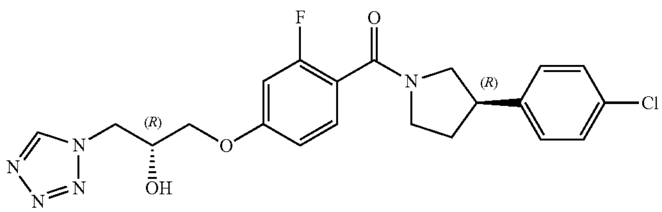 | +++ | R,R |
| 34 | 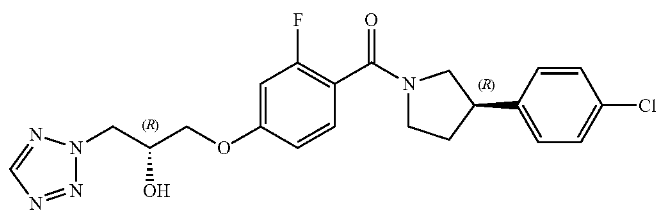 | ++++ | R,R, |
| 35a | 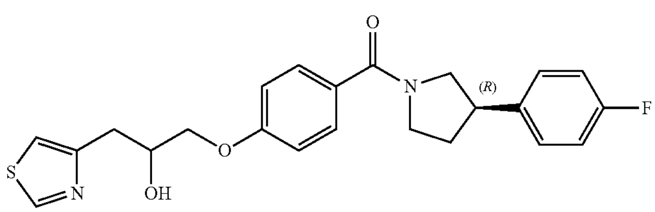 | ++++ | Isom1,R |
| 35b | 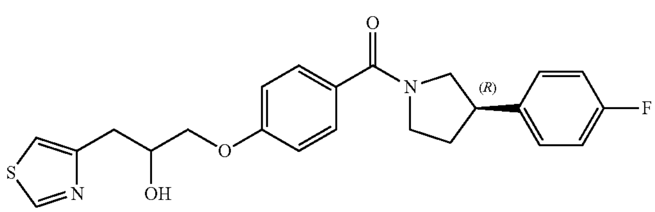 | +++ | Isom2,R |
| 36a | 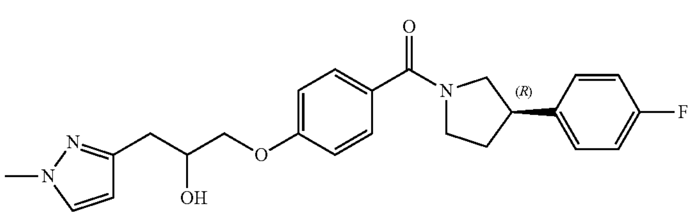 | ++++ | Isom1,R |

-continued

| Example | Structure | PfIC50 Media (uM) | Isomer[a] |
|---|---|---|---|
| 36b | 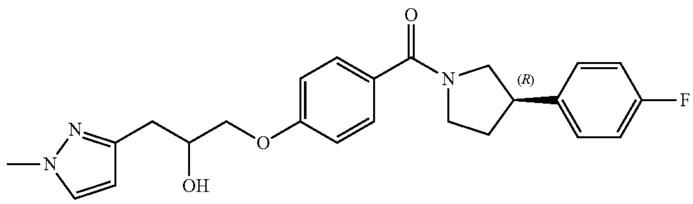 | † | Isom1,R |
| 37 | 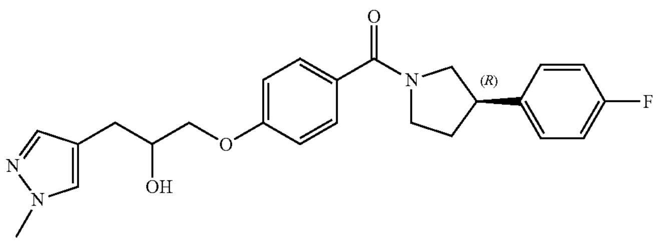 | + | Rac,R |
| 38 | 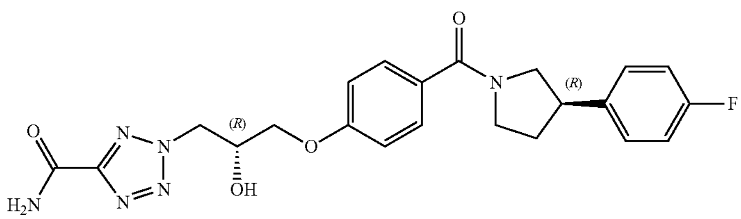 | +++ | R,R |
| 39 | 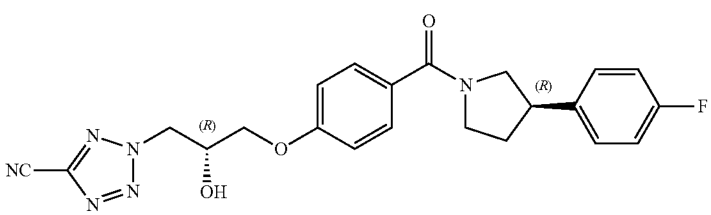 | +++ | R,R |
| 40a | 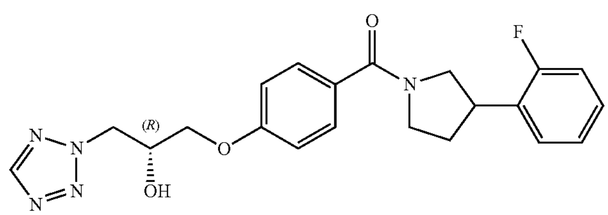 | ++++ | R,isom.1 |
| 40b | 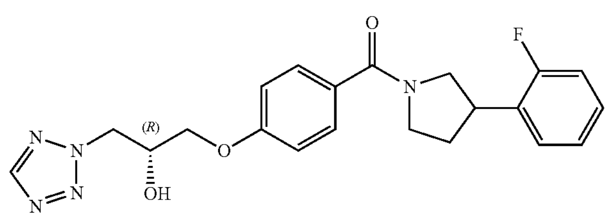 | +++ | R,isom.2 |
| 41a | 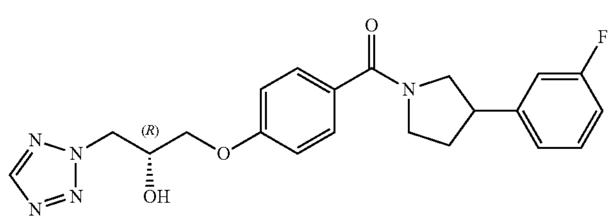 | ++++ | R,isom.1 |

-continued

| Example | Structure | PfIC50 Media (uM) | Isomer[a] |
|---------|-----------|-------------------|-----------|
| 41b | 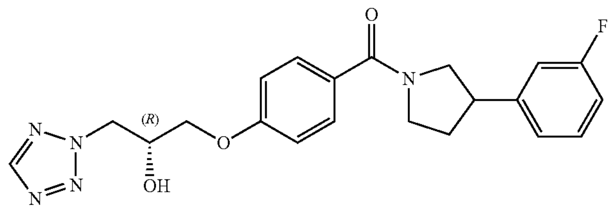 | +++ | R,isom.2 |
| 42a | 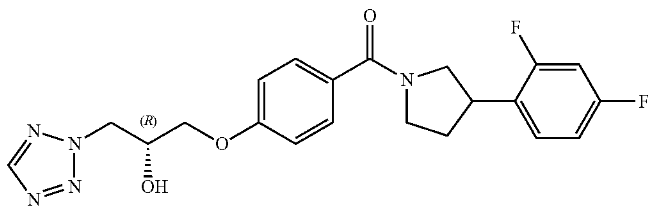 | ++++ | R,isom.1 |
| 42b | 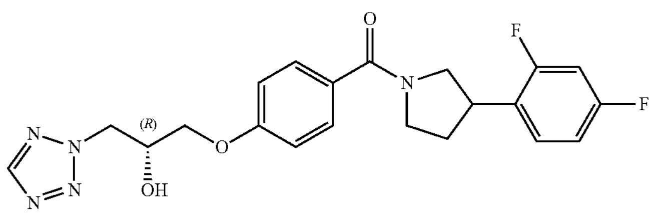 | +++ | R,isom.2 |
| 43a | 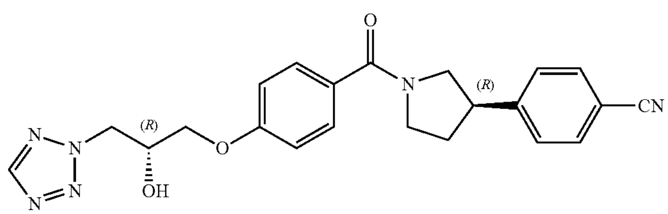 | +++ | R,isom.1 |
| 43b | 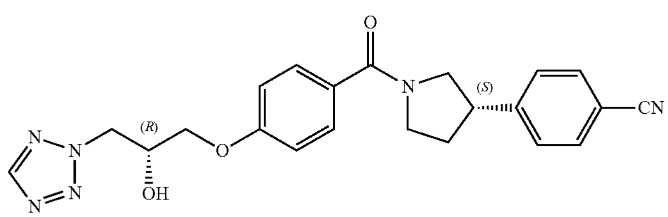 | + | R,isom.2 |
| 44a | 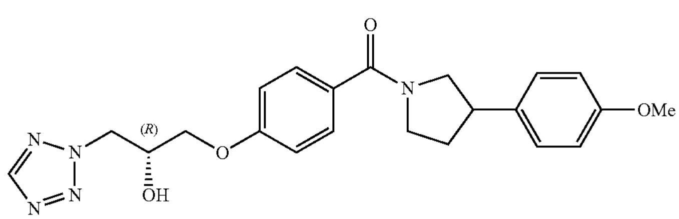 | ++++ | R,isom.1 |
| 44b | 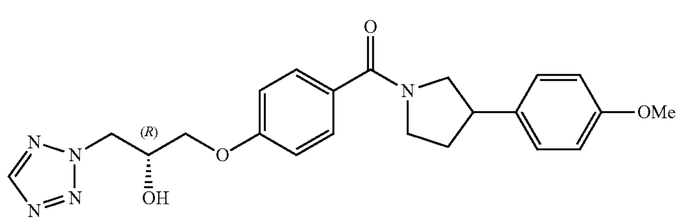 | ++ | R,isom.2 |

-continued

| Example | Structure | PfIC50 Media (uM) | Isomer[a] |
|---|---|---|---|
| 45 | 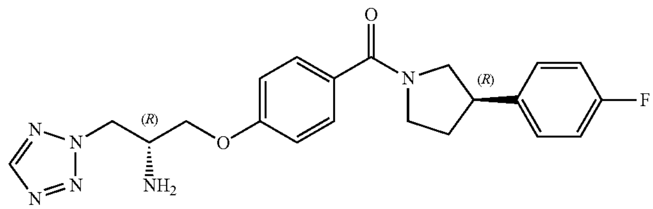 | ++++<br>++++(HCl) | R,R |
| 46 | 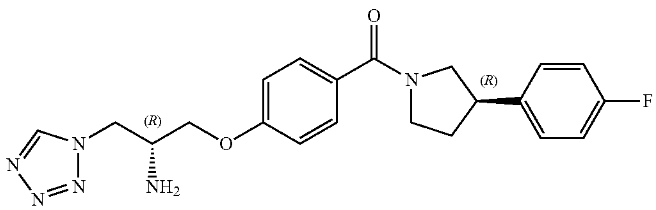 | ++++ | R,R |
| 47 | 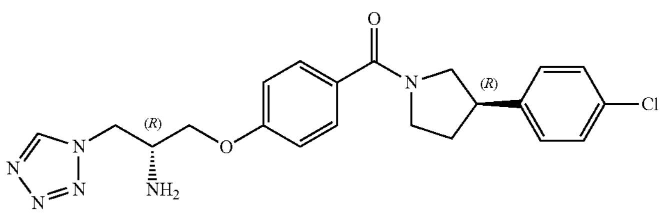 | ++++<br>++++(HCl) | R,R |
| 48 | 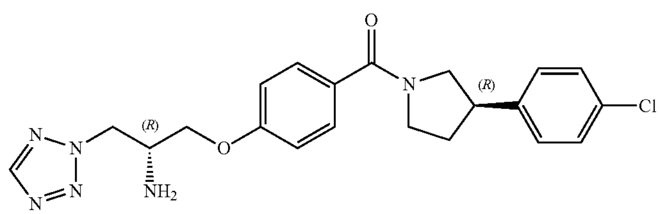 | ++++ | R,R |
| 49 | 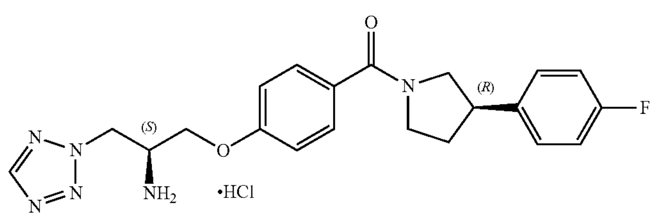 | +++ | S,R |
| 50 | 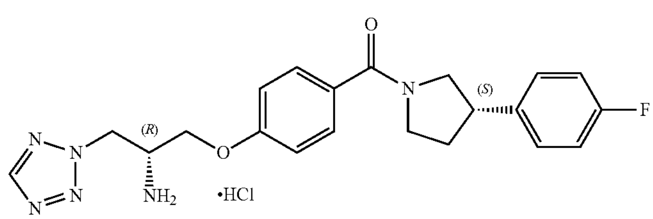 | +++ | R,S |
| 51 | 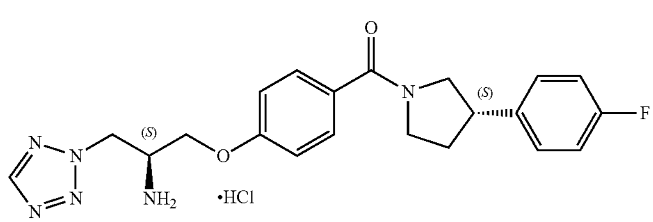 | † | S,S |

| Example | Structure | PfIC50 Media (uM) | Isomer[a] |
|---|---|---|---|
| 52 | 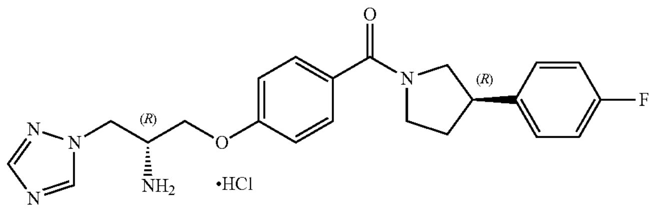 | +++ | R,R |
| 53 | 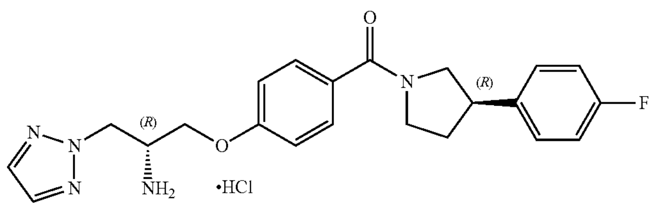 | ++++ | R,R |
| 54 | 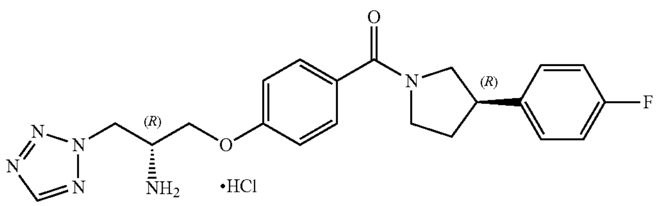 | +++ | R,R |
| 55 | 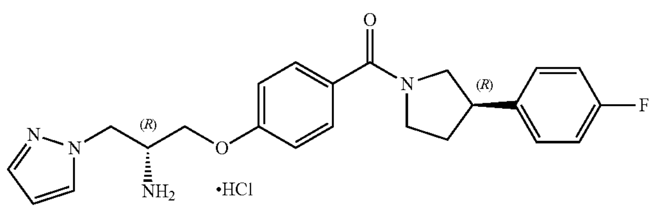 | +++ | R,R |
| 56 | 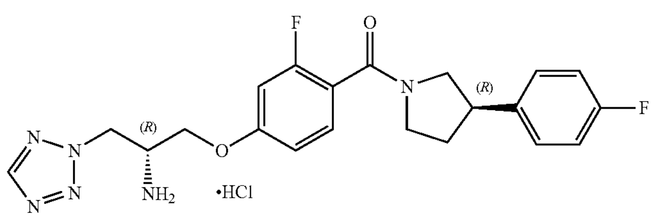 | +++ | R,R |

[a] stereocentres indicated by reference to the compound (as depicted) from left to right.

In particular, each of Examples 3b, 5, 7, 11, 12, 15, 16, 17, 19, 27, 29, 31, 32, 35a, 40a, 41a, 42a, 4 and, 48 were found to have an average PfIC50 of ≤50 nM (i.e. ≤0.05 μM).

Example 8 was found to have an average PfIC50 of 52 nM.

Example 13 was found to have an average PfIC50 of 54 nM.

Example 14 was found to have an average PfIC50 of 1.2 μM.

Example 45 was found to have an average PfIC50 of 18 nM. The hydrochloride salt of the same example was found to have an average PfIC50 of 30 nM.

The hydrochloride salt of Example 49 was found to have an average PfIC50 of 310 nM.

The hydrochloride salt of Example 50 was found to have an average PfIC50 of 219 nM.

The hydrochloride salt of Example 51 was found to have an average PfIC50 of >5 μM.

The invention claimed is:

1. A compound according to Formula (I) or a pharmaceutically acceptable salt thereof:

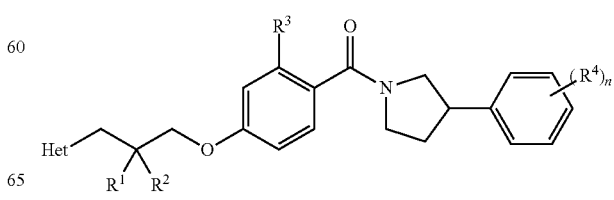

(I)

wherein
R¹ is hydrogen, fluoro or methyl, wherein
when R¹ is hydrogen, R² is fluoro, methyl, hydroxyl or amino,
when R¹ is fluoro, R² is fluoro, and
when R¹ is methyl, R² is methyl or hydroxyl;
R³ is hydrogen or fluoro;
R⁴ is fluoro, chloro, cyano or methoxy;
n is 1 or 2; and
Het is imidazole, pyrazole, thiazole, isothiazole, oxazole, isoxazole, triazole or tetrazole, wherein each Het is optionally substituted by $C_1$-$C_4$ alkyl, cyano or —C(O)NH₂.

2. The compound or pharmaceutically acceptable salt thereof according to claim 1, wherein R¹ is hydrogen.

3. The compound or pharmaceutically acceptable salt thereof according to claim 1, wherein R² is hydroxyl or amino.

4. The compound or pharmaceutically acceptable salt thereof according to claim 1, wherein R³ is hydrogen.

5. The compound or pharmaceutically acceptable salt thereof according to claim 1, wherein n is 1.

6. Thesompound or pharmaceutically acceptable salt thereof according to claim 1, wherein R⁴ is at the para position.

7. The compound or pharmaceutically acceptable salt thereof according to claim 1, wherein R⁴ is fluoro or chloro.

8. The compound or pharmaceutically acceptable salt thereof according to claim 1, wherein the compound is defined according to Formula Ib:

(Ib)

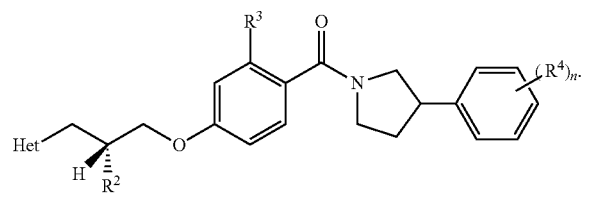

9. The compound or pharmaceutically acceptable salt thereof according to claim 1, wherein the compound is defined according to Formula (Id):

(Id)

10. The compound or pharmaceutically acceptable salt thereof according to claim 1, wherein Het is selected from one of the following groups, where * represents the point of attachment:

11. The compound or pharmaceutically acceptable salt thereof according to claim 1, wherein Het is selected from one of the following groups, where * represents the point of attachment:

12. The compound or pharmaceutically acceptable salt thereof according to claim 1, wherein Het is tetrazole.

13. The compound or pharmaceutically acceptable salt thereof according to claim 1, wherein the compound is selected from the group consisting of:
((R)-3-(4-fluorophenyl)pyrrolidin-1-yl)(4-(2-methyl-3-(1H-tetrazol-1-yl) propoxy)phenyl)methanone;
(R)-(4-(2,2-dimethyl-3-(1H-tetrazol-1-yl)propoxy)phenyl)(3-(4-fluorophenyl)pyrrolidin-1-yl)methanone;

(4-(2-fluoro-3-(1H-tetrazol-1-yl)propoxy)phenyl)((R)-3-(4-fluorophenyl)pyrrolidin-1-yl)methanone;

(R)-(4-(2,2-difluoro-3-(1H-tetrazol-1-yl)propoxy)phenyl)(3-(4-fluorophenyl)-pyrrolidin-1-yl)methanone;

((R)-3-(4-fluorophenyl)pyrrolidin-1-yl)(4-((R)-2-hydroxy-3-(1H-tetrazol-1-yl) propoxy)phenyl)methanone;

((R)-3-(4-fluorophenyl)pyrrolidin-1-yl)(4-((S)-2-hydroxy-3-(1H-tetrazol-1-yl) propoxy)phenyl)methanone;

((R)-3-(4-fluorophenyl)pyrrolidin-1-yl)(4-((R)-2-hydroxy-3-(2H-tetrazol-2-yl) propoxy)phenyl)methanone;

((R)-3-(4-fluorophenyl)pyrrolidin-1-yl)(4-((S)-2-hydroxy-3-(2H-tetrazol-2-yl)propoxy)phenyl)methanone;

((R)-3-(4-fluorophenyl)pyrrolidin-1-yl)(4-(2-hydroxy-2-methyl-3-(2H-tetrazol-2-yl)propoxy)phenyl)methanone;

((R)-3-(4-fluorophenyl)pyrrolidin-1-yl)(4-(2-hydroxy-2-methyl-3-(1H-tetrazol-1-yl)propoxy)phenyl)methanone;

(4-((R)-2-fluoro-3-(2H-tetrazol-2-yl)propoxy)phenyl)((R)-3-(4-fluorophenyl) pyrrolidin-1-yl)methanone);

(4-((S)-2-fluoro-3-(2H-tetrazol-2-yl)propoxy)phenyl)((R)-3-(4-fluorophenyl) pyrrolidin-1-yl)methanone);

((S)-3-(4-fluorophenyl)pyrrolidin-1-yl)(4-((R)-2-hydroxy-3-(2H-tetrazol-2-yl)propoxy)phenyl)methanone;

((S)-3-(4-fluorophenyl)pyrrolidin-1-yl)(4-((S)-2-hydroxy-3-(2H-tetrazol-2-yl)propoxy)phenyl)methanone;

((R)-3-(4-fluorophenyl)pyrrolidin-1-yl)(4-((R)-2-hydroxy-3-(1H-1,2,4-triazol-1-yl)propoxy)phenyl) methanone;

((R)-3-(4-fluorophenyl)pyrrolidin-1-yl)(4-((R)-2-hydroxy-3-(2H-1,2,3-triazol-2-yl)propoxy)phenyl) methanone;

((R)-3-(4-fluorophenyl)pyrrolidin-1-yl)(4-((R)-2-hydroxy-3-(1H-1,2,3-triazol-1-yl)propoxy)phenyl) methanone;

((R)-3-(4-fluorophenyl)pyrrolidin-1-yl)(4-((R)-2-hydroxy-3-(4H-1,2,4-triazol-4-yl)propoxy)phenyl) methanone;

((R)-3-(4-fluorophenyl)pyrrolidin-1-yl)(4-((R)-2-hydroxy-3-(1H-pyrazol-1-yl)propoxy)phenyl)methanone;

((R)-3-(4-fluorophenyl)pyrrolidin-1-yl)(4-((R)-2-hydroxy-3-(1H-imidazol-1-yl)propoxy)phenyl)methanone;

((R)-3-(4-fluorophenyl)pyrrolidin-1-yl)(4-((R)-2-hydroxy-3-(5-methyl-1H-tetrazol-1-yl)propoxy)phenyl)methanone;

((R)-3-(4-fluorophenyl)pyrrolidin-1-yl)(4-((R)-2-hydroxy-3-(5-methyl-2H-tetrazol-2-yl)propoxy)phenyl)methanone;

((R)-3-(4-fluorophenyl)pyrrolidin-1-yl)(4-((R)-2-hydroxy-3-(2-methyl-2H-tetrazol-5-yl)propoxy)phenyl)methanone;

((R)-3-(4-fluorophenyl)pyrrolidin-1-yl)(4-((R)-2-hydroxy-3-(1-methyl-1H-tetrazol-5-yl)propoxy)phenyl)methanone;

((R)-3-(4-fluorophenyl)pyrrolidin-1-yl)(4-((R)-2-hydroxy-3-(1H-tetrazol-5-yl)propoxy)phenyl)methanone;

(2-fluoro-4-((R)-2-hydroxy-3-(1H-tetrazol-1-yl)propoxy)phenyl)((R)-3-(4-fluorophenyl)pyrrolidin--yl)methanone;

(2-fluoro-4-((R)-2-hydroxy-3-(2H-tetrazol-2-yl)propoxy)phenyl)((R)-3-(4-fluorophenyl)pyrrolidin-1-yl)methanone;

((R)-3-(4-chlorophenyl)pyrrolidin-1-yl)(4-((R)-2-hydroxy-3-(1H-tetrazol-1-yl)propoxy)phenyl)methanone;

((R)-3-(4-chlorophenyl)pyrrolidin-1-yl)(4-((R)-2-hydroxy-3-(2H-tetrazol-2-yl)propoxy)phenyl)methanone;

((R)-3-(4-chlorophenyl)pyrrolidin-1-yl) (4-((R)-2-hydroxy-3-(1H-1,2,4-triazol-1-yl)propoxy)phenyl) methanone;

((R)-3-(4-chlorophenyl)pyrrolidin-1-yl)(4-((R)-2-hydroxy-3-(2H-1,2,3-triazol-2-yl)propoxy)phenyl) methanone;

((R)-3-(4-chlorophenyl)pyrrolidin-1-yl)(4-((R)-2-hydroxy-3-(1H-1,2,3-triazol-1-yl)propoxy)phenyl) methanone;

((R)-3-(4-chlorophenyl)pyrrolidin-1-yl) (2-fluoro-4-((R)-2-hydroxy-3-(1H-tetrazol-1-yl)propoxy)phenyl)methanone;

((R)-3-(4-chlorophenyl)pyrrolidin-1-yl) (2-fluoro-4-((R)-2-hydroxy-3-(2H-tetrazol-2-yl)propoxy)phenyl)methanone;

((R)-3-(4-fluorophenyl)pyrrolidin-1-yl)(4-(2-hydroxy-3-(thiazol-4-yl)propoxy)phenyl)methanone;

((R)-3-(4-fluorophenyl)pyrrolidin-1-yl)(4-(2-hydroxy-3-(1-methyl-1H-pyrazol-4-yl)propoxy)phenyl)methanone;

2-((R)-3-(4-((R)-3-(4-fluorophenyl)pyrrolidine-1-carbonyl)phenoxy)-2-hydroxypropyl)-2H-tetrazole-5-carboxamide;

2-((R)-3-(4-((R)-3-(4-fluorophenyl)pyrrolidine-1-carbonyl)phenoxy)-2-hydroxypropyl)-2H-tetrazole-5-carbonitrile;

(3-(2-fluorophenyl)pyrrolidin-1-yl)(4-((R)-2-hydroxy-3-(2H-tetrazol-2-yl)propoxy)phenyl)methanone;

(3-(3-fluorophenyl)pyrrolidin-1-yl)(4-((R)-2-hydroxy-3-(2H-tetrazol-2-yl)propoxy)phenyl)methanone;

(3-(2,4-difluorophenyl)pyrrolidin-1-yl)(4-((R)-2-hydroxy-3-(2H-tetrazol-2-yl)propoxy)phenyl)methanone;

4-(1-(4-((R)-2-hydroxy-3-(2H-tetrazol-2-yl)propoxy)benzoyl) pyrrolidin-3-yl)benzonitrile;

(4-((R)-2-hydroxy-3-(2H-tetrazol-2-yl)propoxy)phenyl)(3-(4-methoxyphenyl)pyrrolidin-1-yl)methanone;

(4-((R)-2-amino-3-(2H-tetrazol-2-yl)propoxy)phenyl)((R)-3-(4-fluorophenyl) pyrrolidin-1-yl)methanone;

(4-((R)-2-amino-3-(1H-tetrazol-1-yl)propoxy)phenyl)((R)-3-(4-fluorophenyl) pyrrolidin-1-yl)methanone;

(4-((R)-2-amino-3-(1H-tetrazol-1-yl) propoxy)phenyl)((R)-3-(4-chlorophenyl) pyrrolidin-1-yl)methanone;

(4-((R)-2-amino-3-(2H-tetrazol-2-yl) propoxy)phenyl)((R)-3-(4-chlorophenyl) pyrrolidin-1-yl)methanone;

(4-((S)-2-amino-3-(2H-tetrazol-2-yl) propoxy)phenyl)((R)-3-(4-fluorophenyl) pyrrolidin-1-yl)methanone;

(4-((R)-2-amino-3-(2H-tetrazol-2-yl) propoxy)phenyl)((S)-3-(4-fluorophenyl) pyrrolidin-1-yl)methanone;

(4-((S)-2-amino-3-(2H-tetrazol-2-yl) propoxy)phenyl)(S)-3-(4-fluorophenyl) pyrrolidin-1-yl)methanone;

(4-((R)-2-amino-3-(2H-1,2,3-triazol-2-yl) propoxy)phenyl)((R)-3-(4-fluorophenyl)pyrrolidin-1-yl)methanone;

(4-((R)-2-amino-3-(1H-1,2,3-triazol-1-yl) propoxy)phenyl)((R)-3-(4-fluorophenyl)pyrrolidin-1-yl)methanone;

(4-((R)-2-amino-3-(1H-pyrazol-1-yl) propoxy)phenyl)((R)-3-(4-fluorophenyl) pyrrolidin-1-yl)methanone; and (4-((R)-2-amino-3-(2H-tetrazol-2-yl)propoxy)-2-fluorophenyl)((R)-3-(4-fluorophenyl)pyrrolidin-1-yl)methanone.

14. A pharmaceutical composition comprising (a) a compound or pharmaceutically acceptable salt thereof according to claim 1; and (b) a pharmaceutically acceptable excipient.

15. A method for the treatment of a parasitic protozoal infection in a human in need thereof, comprising administering to the human a pharmaceutically effective amount of a compound or pharmaceutically acceptable salt thereof according to claim 1, wherein the parasitic protozoal infection is a *Plasmodium falciparum* infection.

16. The method according to claim 15, wherein the parasitic protozoal infection is malaria.

17. The compound or pharmaceutically acceptable salt thereof according to claim 1, wherein the compound is ((R)-3-(4-fluorophenyl)pyrrolidin-1-yl)(4-((R)-2-hydroxy-3-(2-H-tetrazol-2-yl) propoxy)phenyl)methanone.

18. A compound which is

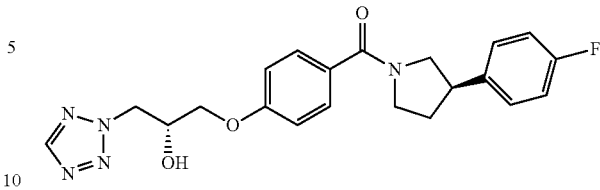

or a pharmaceutically acceptable salt thereof.

19. A method for the treatment of a parasitic protozoal infection in a human in need thereof, comprising administering to the human a pharmaceutically effective amount of a compound or pharmaceutically acceptable salt thereof according to claim 18, wherein the parasitic protozoal infection is malaria.

* * * * *